US011351270B2

(12) United States Patent
Song et al.

(10) Patent No.: US 11,351,270 B2
(45) Date of Patent: Jun. 7, 2022

(54) JUNCTOPHILIN-2 FRAGMENTS AND USES THEREFOR

(71) Applicant: University of Iowa Research Foundation, Iowa City, IA (US)

(72) Inventors: Long-Sheng Song, Coralville, IA (US); Ang Guo, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 475 days.

(21) Appl. No.: 16/307,807

(22) PCT Filed: Jun. 7, 2017

(86) PCT No.: PCT/US2017/036392
§ 371 (c)(1),
(2) Date: Dec. 6, 2018

(87) PCT Pub. No.: WO2017/214296
PCT Pub. Date: Dec. 14, 2017

(65) Prior Publication Data
US 2019/0307899 A1 Oct. 10, 2019

Related U.S. Application Data

(60) Provisional application No. 62/346,794, filed on Jun. 7, 2016.

(51) Int. Cl.
| | | |
|---|---|---|
| C12N 15/79 | (2006.01) |
| C07H 21/04 | (2006.01) |
| A61K 48/00 | (2006.01) |
| A61P 9/00 | (2006.01) |
| A01K 67/027 | (2006.01) |
| A61K 38/17 | (2006.01) |
| C07K 14/47 | (2006.01) |
| C12N 15/86 | (2006.01) |

(52) U.S. Cl.
CPC ...... *A61K 48/0058* (2013.01); *A01K 67/0278* (2013.01); *A61K 38/17* (2013.01); *A61K 38/1719* (2013.01); *A61K 48/00* (2013.01); *A61P 9/00* (2018.01); *C07K 14/4716* (2013.01); *C12N 15/86* (2013.01); *A01K 2217/206* (2013.01); *A01K 2227/105* (2013.01); *C07K 2319/21* (2013.01)

(58) Field of Classification Search
CPC ........ C12N 15/79; C12N 15/85; C12N 15/86; C07H 21/04
See application file for complete search history.

(56) References Cited

FOREIGN PATENT DOCUMENTS

| | | |
|---|---|---|
| CN | 106011085 A | 10/2016 |
| WO | WO-0028020 A2 | 5/2000 |
| WO | WO-2017214296 A1 | 12/2017 |

OTHER PUBLICATIONS

Emtage et al., 2005, Geneseq Accession No. AEB77267, computer printout, pp. 1-2.*
Padigaru et al., 2002, Geneseq Accession No. ABU65176, computer printout, pp. 1-2.*
Emtage et al., 2005, US 20050164202 A1, Emtage A.*
Emtage et al., 2005, Geneseq Accession No. AEB77267, computer printout, pp. 1-2, Emtage C.*
"International Application Serial No. PCT/US2017/036392, International Search Report dated Oct. 17, 2017", 6 pgs.
"International Application Serial No. PCT/US2017/036392, Written Opinion dated Oct. 17, 2017", 9 pgs.
A, Guo, et al., "Overexpression of junctophilin-2 does not enhance baseline function but attenuates heart failure development after cardiac stress", Proceedings National Academy of Sciences PNAS vol. 111 No. 33, (Aug. 4, 2014), 12240-12245.
Ang, Guo, et al., "Molecular Determinants of Calpain-dependent Cleavage of Junctophilin-2 Protein in Cardiomyocyte", Journal of Biological Chemistry vol. 290 No. 29, (Jul. 17, 2015), 17946-17955.
Takeshima, Hiroshi, et al., "Junctophilins: A Novel Family of Junctional Membrane Complex Proteins", Journal of Molecular Cell, 6 (1), (Jul. 2000), 11-22.
"International Application Serial No. PCT US2017 036392, International Preliminary Report on Patentability dated Dec. 20, 2018", 8 pgs.
Wu, Chia-Yen, et al., "Calpain-Dependent Cleavage of Junctophilin-2 and T-Tubule Remodeling in a Mouse Model of Reversible Heart Failure", American Heart Association, (2014), 18 pgs.

* cited by examiner

*Primary Examiner* — Shin Lin Chen
(74) *Attorney, Agent, or Firm* — Schwegman Lundberg & Woessner, P.A.

(57) ABSTRACT

Truncated junctophilin-2 related proteins, transcriptional repressor domains, vectors encoding the proteins or domains, and methods of using the proteins and domains, are provided.

8 Claims, 89 Drawing Sheets
Specification includes a Sequence Listing.

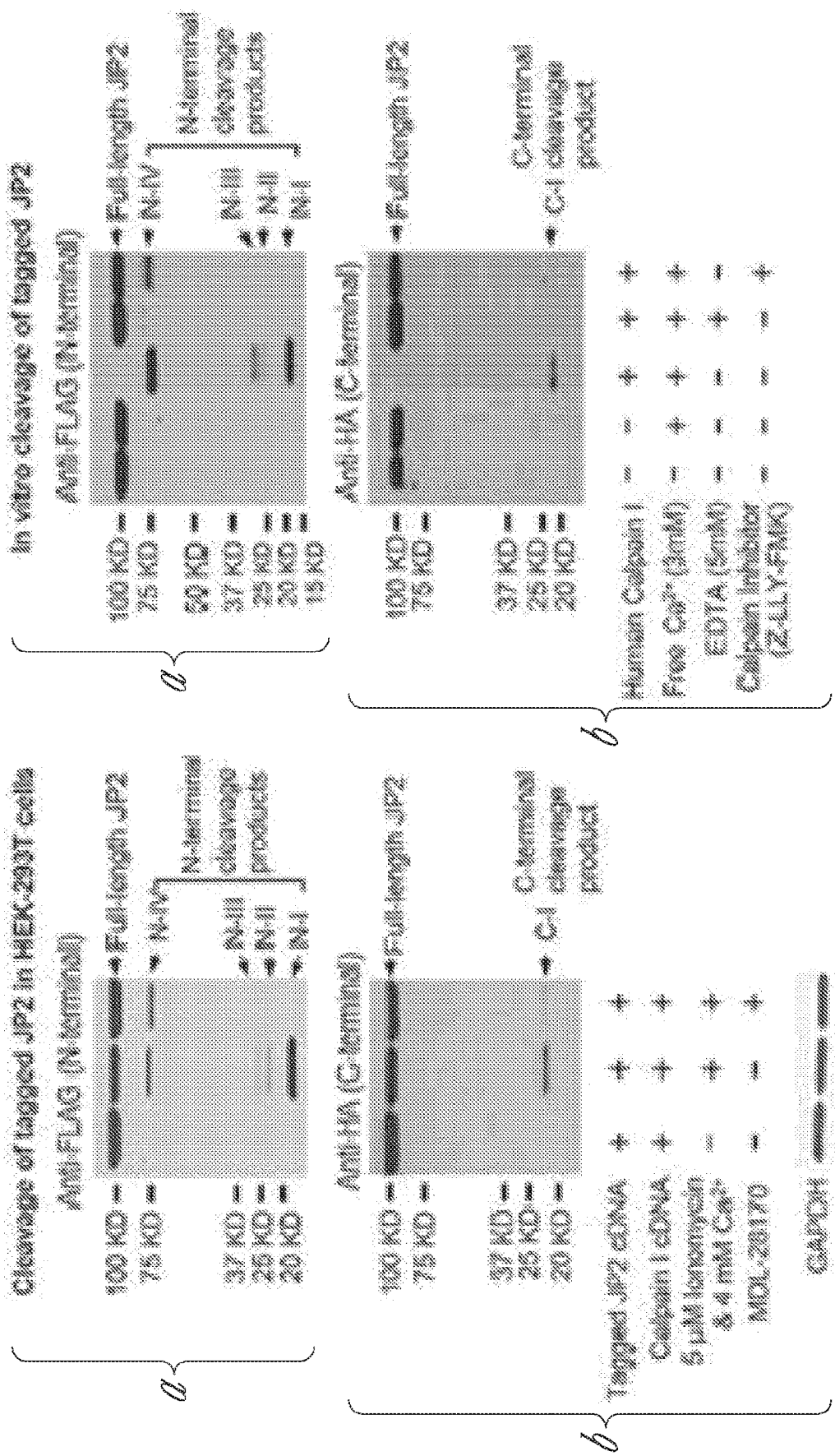

JPH2_HUMAN

```
  1 msggrfdfdd ggaycggweg gkahghglct gpkgggeysg swnfgfevag vytwpsgntf
 61 egywsggkrh glgietkgrw lykgewthgf kgrygirqss ssgakyegtw nnglqdgygt
121 etyadggtyg gqftngmrhg ygvrqsvpyg mavvvrsplr tslssIrseh sngtvapdsp
181 aspasdgpal pspaiprggf alsllanaea aarapkgggl fqrgaligkl rraesrtsvg
241 sqrsrvsflk sdlssgasda astaslgeaa egadeaapfe adidatttet ymgewkndkr
301 sgfgvserss glryegewld nlrhyggctt lpdghreegk yrhnvlvkdt krrmlqlksn
361 kvrqkvehsv egagraaaia rqkaeiaasr tshakakaea aegaalaang esniartlar
421 elapdfyqpg peygkrrllg eilensesll eppdrgagaa glpqppresp glheretprp
481 eggspspagt ppqpkrprpg vskdgllspg awngepsgeg srsvtpsega grrsparpat
541 ermaiealga ppapsrepev alyqgvhsya vrttppeppp fedqpepevs gsesapsspa
601 taplqaptlr gpeparetpa klepkpiipk aeprakarkt eargltkaga kkkarkeaal
661 aaeaevevee vpntilicmv illniglail fvhllt (SEQ ID NO:1)
```

Fig. 8A

NP_065166 (human)

```
  1 msggrfdfdd ggaycggweg gkahghglct gpkggqeysg swnfgfevag vytwpsgntf
 61 egywsqgkrh glgietkgrw lykgewthgf kgrygirqss ssgakyegtw nnglqdgygt
121 etyadggtyg gqftngmrhg ygvrqsvpyg mavvvrsplr tslsslrseh sngtvapdsp
181 aspasdgpal pspaiprggf alsllanaea aarapkgggl fqrgaligkl rraesrtsvg
241 sqrsrvsflk sdlssgasda astaslgeaa egadeaapfe adidatttet ymgewkndkr
301 sgfgvserss glryegewld nlrhgygctt lpdghreegk yrhnvlvkdt krrmlqlksn
361 kvrqkvehsv egaqraaaia rqkaeiaasr tshakakaea aeqaalaanq esniartlar
421 elapdfyqpg peyqkrrllq eilensesll eppdrgagaa glpqppresp qheretprp
481 eggspspagt ppqpkrprpg vskdglispg awngepsgeg srsvtpsega grrsparpat
541 ermaiealga ppapsrepev alyqgyhsya vrttppeppp fedqpepevs gsesapsspa
601 taplgaptlr gpeparetpa klepkpiipk aeprakarkt eargltkaga kkkarkeaal
661 aaeaevevee vpntilicmv illnigliail fvhllt    (SEQ ID NO:2)
```

*Fig. 8B*

NP_001192005 (mouse)

```
  1  msggrfdfdd  ggaycggweg  gkahghglct  gpkqgeysg   swnfgfevag  vytwpsgntf
 61  egywsggkrh  glgietkgrw  lykgewthgf  kgrygirqst  nsgakyegtw  nnglqdgygt
121  etyadggtyq  gqftngmrhg  ygvrqsvpyg  mavvvrsplr  tslsslrseh  sngtvapdsp
181  aadgpmlpsp  pvprggfalt  llataeaarp  ggliftrgtll grirrsesrt  slgsqrsrls
241  flkselssga  sdaastgsla  egaegpddaa  apfdadidat  ttetymgewk  ndkrsgfgvs
301  erssglryeg  ewldnlrhgy  grttlpdghr  eegkyrhnvl  vkgtkrrvlp  lksskvrqkv
361  ehgvegaqra  aaiarqkaei  aasrtshaka  kaeaaeqaal  aanqesniar  tlakelapdf
421  yqpgpeyqkr  rllqeilens  esllepperg  lgtglperpr  espqlheret  pqpeggppsp
481  agtpppqkrp  rpgaskdgll  spgswngepg  gegsrpatps  dgagrrspar  pasehmaiea
541  lqpppapsge  pevamyrgyh  syavrtgppe  pppledeqep  epepepevrr  sdsappspvs
601  atvpeeeppa  prspvpakqa  tlepkpivpk  aepkakarkt  eargiskaga  kkkgrkevaq
661  akeaevevee  vpntvlicmv  illniglail  fvhllt      (SEQ ID NO:3)
```

Fig. 8C

Rabbit

```
  1 msggrfdfdd ggaycggweg gkahghglct gpkgggeysg swnfgfevag vytwpsgntf
 61 egywsqgkrh glgietkgrw lykgewthgf kgrygtrqst ssgakyegtw nnglqdgygt
121 etyadggtyg gqftngmrhg ygvrqsvpyg mavvvrsplr tslsslrseh sngtvapdsp
181 aspaadgpal pspaiprggf alsllanaea arapkggglf prgaligklr raesrtsvgs
241 qrsrvsflks dlssgasdaa staslgegae gaddaapfea didatttety mgewkndkrs
301 gfgvserssg lryegewldn lrhgygcttl pdghreegky rhnvlvkgtk rrvlplksnk
361 vrqkvehsve gaqraaaiar qkaeiavsrt sharakaeaa eqaalaange sniarslare
421 lapdfyqpgp eyqkrrllge ilehsesile ppdrgaaglp qpprespqlh eretprpegg
481 ppspagtppq pkrprpgask dgllgpgawn gepsggsgge gsrpatpaaa gagrrsparp
541 asehmaieal qappapsrep evalyrgyhs yavrtappap pfeddpqpe aadpdsapas
601 patapgqapa lgnpepapes paklepkpiv pkakarktea rglsktgakk kprkeaaqaa
661 eaeveveevp ntvlicmvil lniglailfv hllt (SEQ ID NO:4)
```

*Fig.8D*

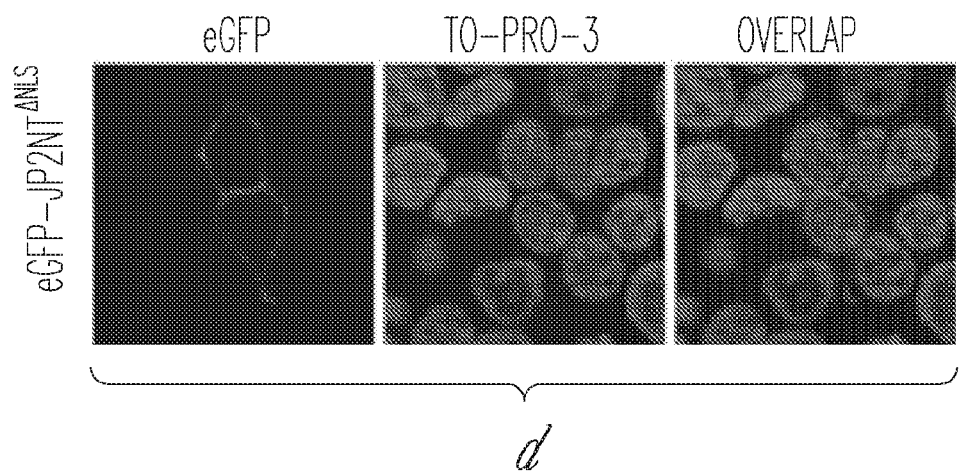
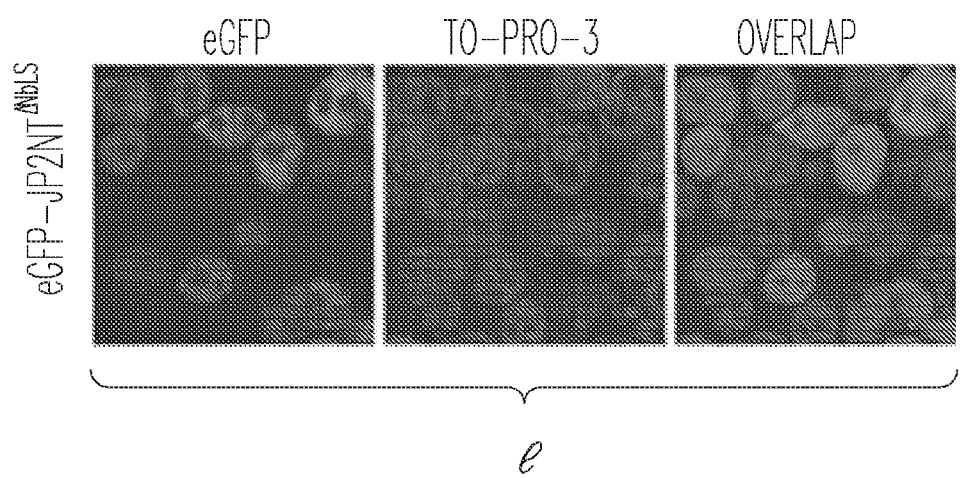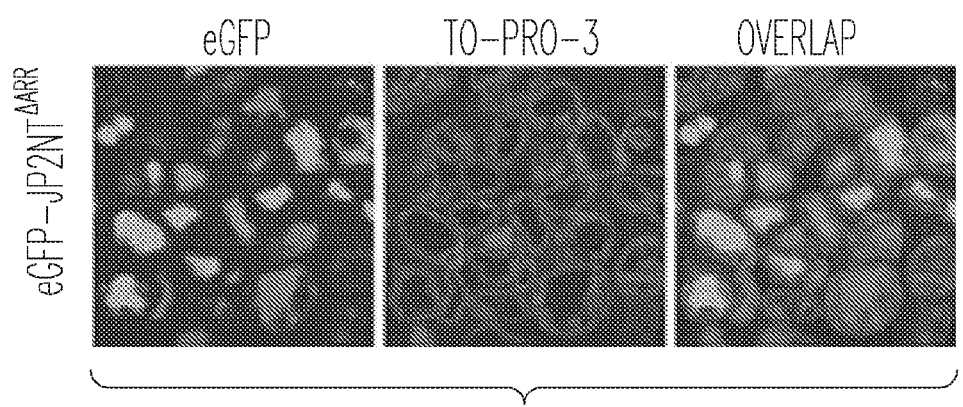
Fig. 10B

Mutant TATA BOX
(promoter^Myc)
GGGATCCTGAGTCGGCAGTATATTA
AGAAGCTTTTCGGGCGTT

| TATA BOX CORE<br>SEQUENCE VARIATION | BINDING<br>BY JP2NT |
|---|---|
| TATAAA | YES |
| TATAAT | YES |
| TATATA | YES |
| TATATT | NO |
| TATTAA | NO |
| TTTAAA | NO |

*Fig. 11F*

GST-JP2NT    GST
200 ng 100 ng 50 ng   200 ng  Blank

*Fig. 11E*

WT TATA BOX (promoter^Myc)
GGGATCCTGAGTCGGCAGTATAAAAGAAGCTTTTCGGGCGTT

← Free probes

GST-JP2NT^WDR5-I-M    GST    GST-JP2NT^WDR5-I-M    GST
200 ng 100 ng 50 ng 200 ng Blank  200 ng 100 ng 50 ng 200 ng Blank

*Fig. 11G*

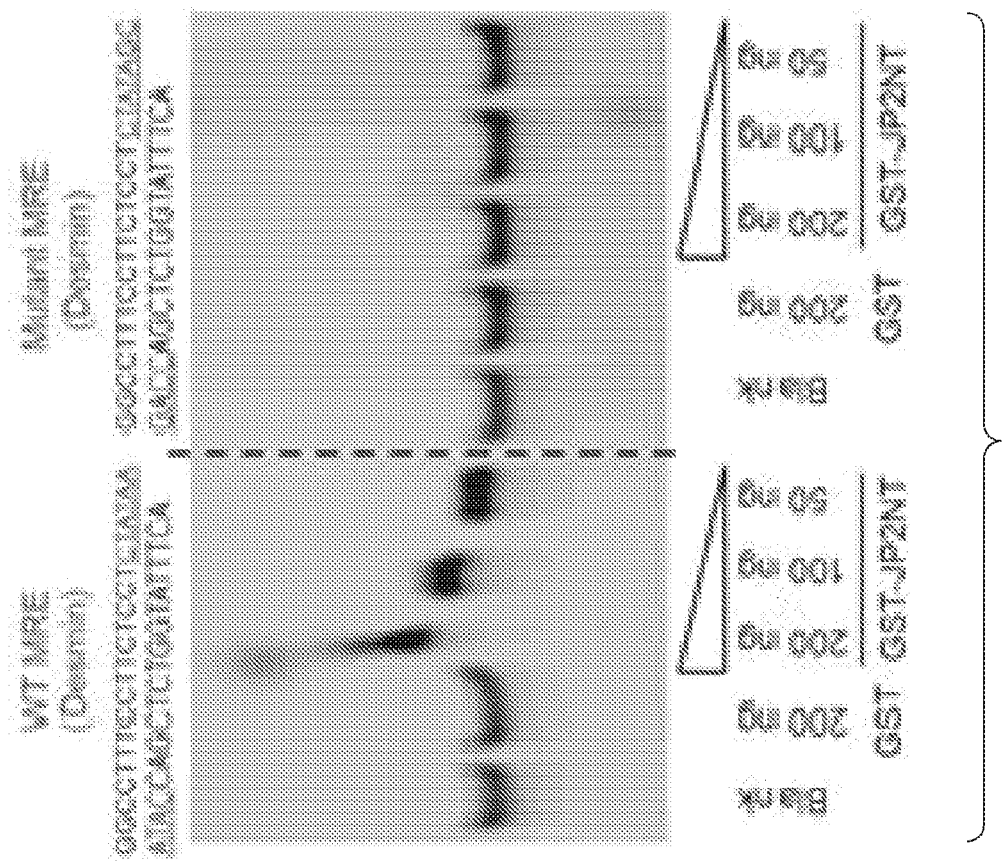
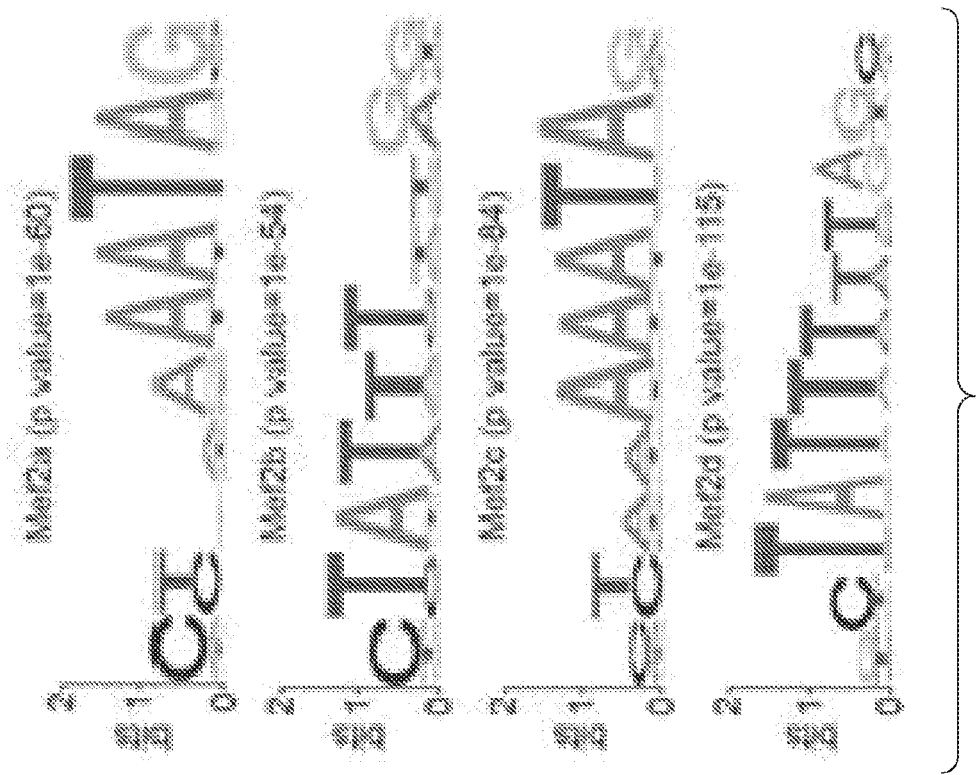
Fig. 12A
Fig. 12B

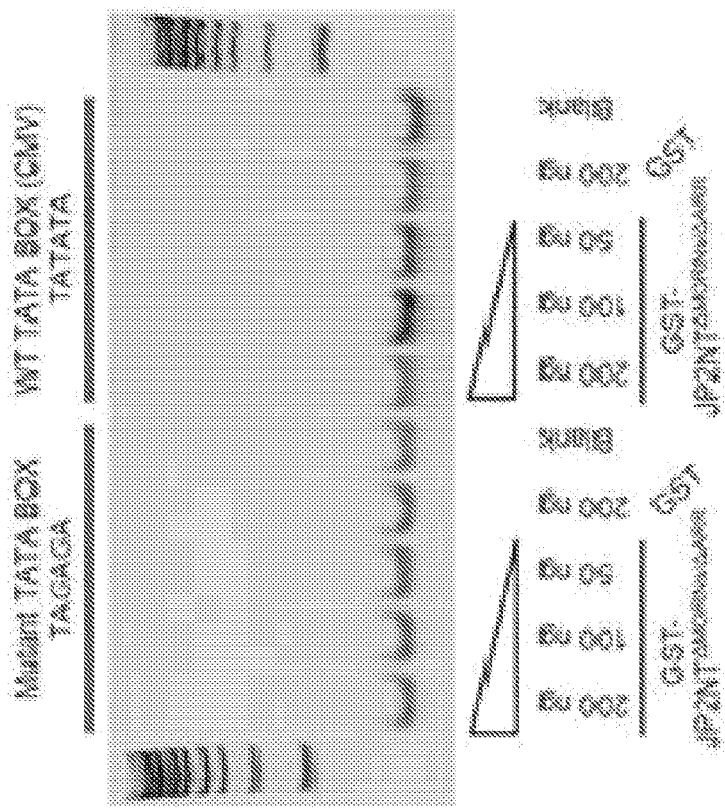
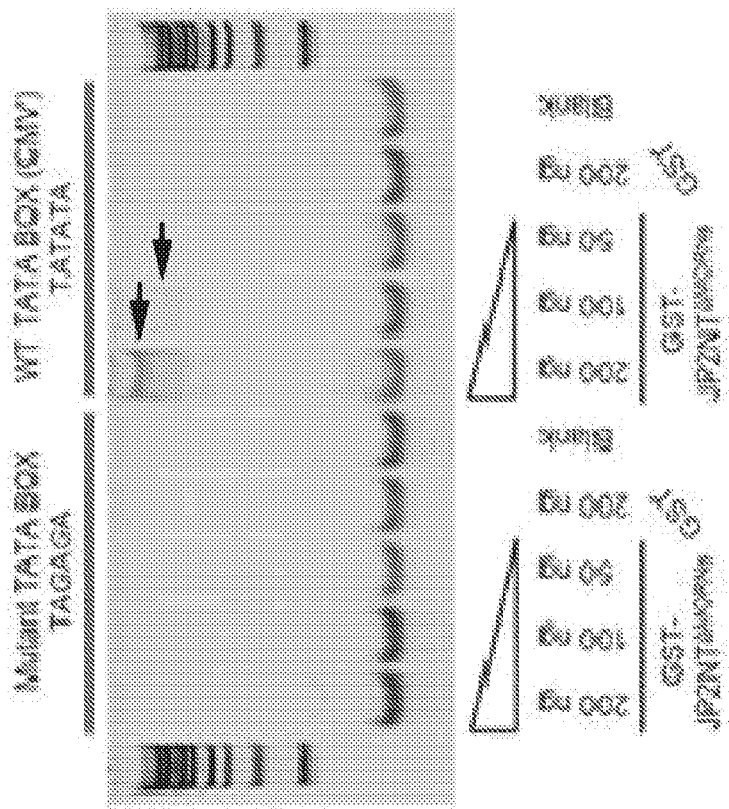
Fig. 17C

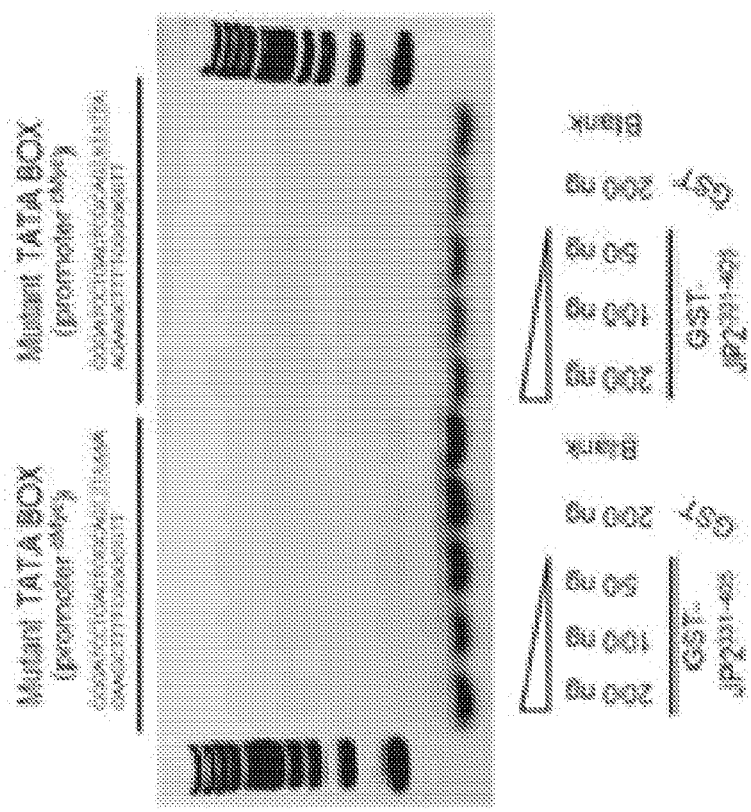
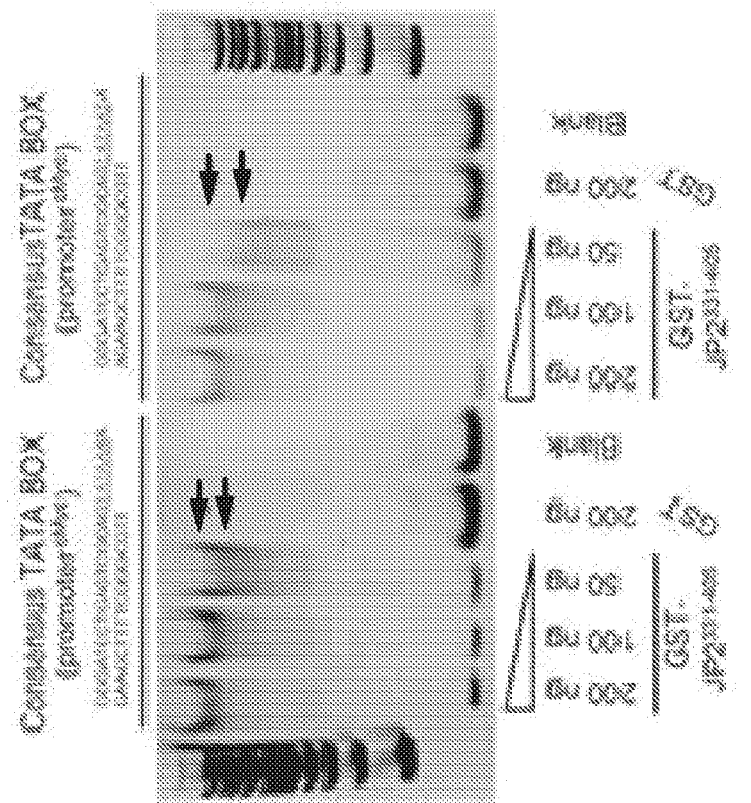
Fig. 17D

| UPSTREAM REGULATOR | EXP LOG RATIO | MOLECULE TYPE | PREDICTED ACTIVATION STATE | ACTIVATION Z SCORE | P-VALUE OF OVERLAP | TARGET MOLECULES IN DATASET | MECHANISTIC NETWORK |
|---|---|---|---|---|---|---|---|
| NR4A3 | 5.626 | LIGAND DEPENDENT NUCLEAR RECEPTOR | ACTIVATED | 2.447 | 0.055 | COL16A1,COL1A1,COL6A1,COL6A2,IL2RA,TGFB3 | |
| NR4A3 | 1.795 | LIGAND DEPENDENT NUCLEAR RECEPTOR | ACTIVATED | 2.615 | 0.00068 | CCND1,COL16A1,COL1A1,COL6A2,COL6A1,HIF1A,IL2RA,NDUFB9,TGFB3 | |
| FBN1 | -0.74 | OTHER | ACTIVATED | 2.207 | 0.00131 | COL1A2,COL3A1,COL4A2,FBN1,LTBP3 | |
| FOXO4 | 0.222 | TRANSCRIPTION REGULATOR | ACTIVATED | 2.433 | 0.00041 5 | AKR1C14,CCND1,DHCR24,FDFT1,HIF1A,NAMPT,SOD2,VEGFA | |
| EGLN1 | 0.299 | ENZYME | ACTIVATED | 2.157 | 0.0203 | HIF1A,SDC4,TGFB1,TGFB2,TGFB3,VEGFA | |
| INSR | | KINASE | ACTIVATED | 3.535 | 1.8E-17 | ACAA2,ACADS,ACADVL,ACSL1,ACTN4,ALDH6A1,ARHGDIA,ATP5H,BCL2A1,CCND1,CD36,CFL1,CPT2,CRAT,CYCS,DECR1,DES,ECI1,EREG,ETFA,ETFB,ETFDH,FDFT1,HADHA,HADHB,HSPD1,IDH3A,IGF1,IQGAP1,ITGB5,LGALS1,MAOB,MYH7,NAMPT,NDUFA3,NDUFV2,NFKB2,NPPA,PHLDA1,PTPRN,RRM2,RTN2,SC5D,SCP2,STX4,SLC20A1,SLC2A4,SMPX,SOCS2,SUCLA2,TGFB1,TGFB3,TGIF1 | |
| HALOFUGI NONE | | CHEMICAL DRUG | ACTIVATED | 2.415 | 2.06E-13 | ANXA4,BGN,CKB,COL1A1,COL1A2,CYGB,DBN1,ELN,EMP1,F2R,FBLN5,FBN1,FSTL1,FXYD6,GATM,HK1,IGFBP3,LGALS1,LOX,NUPR1,PCOLCE,PKM,PLPP3,PMP22,PTGFRN,SPARC,TGFB1,TGFB3,TIMP1 | |
| ROSIGLIT AZONE | | CHEMICAL DRUG | ACTIVATED | 4.577 | 2.32E-13 | ACAA2,ACADS,ACADVL,ACSL1,ADAM9,ADAMTS1,AQP7,BCL2,COL11,CCND1,CD36,COL1A1,COX7A1,CPT2,CSF1,CYCS,DECR1,DIO2,ECHL,EGLN1,ETFA,ETFDH,FN1,HADH,HADHB,HSD11B1,IDH3A,IGF1,PEX11A,PHYH,PLIN5,PLPP3,PLTP,POSTN,POU2F1,PTPN1,SAMHD1,SERPINF1,SLC2A4,SLC9A3,SOD2,TGFB3,TIMP1,TPM3,VEGFA,VLDLR,WTR1 | |
| AHR | | LIGAND DEPENDENT NUCLEAR RECEPTOR | ACTIVATED | 3.716 | 2.78E-12 | ACTN1,ADAMTS2,CCL21,CCND1,CD36,CDC42,COL11A1,COL12A1,COL16A1,COL1A1,COL1A2,COL27A1,COL3A1,COL4A2,COL5A1,COL5A2,COL6A1,DCLK3,DUSP6,EFEMP1,EMILIN1,FBLN2,FBLN5,FN1,GSTM5,HECTD2,HIF1A,HSPB1,ITGBL1,LTBP2,LTBP3,MYH7,MYL2,PLAT,PLXR1,REP1,SHB,SOD2,STAT3,TGFB1,TGFB2,TGFB3,VEGFA,VIM | |

Fig. 21A

| | | | |
|---|---|---|---|
| PPARA | LIGAND DEPENDENT NUCLEAR RECEPTOR | ACTIVATED | 3.217 | 4.41E-11 | ABCA1,ABCD3,ACAA2,ACADS,ACADVL,ACOT1,ACSL1,ANXA2,AQP7,ARHGDIA,ASS1,BCL2,CCND1,CD36,CD63,CPT2,CYCS,DECR1,DIO2,ECHI,ECI1,FDFT1,GSTK1,HADH,HADHA,HADHB,HIF1A,HIST1H1C,IGFBP3,KYAT3,LIFR,MAT2A,MLYCD,NPPA,PEX11A,PHLDA1,PLIN5,PLTP,PLTP,PREM16,REISAT,RTN4,SC5D,SCP2,SELENBP1,SLC2A4,SOCS2,SORD,TSPO,VEGFA |
| SIROLIMUS | CHEMICAL DRUG | ACTIVATED | 3.5 | 1.68E-10 | ACADVL,AKT1,ANXA5,ASS1,ATP6V1B2,BCL2,BCL2A1,CCND1,CLIC1,COL1A1,COL1A2,CRAT,CREG1,CSF1,CYCS,DDT,DES,EEF1A1,ENO1,ERCC1,FN1,H3F3A/H3F3B,HIF1A,HSPD1,IDH1,IL2RA,LDHB,LGALS3,LMNA,MAPT,MMP14,MYH6,MYL2,NR4A3,ODC1,PKM,POSTN,PRKAR1A,RPL13,SLC1A5,SLC2A4,SLC36A3,TGFB1,TIMP1,TMPO,TFM3,TUBB2A,UCK2,VEGFA,VIM |
| PD98059 | CHEMICAL KINASE INHIBITOR | ACTIVATED | 2.572 | 2.28E-10 | ABCA1,ACE,ALDOA,BCL2,BDH1,BGN,CCL11,CCND1,CD36,CLU,COL1A1,COL1A2,COL3A1,CT3K,CYCS,DES,DIO2,DUSF6,EEF1A1,ELN,EMP1,ENO1,F3R,FN1,HADHB,HIF1A,IGF1,IGFBP3,IL2RA,ITGB5,LIFR,MAT2A,MMP14,MYH7,NPPA,FABPC1,PHLDA1,PLAT,POSTM,RAB20,RETSAT,RRM2,SELENBP1,SOCS2,SPRR1A,STAR,STAT3,TEAD2,TGFB1,TGFB3,TIMP1,TLR2,TUBB2A,VCAN,VEGFA,VIM |
| ALPHA CATENIN | GROUP | ACTIVATED | 4.703 | 4.34E-10 | ADAM8,ADAMTS1,ADAMTS12,ADAMTS2,BGN,COL15A1,COL1A1,COL1A2,COL3A1,COL5A1,COL5A2,COL6A1,COL6A2,ELN,EREG,FSTL1,IGF1,IGFBP7,MMP23B,NFKBIZ,RHOC,TIMP1,VIM |
| PYRINIXIC ACID | CHEMICAL TOXICANT | ACTIVATED | 3.421 | 4.96E-10 | ABCA1,ABCD3,ACAA2,ACADS,ACADVL,ACOT1,ACSL1,AKR1B10,AlAS1,ANXA2,ANXA7,CCND1,CCT3,CD36,CD63,CLU,COL1A1,CPT2,DECR1,ECH1,ECI1,ETFDH,HADHA,HADHB,HIF1A,HIST1H1C,HSD12,HSPD1,ITGB5,LDHB,LGALS3,LIFR,MLYCD,NUDT7,PEX11A,PHLDA1,PLIN5,PLTP,PPIC,PTPRF,RTN4,SC5D,SCP2,SLC22A5,SLC2A4,TSPO,VEGFA |
| LOSARTAN POTASSIUM | CHEMICAL DRUG | ACTIVATED | 2.724 | 1.08E-08 | ACE,ATP2A2,ATP5H,CD36,COL1A1,COL3A1,CST3,FN1,ITGB5,MAP1,MYH7,NPPA,POSTN,STAR,TGFB1,TGFB2,TGFB3,TIME1,TUBB3,VEGFA |
| KLF15 | TRANSCRIPTION REGULATOR | ACTIVATED | 3.048 | 1.26E-08 | ACADS,ACADVL,ACOT1,ACSL1,CD36,CPT2,DECR1,HADHA,HADHB,MLYCD,NPPA,SLC2A4,SYNPO |
| CRI1 | OTHER | ACTIVATED | 3.317 | 2.85E-03 | BGN,COL15A1,COL1A1 COL1A2,COL3A1,COL4A2,COL5A1,COL6A1,COL8A1,FBN1,TGFB1 |
| ESTROGEN RECEPTOR | GROUP | ACTIVATED | 2.412 | 8.67E-03 | ABCA1,BCL2,CAPG,CCND1,COL12A1,COL4A2,COL5A1,COL6A2,COL9A2,DCHS1,EREG,FN1,IGF1,KRT |

Fig. 21B

| | | | | |
|---|---|---|---|---|
| MYCN | TRANSCRIPTION REGULATOR | ACTIVATED | 3.212 | 0.00000013 | 18,LOXL2,MAP1B,MAPT,MMP14,MSN,SPARC,SYNPO,TGFB1,TGFB3,TGFBR3,TIMP1,VEGFA,VIM |
| MYCN | TRANSCRIPTION REGULATOR | ACTIVATED | 3.212 | 0.00000013 | ACTG1,ACTN4,ALDOA,ARPC1B,CCND1,CKAP4,CLU,COL1A1,COL5A2,COL8A1,DPYSL3,DUSP7,EEF1A1,FBN1,FN1,HSPD1,IGFBP7,LGALS1,MAP4,MRC2,MYH9,OBC1,RGS5,RPL3,RUSC2,SORD,SPARC,TUBA1B,TUBE,VIM |
| MIR-29B-3P (AND OTHER MIRNAS W/SEED AGCACCA) | MATURE MICRORNA | ACTIVATED | 3.648 | 0.00000148 | COL15A1,COL1A1,COL1A2,COL3A1,COL4A2,COL5A2,FBN1,LAMC1,LOXL2,PMP22,PPIC,SPARC,TGFB3,TUBB2A |
| METHOTREXATE | CHEMICAL DRUG | ACTIVATED | 2.772 | 0.00000181 | ABCA1,ABCD3,ACAA2,ACADVL,ACTG1,AGPAT3,ALDOA,AMACR,ANKH,ANKA4,ASS1,AUH,CCL11,CCL21,CCND1,CES1,CLEC11A,CSF1,CYCS,ECH1,HADHA,HADHB,HSD11B1,IGFBP3,ITIH4,NR4A2,PHYH,TEF,TGFB1 |
| MONO-(2-ETHYLHEXYL)PHTHALATE | CHEMICAL TOXICANT | ACTIVATED | 4.357 | 0.00000235 | ACADVL,ACSL1,ATP5F1,BCL2,CD36,CPT2,ENO1,HADH,HADHA,IDH3A,MLYCD,NAMPT,NDUFS1,NDUFS2,NDUFS7,NDUFV2,RSRP1,SC5D,SLC2A4,SUCLG1,SUCLG2,TSPO |
| RAMIPRIL | CHEMICAL DRUG | ACTIVATED | 2.985 | 0.00000497 | COL1A1,COL1A2,COL3A1,COL4A2,FN1,LAMC1,TGFB1,TIMP1,VEGFA |
| SPDEF | TRANSCRIPTION REGULATOR | ACTIVATED | 3.413 | 0.00000499 | CD34,COL16A1,COL1A1,COL4A2,COL5A1,COL5A2,COL6A1,COL6A2,HIF1A,LAMC1,PTPRF,TGFB1,VASP,VIM |
| FENOFIBRATE | CHEMICAL DRUG | ACTIVATED | 4.244 | 0.00000051 | ABCD3,ACAA2,ACADVL,ACOT1,ACSL1,CCL21,CCND1,CD36,CLU,CPT2,DECR1,ECH1,HADHA,HADHB,HIF1A,LDHB,MLYCD,MYH7,NUDT7,PANK1,PLTP,PPIC,PTPRF,SC5D,SLC2A4,SOD2,STAR,SUCLG1,TGFB1 |
| FAS | TRANSMEMBRANE RECEPTOR | ACTIVATED | 2.482 | 0.00000518 | AKAP2,ANXA2,ARHGDIA,BCL2,BCL2A1,BGN,COL15A1,COL1A1,COL1A2,COL3A1,COL4A2,COL5A1,COL6A1,COL9A1,CSF1,DGCR2,ERCC1,F2RL1,FBN1,FGL2,GADD45G,LGALS3,MME,NR4A2,PDLIM7,PPFIA1,PTPN1,PTPRN,RASGRP2,SOD2,SPTBN1,TAGLN2,TGFB1,TLR2,TNK2,VEGFA,WNK1 |
| PTEN | PHOSPHATASE | ACTIVATED | 3.104 | 0.00000875 | ACAA2,ACSL1,AKT1,ARHGDIA,BCL2,CCND1,CKS2,FDFT1,HADH,HADHA,HADHB,HIF1A,IDH3A,IDH3G,IGF1,IGFBP3,ING4,KLHL24,LDHB,LGALS3,LHMS1,LRRFIP1,MAT2A,MME,MMP14,MMP23B,NPPA,NR4A2,PLK1,SDC4,SLC20A1,SORD,STAT3,STX5,SUCLA2,SUCLG2,SUCLG2,TGFB1,TMSB4X (INCLUDES OTHERS),TOM1,VEGFA |

Fig. 21C

| | | | | |
|---|---|---|---|---|
| SMAD7 | TRANSCRIPTION REGULATOR | ACTIVATED | 3.054 | 0.000000952 | ADAMTS2,BGN,COL1A1,COL1A2,COL3A1,COL6A1,FFEMP1,FN1,ITGBL1,LTBP2,LTBP3,PLAT,PMEPA1,TGFB1,TGFB2,TGFB3,TIMP1,TPM3,VEGFA |
| PPARGC1A | TRANSCRIPTION REGULATOR | ACTIVATED | 2.752 | 0.000000118 | ACADVL,ALAS1,ATP5H,CD36,CIDEB,CYCS,DIO2,FMDC5,GPX1,IDH3A,KYAT3,LIFR,MAOB,MYH6,MYH7,NDUFS1,NDUFV2,NPPA,PDK2,PHYH,PLIN5,PRDX3,SESN2,SLC2A4,SOD2,VEGFA |
| ALDH1A2 | ENZYME | ACTIVATED | 2.333 | 0.000000267 | BGN,CDC42,COL1A2,COL3A1,CSF1,NPPA,PCOLCE,SPARC,TIMP1 |
| NPPB | OTHER | ACTIVATED | 2 | 0.000000274 | ACE,COL1A1,NPPA,TGFB3 |
| U0126 | CHEMICAL - KINASE INHIBITOR | ACTIVATED | 3.493 | 0.000000325 | BCL2,BRAP,CCL11,CCND1,CD36,COL1A1,DCHS1,DES,DUSP6,DUSP7,EEF1A1,EMP1,ENPP2,ERCC1,EREG,ETV5,FN1,HIF1A,ITGB5,KDM6B,LIFR,MAT2A,MYH7,NPPA,NR4A2,NR4A3,PABPC1,PHLDA1,POSTN,SFT1,SHE,SPRR1A,STAR,STAT3,TGFB2,TGFB3,TLR2,TOM1,TPM3,VEGFA,VIM,WNT5A |
| BISINDOLYLMALEIMIDE I | CHEMICAL - KINASE INHIBITOR | ACTIVATED | 2.383 | 0.000000336 | ACE,BCL2,BCL2A1,CLU,FN1,IGF1,MAT2A,MYH6,MYH7,NPPA,NR4A2,PITPNB,PRKCD,SOD2,TGFB3,VEGFA |
| GLIS2 | TRANSCRIPTION REGULATOR | ACTIVATED | 2.63 | 0.000000391 | CCND1,COL1A1,LTBP2,MMP14,SPARC,TGFB1,VIM |
| NPR1 | ENZYME | ACTIVATED | 2.774 | 0.000000598 | ACE,COL1A1,COL3A1,FN1,MYH7,NPPA,TGFB1,TGFB3 |
| PPARD | LIGAND-DEPENDENT NUCLEAR RECEPTOR | ACTIVATED | 2.837 | 0.000000761 | ACAA2,ACADVL,ACY1,ADORA1,AQP7,BCL2,CCND1,CD36,CPT2,DCT1,ECH1,FN1,KYAT3,LDHB,MLYCD,PDE4C,RBP1,S100A6,SFT1,SLC2A4,SORD,VEGFA,VLDLR |
| L-DOPA | CHEMICAL - ENDOGENOUS MAMMALIAN | ACTIVATED | 2.672 | 0.000000793 | ACY1,ATP2A2,BCL2,CACNB2,CAP1,CAPG,CCND1,CD63,CITED4,CMTM8,COMT,COTL1,DUSP6,FAM114A1,FBLN2,FCGRT,GNE,GOLIM4,IL18BP,IQGAP1,KCND2,LMNA,MAT2A,METAP1D,MMP14,NAGLU,NAV1,NDUFS4,OMA1,PARM1,PFKP,PKIA,PLCG2,PPM1L,PPP2R2C,RHBDL3,RILPL1,SBK1,SDR39U1,SH3BGRL3,SH3PXD2B,SLAMF9,STRN,TDRKH,TIRAP,TMCC2,VAT1,VLDLR,VTN,WDR1,WWTR1,ZNRF1 |
| TFAM | TRANSCRIPTION REGULATOR | ACTIVATED | 2.646 | 0.000000886 | ACADS,AUH,CPT2,ECH1,HK1,MT-ATP8,PFKP |
| CLOFIBRATE | CHEMICAL DRUG | ACTIVATED | 2.832 | 0.0000111 | ABCA1,ABCD3,ACADVL,ACOT1,ANXA7,CCND1,CD36,CPT2,DECR1,ECH1,ECI1,HADHA,HADHB,PEX11A,RTN4 |

Fig. 21D

| | | | | | |
|---|---|---|---|---|---|
| SPIRONOL ACTONE | CHEMICAL DRUG | ACTIVATED | 3.44 | 0.00001 28 | ACE,BCL2,COL1A1,COL1A2,COL3A1,DES,FN1,LOX,NP PA,FKBM16,STAR,TGFB1,VEGFA |
| TROGLITA ZONE | CHEMICAL DRUG | ACTIVATED | 2.459 | 0.00001 41 | ABCA1,ACADS,ACOT1,ACSL1,ALAS1,ANXA2,AQP7,ARF 4,BCL2,CCND1,CD36,CFL1,COL15A1,COL1A1,COL1A2 ,COX7A1,CPT2,CTNNAL1,DGKA,ECH1,ENTPD5,FN1,LO C102724788/PRODH,MAO5,MME,NAGK,NPPA,NR4A3,PE X11A,POU2F1,SLC2A4,TGFB1,TGIF1,VEGFA |
| LY294002 | CHEMICAL - KINASE INHIBITOR | ACTIVATED | 4.46 | 0.00001 66 | ABCA1,ADAMTS1,AKT1,BCL2,BRAP,CCND1,CD36,CKS2 ,COL1A1,COL1A2,CST3,DHCR24,DUSP6,EMILIN1,ERC C1,EREG,F2R,FDFT1,FN1,HIF1A,IFRD2,IGF1,IGFBP 3,INPP4B,ITGB1I,LMNA,MAT2A,MMP14,NR4A2,NR4A3 ,PHLDA1,POSTN,PTPN2,SLC2A4,SLC38A3,SOCS2,TGF B1,TLR2,VCAN,VEGFA,VIM |
| ABCB4 | TRANSPORT ER | ACTIVATED | 2.81 | 0.00002 52 | COL1A2,COL1A2,LGALS3,NFKB2,SPARC,TGFB1,TGFB2 ,TIMP1 |
| UXT | TRANSCRIP TION REGULATOR | ACTIVATED | 2.039 | 0.00003 24 | B4GALT1,BUB1,IL2RA,KDELR3,KRT18,PMEPA1,SEC24 D,SORD |
| WORTMANN IN | CHEMICAL - KINASE INHIBITOR | ACTIVATED | 2.978 | 0.00003 4 | AKT1,BCL2,CKB,COL1A1,COL1A2,COL3A1,CSF1,CX3C L1,F2R,FN1,HIF1A,IGF1,IL2RA,MMP14,MSN,NR4A3, OGT,POSTN,SOCS2,VEGFA,VIM |
| MIR-1 | MICRORNA | ACTIVATED | 3.537 | 0.00003 59 | ANXA2,CACNE2,CAP1,FN1,H3F3A/H3F3B,HSPD1,IGF1 ,IRX5,PFTB,SEC61A1,SH3BGRL3,SULF1,TAGLN2,TMX 1,VEGFA |
| MIR-1-3P (AND OTHER MIRNAS W/SEED GGAAUGU) | MATURE MICRORNA | ACTIVATED | 4.516 | 0.00004 63 | ANXA2,ARF4,ATP6V1B2,BCL2,CAP1,EBLN2,FSTL1,H3 F3A/H3F3B,IGF1,IRX5,MKC2,PDLIM7,PPIB,PTPRF,S DC4,SH3BGRL3,SH3PXD2B,SPHK1,TAGLN2,TMSB4X (INCLUDES OTHERS),TPM3 |
| TOPOTECA N | CHEMICAL DRUG | ACTIVATED | 2.205 | 0.00006 08 | ACSL1,ARPC1B,BUB1,CAMTA1,ENO1,FAT1,GPC6,GPX1 ,HIF1A,HSPD1,MAT2A,OSBPL8,PCDH,PHKG1,PLK1,R BFOX1,SESN2,SLC7A5,UBE2B,VEGFA |
| TRIENTIN E | CHEMICAL DRUG | ACTIVATED | 2.236 | 0.00006 92 | COL3A1,FN1,IGF1,IGFBP3,IGFB1 |
| TRICHLOR OETHYLEN E | CHEMICAL TOXICANT | ACTIVATED | 2.53 | 0.00010 6 | CD47,CD63,COL1A1,COL3A1,DHCR24,IGFBP3,NDUFS1 ,PTPRF,RTN4,SPARC |
| BENZENE | CHEMICAL TOXICANT | ACTIVATED | 2.53 | 0.00010 6 | CD47,CD63,COL1A1,COL3A1,DHCR24,IGFBP3,NDUFS1 ,PTPRF,RTN4,SPARC |
| BENZO(A) PYRENE | CHEMICAL TOXICANT | ACTIVATED | 2.034 | 0.00011 6 | AGTPBP1,ARHGDIA,BCL2,BLK,COL3A1,COMT,ENTPD5, EREG,GNAO1,GPC1,IGF1,MAFF,MX1/MX2,PDLIM1,RGS 5,RHOC,RSRP1,SELENBP1,STX5,TGFB1,TGFB2,VEGFA |

Fig. 21E

| | | | | |
|---|---|---|---|---|
| MASLINIC ACID | CHEMICAL - ENDOGENOUS NON-MAMMALIAN | ACTIVATED | 2.236 | 0.000117 | ACTN1,AKT1,ARPC4,BCL2,CCND1,CD47,CFL1,DVL1,MAP3K7,MSN,TGFB1,YWHAG |
| BEZAFIBRATE | CHEMICAL DRUG | ACTIVATED | 3.062 | 0.000138 | ABCD3,ACADVL,ACOT1,ACSL1,CD36,ECH1,ECI1,HADHA,HADHB,LGALS3,PANK1,PEX11A,TSPO |
| MIR-122 | MICRORNA | ACTIVATED | 3.462 | 0.000232 | ALDOA,IQGAP1,LAMC1,MAP1B,MAP4,MAPRE1,PKM,PTPN1,RBM3,SH3BGRL3,SLC1A5,VIM |
| SB-431542 | CHEMICAL REAGENT | ACTIVATED | 2.897 | 0.000318 | BGN,CCND1,COL1A1,FN1,IGF1,IGFBP7,KCNN2,KRT18,STAT3,TGFB1,TGFB2,TGIF1 |
| METHYLMERCURY | CHEMICAL TOXICANT | ACTIVATED | 2.53 | 0.000319 | CD47,CD63,COL1A1,COL3A1,DHCR24,TGFBP3,NDUFS1,PTPRF,RTN4,SPARC |
| TACROLIMUS | CHEMICAL DRUG | ACTIVATED | 2.026 | 0.000383 | ABCD3,BCL2,CAMKK2,CCND1,CD36,COL1A1,COL3A1,DPYSL3,FLNA,FN1,HSPD1,KIAA0430,MYH10,MYH7,NEPA,ODC1,PTPRF,SDC3,SOD2 |
| CANDESARTAN | CHEMICAL DRUG | ACTIVATED | 2.158 | 0.000415 | ACE,COL1A2,COL3A1,FN1,MYH7,NPPA,SLC9A3,TGFB1 |
| ACTINOMYCIN D | CHEMICAL DRUG | ACTIVATED | 2.289 | 0.000471 | ABCA1,ASS1,BCL2,CCL11,CCND1,CLEC11A,COL1A2,FLNA,FN1,GSTM5,HIF1A,HK1,SDC3,SLC20A1,SLC40A1,SPHK1,TGFB1,TLR2,UBE2B,VEGFA |
| FMR1 | TRANSLATION REGULATOR | ACTIVATED | 2.613 | 0.000564 | ALDOA,ATPIF1,CFL1,ENO1,KCND2,MAP1B,PFKP,PLAT |
| NR1H | GROUP | ACTIVATED | 2.065 | 0.000808 | ABCA1,ACE,BCL2,CPT2,CSF1,F2R,GGT5,MX1/MX2,MYLIP,NFKB2,NFKBIZ,PLTP,SLC2A4,STAR,VLDLR |
| COL18A1 | OTHER | ACTIVATED | 2.703 | 0.000971 | BCL2,CCND1,CD34,EGLN1,F2R,F2RL1,FN1,HIF1A,STAT3,TUBA1A,VEGFA |
| MIR-296-5P (MIRNAS W/SEED GGGCCCC) | MATURE MICRORNA | ACTIVATED | 2.213 | 0.001031 | AKT1,BCL2,CCND1,COL1A1,VEGFA |
| PRKG1 | KINASE | ACTIVATED | 2.219 | 0.001150 | BCL2,CCND1,COL1A1,COL3A1,FN1,TGFB1 |
| ALITRETINOIN | CHEMICAL DRUG | ACTIVATED | 2.524 | 0.0014 | ABCA1,ANXA5,BCL2,BCL2A1,CCND1,CD36,CYCS,FN1,IL2RA,MLYCD,MYH6,NPPA,PLTP,RBP1,TGFB1 |
| DSP | OTHER | ACTIVATED | 2 | 0.00197 | COL1A1,COL1A2,COL3A1,MMP14 |
| PREGNA-4,17-DIENE-3,16-DIONE | CHEMICAL - ENDOGENOUS NON-MAMMALIAN | ACTIVATED | 2.179 | 0.00202 | BCL2,BCL2A1,CCND1,CES1,VEGFA |

Fig. 21F

| Name | Type | Status | Value | p-value | Genes |
|---|---|---|---|---|---|
| LET-7 | MICRORNA | ACTIVATED | 3.211 | 0.0023 | BUB1,CCND1,COL1A1,COL1A2,COL27A1,COL3A1,DLC1,FARP1,FN1,ORC6,PKM,RRM2,STAT3,VIM |
| IMATINIB | CHEMICAL DRUG | ACTIVATED | 2.598 | 0.00237 | BCL2,CCND1,COL1A1,COL3A1,FN1,MME,SOCS2,STAT3,TGFB1,VEGFA |
| PARICALCITOL | CHEMICAL DRUG | ACTIVATED | 2.433 | 0.00265 | BCL2,COL3A1,FN1,NPPA,TGFB1,TIMP1 |
| MIR-29 | MICRORNA | ACTIVATED | 2.021 | 0.00268 | AOX1,BCL2,CDC42,COL1A1,EIN,IGF1,IL2RA,EMP22 |
| PROPRANOLOL | CHEMICAL DRUG | ACTIVATED | 2.213 | 0.00407 | ACE,ATP2A2,DIO2,IGF1,PLN,VEGFA |
| MIR-199A-3P (AND OTHER MIRNAS W/SEED CAGUAGU) | MATURE MICRORNA | ACTIVATED | 2 | 0.00426 | CALU,FN1,PON2,VCAN |
| NO 1886 | CHEMICAL DRUG | ACTIVATED | 2 | 0.00426 | ACAA2,CES1,CPT2,HADHA |
| FOXO3 | TRANSCRIPTION REGULATOR | ACTIVATED | 2.56 | 0.00439 | ACOT1,AQP4,CCND1,FOXO4,GPX1,GSTM5,IGF1,NAMPT,PLK1,PRDX3,SLC40A1,SOD2,TGFB1,TGFB2,VIM |
| SALIRASIB | CHEMICAL DRUG | ACTIVATED | 2.646 | 0.00493 | COL5A1,COL5A2,HIF1A,LGALS1,PKM,PLAT,VEGFA |
| PIOGLITAZONE | CHEMICAL DRUG | ACTIVATED | 2.611 | 0.00593 | ABCA1,AQP7,ATP2A2,BCL2,CCND1,CD36,FN1,NPPA,NR4A3,SLC2A4,SLC9A3,SOD2,TGFB1,VLDLR |
| RBL2 | OTHER | ACTIVATED | 2.298 | 0.00661 | BUB1,CAMKK2,CCND1,CDR2,HADH,NEK2,PLK1,RRM2,UCK2,VEGFA |
| LET-7A-5P (AND OTHER MIRNAS W/SEED GAGGUAG) | MATURE MICRORNA | ACTIVATED | 2.564 | 0.00847 | CAPG,CARHSP1,CCND1,COL1A1,COL1A2,COL27A1,COL3A1,GEMIN7,MTRR,SNAP23,SEC3,STAT3,VIM |
| SU6656 | CHEMICAL TOXICANT | ACTIVATED | 2.236 | 0.0102 | CCND1,CSF1,NR4A2,PHLDA1,VEGFA |
| FOXP1 | TRANSCRIPTION REGULATOR | ACTIVATED | 2 | 0.0102 | ACY1,MYH6,MYH7,NPPA,RASGRF2 |
| ZBED6 | OTHER | ACTIVATED | 2.236 | 0.0116 | ARL4C,PMEPA1,SPTBN1,TUBB3,WNT1 |
| METFORMIN | CHEMICAL DRUG | ACTIVATED | 2.143 | 0.0128 | ABCA1,BCL2,ERN1,FN1,IGF1,PEA15,PKM,SERPINE1,SLC2A4,SORT1,STAR,TGFB1 |
| GELDANAMYCIN | CHEMICAL | ACTIVATED | 2.714 | 0.0149 | BCL2,BGN,CCND1,CL9,COL6A2,FBLN2,GNAO1,HIF1A,HSPD1,NAPT,NPPA,NTN1 |

Fig. 21G

| | | | | |
|---|---|---|---|---|
| MAFB | ENDOGENOUS NON-MAMMALIAN TRANSCRIPTION REGULATOR | ACTIVATED | 2.216 | 0.0183 | ACTN1,AKR1B10,ARHGDIA,CAP1,CNN2 |
| AG490 | CHEMICAL - KINASE INHIBITOR | ACTIVATED | 2.18 | 0.021 | ACE,BCL2,IGF1,MYH10,SOD2,STAR,TIMP1,VEGFA |
| BERBERINE | CHEMICAL DRUG | ACTIVATED | 2.197 | 0.0261 | BCL2,CCND1,FN1,HIF1A,SPHK1,TGFB1,TIMP1,VEGFA,VIM |
| ZNF217 | TRANSCRIPTION REGULATOR | ACTIVATED | 2 | 0.0271 | ANK3,COL8A1,IGFBP3,KCNK2,KRT18,PLAT,SOCS2 |
| EFNA4 | KINASE | ACTIVATED | 2.236 | 0.0272 | DUSP6,ETV5,KRT18,PLAT,SLC20A1 |
| EFNA3 | KINASE | ACTIVATED | 2.236 | 0.0297 | DUSP6,ETV5,KRT18,PLAT,SLC20A1 |
| 2-AMINO-5-PHOSPHONOVALERIC ACID | CHEMICAL - OTHER | ACTIVATED | 2.137 | 0.0309 | ADAMTS1,ADAMTS2,C16ORF8,DUSP6,GADD45G,NR4A2,NR4A3,PHLDA1,RIT1,RPS6KA5,SPRY4 |
| EPLERENONE | CHEMICAL DRUG | ACTIVATED | 2 | 0.0323 | ACE,FN1,TGFB1,VEGFA |
| EFNA5 | KINASE | ACTIVATED | 2.236 | 0.0353 | DUSP6,ETV5,KRT18,PLAT,SLC20A1 |
| CURCUMIN | CHEMICAL DRUG | ACTIVATED | 2.251 | 0.0436 | ABCA1,AQP4,BANP,BCL2,CCND1,CD36,CLIC1,COL1A1,COL1A2,ENTPD5,FASTK,HIF1A,MAPT,MMP14,NAMPT,NPPA,SLC2A4,STAT3,TLR2,VEGFA,VIM |
| HIPK2 | KINASE | ACTIVATED | 2.198 | 0.0518 | BCL2,EEB41,HIF1A,LGALS3,VEGFB,VIM |
| FST | OTHER | ACTIVATED | 2.19 | 0.052 | ACSL1,CD36,CYCS,FN1,PRDM16 |
| RBPJ | TRANSCRIPTION REGULATOR | ACTIVATED | 2.611 | 0.0559 | CCND1,CSF1,FBXL19,FGF18,GMA12,HEY1,IGF1,TGFB2,TGFB3,VEGFA |
| DI (2-ETHYLHEXYL) PHTHALATE | CHEMICAL TOXICANT | ACTIVATED | 2.213 | 0.0772 | ABCD3,ACOT1,CD36,PEX11A,TSPO |
| EFNA2 | KINASE | ACTIVATED | 2.236 | 0.0819 | DUSP6,ETV5,KRT18,PLAT,SLC20A1 |
| IRGM1 | OTHER | ACTIVATED | 2 | 0.0968 | BUB1,NEK2,NUPR1,RRM2 |
| ASPIRIN | CHEMICAL DRUG | ACTIVATED | 2.606 | 0.0968 | ABCA1,BCL2,CCND1,CSF1,CX3CL1,NPPA,TGFB1 |
| ROTTLERIN | CHEMICAL TOXICANT | ACTIVATED | 2.434 | 0.0982 | ABCA1,CCND1,COL1A1,COL3A1,PLSCR1,PRKCD |

*Fig. 21H*

| | | | | | |
|---|---|---|---|---|---|
| CIGLITAZONE | | CHEMICAL DRUG | ACTIVATED | 2.416 | 0.108 | ABCA1,BCL2,CCND1,CD36,DGKA,FN1 |
| CELECOXIB | | CHEMICAL DRUG | ACTIVATED | 2.2 | 0.113 | AKT1,BCL2,BCL2A1,BLK,CCND1,CISK,DES,TLR2 |
| BORTEZOMIB | | CHEMICAL DRUG | ACTIVATED | 2.134 | 0.137 | BCL2,BCL2A1,CALR,CCND1,CDR2,CXCR5,ERN1,IGF1,IGFBP3,IL2RA,ODC1,TGFB1,VIM |
| FOXA1 | | TRANSCRIPTION REGULATOR | ACTIVATED | 2.397 | 0.142 | AKR1C4,ALDH6A1,FKBP4,FSTL1,HADH,HK1,LHFP,NR4A2,THBS3 |
| Y 27632 | | CHEMICAL DRUG | ACTIVATED | 2 | 0.246 | ACTG1,NPPA,TGFB1,VIM |
| GFI1 | | TRANSCRIPTION REGULATOR | ACTIVATED | 2 | 0.545 | AKT1,CSF1,F2R,NFKB2 |
| NANOG | | TRANSCRIPTION REGULATOR | ACTIVATED | 2 | 1 | COL3A1,LGALS1,MAP1B,S100A6 |
| CSF1 | -4.333 | CYTOKINE | INHIBITED | -3.112 | 0.00415 | BCL2,CCND1,CD163,CSF1,CISK,F2R,F2RL1,FCGR2A,FN1,IGF1,IL18BP,ITGB5,NFKB2,TLR2,VEGFA |
| VEGFA | -4.247 | GROWTH FACTOR | INHIBITED | -2.806 | 0.000000335 | ACE,ACSL1,ADAMTS1,AKT1,ALAS1,BCL2,BCL2A1,CCND1,CD34,COL1A1,CSF3,DBT,DECR1,ETFA,ETV5,FN1,HIF1A,HK1,LMNA,MRPL3,MVP,NR4A2,PLAT,PLPP3,SOD2,SPARC,STARD8,TGFB1,TSPO,VEGFA |
| IGF1 | -3.708 | GROWTH FACTOR | INHIBITED | -3.752 | 0.00000314 | AKT1,AQP4,BCL2,BCL2A1,BGN,CCND1,CDC42,CLEC11A,CLU,COL1A1,COL3A1,CSF1,DCLK1,ELN,FN1,HIF1A,HSD11B1,IGF1,IGFBP3,ITGB5,MAPT,MMP14,MYH6,NPPA,NTN1,NUPR1,ODC1,PCOLCE,PHLDA1,SLC20A1,SLC2A4,STAR,TGFB1,TUBB3,UBE2B,VEGFA,VIM |
| TIMP1 | -1.861 | CYTOKINE | INHIBITED | -2 | 0.0398 | IGFBP3,MME,PLAT,PLTP |
| BCL2 | -0.671 | TRANSPORTER | INHIBITED | -2.817 | 0.0113 | ATP2A2,BCL2,CCND1,HIF1A,MCAM,SNAP91,SPHK1,TGFB2,TIMP1,VEGFA |
| HIF1A | -0.602 | TRANSCRIPTION REGULATOR | INHIBITED | -2.306 | 3.14E-11 | ADAMTS1,AKT1,ALDOA,AQP4,ARPC2,ATP2A2,BCL2,BGN,CCND1,CTPS1,EGLN1,ENO1,EREG,FN1,HIF1A,HIST1H1C,IGF1,IGFBP3,KRT18,LGALS1,LIFR,LOX,LOXL2,MAFF,METTL23,NR4A3,P4HA2,PKM,RAB20,SDC4,SESN2,SLC2A4,SOD2,SPHK1,STAT3,SULF1,TGFB1,TGFB2,TGFB3,TLR2,TMEM45A,TRIM21,VASP,VEGFA,VIM |
| TGFB2 | -0.557 | GROWTH FACTOR | INHIBITED | -3.006 | 0.000000065 | ABCA1,CD36,COL1A1,COL2A1,COL3A1,DES,FN1,HEY1,ITGB5,SPHK1,TGFB1,TGFB2,TGFBR3,TIMP1,VCAN,VEGFA |
| PKM | -0.463 | KINASE | INHIBITED | -2.129 | 0.00299 | ACLY,CCND1,ENO1,PKM,STAT3 |

*Fig. 21I*

| | | | | | |
|---|---|---|---|---|---|
| PRKCD | -0.428 | KINASE | INHIBITED | -3.903 | 0.00003 21 | ABCA1,BCL2,BCL2A1,CCND1,CDC42,COL1A1,COL1A2,CX3CL1,FBN1,NFKB2,ODC1,PDLIM7,PLSCR1,SETBP1,SPHK1,STAR,STAT3,TLR2,TUBB2A,VEGFA |
| TGFB3 | -0.421 | GROWTH FACTOR | INHIBITED | -2.259 | 2.66E-08 | BCL2,CD46,COL11A1,COL1A1,COL1A2,COL3A1,COL5A1,ELN,F2RL1,FN1,LTBP2,MICAL2,MYO10,PLK1,SDC3,TGFB1,TGFB3,TGFBR3,VEGFA |
| TGFB1 | -0.407 | GROWTH FACTOR | INHIBITED | -8.034 | 2.8E-32 | ABCA1,ABLIM3,ACAA2,ACE,ACLY,ACOT1,ACTN1,ADAMTS12,ADAMTS2,ADI1,ADGRA1,AKT1,ALDH5A1,ANKH,ANXA11,ANXA2,ARF4,ARPC2,ASS1,BCL2,BDH1,BGN,BUB1,CAP1,CBFA2T3,CCL11,CCND1,CD163,CD34,CD36,CD46,CENPA,CFL1,CHD4,CKS2,CLU,CNN2,COL11A1,COL12A1,COL16A1,COL1A1,COL1A2,COL3A1,COL4A2,COL5A1,COL6A2,COL8A1,COTL1,CSF1,CSRP2,CST3,CTPS1,CTSK,CTTN,CX3CL1,CXCR6,DES,DPYSL3,EEF1A1,EGLN1,ELN,EMILIN1,EREG,F2R,F2RL1,FBLN2,FBLN5,FBN1,FLNA,FN1,FNDC5,FXYD6,GATM,GDF6,GNAO1,GSE1,HADH,HEY1,HIF1A,HMOX2,HNRNPC,HOOK1,IGF1,IGFBP3,IGFBP7,IL2RA,ITGB5,ITGBL1,KCNJ3,KDELR3,KDM6B,KRT18,LAMC1,LGALS3,LIFR,LIMS1,LITAF,LOC102724788/PRODH,LOX,LOXL1,LOXL2,LTBP2,LTBP3,MAF4,MARCH7,MFAP4,MMP14,MSN,MTR3,MYH7,MYH9,MYL6,MYO10,MYO1C,MYOF,NAMPT,NDRG4,NDUFS4,NEK2,NPPA,NR4A2,NR4A3,NUPR1,P2RY1,PDE7A,PDK2,PDLIM5,PDLIM7,PLAT,PLSCR1,PMEPA1,POSTN,PTPRN,RAB31,RBM3,RHOC,S100A6,SAMHD1,SDC4,SELENBP1,SEMA3B,SERPINH1,SHISA5,SLC20A1,SLC39A1,SLC7A5,SMOC2,SOD2,SPARC,SFRK1,SRI,STAR,STAT3,TGFB1,TGFB2,TGFB3,TGFBR3,TGIF1,TIMP1,TLR2,TPM3,TPM4,TUBA1A,TUBB2A,TUBB3,UCK2,VASP,VAT1,VCAN,VEGFA,VIM,WNK1 |
| STAT3 | -0.325 | TRANSCRIPTION REGULATOR | INHIBITED | -2.27 | 0.00009 06 | AKT1,BCL2,CCL11,CCND1,CD46,COL1A1,COL1A2,COL3A1,COL5A1,CTTN,CX3CL1,FGL2,FN1,GADD45G,HERC6,HEY1,HIF1A,IL2RA,LDHB,MX1/MX2,MYH7,NAMPT,NFKBIZ,NPPA,NR4A2,PEG10,PHLDA1,PLSCR1,PGU2F1,PTPN2,SLC9A3,SLFN2,SOD2,STAT3,SYNPO,TGFB1,TIMP1,VCAN,VEGFA,VIM |
| CALR | -0.301 | TRANSCRIPTION REGULATOR | INHIBITED | -2.587 | 0.00012 1 | ATP2A2,COL1A1,COL1A2,FN1,MYL2,RYR2,TGFB1,TRDN |
| AKT1 | -0.234 | KINASE | INHIBITED | -2.822 | 3.87E-09 | ACLY,AKR1B10,AKT1,ANKH,ASS1,BCL2,BCL2A1,CCND1,CKS2,COL3A1,CSF3,FN1,FSTL1,GSTM5,HIF1A,LBH,MMP14,NFKB2,NPPA,PCOLCE,PEXL1A,PHLDA1,PRKAB,... |

*Fig. 21J*

| | | | | | |
|---|---|---|---|---|---|
| MKL2 | 0.291 | TRANSCRIPTION REGULATOR | INHIBITED | -2.236 | 0.0065 | R1A,SERPINF1,SORT1,TGFB2,TGFBR3,TIMP1,VCAM,VCP,VEGFA,VIM CNN2,DHCR24,F2R,FLNA,GSDM5,MYH9,P2RY1,SLC20A1,TEM4 |
| TMPO | 0.896 | OTHER | INHIBITED | -2 | 0.00008 68 | COL1A1,COL1A2,COL2A1,COL3A1 |
| ERBB2 | | KINASE | INHIBITED | -2.04 | 1.54E-21 | ABHD5,ACAA2,ADAM8,AKT1,ALAS1,ANXA2,BCL2,BUB1,CBFA2T3,CCDC80,CCL11,CCNE1,CD34,CD36,CD47,CEMFA,CES1,CKS2,CLEC11A,CLU,COL1A,COL3A1,COL5A1,COL5A2,COL6A1,COL6A2,CPT2,CYP4B1,DAP,DEC R1,DHRS7,DEPP1,DUSP6,EMP1,EREG,ETFB,ETV5,F2R,FBLN2,FN1,FSTL1,GPC1,HADHB,HIF1A,IDH1,IGFBP3,IRX3,LGALS1,LGALS3,LITAF,LRRFIP1,LTBP2,LTBP3,MAP1B,MAP4,MCCC1,MME,MMP14,MYO10,NDRG4,NDUFAB1,NEK2,NFKB2,NRG1,P4HA2,PHYH,PLAT,PMEPA1,PTFN1,RAB31,RNF149,RRM2,S100A6,SEC61A1,SHROOM3,SOCS2,SPARC,STAT3,TGIF1,TMSB4X (INCLUDES OTHERS),TUBA1A,VCAM,VEGFA,VIM |
| THIOACETAMIDE | | CHEMICAL TOXICANT | INHIBITED | -4.351 | 3.88E-18 | ADAMTS1,ANXA2,ANXA4,BGN,CKB,CLU,COL1A1,COL1A2,COL3A1,CSRP2,CTSF,CYGB,DBN1,ELN,EMP1,F2R,FBLN5,FBN1,FCGR2A,FSTL1,FXYD6,GATM,HK1,IGF1,IGFBP3,LGALS1,LGALS3,LOX,MMP14,NUPR1,ODC1,PCOLCE,PKM,PI,PP3,PMP22,PSMB10,PTGFRN,RBM3,SLC22A5,SPARC,SPRR1A,TGFB1,TGFB3,TGIF1,TIMP1,TMEM45A |
| PRL | | CYTOKINE | INHIBITED | -2.533 | 6.07E-18 | ANXA2,ANXA5,ATP2A2,ATP5H,BCL2,BOK,CCND1,CLU,COL1A1,COL1A2,COL3A1,COL5A1,CST3,DES,DVL1,EN O1,FN1,GNA12,HERC6,HSPD1,IGFBP3,IL2RA,LAMC1,MME,MMP14,MSN,NUPR1,ODC1,P4HB,PARM1,PCOLCE,PDK2,PLAT,PLSCR1,PTGFR,SAMHD1,SCP2,SHISA5,SOCS2,SPARC,STAR,TGFB1,TIMP1,TMSB4X (INCLUDES OTHERS),TPM3,TUBA1B,VIM,YWHAG |
| BETA-ESTRADIOL | | CHEMICAL - ENDOGENOUS MAMMALIAN | INHIBITED | -2.198 | 2.75E-17 | ABCA1,ABHD5,ACAA2,ACADVL,ACE,ACOT1,ACSL1,ADAMTS1,ADCY1,ADORA1,ALDOA,ANKH,ANXA4,APBB1,ATP5F1,BACE2,BCL2,BCL2A1,BUB1,C1QTNF6,CALR,CBFA2T3,CCDC80,CCL21,CCND1,CKB,CLU,CNN2,COL1A1,COL1A2,COL3A1,COL6A6,COLEC12,COMT,CTPS1,CTSK,CTTN,CYP4B1,DBN1,DCAF6,DCLK1,DECR1,DUSP6,ECH1,EMP1,ENO1,ENPP2,F2RL1,FBLN2,FBN1,FCGR2A,FCGRT,FDFT1,FMO1,FN1,FNDC5,FSTL1,GADD45G,GNE,GPC1,GPX1,HADH,HSD11B1,HSPD1,HSPH1,IFRD2,IGF1,IGFBP3,INPP4B,IP6K1,IQGAP1,ITGBL1,ITIH4,KCN |

Fig.21K

| | | | |
|---|---|---|---|
| LIPOPOLY SACCHARI DE | CHEMICAL DRUG | INHIBITED | -3.552 | 3.31E-16 | D3,KDELR3,KLHL38,KRT18,LGALS3,LITAF,LMNA,MAP1,M6ME,MTMR4,MX1/MX2,MYH6,MYH7,MYOF,NAMPT,NDRG2,NPPA,NR4A3,NRTN,NTN1,NUPR1,ODC1,OSRPL3,P4KZ,FHL1DA1,PRM,PLAT,PME22,PON2,PFIB,PPP2R2C,PRCD,PTGFR,PTFN1,PTPN2,PTPRN,RAB31,RASGRP2,RBM39,KRM2,RTN2,S100A6,SBK1,SDC3,SDC4,SELENBP1,SEMA3B,SLC10A1,SLC22A5,SLC7A5,SLK,SOCS2,SORD,SPARC,SERR1A,STAR,STAT3,SUCLA2,SYNPO,TGFB1,TGFB2,TGFB3,TGFBR3,TIMP1,TLR2,TMEM44,TMPO,TSPO,UBE2B,UCK2,VCAM,VEGFA,VIM,ZNRF1 ABCAL,ACE,ACLY,ACOT1,ACSL1,ACTN4,ADORA1,AKAP2,ANXA5,ANXA7,AQP4,AQP7,ARF2,ARL4C,ARPC1B,AS1,ATP2A2,BCL2,BCL2A1,BGN,CALR,CCL11,CCL21,CCND1,CD163,CD36,CD46,COL12A1,COL1A1,COL1A2,COL3A1,COL4A2,COL5A1,COL5A2,COL6A1,COL7A1,CSF1,CST3,CTSK,CUX2,CX3CL1,CYCS,DHCR24,DIO2,ENO1,ENPP2,ERCC1,EREG,ERN1,ETV5,F2R,F2RL1,FBLN2,FBN1,FCGRT,FN1,GPC4,HADHB,HEY1,HIF1A,IDH1,IGF1,IGFBP3,IL2RA,ITGB5,ITIH4,LGALS1,LGALS3,LIFR,LIMS1,LITAF,LRRFIP1,MAFF,MAFT,MARCH7,MFN1,M2ME,MMP14,MMP23B,MSN,MX1/MX2,MYH7,MYH9,MYL2,NAMFT,NDUFV2,NFKB2,NFKBIZ,NLRC5,NPPA,NR4A2,MR4A3,NRTN,NUPR1,ODC1,P4HB,PANX1,PCOLCE,PHLDA1,PLA2G5,PLAT,PLK1,PLSCR1,POU2F1,PSMB10,RAB20,SDC4,SERPINF1,SERPINH1,SLC1A5,SLC30A4,SLC40A1,SLC9A3,SLFN2,SNAP23,SOCS2,SOD2,SPARC,SPHK1,SFTLC2,STAR,STAT3,SYNPO,TGFB1,TGFB2,TIMP1,TIRAP,TLR2,TNK2,TNNI3,TRIM21,TSPO,VCAN,VEGFA,VIM,VLDLR,VTN,YWHAG |
| F2 | PEPTIDASE | INHIBITED | -3.813 | 2.03E-13 | AKR1B1,B3GNT5,B4GALT1,CALR,CCND1,CD63,CITED4,CKAP4,CLIC1,CLU,COL1A1,COL11,CTPS1,CX3CL1,EHD4,EPB41,EREG,F2R,F2RL1,FN1,HIF1A,IFRD2,IGF1,LOXL2,MEOX1,MFHAS1,MYH9,NR4A3,PLAT,SDC4,SLC2A12,SOD2,TAGLN2,TGFB2,TGFB3,TUBB3,UCK2,VASP,VEGFA,VTN |
| CTGF | GROWTH FACTOR | INHIBITED | -2.097 | 2.8E-13 | ADAMTS1,AKT1,BCL2,BCL2A1,CCND1,COL1A1,COL4A2,COL8A1,EMILIN1,ENO1,FN1,HIF1A,IGF1,LIMS1,LOX,LTBP3,MMP14,PDE7A,PTGFR,SDC4,SPARC,TGFB1,TIMP1,VEGFA,WNK1 |
| FORSKOLIN | CHEMICAL TOXICANT | INHIBITED | -3.513 | 6.18E-13 | ABCA1,ACE,ACTN1,ADAMTS1,ALDOA,ARL4C,ATP6V1B2,B4GALT1,BCL2,CALR,CCL11,CCND1,CITED4,CLU,COL15A1,COL1A1,CREBL2,CRIP2,CSF1,CTTN,DIO2,EREG,FBLN5,FN1,GADD45G,GSTM5,H3F3A/H3F3B,HIF1A, |

| | | | | |
|---|---|---|---|---|
| FGF2 | GROWTH FACTOR | INHIBITED | -3.383 | 9.2E-13 | HSD11B1,IGF1,IGFBP3,IL2RA,ITGB5,KRT18,LITAF, MAT2A,MFN1,MMP23B,NAMPT,NPPA,NR4A2,NR4A3,ODC1,P4HA2,PDE4C,PEG10,PLAT,PKAR1A,PTPN1,PTPRF,PTPRM,RAB20,RAB31,RGS5,RRM2,SLC2A4,SOD2,STAR,STAT3,SYNJ2,SYNPO,TAGLN2,TIMP1,TMB1M1,TPM4,TUBA1A,VCAN,VEGFA,VIM |
| PDGF BB | COMPLEX | INHIBITED | -2.662 | 5.14E-12 | ACE,AKR1B1,AKR1B10,AKT1,BCL2,BGN,CCND1,COL1A1,COL1A2,COL3A1,CSF1,CTSK,ELN,ENO1,ENPP2,EREG,ETV5,FBN1,FLNA,FN1,FOXO4,HIF1A,IGF1,IGFBP3,LMNA,LOX,MAFF,MCAM,NES,NR4A2,ODC1,PLAT,PRKCD,PTMA (INCLUDES OTHERS),SLC20A1,SPARC,SPHK1,SPRY4,STAR,TGFB1,TGFB2,TGFBR3,TIMP1,TMSB4X (INCLUDES OTHERS),TUBB3,VEGFA,VIM |
| CD44 | ENZYME | INHIBITED | -2.764 | 5.33E-12 | AKR1C14,AKR7A2,ANXA11,ATP2A2,BRAP,CCND1,COL3A1,CSF1,CSRP2,CYCS,DUSP6,EREG,FBLN5,FLNA,FMO1,FN1,IGF1,KLHL21,LGALS3,LMNA,MAT2A,MMP14,NAMPT,NDUFB8,NR4A2,NR4A3,ODC1,PCOLCE,PDLIM1,PHLDA1,PLAT,PLCG2,POSTN,RBP1,SLC6A6,SOD2,SPHK1,STAT3,TGFB1,TGFB3,TIMP1,VCAN,VEGFA |
| PROGESTERONE | CHEMICAL - ENDOGENOUS MAMMALIAN | INHIBITED | -2.118 | 2.54E-11 | ABCA2,ADAM8,ANXA11,BCL2,BGN,CALR,CCND1,CD36,CD63,CLU,COL1A1,COL3A1,COL5A2,CTSK,CXCL11,CYB5R3,EMILIN1,FKBP4,FN1,FLRA,ITGBL1,LAMC1,LGALS1,LGALS3,LTBP2,MMP14,NFKB2,PLPP3,PMEPA1,SBK1,SDC4,VCP,VIM |
| IL5 | CYTOKINE | INHIBITED | -2.791 | 8.9E-11 | ACE,ACOT1,ACSL1,ADAMTS1,AK3,AMY2A,ANKH,ATP6V1B2,BCL2,CCND1,CES1,CNDP2,COL15A1,COMT,CREB3L2,CSF1,CST3,CTSF,DLC1,ENPP2,F2R,F2RL1,FKBP4,FN1,HEY1,HIF1A,HSD11B1,IGF1,IGFBP3,TNMT,LGALS1,LGALS3,LITAF,MME,MYO10,NDRG2,PARM1,PDLIM1,PKM,PLPP3,PMP22,POSTN,PTGFR1,RAP1B,RBP1,RRM2,RTN4,S100A6,SFT1,SIX4,SLC1A5,SOD2,SPHK1,TGFB1,TGFB2,TGFB3,TGFBR3,TIMP1,VEGFA,VIM,YWHAG |
| NR3C2 | LIGAND-DEPENDENT NUCLEAR RECEPTOR | INHIBITED | -2.829 | 2.46E-10 | ACAA2,AK3,ALDOA,ANXA2,ASS1,BCL2,CA4,CD63,CIS,D1,CKAP4,DUSP6,EGLN1,ENO1,FGL2,GADD45G,HIF1A,HSPH1,IL18BP,IL2RA,MAT2A,NARP1,NEK2,PDLIM1,PFRP,PKM,PMP22,RASGRP2,RBM3,S100A6,SLC1A5,SLC7A5,SNAP23,SOCS2,SRI,TGFB1,TUBB2B,UCK2,VIM,ADAMTS1,AQP4,ARFC2,BCL2,BCL2A1,CMYA5,COL1A1,COL3A1,DES,FKBP4,FN1,GPX1,HMOX2,HPC,NDRG2,NPPA,NR4A2,PPIB,TGFB1,TUBB3,VEGFA,VLDLR |

| | | | | |
|---|---|---|---|---|
| MAP4K4 | KINASE | INHIBITED | -3.841 | 1.07E-09 | ACAA2,ACADS,ACADVL,ACLY,AGPAT3,AUH,CHPT1,HADH,HADHA,HADHB,KYAT3,LDHB,NDUFA3,NDUFAB1,NDUFS1,NDUFS4,PEX11A,PHYH,PON2,SCP2,SLC2A4,SUCLG1 |
| D-GLUCOSE | CHEMICAL - ENDOGENOUS MAMMALIAN | INHIBITED | -2.316 | 1.07E-09 | ABCA1,ACAA2,ACE,ACLY,ACSL1,AKR1B1,ALDOA,ARF4,ASS1,ATP2A2,BCL2,CALR,CAP1,CCND1,CD36,CLU,COL1A1,COL3A1,CPT2,CX3CL1,DECR1,ENO1,FN1,HIF1A,HK1,HSPD1,IDH1,IGF1,LAMC1,LOC102724788/PRODH,MMP14,NAMPT,NR4A2,NR4A3,ODC1,PFKP,PKM,PON2,PPIB,PTPRN,RAP1B,RRM2,SEC61A1,SLC2A4,SOD2,SPRK1,SUCLA2,TGFB1,TGIF1,TIMP1,TLR2,TUBB3,VEGFA |
| TGF BETA | GROUP | INHIBITED | -2.636 | 1.48E-09 | ABCA1,AMHH,BCL2,BGN,CCL11,CCND1,CLU,COL1A1,COL1A2,CSF1,CTSK,FBLN2,FN1,FSTL1,HEY1,IGF1,IGFBP3,IGHA,KDM6B,LOX,NR4A2,PLAT,PLPP3,PMEPA1,POSTN,RYR2,SPARC,TGFB1,TIMP1,TLR2,VEGFA,VIM |
| METHAPYRILENE | CHEMICAL DRUG | INHIBITED | -2 | 2.01E-09 | ACADS,ACTG1,ALDOA,AMACR,ANXA2,ANXA5,ASS1,ATP6V1B2,AZIN1,CCND1,CD36,CES1,CST3,DECR1,EEF1A1,EMPP2,IGF1,ITIH4,MAOB,MIFEP,NX1/MX2,ODC1,SCP2,TUBB |
| PTH | OTHER | INHIBITED | -2.133 | 2.64E-09 | ADAMTS1,ANK3,ATP2A2,BCL2,CCND1,COL1A1,COL1A2,CSF1,FN1,IGF1,IGFBP3,LMNA,MME,NDRG2,NR4A2,ODC1,POSTN,SDC4,SLC2A4,SLC9A3,SMPX,SORT1,TGFB1,TMEM119,WIF1 |
| NITROFURANTOIN | CHEMICAL DRUG | INHIBITED | -3.213 | 3.73E-09 | ACADVL,ACTG1,ADAMTS1,AMACR,ANXA2,ANXA5,ASS1,CCND1,CES1,CLU,CST3,EEF1A1,IGF1,IGFBP3,ITIH4,LGALS3,LOX,MMP14,ODC1,PLAT,SCP2,SELENBP1,TIMP1,TUBA1A,TUBB,VEGFA |
| AGT | GROWTH FACTOR | INHIBITED | -3.757 | 4.14E-09 | ACE,ANK3,BCL2,BGN,BGR,CALR,CCND1,CD36,COL1A1,COL1A2,COL3A1,COL6A1,COX7A1,DCUN1D3,DDAH2,EFEMP1,EREG,FDFT1,FN1,GSTM5,HEY1,HIF1A,IDH1,IGF1,IGFBP3,ITGB5,KCND3,MAPT,MYH10,MYH5,MYH7,NFKB2,NPPA,NR4A2,PFN1,POSTN,PTGFR,SOD2,STAR,TBX20,TGFB1,TGFB2,TGFB3,TIMP1,TUBB3,VEGFA |
| PGR | LIGAND-DEPENDENT NUCLEAR RECEPTOR | INHIBITED | -2.023 | 8.22E-09 | ACSL1,ADAMTS1,AK3,BU51,CCND1,CKAP4,COL6A1,COL6A2,COMT,CPT2,CREB3L2,F2RLL1,FN1,HIF1A,KRT18,MAT2A,MFAP5,MVP,MYO1G,P4HA2,PCDHGC3,PDLIM1,PFKP,POSTN,RASGRP2,RHOC,S100A6,SFT1,SLC7A5,STAT3,TGFB3,UCK2,VASP,VCAN |
| EGF | GROWTH FACTOR | INHIBITED | -4.149 | 9.83E-09 | ACTN1,AKT1,ATP2A2,B4GALT1,BCL2,CCND1,CKS2,CLU,COL1A1,COL1A2,COL3A1,DIO2,DUSP6,EEF1A1,ERCC1,EREG,FN1,FSTL1,GGT5,HIF1A,IDH1,IGF1,IGFBP3,NPPA,NR4A2,NR4A3,NRG1,ODC1,PLAT,PLPP3,PLSCR3 |

Fig. 21N

| | | | | |
|---|---|---|---|---|
| CG | COMPLEX | INHIBITED | -3.635 | 1.42E-08 | R1,EPIB,FTPRN,RRM2,SLC2A4,SLC9A3,SPARC,SPHK1,SPRY4,STAR,TGFB1,TGFB3,TGIF1,TIMP1,ULK1,VASP,VCAN,VEGFA,VIM |
| CD38 | ENZYME | INHIBITED | -2.557 | 2.11E-08 | ACSL1,ADAMTS1,AKR1B10,BCL2,CBFA2T3,CLU,COL11A1,DUSP6,EFEMP1,EMP1,ENPP2,EPHB6,EREG,F2RL1,FGL2,GPC1,HIF1A,HSD11B1,IGF1,IGFBP3,ITGB5,RCNU3,MCAM,FHLDA1,PKIA,PLAT,PLEP1,PTGER,S100A6,SEC4,SLC20A1,SERPINA,ST6SIA4,STAR,TGFB2,TGFBR3,TIMP1,VCAN,VEGFA |
| MKNK1 | KINASE | INHIBITED | -2.524 | 2.25E-08 | AK3,ALDOA,ANXA2,ASS1,CISD1,CRAF4,CPEB3,EGLN1,FGL2,GADD45G,IL2RA,LGALS3,MABP1,NEK2,PDLIM1,PFKP,PKM,RASGRP2,S100A6,SLC7A5,SOCS2,TUBB2B,UCK2,VIM |
| SP1 | TRANSCRIPTION REGULATOR | INHIBITED | -2.741 | 2.33E-08 | ANXA2,ANXA5,DPYSL3,FLNA,GNAO1,GPC4,HADHA,RIF1B,LAMC1,MAF1B,MAP7,MR4A3,PDLIM5,PLTP,PLXNE2,SERPINH1,SPARC,VIM,YWHAG |
| MTPN | TRANSCRIPTION REGULATOR | INHIBITED | -4.049 | 2.72E-08 | ABCA1,ACSL1,ADAMTS1,ANKH,ASS1,ATP2A2,BACE2,BCL2,CCND2,CES1,CIRBP,CKB,COL1A1,COL1A2,COL3A1,DHCR24,DLC1,EREG,F2R,FLNA,FN1,HADHA,HADHB,HIF1A,IGF1,IGFBP3,ITGB5,KRT18,LTBP3,MAOB,MAT2A,MMP14,MYH7,NPPA,PKM,PRKCD,PTPN1,RASGRP2,SLC2A12,SLC9A3,SOD2,SPARC,STAR,TGFB1,TGFB2,TGFBR3,TIMP1,TLR2,TSPO,VEGFA,VIM |
| EDN1 | CYTOKINE | INHIBITED | -4.012 | 3.91E-08 | BCL2,BCL2A1,CCND1,COL1A1,COL1A2,COL8A1,FN1,IGF1,MYH7,NPPA,PLAT,S100A6,SPARC,TGFB1,TGFB2,TGFB3,TUBA1A |
| CTNNB1 | TRANSCRIPTION REGULATOR | INHIBITED | -2.898 | 6.42E-08 | ANXA4,ANXA5,ATP2A2,BCL2,BCL2A1,CCND1,COL1A2,COL5A1,CST3,EREG,FN1,HEY1,HIF1A,MCAM,MSN,MYH7,MYL2,MYL6,NPPA,NUPR1,ODC1,PRKCD,TIMP1,TPM3,VCAN,VEGFA,VIM |
| ERK | GROUP | INHIBITED | -4.537 | 8.67E-08 | ACTN4,AKR1C14,AQF4,AREGAP3,ARHGD1A,BCL2,BGN,CCND1,CD34,CLU,CNN2,COL1A1,COL2A1,COL4A2,CRAT,CTSF,DES,DIO2,DPEP1,ENPP2,EWSR1,F2R,FBLN2,FGF18,FN1,GADD45G,GNA12,GNAO1,IL2RA,LAP3,LGALS3,LMNA,MAP4,MEOX1,MLLT6,MME,MMP14,MMP23B,NDRG2,NTN1,NUDT7,NUMB,PCDH9,PFN1,FLK1,FMP22,RAD23A,RAI14,SEC61A1,SLC1A5,STAT3,TBX20,TGFB3,TGIF1,TIMP1,VCAN,VEGFA,VIM,WIF1,ABCA1,ACTN1,ARPC2,BCL2,BGN,CCND1,CKS2,CLU,COL1A1,COL3A1,CTSK,CTTN,DIO2,EREG,FN1,HEY1,KRT18,MAFF,MCAM,MMP14,NFKBIZ,ODC1,SCRT1,SPTBN1,TIMP1,TUBA1A,VASP,VCAN,VEGFA |

*Fig. 210*

| | | | | |
|---|---|---|---|---|
| EPAS1 | TRANSCRIPTION REGULATOR | INHIBITED | -2.391 | 9.91E-08 | BCL2,CCND1,CKB,DUSP7,ENO1,FBLN2,FN1,GPX1,HIF1A,HIST1H1C,IGFBP3,ITIH5,LOX,LOXL2,MAFF,MME1 4,OMA1,SLC2A4,SLC40A1,SLC7A5,SOD2,SPHK1,TGFB3,TMEM45A,TRIM21,VEGFA |
| MIBOLERONE | CHEMICAL DRUG | INHIBITED | -2.19 | 0.000000149 | ACSL1,ARF4,CALR,CALU,CCDC80,CCND1,CLEC11A,CLU,COL1A1,COL1A2,GADD45G,IDH3G,IGF1,IGFBP3,MAT2A,MME,NANS,P4HB,PPIB,SLC22A5,TUBA1A |
| HGF | GROWTH FACTOR | INHIBITED | -2.837 | 0.000000152 | ADAMTS1,AKT1,ANK3,BCL2,BCL2A1,BUB1,CCND1,CD46,COL1A1,COL1A2,COL3A1,CSF1,CTSK,DES,DUSP6,EMP1,FASTK,FLNA,FN1,HK1,IGF1,IGFBP3,KRT18,MAT2A,MMP14,MAMF1,NEK2,NR4A2,NR4A3,NRG1,PHLDA1,PTR1,PLPP3,PMP22,PTPN2,PTPRF,SLC20A1,SLK,SOCS2,TAGLN2,TGFB1,TGFB2,TIMP1,TRDN,VEGFA,VIM |
| INS1 | OTHER | INHIBITED | -2.765 | 0.000000236 | ACOT1,AKT1,ALAS1,AP2M1,AQP7,BDH1,CCND1,COL1A1,CRAT,ECI1,ERCC1,FDFT1,IGF1,IGFBP3,LDHB,LIFR,MAPT,NDUFS4,NPPA,ODC1,PLAT,PPIB,PTGFRN,PTPRN,RETSAT,RRM2,SLC2A4,SOCS2,SOD2,SPARC,STAT3,TIMP1,VEGFA,VIM |
| NRG1 | OTHER | INHIBITED | -2.647 | 0.000000331 | ABCA1,ACTN1,ARPC4,BCL2,CCND1,CKS2,COL1A1,DUSP6,EEF1A1,ETFB,FN1,FSTL1,HIF1A,IMMT,ITGB5,LIFR,MYH6,MYL2,NDUFS1,NPPA,NR4A3,PHKG1,PYGM,SLC2A4,TNNI3,VEGFA,VIM |
| CREB1 | TRANSCRIPTION REGULATOR | INHIBITED | -2.566 | 0.000000412 | ABCA1,ALAS1,BCL2,CACNA2D1,CAMKK2,CCND1,CDK19,CLMP,CSRP2,DGKA,DIO2,EHD4,FGL2,FN1,GADD45G,HN1,HSD11B1,IL2RA,ITGB1,KCND2,KCNIP2,KDELR3,LITAF,MAT2A,MCAM,MYH10,NR4A3,PEG10,PITPNB,PLAT,PTPRN,ROBO1,RP1,SCN3B,SLC2A4,SOCS2,SOD2,STAR,STAT3,SYNJ2,TAGLN2,TGIF1,TMBIM1,TOM1,TPM4,VEGFA,VIM |
| TWIST1 | TRANSCRIPTION REGULATOR | INHIBITED | -3.578 | 0.000000715 | ADAMTS1,BCL2,CLU,COL1A1,COL6A1,EMILIN1,FN1,GPC1,ITGB5,LMNA,MME,MRC2,OLFML3,PCOLCE,RHOC,SDC3,SPHK1,TGFB1,VCAN,VEGFA,VIM |
| ANGPT2 | GROWTH FACTOR | INHIBITED | -3.048 | 0.000000913 | ARL4C,BCL2,CALR,COL1A1,COL1A2,COL3A1,COMT,EKBP10,FKBP4,FN1,HIF1A,HSPD1,KDM6B,KIF1C,MYH6,MYH7,NPPA,P4HB,PHLDA1,POSTN,SOD2,TOR1AIP2,TUBB3,VIM |
| AR | LIGAND-DEPENDENT NUCLEAR RECEPTOR | INHIBITED | -2.984 | 0.00000104 | ABCA1,AK3,AKT1,ATF2A2,BUB1,CA4,CALU,CAMKK2,CCND1,CKAP4,COL3A1,CUX2,DDT,DES,DHCR24,ERN1,FKBP4,HSPH1,IGF1,IGFBP3,INPP4B,KCNJ3,MME,MYH6,NEK2,NUPR1,ODC1,PLAT,PLK1,PLN,PMEPA1,PRKCD,SGRD,STAR,TGFB1,TGFB2,TUBB3,VCAN,VEGFA,VIM |
| INSULIN | GROUP | INHIBITED | -2.401 | 0.0000013 | ACLY,ACSL1,AK1,ALDOA,BCL2,CCND1,CD36,COL1A1,FN1,HIF1A,HSD11B1,IGF1,IGFBP3,KCNJ3,MAOB,MA |

*Fig. 21P*

| | | | | | |
|---|---|---|---|---|---|
| VANCOMYCIN | BIOLOGIC DRUG | INHIBITED | -3.231 | 0.00000184 | PT,MTCH2,NR4A2,MR4A3,ODC1,OGT,PDK2,PKM,PRKCD,PTKRN,SLC2A4,SLC38A3,SORT1,STAR,STAT3,TGFB1,TLR2,VEGFA,VLDLR |
| NOS2 | ENZYME | INHIBITED | -2.076 | 0.00000202 | ADAMTS1,ANXA2,CLU,EFEMP2,FCGR2A,GSTK1,LGALS3,PSMB10,RBM3,RTN4,SOD2,TGIF1,TIMP1,TUBB,VIM,ATP2A2,BCL2,BCL2A1,COX7A1,CYC3,HIF1A,ITIH4,MYH6,MYH7,MYL2,NEPA,NKTN,PLSCR1,SERPINH1,SLC1A5,SLC2A4,SLC40A1,SLFN2,TGFB1,TIMP1,TNK2,TNNT3,VEGFA |
| BLEOMYCIN | CHEMICAL DRUG | INHIBITED | -3.634 | 0.0000021 | AKT1,BCL2,COL1A1,COL1A2,COL3A1,CTSK,ELN,F2R,FN1,HEY1,IGF1,MAP4,MMP14,MSN,PLAT,SDC4,SOCS2,SPHK1,TGFB1,TIMP1,TLR2 |
| N-NITRO-L-ARGININE METHYL ESTER | CHEMICAL DRUG | INHIBITED | -2.16 | 0.00000214 | ACE,BCL2,BGN,CCL11,COL1A2,COL3A1,CSF1,FN1,MAP1B,MYH7,NPPA,TGFB1,TIMP1,TLR2,VEGFA |
| CYP1A1 | ENZYME | INHIBITED | -2 | 0.00000276 | ACOT11,ANXA4,ANXA7,AP2M1,CCND1,CNN2,CTTN,GPC1,IGF1,LMNA,MAPT,MYO10,ODC1,SOCS2,TMPO,VLDLR |
| KLF4 | TRANSCRIPTION REGULATOR | INHIBITED | -2.675 | 0.00000288 | ADAMTS1,ATP2A2,CCND1,CD34,COL1A1,COL8A1,EFEMP1,FARP1,FN1,HEY1,IRX3,MYH6,MYH7,NPPA,ODC1,PFKP,PLAT,SERPINH1,SOD2,SPHK1,SERPIA,TEAD2,TGFB1,TGFB2,TGFB3,VEGFA,VTN |
| 2-BROMOETHYLAMINE | CHEMICAL REAGENT | INHIBITED | -3.286 | 0.00000341 | ADAMTS1,ANXA2,CLU,EFEMP2,FCGR2A,LGALS3,RBM3,TGIF1,TIMP1,TUBB,VIM |
| CSF2 | CYTOKINE | INHIBITED | -3.055 | 0.00000341 | ABCA1,ACE,ADAM8,BCL2,BCL2A1,BUB1,CCND1,CD63,COL8A1,CSF1,DUSP6,EFEMP2,ELN,F2R,F2RL1,HSPD1,HSPH1,IGF1,IL2RA,ITGB5,MAT2A,MME,MMP14,NEK2,NFKB2,NR4A2,ODC1,PLK1,PMP22,RBM3,RRM2,SGC1,SLC1A5,SLC30A4,SLFN2,SNAP23,SOCS2,SOD2,TGFB1,TLR2 |
| SMAD3 | TRANSCRIPTION REGULATOR | INHIBITED | -3.027 | 0.00000417 | ADORA1,BCL2,BGN,CCND1,COL1A1,COL1A2,COL3A1,COL6A1,DES,ELN,EREG,FN1,FNDC5,HEY1,IL2RA,ITGB5,PMEPA1,STAT3,TGFB1,TGFB2,TGFB3,TIMP1,TPM3,VEGFA,VIM |
| GENTAMICIN C | CHEMICAL DRUG | INHIBITED | -3.464 | 0.00000765 | ADAMTS1,ANXA2,CLU,EFEMP2,FCGR2A,LGALS3,PSMB10,RBM3,TGIF1,TIMP1,TUBB,VIM |
| PHORBOL MYRISTATE ACETATE | CHEMICAL DRUG | INHIBITED | -3.274 | 0.00000789 | ABCA1,ACE,ADAM6,ADAMTS1,AKR1B10,AKT1,ALAS1,AQP4,ARF4,ATP2A2,B3GNT5,BCL2,BCL2A1,C14ORF159,CAPG,CCND1,CD163,CD36,CES1,CTTN,DES,EGSF6,ERCC1,FBN1,HIF1A,HNRNPC,HSD1B1,IGF1,IGFBP3,IL2RA,KCNK2,LOXL2,LRRFIP1,MACB,METTL7A,M... |

*Fig. 21Q*

| | | | | |
|---|---|---|---|---|
| GENTAMIC IN | CHEMICAL DRUG | INHIBITED | -3.028 | 0.00000 869 | ME,MMP14,MTRR,MYH7,MYH9,NPPA,NR4A2,ODC1,PDLI M7,PEA15,PKM,PLAT,PLN,PRKAR1A,PRKCD,PTGFR,PT PRF,PIERN,SETBP1,SLC9A2,SOD2,SPARC,SPHK1,SER R1A,STAR,STAT3,TEAD2,TEF,TGFB1,TIE1,TIMP1,TL R2,TPM3,VCAN,VEGFA,VIM,VLDLR |
| FINASTER IDE | CHEMICAL DRUG GROUP | INHIBITED | -2.607 | 0.00000 836 | AZIN1,CA4,CALR,CLU,CSRP2,DECR1,DPEP1,EEF1A1, ENPEP2,ETFDH,FMO1,GATM,GSTM5,H3F3A/H3F3B,IDH1 ,IGFBP3,LITAF,PTPN1,SLC22A5,SLC9A3,TANGO2,TG FB1,TIMP1,TUBB,UBQLN1,VAT1 |
| P38 MAPK | CHEMICAL DRUG | INHIBITED | -2.941 | 0.00000 893 | BCL2,CLU,HIF1A,TGFB1,TGFB2,TGFB3,VEGFA |
| | | | | | ABCA1,ANXA5,AQP4,ASS1,BCL2,BCL2A1,BGN,CCL11, CCND1,CD36,CD46,COL3A1,CTSK,DES,DGKA,DIO2,FL NA,FN1,HIF1A,IL2RA,KDELR3,MAP4,NES,NPPA,NR4A 3,POSTN,RBP1,TGFB1,TIMP1,TLR2,ULK1,VEGFA,VLD LR |
| TRIAMTER ENE | CHEMICAL DRUG | INHIBITED | -3.44 | 0.00001 26 | ADAMTS1,ANXA2,CLU,EFEMP2,FCGR2A,LGALS3,PSMB1 0,RBM3,TGIF1,TIMP1,TUBB,VIM |
| ERR1/2 | GROUP | INHIBITED | -2.771 | 0.00001 4 | ABCA1,AKR1B10,ANKRD2,BCL2,BCL2A1,CALR,CCL11, CCND1,CLEC11A,COL1A1,COL3A1,ENO1,HIF1A,IGFBP 3,IL2RA,NAMPT,NPPA,NR4A3,NRG1,POSTN,PSMB10,R HOC,S100A6,SERP4,STAR,TIMP1,VCAN,VEGFA |
| CISPLATI N | CHEMICAL DRUG | INHIBITED | -2.247 | 0.00001 55 | ACADVL,ADAMTS1,AKT1,ANXA2,ANXA4,ANXA5,BCL2,B CL2A1,CCND1,CLU,COL1A1,CPT2,CSF1,DGKA,DUSP6, EFEMP2,ERCC1,FCGR2A,FN1,HADHA,HEYL,HIF1A,HK1 ,IGFBP3,TQSEC2,LDHB,LGALS3,LMNA,ODC1,OMA1,PE X6,PLAT,PLK1,POU2F1,PSMB10,RBM3,RPM2,SESN2,S LC22A5,SLC6A6,STAT3,TARSL2,TGFB1,TGIF1,TIME1 ,TMSB4X (INCLUDES OTHERS),TNK2,TUBB,VIM |
| SOX4 | TRANSCRIP TION REGULATOR | INHIBITED | -2.457 | 0.00001 63 | ACOT1,APBB1,B3GNT5,BCL2,BLK,DDAH2,EMP1,FN1,I GF1,LHFP,NAV1,PPIC,S100A11,SDR39U1,SORT1,TDR KH,TMSB4X (INCLUDES OTHERS),TPM4,TUBA1A,TUBB2B,VIM |
| SEMA7A | TRANSMEMB RANE RECEPTOR | INHIBITED | -2.646 | 0.00001 82 | COL1A1,COL1A2,COL3A1,ELN,FN1,TGFB1,TIMP1 |
| FENAMIC ACID | CHEMICAL REAGENT | INHIBITED | -3.429 | 0.00002 02 | ADAMTS1,ANXA2,CLU,EFEMP2,FCGR2A,LGALS3,PSMB1 0,RBM3,TGIF1,TIMP1,TUBB,VIM |
| HDAC6 | TRANSCRIP TION REGULATOR | INHIBITED | -2.36 | 0.00002 6 | ADAMTS1,BCL2,COL1A1,GDF5,HIF1A,IGF1,LTBP2,TG FB1,VIM |
| PHENYLBU TAZONE | CHEMICAL DRUG | INHIBITED | -2.795 | 0.00002 66 | ADAMTS1,ANXA2,CCND1,CLU,EFEMP2,FCGR2A,LGALS3 ,RBM3,TIMP1,TUBB,VIM |

Fig. 21R

| | | | | | |
|---|---|---|---|---|---|
| VEGF | GROUP | INHIBITED | -3.312 | 0.000032 | ACE,ADAMTS1,AKR1C14,AQP4,BCL2,BCL2A1,BUB1,CD46,COL4A3,CTYB1,DUSP6,ELN,EMP1,ENPP2,ETV5,FLNA,FN1,HIF1A,IGFBP3,MAOB,MMP14,NAMPT,NEK2,NR4A2,NR4A3,PHLDA1,PLK1,PLEP3,PLVAP,EMP22,SCML4,SLC20A1,SLK,SOCS2,ST8SIA4,STAT3,TGFB1,TIMP1,VEGFA,VIM |
| ACETAMINOPHEN | CHEMICAL DRUG | INHIBITED | -2.086 | 0.0000375 | ACTG1,AMACR,BCL2,CCND1,CES1,GPX1,HIF1A,HSPD1,IGF1,IGFBP3,NDRG2,ODC1,PTPN1,SCP2,SERPINF1,TUBA1A,TUBB,VEGFA |
| MEF2D | TRANSCRIPTION REGULATOR | INHIBITED | -2.223 | 0.0000395 | CCND1,COL1A2,COL3A1,MYH7,NPPA,SLC2A4,TGFB1,TGFB2,TGFB3 |
| RUNX2 | TRANSCRIPTION REGULATOR | INHIBITED | -2.542 | 0.0000401 | AKT1,BCL2,CCND1,COL1A1,COL1A2,COL1A2,DPYSL3,FGF18,FN1,HIF1A,ITGBL1,LGALS3,MMP14,TIMP1,VEGFA |
| IL3 | CYTOKINE | INHIBITED | -2.595 | 0.0000403 | ABCA2,BCL2,CALR,CAMKK2,CCL11,CCND1,CD63,CLEC11A,CRAT,CSF1,CTTN,ECH1,EEF1A1,F2R,FCGR2A,GADD45G,GNAO1,GPX1,HK1,IL2RA,KIF1B,MYO1C,ODC1,RBM3,RPL3,TLR2,VASP,VEGFA,WNK1,YWHAG |
| RESIQUIMOD | CHEMICAL DRUG | INHIBITED | -2.096 | 0.0000451 | ACADS,ANXA4,ATP6V1B2,BCL2,BCL2A1,CCL11,CMTM8,GPX1,HEY1,IL2RA,LAP3,LMNA,MSN,NAMPT,NFKBIZ,PKM,PLAT,SOD2,TLR2 |
| IL2 | CYTOKINE | INHIBITED | -2.62 | 0.0000483 | ABCA1,ADAM8,ARHGDIA,BCL2,BCL2A1,CCL11,CCND1,CD46,CD47,CSF1,CTFS1,CXCR6,CYCS,DAP,DUSP6,DUSP7,EMP1,ENPP2,FGL2,GADD45G,HISTH1C,HSPD1,IL13BP,IL2RA,ING4,LIFR,MME,NAVI,PEA15,PHLDA1,PLK1,RHOC,RPS6KA5,SNAP23,SOCS2,STAT3,TFDP2,TGFB1,TIMP1,TLR2,UCK2,VEGFA,VIM |
| JNK | GROUP | INHIBITED | -2.124 | 0.0000536 | ABCA1,ANKA5,CCL11,CCND1,COL1A1,COL3A1,F2RL1,FN1,IGF1,HEY1,IL2RA,MMP14,MRC2,PLAT,PLSCR1,PON2,POSTN,SESN2,SOD2,TGFB1,TIMP1,VCAN |
| ISOPROTERENOL | CHEMICAL DRUG | INHIBITED | -3.526 | 0.0000573 | ACE,AQP4,BCL2,DIO2,HMOX2,MYH7,NAMPT,NPPA,ODC1,PLAT,PLN,RGS5,TGFB1,TIMP1,TUBB,TUBB3,VEGFA |
| RETNLB | OTHER | INHIBITED | -2.891 | 0.0000624 | AKT1,COL1A1,COL1A2,ELN,FN1,HEY1,IGF1,MSN,SOCS2,TGFB1,TIMP1,TLR2 |
| CSF3 | CYTOKINE | INHIBITED | -2.428 | 0.0000627 | ARHGDIA,BCL2,CAPG,CD34,CST3,DES,DUSP6,ENPP2,GADD45G,HSPD1,IGF1,ODC1,PLSCR1,SLC20A2,STAT3,TGFB1,TLR2,TNNI3,VEGFA |
| TGFBR2 | KINASE | INHIBITED | -2.207 | 0.0000764 | BGN,CCND1,CLU,COL1A1,COL1A2,FN1,GATM,HSD11B1,KCNN2,KRT18,MMP14,MYOF,SPARC,STAT3,TGFB1,TGFB2,TGFB3,TGIF1,TIMP1,VEGFA |
| BISPHENOL A | CHEMICAL | INHIBITED | -2.331 | 0.0000911 | ALAS1,ALDH5A1,BCL2,CLU,CTTN,ENO1,EREG,IGF1,NR4A3,NR4A3,PKM,SLC1A5,SLC2A4,STAT3,TGFB3 |

Fig. 21S

| | | | | |
|---|---|---|---|---|
| IGF2BP1 | ENDOGENOUS NON-MAMMALIAN TRANSLATION REGULATOR | INHIBITED | -2.449 | 0.000107 | COL1A1,COL1A2,COL3A1,COL6A2,LGALS1,SERPINH1 |
| CEBPB | TRANSCRIPTION REGULATOR | INHIBITED | -2.11 | 0.000106 | AKR1B10,BCL2,BCL2A1,CCND1,CIRBP,COL1A1,COL1A2,COL5A2,HSD11B1,HSPD1,IGF1,IGFBP3,IL18BP,INMT,KRT18,LAMC1,NDRG4,NFKBIZ,NRG1,NUPR1,ODC1,PEA15,PRKCD,PTGFR,SPRR1A,STAR,STAT3,TGFB1,TUBB3,UBR2,VCAN,VIM,VLDLR |
| PDGF (COMPLEX) | COMPLEX | INHIBITED | -2.151 | 0.000124 | AKT1,BCL2,CCND1,FN1,HEY1,HIF1A,NR4A2,ODC1,SPARC,TGFB1,TGFB3,TIMP1,VEGFA |
| GH1 | GROWTH FACTOR | INHIBITED | -2.312 | 0.000126 | ACSL1,AKR1B1,BCL2,CLU,COL3A1,COMT,DDT,DECR1,FN1,GTF2H1,HADH,HADHB,IGF1,IGFBP3,NDRG2,NPPA,PRDX3,RAD23A,SOCS2,TUBA1A,VIM |
| PDGFC | GROWTH FACTOR | INHIBITED | -2.425 | 0.000144 | CCND1,COL1A2,COL4A2,TGFB1,TIMP1,VEGFA |
| ALLOPURINOL | CHEMICAL DRUG | INHIBITED | -3.464 | 0.000148 | ADAMTS1,ANXA2,CLU,EFEMP2,FCGR2A,LGALS3,PSMB10,RBM3,TGIF1,TIMP1,TUBB,VIM |
| PROSTAGLANDIN E2 | CHEMICAL | INHIBITED | -2.626 | 0.000171 | ADAMTS1,AKR1C14,ANXA2,BCL2,CCND1,CD46,COL1A1,CSF1,EREG,F2R,F2RL1,FBXO31,FN1,HIF1A,IGF1,IGFBP7,IL2RA,LMNA,MMP14,NR4A2,SOCS2,SPHK1,STAR,TGFB1,TGFB3,VEGFA |
| IPMK | MAMMALIAN KINASE | INHIBITED | -2.449 | 0.000192 | FLNA,MYL6,PDLIM5,PFN1,PMP22,TAGLN2 |
| INOSINE | CHEMICAL | INHIBITED | -2.949 | 0.000194 | ANXA2,ANXA5,ARPC1B,CD63,RHOC,TIMP1,TSPO,TUBA1A,VIM |
| GLI1 | ENDOGENOUS MAMMALIAN TRANSCRIPTION REGULATOR | INHIBITED | -2.318 | 0.000206 | ACADVL,AKT1,BCL2,C11ORF96,CCND1,CLU,COL1A1,CSF1,DIO2,FUCA2,IGF1,IGFBP7,IL2RA,LMNA,NDRG2,TOM1,ULK1,VEGFA,VIM,WIF1 |
| EHHADH | ENZYME | INHIBITED | -2.236 | 0.000237 | ABCD3,ACSL1,CD36,FXYL1A,SCP2 |
| BSG | TRANSPORTER | INHIBITED | -2.566 | 0.000251 | CCND1,HIF1A,IL2RA,PLEK1,TGFB1,VEGFA,VIM |
| NEAT (FAMILY) | GROUP | INHIBITED | -2.309 | 0.000258 | B4GALT1,BCL2,CTSK,CX3CL1,EHD4,F2RL1,FGF18,SDC4,SOD2,TGFB2,TNNI3,TUBB3 |

| | | | | | |
|---|---|---|---|---|---|
| AKT | GROUP | INHIBITED | -2.757 | 0.000262 | ANKRD2,BCL2,BCL2A1,CCND1,CD36,COL3A1,FN1,GST K1,HIF1A,IGF1,LMNA,MCAM,MMP14,NPPA,PEA15,PRD M1.6,RRM2,SLC2A4,SOD2,TLR2,VCAN,VEGFA |
| RAC1 | ENZYME | INHIBITED | -2.127 | 0.000283 | AKT1,AFBB1,CCND1,COL1A2,FN1,HIF1A,MMP14,MYH7,NPPA,SOD2,STAT3,TGFB1,VEGFA |
| CARBON TETRACHL ORIDE | CHEMICAL TOXICANT | INHIBITED | -2.268 | 0.000286 | AOX1,ASS1,COL1A1,COL1A2,COL3A1,DES,FN1,GSTK1,HSPD1,IGF1,NDRG2,GDC1,RBP1,S100A6,SOD2,SORD,SEHK1,TGFB1,TGFB2,TIMP1 |
| S100A9 | OTHER | INHIBITED | -2.668 | 0.000296 | ADAMTS1,BACE2,CCL11,CCND1,ELN,ENPP2,ETV5,FCG R2A,IGF1,LOC102724788/PRODH,NR4A3,PHLDA1,POS TN,RAB20,RBFOX1,SEMA3B,VCAN |
| MKL1 | TRANSCRIP TION REGULATOR | INHIBITED | -2.144 | 0.000326 | ARPC1B,ARPC4,CNN2,COMT,COX7A1,CTTN,DHCR24,F2 R,FLNA,GSTM5,MYH9,NPPA,P2RY1,SLC20A1,TPM4 |
| SKIL | TRANSCRIP TION REGULATOR | INHIBITED | -2.63 | 0.000354 | CKS2,COL1A2,DCHS1,PLSCR1,RHOBTB1,SLC16A6,SLC 1A5,VAT1 |
| DIMETHYL NITROSAM INE | CHEMICAL TOXICANT | INHIBITED | -2.804 | 0.000415 | COL1A1,COL1A2,COL3A1,DES,SOD2,TGFB1,TIMP1,VI M |
| SMAD2/3-SMAD4 | COMPLEX | INHIBITED | -2.236 | 0.000456 | BCL2,COL1A1,COL1A2,IGFBP3,ITGB5 |
| HEXACHLO ROBENZEN E | CHEMICAL TOXICANT | INHIBITED | -2.985 | 0.000461 | ANKA2,CLU,EFEMP2,FCGR2A,LGALS3,PSMB10,TGIF1,TIMP1,VIM |
| ALDOSTER ONE | CHEMICAL - ENDOGENOU S MAMMALIAN | INHIBITED | -2.552 | 0.000583 | ACE,ADAMTS1,AQP4,COL1A1,COL1A2,COL3A1,ELN,FN 1,LOX,NDRG2,NPPA,PTPN1,TGFB1,WNK1 |
| S100A8 | OTHER | INHIBITED | -2.5 | 0.000641 | ADAMTS1,BCL2,CCL11,CCND1,ELN,ENPP2,ETV5,FCGR 2A,IGF1,LOC102724788/PRODH,NR4A3,PHLDA1,POST N,RAB20,RBFOX1,SEMA3B,VCAN |
| AGTR1 | G-PROTEIN COUPLED RECEPTOR | INHIBITED | -2.315 | 0.000643 | CCND1,COL3A1,FN1,GSTM5,NPPA,TGFB1,TGFB3 |
| GDF2 | GROWTH FACTOR | INHIBITED | -2.111 | 0.000726 | ANKH,COL1A1,ENPP2,HIF1A,IGF1,POSTN,SEMA3B,SE RPINF1,SLC6A6,SOCS2,TUBB3 |
| MAP2K1 | KINASE | INHIBITED | -2.937 | 0.000732 | BCL2,BCL2A1,CCND1,COL1A1,COL1A2,COL3A1,DUSP6,ENO1,ETV5,F2R,FLNA,HIF1A,LGALS3,MAOB,MMP14,STAR,VEGFA |

| | | | | |
|---|---|---|---|---|
| URSODEOX YCHOLIC ACID | CHEMICAL - ENDOGENOU S | INHIBITED | -2.121 | 0.00086 8 | COL1A1,COL1A2,DLC1,LGALS3,NFKB2,SPARC,TGFB1, TGFB2,TIMP1 |
| FOXM1 | MAMMALIAN TRANSCRIP TION REGULATOR | INHIBITED | -3.108 | 0.00089 5 | CCL11,CCND1,CENPA,CKS2,IGF1,LOX,NEK2,NES,PLK 1,STAT3,VCAN,VEGFA,VIM |
| CARBOPLA TIN | CHEMICAL DRUG | INHIBITED | -2.138 | 0.00099 | CLU,FCGR2A,LGALS3,RBM3,TGIF1,TIMP1,TUBB,VIM |
| NOREPINE PHRINE | CHEMICAL - ENDOGENOU S | INHIBITED | -3.037 | 0.00105 | ABCA1,ATP2A2,CITED4,DCLK3,DES,DTG2,DNM2,FN1, MAT2A,MCAM,MYH7,NPPA,NR4A3,SLC2A4,VEGFA,WHRN |
| BMP6 | MAMMALIAN GROWTH FACTOR | INHIBITED | -2.284 | 0.00107 | ADAMTS1,ETV5,MYH10,PMEPA1,PMP22,SLC20A1,SORD ,STAR,TEF,TIMP1,VEGFA |
| LOMUSTIN E | CHEMICAL DRUG | INHIBITED | -3 | 0.0011 | ANXA2,CLU,FCGR2A,LGALS3,RBM3,TGIF1,TIMP1,TUB B,VIM |
| RAF1 | KINASE | INHIBITED | -2.186 | 0.00113 | ANKRD2,BCL3,CCND1,DTG2,DUSP6,EMP1,HIF1A,IGFB P3,ITGB5,LIFR,MAOB,NPPA,PHLDA1,PLAT,RRM2,SEL ENBP1,TIMP1,TUBB2A,VEGFA |
| PI3K (COMPLEX ) | COMPLEX | INHIBITED | -2.95 | 0.00125 | ABCA1,AKT1,AQP7,BCL2,CCND1,COL1A1,FN1,GSTM5, HIF1A,HK1,IGF1,LTBP2,MCAM,MMP14,NFKB2,NPPA,N R4A2,NUPR1,PLA2G5,POSTN,SAMHD1,TUBB3,VEGFA |
| DECITABI NE | CHEMICAL DRUG | INHIBITED | -2.272 | 0.00139 | ANXA2,CCND1,CLU,COL1A1,COL1A2,COL3A1,COMT,CY P4B1,DLC1,EEF1A1,EPHB6,FN1,GADD45G,GPX1,IGFB P3,IGFBP7,KRT18,LGALS3,LOX,MAOB,MMP14,NEK2,P ABPC1,PCDH9,ROBO1,SERPINH1,SPARC,STAR,TBX20, TGFB2,VCAN,VIM,VTN,WIF1 |
| PIM1 | ENZYME | INHIBITED | -2.36 | 0.00164 | BCL2A1,BUB1,CCND1,CENPA,COL3A1,FN1,TGFB1,TIM P1 |
| MAP2K4 | KINASE | INHIBITED | -2.433 | 0.00185 | BCL2,CCND1,FLNA,MYH7,NPPA,STAT3,TGFB1,TUBB2A |
| TLR4 | TRANSMEMB RANE RECEPTOR | INHIBITED | -2.688 | 0.00213 | BCL2,CD163,CTSK,EREG,FGL2,GADD45G,IL18BP,IL2 RA,METTL1,MX1/MX2,NFKB2,NFKBIZ,NR4A2,NR4A3,N SMAF,PLAT,RILPL1,SH3BP5,SOD2,SFRP1,SFTLC2,TG FB1,TLR2,TOR1AIP2,TRIM21,TSPO |
| MEK | GROUP | INHIBITED | -3.141 | 0.00216 | CCND1,CLU,COL1A2,DUSP6,EREG,ETV5,HIF1A,MAFF, MMP14,OSBPL8,PHLDA1,PIPP3,RETSAT,SLC16A6,SLC 20A1,SPRY4,VIM |
| CHOLECAL CIFEROL | CHEMICAL - ENDOGENOU | INHIBITED | -2.03 | 0.00237 | BCL2,COL1A1,CSF1,CTSK,IGF1,IGFBP3,MYH6,NDUFA F4,SLC20A1,TGFB1 |

*Fig. 21V*

| | | | | |
|---|---|---|---|---|
| TESTOSTE RONE | MAMMALIAN CHEMICAL - ENDOGENOUS MAMMALIAN | INHIBITED | -2.063 | 0.00239 | ACSL1,ALDOA,ATP5F1,BCL2,CCND1,CLU,DHCR24,FN1,GPC1,HIF1A,HSPD1,IGF1,MX1/MX2,NFKB2,ODC1,PMP22,RAI14,SOD2,STAR,STAT3,TGFB2,TUBB2A,TUBB3,UBE2B,VCAN |
| TWIST2 | TRANSCRIPTION REGULATOR | INHIBITED | -2.207 | 0.00247 | FBLN5,FN1,POSTN,TGFB1,VIM |
| HSD17B4 | ENZYME | INHIBITED | -2.236 | 0.00247 | ABCD3,ACSL1,CD36,PEX11A,SCP2 |
| KDM5A | TRANSCRIPTION REGULATOR | INHIBITED | -3.053 | 0.00253 | ATP5K,CCND1,COL1A2,GPT2,MLYCD,MYH6,MYH7,NDUFA3,NDUFB8,NDUFS2,NDUFS4,NDUFS7,SOD2 |
| EDNRA | TRANSMEMBRANE RECEPTOR | INHIBITED | -2 | 0.00261 | COL1A1,COL3A1,TGFB1,TIMP1 |
| C5 | CYTOKINE | INHIBITED | -2.549 | 0.00296 | AKT1,BCL2,CCL11,CCND1,CD46,CD63,CSF1,ERN1,FCGR2A,PLAT,TGFB1,VEGFA |
| LCN2 | TRANSPORTER | INHIBITED | -2.135 | 0.0032 | ACTN1,CAPG,COL1A1,HIF1A,MSN,TAGLN2,TGFB1,VIM |
| REN | PEPTIDASE | INHIBITED | -2.213 | 0.00425 | ACE,COL3A1,MYH6,MYH7,NPPA |
| PKC(S) | GROUP | INHIBITED | -2.062 | 0.00518 | ABCA1,AQP4,BCL2,CD36,COL3A1,ERN1,FN1,HIF1A,MAOB,NR4A2,NR4A3,P4HB,PHLDA1,PTRN,STAR,TGFB1,VEGFA |
| TGFA | GROWTH FACTOR | INHIBITED | -2.157 | 0.00563 | AKT1,CCND1,EREG,NR4A2,PLA2G5,PLAT,TGFB1,VEGFA,VIM |
| GROWTH HORMONE | GROUP | INHIBITED | -2.12 | 0.00575 | BCL2,CCND1,CD36,COL1A1,CX3CL1,FN1,GSTM5,IGF1,IGFBP3,NAMPT,SOCS2,TGFB3 |
| ISOPRENALINE | CHEMICAL DRUG | INHIBITED | -2 | 0.0065 | NPPA,NR4A2,NR4A3,SLC2A4 |
| YAP1 | TRANSCRIPTION REGULATOR | INHIBITED | -2.607 | 0.00746 | AKT1,CCND1,FN1,MYH7,MEK2,NPPA,PLK1,VIM |
| LYSOPHOSPHATIDIC ACID | CHEMICAL - OTHER | INHIBITED | -2.032 | 0.00893 | CACNA2D1,CCL11,CCND1,CD36,CSF1,HIF1A,SPHK1,VEGFA,VIM |
| CA2+ | CHEMICAL - ENDOGENOUS MAMMALIAN | INHIBITED | -2.216 | 0.00931 | ANKH,ATP2A2,BCL2,CALR,CCND1,COL1A1,CTTN,DES,FN1,KCNE2,MCAM,MYH7,NES,NPPA,NR4A3,ODC1,STAR,TGFB1,VEGFA |

Fig. 21W

| | | | | |
|---|---|---|---|---|
| E. COLI B4 LIPOPOLY SACCHARI DE | CHEMICAL TOXICANT | INHIBITED | -2.286 | 0.00994 | ANXA11,B3GNT5,BCL2,CCL11,CENPA,FGL2,GADD45G, LRRFIP1,METTL1,MX1/MX2,PANK1,PDLIM5,RAB20,RH OC,SERPINH1,SLAMF9,SLFN2,SOD2,TLR2,TSPO |
| TCR | COMPLEX | INHIBITED | -2.617 | 0.0105 | ABCD3,BCL2,BCL2A1,ETV5,FLNA,GADD45G,HIF1A,HS PD1,IL2RA,KIAA0430,LSM3,NFKB2,ODC1,P4HB,PREL ID1,SOCS2,SPHK1,STAT3,SYMCRIP,TGFB1,ZNFX1 |
| PTHLH | OTHER | INHIBITED | -2.592 | 0.0106 | ADAMTS1,BCL2,CCND1,CTSK,FN1,IGF1,VEGFA |
| BCL2L1 | OTHER | INHIBITED | -2.611 | 0.0106 | ATP8A2,BCL2,COL6A2,CYCS,FN1,TIMP1,TUBB3 |
| SHH | PEPTIDASE | INHIBITED | -2.079 | 0.0109 | ADAMTS1,BCL2,CCND1,CTPS1,FN1,GPC1,HEY1,IGF1, IL2RA,PLAT,PMP22,TGFB2,TGFB3,TUBB3 |
| MONOCROT ALINE | CHEMICAL TOXICANT | INHIBITED | -2.213 | 0.0116 | ATP2A2,MYH7,NPPA,PLN,TUBB3 |
| ISOBUTYL METHYLXA NTHINE | CHEMICAL TOXICANT | INHIBITED | -2.236 | 0.0121 | ACE,AKT1,CCND1,CD36,NPPA,PLAT,PTGFRN,PTPRN,S OD2,TGFB1,TIMP1,TUBB |
| SMAD4 | TRANSCRIP TION REGULATOR | INHIBITED | -2.465 | 0.0145 | BGN,CCND1,COL1A2,CSF1,EREG,FN1,ITGB5,LOC1027 24788/PRODH,NAMPT,SH3BA5,TGFB1,TGFB2,TIMP1,T PM3,VEGFA,VIM |
| CREBBP | TRANSCRIP TION REGULATOR | INHIBITED | -2.813 | 0.0149 | ALAS1,BCL2,CAPG,CCND1,CKB,COL1A2,CSF1,ERCC1, HSD11B1,IL2RA,KIF1B,MFHAS1,MYH7,NPPA,NR4A2,N R4A3,NTN1,PRKCD,PTPRF,RMND5A,SDC4,STAR,TLR2, TMEM38A,VEGFA |
| Il11 | CYTOKINE | INHIBITED | -2.395 | 0.0155 | ANXA2,BCL2,BCL2A1,IGF1,SPHK1,TIMP1 |
| SRF | TRANSCRIP TION REGULATOR | INHIBITED | -2.641 | 0.0168 | ACTG1,ARHGAP20,BCL2,CAP1,CNN2,CSRP2,DES,DSTN ,FLNA,GADD45G,GSTM5,IGF1,KRIT1,MYH6,MYH7,MYH 9,MYL2,NPPA,NR4A2,PDLIM7,TMEM44,TPM4 |
| TET2 | OTHER | INHIBITED | -3.162 | 0.0191 | ADAM9,ANXA2,FAM129A,FAM129B,HS6ST1,LHFP,MAFF ,NAV1,SLC20A1,TIMP1 |
| PI3K (FAMILY) | GROUP | INHIBITED | -2.209 | 0.0197 | ABCA1,AKR1B10,EGLN1,FOXO4,HIF1A,HK1,PKM,VEGF A |
| ATF4 | TRANSCRIP TION REGULATOR | INHIBITED | -2.547 | 0.0234 | CALR,IGFBP7,LGALS3,NUPR1,PMP22,SERPINF1,SLC1 A5,SLC38A3,SLC7A5,STAT3,VEGFA |
| RETN | OTHER | INHIBITED | -2 | 0.0272 | CX3CL1,MMP14,PLAT,SLC2A4,STAT3 |
| PHENACET IN | CHEMICAL DRUG | INHIBITED | -2.236 | 0.0272 | ANXA2,CLU,LGALS3,TIMP1,VIM |
| 5-N-ETHYLCAR BOXAMIDO ADENOSIN E | CHEMICAL REAGENT | INHIBITED | -2.909 | 0.0276 | CES1,COL1A2,HIF1A,NR4A2,NR4A3,ODC1,TGFB1,VCA N,VEGFA |

*Fig. 21X*

| | | | | | |
|---|---|---|---|---|---|
| ADRB | GROUP | INHIBITED | -2.045 | 0.0282 | ANXA5,BOK,CCND1,DIO2,HSPD1,IDH1,NEK2,NPPA,NR4A2,NR4A3,SLC40A1 |
| FGF8 | GROWTH FACTOR | INHIBITED | -2.183 | 0.0285 | CCL11,CCND1,CITED4,CYCS,DDAH2,ETV5,SPARC,TUBB3 |
| DALFAMPRIDINE | CHEMICAL DRUG | INHIBITED | -2 | 0.0398 | DUSP6,GADD45G,MAFF,NR4A2 |
| CARDIOTOXIN | CHEMICAL - OTHER | INHIBITED | -2.449 | 0.0451 | BGN,CCND1,COL1A2,COL6A2,IGF1,IGFBP7,ITGB5,LRRFIP1,MYH9,STAT3,TIMP1 |
| RORC | LIGAND-DEPENDENT NUCLEAR RECEPTOR | INHIBITED | -2 | 0.0469 | AOX3,CD36,DHCR24,FDFT1,HIF1A,IL2RA,LRTM1,SELENBP1,SPARC,VEGFA,VLDLR |
| LIPOTEICHOIC ACID | CHEMICAL - ENDOGENOUS NON-MAMMALIAN | INHIBITED | -2.189 | 0.0518 | BCL2,HIF1A,NR4A2,NR4A3,TIRAP,TLR2 |
| GDNF | GROWTH FACTOR | INHIBITED | -2.2 | 0.0518 | CCND1,EIF4A2,FN1,LGALS1,SPHK1,VASP |
| EIF4E | TRANSLATION REGULATOR | INHIBITED | -2.368 | 0.0537 | BCL2,CAPG,CCND1,CKS2,EREG,FASTK,HIF1A,HMOX2,ODC1,SPHK1 |
| CYP1B1 | ENZYME | INHIBITED | -2.236 | 0.0726 | ACOT11,CCND1,MCAM,SOCS2,VLDLR |
| RICTOR | OTHER | INHIBITED | -3.011 | 0.0728 | ATP5F1,ATP5H,ATP6V1B2,COX7A1,HIF1A,MX1/MX2,NDUFA3,NDUFAB1,NDUFB8,NDUFS1,NDUFS2,NDUFS4,NDUFS7,NDUFV2,PSMB10,SLFN2 |
| GNRH-A | CHEMICAL REAGENT | INHIBITED | -2.433 | 0.0729 | ACE,AKR1B10,ANXA5,HADH,NFKBIZ,TMBIM1 |
| BICUCULLINE | CHEMICAL - ENDOGENOUS NON-MAMMALIAN | INHIBITED | -2 | 0.0731 | DUSP6,GADD45G,MAFF,NR4A2 |
| ETHIONINE | CHEMICAL TOXICANT | INHIBITED | -2 | 0.0731 | CLU,LGALS3,PSMB10,TIMP1 |
| CD40 | TRANSMEMBRANE RECEPTOR | INHIBITED | -2.674 | 0.0865 | BCL2,BCL2A1,CCND1,CSF1,CX3CL1,DUSP6,IL2RA,LGALS3,MMP14,NFKB2,PSMB10,TLR2,VEGFA |
| MBD2 | TRANSCRIPTION REGULATOR | INHIBITED | -2.213 | 0.0919 | AMY2A,CKS2,NUPR1,ORC6,PLK1 |
| MAPK9 | KINASE | INHIBITED | -2.009 | 0.0958 | ACLY,BCL2,DIO2,FGL2,HIF1A,LMNA,LSM3,PLAT,RILPL1,SOD2 |

*Fig. 21Y*

| | | | | |
|---|---|---|---|---|
| MYD88 | OTHER | INHIBITED | -2.448 | 0.0972 | ACSL1,AK3,CTSK,HIF1A,IGF1,MAFF,MMP14,NES,NFKB2,NFKBIZ,SAMHD1,SH3BP5,TGFB1,TIMP1,TLR2 |
| MAPK | GROUP | INHIBITED | -2.2 | 0.109 | BCL2,CCND1,COL1A1,IGF1,NR4A3,TUBB3,VEGFA |
| CYP1A2 | ENZYME | INHIBITED | -2 | 0.117 | ACOT1,CCND1,SOCS2,VLDLR |
| FGF7 | GROWTH FACTOR | INHIBITED | -2.213 | 0.15 | CCND1,CSF1,ETV5,NRG1,VEGFA |
| ETS1 | TRANSCRIPTION REGULATOR | INHIBITED | -2 | 0.162 | ARL4C,ARPC2,CCND1,COL1A2,FCGR2A,FN1,IL2RA,MCLN,PEG10,RHOBTB3,TGFB2,VEGFA |
| ITK | KINASE | INHIBITED | -2.219 | 0.234 | DENND4A,EHD4,F2R,HIF1A,TIRAP |
| NR5A2 | LIGAND-DEPENDENT NUCLEAR RECEPTOR | INHIBITED | -2.177 | 0.265 | BCL2,CCND1,GADD45G,GATM,STAR |
| ATP | CHEMICAL - ENDOGENOUS MAMMALIAN | INHIBITED | -2 | 0.386 | CCND1,FLNA,IL2RA,SPHK1,TUBB3 |

Fig. 21Z

JUNCTOPHILIN-2 FRAGMENTS AND USES THEREFOR

CROSS-REFERENCE TO RELATED APPLICATIONS

This application is a U.S. National Stage Filing under 35 U.S.C. 371 from International Application No. PCT/US2017/036392, filed on Jun. 7, 2017, and published as WO 2017/2142% on Dec. 14, 2017, which application claims the benefit of the filing date of U.S. application Ser. No. 62/346,794, filed on Jun. 7, 2016, the disclosures of which are incorporated by reference herein.

GOVERNMENT SUPPORT

The invention was made with government support under contract HL-090905 awarded by the National Heart, Lung and Blood Institute. The Government has certain rights in the invention.

BACKGROUND

Myocardial infarction, one of the most common causes of heart failure, is characterized by defects in cardiac excitation-contraction (E-C)$^2$ coupling (Gomez et al., 2001; Litwin et al., 2000). In a normal cardiomyocyte, E-C coupling depends on $Ca^{2+}$-induced $Ca^{2+}$ release, in which L-type $Ca^{2+}$ channel-mediated $Ca^{2+}$ influx triggers $Ca^{2+}$ release from the sarcoplasmic reticulum (SR) via type 2 ryanodine receptors (RyR2) (Bers, 2002; Wang et al., 2001). L-type $Ca^{2+}$ channels and RyR2s are physically and functionally organized into a tightly regulated structure known as the $Ca^{2+}$ release unit, which provides the structural basis for $Ca^{2+}$-induced $Ca^{2+}$ release (Wang et al., 2001; Franzini-Armstrong et al., 1999). The integrity of the $Ca^{2+}$ release unit is maintained by the structural protein junctophilin-2 (JP2) that bridges the T-tubule membrane and the SR (Takeshima et al., 2000; van Oort at al., 2011; Jayasinghe et al., 2012). Disruption of the fine architecture of the E-C coupling machinery impairs $Ca^{2+}$-induced $Ca^{2+}$ release, thereby leading to loss of contractility and heart failure (Song et al., 2006).

JP2, the major junctophilin isoform expressed in the heart, contains eight N-terminal membrane occupation and recognition nexus (MORN) domains that mediate interactions with the plasmalemma, a space-spanning α helix, and a C-terminal transmembrane (TM) domain that anchors JP2 to the SR membrane (Takeshima et al., 2000). Consistent with a role for JP2 in E-C coupling, conditional silencing of JP2 in cardiomyocytes results in contractile dysfunction, abnormal $Ca^{2+}$ handling, and acute heart failure (van Oort et al., 2011; Landstrom et al., 2011; Chen et al., 2013). On the contrary, cardiac-specific overexpression of JP2 attenuated the development of heart failure induced by pressure overload (Guo et al., 2014). Moreover, mutations in the JP2 coding region have been discovered in patients with hypertrophic cardiomyopathy (Landstrom et al., 2007; Takeshima at al., 2015). The pathological relevance of JP2 has been revealed by observations that dysregulation of JP2 protein is associated with pathological progression in multiple models of heart failure, including pressure overload-induced hypertrophy/heart failure and myocardial infarction (Chen et al., 2012; Guo at al., 2013; Minamisawa at al., 2004; Wei at al., 2010; Xu et al., 2012; Xu et al., 2007; Wu et al., 2014). Toward understanding the mechanism of JP2 down-regulation, a recent report has demonstrated that JP2 is targeted by the microRNA miR-24, which may be responsible for the down-regulation of JP2 during long-term pressure overload-induced hypertrophy and heart failure (Xu et al., 2007; Song et al., 2012). Recently, a $Ca^{2+}$-dependent mechanism of junctophilin proteolysis has been reported (Murphy et al., 2013). More specifically, the activity of calpain, a family of $Ca^{2+}$-dependent proteases has been found to be related to the degradation of JP2 (Wu at al., 2014). However, it remains unclear whether JP2 is a direct substrate of calpain and the specific molecular site for JP2 proteolysis.

SUMMARY

JP2 protein is a membrane structural protein that regulates $Ca^{2+}$ handling in cardiomyocytes. As described below. JP2 expression was demonstrated to be down-regulated in failing hearts from patients with ischemic heart disease and is regulated by proteolytic processing by the $Ca^{2+}$-sensitive enzyme calpain. Using a murine model of ischemia/reperfusion (I/R) injury, the $Ca^{2+}$-dependent protease calpain was identified as a mediator of JP2 down-regulation, and the molecular sites for calpain cleavage were determined. JP2 fragments corresponding to the primary cleavage site failed to rescue E-C coupling in JP2-deficient cardiomyocytes, which provides insights into the mechanism by which JP2 expression is lost in failing hearts. However, it was unknown if the cleavage products had any function independent of the structural role of intact JP2. A JP2 truncation (JP2NT, having residues 1-565) was found to be imported into the nucleus via a Nuclear Localization Signal (NLS). Other JP2 truncations, shorter or longer than JP2NT including those from different species, with a DNA binding domain and NLS (heterologous or native NLS) likely function similarly to JP2NT. Moreover, JP2NT changed gene transcription and functions as a cardiac protector against hypertrophy and heart failure, which are very common cardiac diseases. Thus, diseases such as cardiac hypertrophy, heart failure, as well as myocardium infarction, may be prevented, inhibited or treated by administering JP2 protein having C-terminal truncations, e.g., administering isolated protein or nucleic acid encoding that protein, such as a plasmid or viral vector, e.g., an AAV vector including but not limited to any of serotypes AAV1-9, or AAV rh10, that eliminate the membrane anchor, for example, a membrane anchor having the sequence MVILLNIGLAIL (SEQ ID NO:51) or deletion of a portion of that sequence. Since JP2 is also expressed in skeletal muscle, isolated JP2 truncated protein or nucleic acid encoding the truncated protein may also have applicability to prevent, inhibit or treat skeletal muscle diseases and abnormalities, such as muscle fatigue, muscular dystrophy, and the like.

As also described herein, JP2NT binds to genomic DNA through an evolutionarily conserved DNA binding domain located in the α-helix region of JP2 and controls expression of a wide spectrum of genes important for cell growth, differentiation, hypertrophy, inflammation and fibrosis. Transgenic overexpression of JP2NT modifies the transcriptional profile in response to cardiac stress and attenuates hypertrophic remodeling and heart failure progression. These data reveal a self protective mechanism that cardiomyocytes possess to counter the deleterious pathological transcriptional remodeling following cardiac stress. These findings identify a connection between ultrastructural remodeling and transcriptional reprogramming in the heart, and potentially in other muscles as well.

In one embodiment, an isolated truncated JP2 protein having a DNA binding domain and a nuclear localization signal (NLS), which protein has at least 80%, 85%, 87%, 90%, 92%, 93%, 94%, 95%, 98%, 99% or more amino acid identity to SEQ ID NO:1, SEQ ID NO:2 or SEQ ID NO:3, which protein in one embodiment lacks a membrane anchor sequence, and in one embodiment has the activity of residues 1-585 of SEQ ID NO:1, SEQ ID NO:2 or SEQ ID NO:3, is provided. In one embodiment, the truncation is a C-terminal truncation of one or more amino acids found at the C-terminus. In one embodiment, the C-terminal truncation is at least 25, 50, 100, 125, 130, 150, 175, 200, 225, or more (or any integer between 1 and 300) amino acids of the C-terminal sequence. In one embodiment, the C-terminus of the truncated protein is not at a calpain cleavage site. In one embodiment, the protein further comprises a heterologous peptide, e.g., one useful for isolation or detection of the protein. In one embodiment, the heterologous peptide is fused to the N-terminus. In one embodiment, the heterologous peptide is fused to the C-terminus. Exemplary heterologous peptides include but are not limited to HisV5 (HHHHH) (SEQ ID NO:5), HisX6 (HHHHHH) (SEQ ID NO:6), C-myc (EQKLISEEDL) (SEQ ID NO:7). Flag (DYKDDDDK) (SEQ ID NO:8), SteptTag (WSHPQFEK) (SEQ ID NO:9), hemagluttinin, e.g., HA Tag (YPYDVPDYA) (SEQ ID NO:10), GST, thioredoxin, cellulose binding domain, RYIRS (SEQ ID NO:11), Phe-His-His-Thr (SEQ ID NO:12), chitin binding domain, S-peptide, T7 peptide, SH2 domain. C-end RNA tag. WEAAAREAC-CRECCARA (SEQ ID NO:13), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin $D_{9K}$, calbindin $D_{28K}$, and calretinin, inteins, biotin, streptavidin, MyoD, Id, leucine zipper sequences, and maltose binding protein in one embodiment, the heterologous peptide comprises a NLS. In one embodiment, the NLS has the sequence KRPRP (SEQ ID NO:14). In one embodiment, the NLS has RRVLPLKSSKVRQK (SEQ ID NO:15), or a sequence that has at least 90% amino acid identity thereto. In one embodiment, the DNA binding domain has KRRVLPLKSSKVRQKVEHGVEGAQR-AAAIARQKAEIAASRTSHAKAKAEAAEQAALAA (SEQ ID NO:16). KRRMLQLKSNKVRQKVEHSVEG-AQRAAAIARQKAEIAASRTSHAKAKAEAAEQAA-LAA (SEQ ID NO:17), or a sequence with at least 80%, 85%, 87%, 90%, 92%, 95%, or 97% identity thereto. The DNA binding domain may be employed alone as a transcriptional repressor, e.g., expressed from a nucleic acid vector, or linked to a different protein (a non-junctophilin-2 protein), thereby forming a fusion polypeptide, e.g., expressed from a nucleic acid vector.

In one embodiment, a pharmaceutical composition is provided that includes isolated truncated JP2 protein having a DNA binding domain and a NLS, which protein has at least 80%, 85%, 87%, 90%, 92%, 93%, 94%, 95%, 98%, 99% or more amino acid identity to SEQ ID NO:1, SEQ ID NO:2 or SEQ ID NO:3, which protein in one embodiment lacks a membrane anchor sequence and in one embodiment has the activity of residues 1-585 of SEQ ID NO:1, SEQ ID NO:2 or SEQ ID NO:3. In one embodiment, a pharmaceutical composition is provided that includes a nucleic acid vector encoding a truncated JP2 protein having a DNA binding domain and a NLS, which protein has at least 80%, 85%, 87%, 90%, 92%, 93%, 94%, 95%, 98%, 99% or more amino acid identity to SEQ ID NO:1, SEQ ID NO:2 or SEQ ID NO:3, which protein in one embodiment lacks a membrane anchor sequence and in one embodiment has the activity of residues 1-565 of SEQ ID NO:1, SEQ ID NO:2 or SEQ ID NO:3. In one embodiment, the vector is a plasmid, e.g., encapsulated in a liposome, or a microparticle or nanoparticle formed of naturally occurring polymers or synthetic polymers, or a combination thereof.

Further provided is a transgenic non-human mammal the genome of which is augmented with a recombinant DNA comprising an open reading frame encoding a truncated JP2 protein. In one embodiment, the genome is augmented with two different recombinant DNAs, e.g., one recombinant DNA encodes the truncated protein the expression of which is controlled by a DNA binding protein and the other recombinant DNA encodes the DNA binding protein and an activation domain, the expression of which is in one embodiment is inducible or is tissue-specific. Exemplary activation domains include but are not limited to those from VP16, TA2, VP64 (a tetrameric repeat of the minimal activation domain of VP16), signal transducer and activator of transcription 6 (STAT6), reticuloendothellosis virus A oncogene (relA), TATA binding protein associated factor-1 (TAF-1), TATA binding protein associated factor-2 (TAF-2), glucocorticoid receptor TAU-1, or glucocorticoid. Exemplary DNA binding proteins include, but are not limited to transcription factors, Gal4, hypoxia inducible factor (HIF), e.g., HIF1α, cyclic AMP response element binding (CREB) protein, LexA, rtTA, endonucleases, zinc finger binding domains, transcription activator like effectors (TALE) domains), synthetic DNA binding domains, e.g., LTPEQWAIASNIGGKQALEVTVQRLLPVLLQAHG (SEQ ID NO:52), or receptor TAU-2.

In one embodiment, a method to prevent, inhibit or treat a cardiac disease or condition, e.g., cardiac hypertrophy, cardiac fibrosis, cardiac inflammation, heart failure, or myocardial infarction, in a mammal is provided. The method includes administering to a mammal in need thereof, e.g., a mammal at risk of a cardiac condition or a mammal having a cardiac condition, an effective amount of a composition comprising the truncated protein or a nucleic acid vector, or a particle having the protein or nucleic acid vector. In one embodiment, the composition is locally administered. In one embodiment, the composition is systemically administered. In one embodiment, the administration reverses cardiac hypertrophy in a mammal. In one embodiment, the administration inhibits progression of heart failure.

Also provided is a method to prevent, inhibit or treat a skeletal disease or disorder, e.g., one associated with JP2 dysfunction or reduced expression, in a mammal. In one embodiment, the skeletal disease is muscular dystrophy. In one embodiment, the disorder is muscle weakness or fatigue. The method includes administering to a mammal in need thereof. e.g., a mammal at risk of the skeletal disease or disorder or having the disease or disorder, an effective amount of a composition comprising the truncated protein or a nucleic acid vector, or a particle having the protein or nucleic acid vector. In one embodiment, the composition is locally administered. In one embodiment, the composition is systemically administered.

BRIEF DESCRIPTION OF FIGURES

FIGS. 3A-D. Calpain cleaves JP2 at multiple sites in the N- and C-terminal regions. A) Schematic of the N- and C-terminal epitope-tagged full-length JP2 cDNA. B) After cotransfection of 293T cells with calpain I and full-length JP2 containing an N-terminal FLAG tag and a C-terminal HA tag, cells were exposed to 5 µM ionomycin and 4 mM extracellular $Ca^{2+}$ for 1 hour in the absence or presence of 10 µM MDL-28170. JP2 expression and degradation were assessed by Western blotting with anti-FLAG (a) or anti-HA (b) to detect N and C-terminal cleavage fragments, respectively. N-I, II, III, and IV denote the four N-terminal cleavage products detected with anti-FLAG. C-I denotes the major C-terminal cleavage product detected by anti-HA. C) In vitro calpain-I mediated cleavage assay as in FIG. 2 using lysates from 293T cells overexpressing JP2 with N-terminal FLAG and C-terminal HA epitopes. Cleavage products were detected with anti-FLAG (a) or anti-HA (b). D) In vitro calpain proteolysis of tagged JP2 at lower concentrations of $Ca^{2+}$ (500 µM). Data are representative of at least three independent experiments.

FIGS. 8A-D. Exemplary human JP2 sequences (SEQ ID NO:1 and 2), mouse JP2 sequence (SEQ ID NO:3), and rabbit JP2 sequence (SEQ ID NO:4).

FIGS. 10A-D. JP2NT contains a NLS and a chromatin/DNA-binding domain. A-B) A conserved NLS in JP2 N-terminus is essential for nuclear accumulation of JP2NT. a-c, Subcellular localization of eGFP and eGFP-fused JP2 and eGFP-JP2NT in 293T cells. Full length JP2 localizes on both plasma membrane and ER network (b). JP2NT is highly enriched in nuclei (c). d, Deletion of NLS from JP2NT (JP2NT$^{\Delta NLS}$) abolished its nuclear localization and restricted its localization on plasma membrane. e-f, A domain containing a bNLS and an ARR is essential for co-localization of JP2NT with DNA (stained with To-Pro-3). eGFP-fused JP2NT mutants without the bNLS (JP2NT$^{\Delta bNLS}$, e) or without the alanine-rich domain (JP2NT$^{\Delta ARR}$, f) lost co-localization with DNA. C-D) JP2NT associates with chromatin. a, Schematic of the subcellular fractionation approach (adapted from Wisoka et al 2001). b, Subnuclear distribution of JP2NT and fragments/mutants. JP2NT is present in both soluble nuclear (S3) and chromatin fractions (S4). Deletion of the MORN domains (JP2NT JP2NT$^{\Delta MORNs}$) had no effect on subnuclear distribution of JP2NT. However, the amount of chromatin-associated JP2NT was decreased by deletion of the bNLS alone (JP2NT$^{\Delta MORNs/\Delta bNLS}$), deletion of the ARR alone (JP2 JP2NT$^{\Delta MORNs/\Delta ARR}$), or deletion of both the bNLS and ARR (JP2$^{\Delta MORNs/\Delta bNLS/\Delta ARR}$ and JP2NT$^{\Delta bNLS/\Delta ARR}$). Histone H3: chromatin marker.

FIGS. 11A-H. JP2NT is a TATA-box binding protein enriched at transcription start site (TSS) and interacts with basic transcription machinery. A) Genomic DNA binding profile of JP2NT in cardiomyocytes as revealed by ChIP-seq. B) JP2NT is preferentially localized around TSS as revealed by ChIP-seq. C) 293T cells were transfected with HA-tagged JP2NT, followed by crosslinking-reversal immunoprecipitation with anti-HA and immunoblotting with anti-polymerase II (Rpb1) or anti-TATA box binding protein (TBP). D-H) JP2NT binds to TATA box DNA sequences in vitro. D-E) Gel shift assays of GST-purified JP2NT binding to WT (D). or mutated TATA box-containing sequences (E) derived from the cMyc promoter. F) Summary of the results of gel shift assays with various of TATA box variants or mutants. Mutation of the core TATA sequences abolished the interaction with GST-JP2NT. G) Deletion of the ARR, but not the N-terminal MORN domains, eliminated JP2NT binding to the TATA box sequence. H) The peptide JP2$^{331-405}$ containing the ARR specifically binds to WT TATA box sequence.

FIGS. 12A-E. JP2NT represses MEF2-mediated transcription by competing for the MEF2 Response Element (MRE). A) Enrichment of MEF2 binding motifs in ChIP-seq dataset. B) Gel shift assay of JP2NT binding to a desmin promoter-derived DNA sequence containing a WT or mutated MRE in vitro. C) Co-immunoprecipitation of HA-tagged JP2NT binding to MEF2C or Histone H3. D) & E) MEF2 activity assays in 293T cells co-transfected with luciferase under the control of an MRE, MEF2C and WT JP2NT (D) or a mutant lacking the ARR (E, JP2NT$^{\Delta ARR}$). n≥3 independent batches of cells; in each batch of experiments, 3 replicates were performed for each transfection; **p<0.01 vs. Ad-Empty.

FIGS. 17A-D. Cardiac specific expression of JP2NT in bi-transgenic mice. A) GO enrichment of JP2NT binding genes. B) Gel shift assay of GST-purified JP2NT fragment binding to a Myc promoter derived DNA sequence with mutations of TATA box core sequence. C) Gel shift assay of GST-purified JP2NT truncations and mutations binding to a CMV promoter derived DNA sequence with a TATA box (TATATA). Mutation of the core TATA sequence (TAGAGA) abolished the interaction. D) Gel shift assay of a purified peptide containing the DNA binding domain of JP2NT binding to consensus TATA box sequences. Mutation of the core sequence abolished the interaction.

FIG. 21A-Z. Transcripts influenced by JP2NT overexpression that are predicted to inhibit ERK, TGF-beta, CREB and NFkappa-B signaling pathways.

DETAILED DESCRIPTION

Figure 1A:
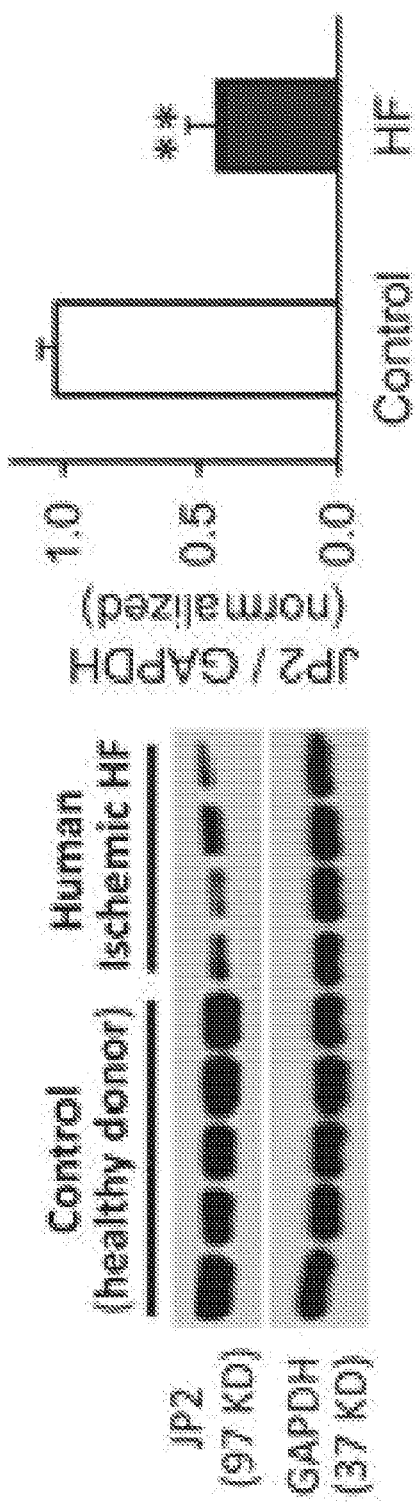
FIGS. 1A-E. JP2 is down-regulated by calpain in response to in vitro and in vivo I/R injury. A) Western blot of JP2 expression in left ventricular lysates from patients with ischemic heart failure (HF) (n=4) or rejected donor hearts (Control) (n=5). B) Representative Western blot and summary data of JP2 expression in WT murine left ventricles after in vitro I/R injury under Langendorff perfusion (at least four hearts for each group). MDL-28170 (10 µM) perfusion after the onset of reperfusion and 10 minutes before ischemia attenuated JP2 down-regulation. C) Representative Western blot and summary data of JP2 expression in left ventricles from calpastatin (CAST) transgenic mice after in vitro I/R injury under Langendorff perfusion (at least three hearts for each group). D) and E) JP2 protein level in left ventricles from WT mice (D) and calpastatin transgenic mice (E) after in vivo coronary artery occlusion-induced I/R injury (at least three hearts for each group). Data are normalized to GAPDH and expressed relative to the values of control or sham-operated hearts for each genotype. *, $p<0.05$; *, $p<0.01$; N.S., not significant.

Junctophilin-2 (JP2) is a 696 amino acid membrane protein expressed in the heart. Since its discovery in 2000, it has been recognized as a structural protein. JP2 provides a structural bridge between the plasmalemma and sarcoplasmic reticulum, is essential for precise $Ca^{2+}$-induced $Ca^{2+}$ release during excitation-contraction coupling in cardiomyocytes. In animal and human falling hearts, expression of JP2 is decreased markedly, but the molecular mechanisms underlying JP2 down-regulation remain incompletely defined. In mouse hearts, ischemia/reperfusion injury resulted in acute JP2 downregulation, which was attenuated by pretreatment with the calpain inhibitor MDL-28170 or by transgenic overexpression of calpastatin, an endogenous calpain inhibitor. Using a combination of computational analysis to predict calpain cleavage sites and in vitro calpain proteolysis reactions, four putative calpain cleavage sites were identified within JP2 with three N-terminal and one C-terminal cleavage sites. Mutagenesis defined the C-terminal region of JP2 as the predominant calpain cleavage site. Exogenous expression of putative JP2 cleavage fragments was not sufficient to rescue $Ca^{2+}$ handling in JP2-deficient cardiomyocytes, indicating that cleaved JP2 is non-functional for normal $Ca^{2+}$-induced $Ca^{2+}$ release.

$Ca^{2+}$ signaling affects almost every aspect of cells from life to death (Clapham, 2007). In heart muscle, excitation-contraction (E-C) coupling is a cascade of $Ca^{2+}$-mediated processes linking membrane depolarization to activation of cell contraction (Bers, 2002). At the cellular level, E-C coupling in working ventricular myocytes depends on precise communication between voltage-gated L-type $Ca^{2+}$ channels located mainly on the transverse (T)-tubule membrane and $Ca^{2+}$-sensitive ryanodine receptors (RyRs) on the terminal cisternae of the sarcoplasmic reticulum (SR) (Cheng et al., 1993; Cannell et al., 1995; Wang et al., 2001). Upon membrane depolarization. Ca-2 influx through the opening of voltage-gated L-type $Ca^{2+}$ channels increases $[Ca^{2+}]$ locally. This high concentration of $[Ca^{2+}]$ sensitizes adjacent RyRs to release a much larger amount of $Ca^{2+}$ from the SR. The SR-released $Ca^{2+}$ together with $Ca^{2+}$ influx activates myofilaments, resulting in myocyte contraction. This intermolecular $Ca^{2+}$ crosstalk between L-type $Ca^{2+}$ channels and RyRs takes place in a confined spatial microdomain, where T-tubules and terminal cisternae of SR form tight junctional couplings with a gap of 12-15 nm, termed "cardiac dyads" (Page et al., 1979). Cardiac dyads provide the structural basis for E-C coupling and are established and maintained by junctophilin-2 (JP2) (Takeshima et al., 2000). JP2 contains eight N-terminal 'membrane occupation and recognition nexus' (MORN) domains that mediate interactions with the T-tubule membrane, a space-spanning α-helix which is thought to control the dyad distance, and a C-terminal transmembrane (TM) domain that anchors JP2 in the SR membrane (Takeshima et al., 2000; Nishi et al., 2000). Genetic manipulation of JP2 by silencing, knockout or overexpression authenticated its role as a structural protein responsible for the formation of cardiac dyads and maintenance of normal E-C coupling in the heart (Takeshima et al., 2000; van Oort et al., 2011; Guo et al., 2014).

Defective E-C coupling is a hallmark of heart failure (Gomez et al., Litwin et al., 2000; Song et al., 2006; Xu et al., 2007; Guo et al., 2013). Recent studies have provided evidence that JP2 is decreased in falling hearts of multiple etiologies including human heart failure, contributing to the loss of ultrastructural integrity of cardiac dyads and E-C coupling dysfunction (Guo et al., 2013; Wei et al., 2010; Xu et al., 2012; M et al., 2012; Zhang et al., 2013; Jiang et al., 2016; Minamisawa et al., 2004). In particular, JP2 proteolytic cleavage by calpain in response to cardiac stress is a mechanism of JP2 downregulation, causing E-C uncoupling, $Ca^{2+}$ mis-handling and heart failure (Wu et al., 2014; Guo et al., 2015). Abnormal $Ca^{2+}$ homeostasis triggers maladaptive remodeling at the transcriptional level, contributing to pathological myocardial remodeling and development of heart failure (Molkentin et al., 1998; Frey et al., 2000; Passier et al., 2000; Backs et al., 2006; V W et al., 2006; Colella et al., 2008; Houser et al., 2008). However, it was not clear whether cardiomyocytes undergoing E-C uncoupling possess a self-protective or homeostatic mechanism that mitigates adverse myocardial remodeling. It was also unknown whether there is an intrinsic connection between cardiac ultrastructural remodeling at E-C coupling junctions and transcriptional reprogramming in stressed hearts.

As discussed below, when JP2 is truncated, it can be transported into the nucleus of cells and alter the gene transcription profile, resulting in repression of cardiac hypertrophy and heart failure. Generation of a JP2 fragment during cardiac stress is a marker of E-C uncoupling, and serves as a negative feedback mechanism to antagonize maladaptive cardiac remodeling. This fragment translocates to the nucleus and represses transcriptional reprogramming, in part through regulating a key muscle transcription factor MEF2. Specifically, the α-helix domain of JP2 contains a DNA binding domain that is evolutionarily conserved. Under stress conditions, proteolytic processing of JP2 by calpain converts it from a structural protein to a transcriptional regulator, indicating a connection between cardiomyocytes ultrastructural remodeling and transcriptional reprogramming in the heart.

Thus, JP2 is a potential therapeutic target for cardiac hypertrophy and heart failure by resolving transcriptional remodeling in heart cells. This has high value because heart disease is a leading cause of death in the US, occurring in about 1 In 16 adults over 18, and costs the US economy an estimated $444 billion yearly (http://www.cdc.gov). Cardiac hypertrophy and heart failure are common and dangerous myocardium diseases. The philosophy of current therapies for cardiac diseases is to control the work load of hearts rather than control the intrinsic mechanisms (gene expression) of disease development. Since remodeling of the gene transcription profile is responsible for myocardium diseases, the use of truncated form of JP2 addresses a deficiency in the present technology by revealing an unappreciated protective mechanism of heart failure.

Definitions

"JP2" refers to junctophilin-2 protein and "JPH2" refers to the gene encoding junctophilin-2 protein.

A "vector" or "delivery" vehicle refers to a macromolecule or association of macromolecules that comprises or associates with a polynucleotide or polypeptide, and which can be used to mediate delivery of the polynucleotide or polypeptide to a cell or intercellular space, either in vitro or in vivo. Illustrative vectors include, for example, plasmids, viral vectors, liposomes, nanoparticles, or microparticles and other delivery vehicles. In one embodiment, a polynucleotide to be delivered, sometimes referred to as a "target polynucleotide" or "transgene," may comprise a coding sequence of interest in gene therapy (such as a gene encoding a protein of therapeutic interest), a coding sequence of interest and/or a selectable or detectable marker.

"Transduction," "transfection," "transformation" or "transducing" as used herein, are terms referring to a process for the introduction of an exogenous polynucleotide into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels), e.g., by ELISA, flow cytometry and Western blot, measurement of DNA and RNA by heterologousization assays, e.g., Northern blots. Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

An "Infectious" virus or viral particle is one that comprises a polynucleotide component which is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, such as mammalian cells including human cells, useful in the present invention. e.g., to produce recombinant virus or recombinant polypeptide. These cells include the progeny of the original cell that was transduced. It is understood that the progeny of a single cell may not necessarily be completely identical (in morphology or in genomic complement) to the original parent cell.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The terms "polypeptide" and "protein" are used interchangeably herein to refer to polymers of amino acids of any length. The terms also encompass an amino acid polymer that has been modified; for example, disulfide bond formation, glycosylation, acetylation, phosphorylation, lipidation, or conjugation with a labeling component.

An "Isolated" polynucleotide, e.g., plasmid, virus, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded). Enrichment can be measured on an absolute basis, such as weight per volume of solution, or it can be measured in relation to a second, potentially interfering substance present in the source mixture. For example, a 2-fold enrichment, 10-fold enrichment, 100-fold enrichment, or a 1000-fold enrichment.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature, e.g., an expression cassette which links a promoter from one gene to an open reading frame for a gene product from a different gene.

"Transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%), or not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more homologous if their amino acids are greater than or equal to 50% identical when optimally aligned using the ALIGN program.

The term "corresponds to" is used herein to mean that a polynucleotide sequence is structurally related to all or a portion of a reference polynucleotide sequence, or that a polypeptide sequence is structurally related to all or a portion of a reference polypeptide sequence, e.g., they have at least 80%, 82%, 85%, 87%, 90%, 92%, 95%, 97% or more, e.g., 99% or 100%, sequence identity. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or 1) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As used herein, "substantially pure" or "purified" means an object species is the predominant species present (i.e., on a molar basis it is more abundant than any other individual species in the composition), for instance, a substantially purified fraction is a composition wherein the object species comprises at least about 50 percent (on a molar basis) of all macromolecular species present. Generally, a substantially pure composition will comprise more than about 80 percent of all macromolecular species present in the composition, or more than about 85%, about 90%, about 95%, and about 99%. The object species may be purified to essential homogeneity (contaminant species cannot be detected in the composition by conventional detection methods) wherein the composition consists essentially of a single macromolecular species.

Preparation of Expression Cassettes

To prepare expression cassettes encoding JP2 or truncated forms thereof, a peptide thereof, or a fusion thereof, for transformation, the recombinant DNA sequence or segment may be circular or linear, double-stranded or single-stranded. A DNA sequence which encodes an RNA sequence that is substantially complementary to a mRNA sequence encoding a gene product of interest is typically a "sense" DNA sequence cloned into a cassette in the opposite orientation (i.e., 3' to 5' rather than 5' to 3). Generally, the DNA sequence or segment is in the form of chimeric DNA, such as plasmid DNA, that can also contain coding regions flanked by control sequences which promote the expression of the DNA in a cell. As used herein, "chimeric" means that a vector comprises DNA from at least two different species, or comprises DNA from the same species, which is linked or associated in a manner which does not occur in the "native" or wild-type of the species.

Aside from DNA sequences that serve as transcription units, or portions thereof, a portion of the DNA may be untranscribed, serving a regulatory or a structural function. For example, the DNA may itself comprise a promoter that is active in eukaryotic cells, e.g., mammalian cells, or in certain cell types, or may utilize a promoter already present in the genome that is the transformation target of the lymphotrophic virus. Such promoters include the CMV promoter, as well as the SV40 late promoter and retroviral LTRs (long terminal repeat elements), although many other promoter elements well known to the art may be employed, e.g., the MMTV, RSV, MLV or HIV LTR in the practice of the invention. In one embodiment, expression is inducible. In one embodiment, a tissue-specific promoter (or enhancer) is employed, e.g., a cardiac-specific promoter or enhancer or a skeletal muscle-specific promoter or enhancer. Such control elements include, but are not limited to, those derived from the actin and myosin gene families, such as from the myoD gene family (Weintraub et al., *Science,* 251, 761 (1991)); the myocyte-specific enhancer binding factor MEF-2; control elements derived from the human skeletal actin gene, and the cardiac actin gene; muscle creatine kinase sequence elements and the murine creatine kinase enhancer (mCK) element; control elements derived from the skeletal fast-twitch troponin C gene, the slow-twitch cardiac troponin C gene and the slow-twitch troponin I genes. Cardiac cell restricted promoters include but are not limited to promoters from the following genes; a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA to be introduced into the cells may contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, puro, hyg, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Exemplary reporter genes include the chloramphenicol acetyl transferase gene (cat) from Tn9 of E. coli, the beta-glucuronidase gene (gus) of the uidA locus of E. coli, the green, red, or blue fluorescent protein gene, and the luciferase gene. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein.

The recombinant DNA can be readily introduced into the host cells, e.g., mammalian, bacterial, yeast or insect cells, or prokaryotic cells, by transfection with an expression vector comprising the recombinant DNA by any procedure useful for the introduction into a particular cell, e.g., physical or biological methods, to yield a transformed (transgenic) cell having the recombinant DNA so that the DNA sequence of interest is expressed by the host cell. In one embodiment, the recombinant DNA is stably integrated into the genome of the cell.

Physical methods to introduce a recombinant DNA into a host cell include calcium-mediated methods, lipofection, particle bombardment, microinjection, electroporation, and the like. Biological methods to introduce the DNA of interest into a host cell include the use of DNA and RNA viral vectors. Viral vectors, e.g., retroviral or lentiviral vectors, have become a widely used method for inserting genes into eukaryotic cells, such as mammalian, e.g., human cells. Other viral vectors can be derived from poxviruses, e.g., vaccinia viruses, herpes viruses, adenoviruses, adeno-associated viruses, baculoviruses, and the like.

To confirm the presence of the recombinant DNA sequence in the host cell, a variety of assays may be performed. Such assays include, for example, molecular biological assays well known to those of skill in the art, such as Southern and Northern blotting, RT-PCR and PCR; biochemical assays, such as detecting the presence or absence of a particular gene product, e.g., by immunological means (ELISAs and Western blots) or by other molecular assays.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

Wile Southern blotting and PCR may be used to detect the recombinant DNA segment in question, they do not provide information as to whether the recombinant DNA segment is being expressed. Expression may be evaluated by specifically identifying the peptide products of the introduced DNA sequences or evaluating the phenotypic changes brought about by the expression of the introduced DNA segment in the host cell.

Vectors for Delivery

Delivery vectors include, for example, viral vectors, microparticles, nanoparticles, liposomes and other lipid-containing complexes, and other macromolecular complexes capable of mediating delivery of a gene to a host cell, e.g., to provide for recombinant expression of a polypeptide encoded by the gene. Vectors can also comprise other components or functionalities that further modulate gene delivery and/or gene expression, or that otherwise provide beneficial properties. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Vectors for gene within the scope of the invention include, but are not limited to, isolated nucleic acid, e.g., plasmid-based vectors which may be extrachromosomally maintained, and viral vectors. e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene viral vectors are described below. Vectors may be administered via any route including, but not limited to, intramuscular, buccal, rectal, intravenous or intracoronary administration, and transfer to cells may be enhanced using electroporation and/or iontophoresis. In one embodiment, vectors are locally administered.

In one embodiment, an isolated polynucleotide or vector having that polynucleotide comprises nucleic acid encoding a polypeptide or fusion protein that has substantial identity, e.g., at least 80% or more, e.g., 85%, 87%, 90%, 92%, 95%, 97%, 98%, 99% and up to 100%, amino acid sequence identity to one of SEQ ID NOs. 1-4, and may, when administered, promote cartilage growth or repair.

Peptides, Polypeptides and Fusion Proteins

The peptide or fusion proteins of the invention can be synthesized in vitro, e.g., by the solid phase peptide synthetic method or by recombinant DNA approaches (see above). The solid phase peptide synthetic method is an established and widely used method. These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, chemically modified derivatives of a given peptide or fusion thereof, can be readily prepared. For example, amides of the peptide or fusion thereof of the present invention may also be prepared by techniques well known in the art for converting a carboxylic acid group or precursor, to an amide. One method for amide formation at the C-terminal carboxyl group is to cleave the peptide or fusion thereof from a solid support with an appropriate amine, or to cleave in the presence of an alcohol, yielding an ester, followed by aminolysis with the desired amine.

Salts of carboxyl groups of a peptide or fusion thereof may be prepared in the usual manner by contacting the peptide, polypeptide, or fusion thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide or fusion thereof may be prepared by utilizing an N-acyl protected amino acid for the final condensation, or by acylating a protected or unprotected peptide, polypeptide, or fusion thereof. O-acyl derivatives may be prepared, for example, by acylation of a free hydroxy polypeptide or polypeptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide. Other amino-terminal modifications include aminooxypentane modifications.

In one embodiment, a peptide or fusion protein has substantial identity. e.g., at least 80% or more, e.g., 85%, 87%, 90%, 92%, 95%, 97%, 98%, 99% and up to 100%, amino acid sequence identity to one of SEQ ID NOs. 1-4, and may, when administered, promote cartilage growth or repair.

Substitutions may include substitutions which utilize the D rather than L form, as well as other well known amino acid analogs, e.g., unnatural amino acids such as α, α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

Conservative amino acid substitutions may be employed—that is, for example, aspartic-glutamic as acidic amino acids; lysine/arginine/histidine as polar basic amino acids; leucine/isoleucine/methionine/valine/alanine/proline/glycine non-polar or hydrophobic amino acids; serine/threonine as polar or hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting peptide, polypeptide or fusion polypeptide. Whether an amino acid change results in a functional peptide, polypeptide or fusion polypeptide can readily be determined by assaying the specific activity of the peptide, polypeptide or fusion polypeptide.

Amino acid substitutions falling within the scope of the invention, are, in general, accomplished by selecting substitutions that do not differ significantly in their effect on maintaining (a) the structure of the peptide backbone in the area of the substitution. (b) the charge or hydrophobicity of the molecule at the target site, or (c) the bulk of the side chain. Naturally occurring residues are divided into groups based on common side-chain properties:

(1) hydrophobic: norleucine, met, ala, val, leu, lie;
(2) neutral hydrophilic: cys, ser, thr;
(3) acidic: asp, glu;
(4) basic: asn, gin, his, lys, arg;
(5) residues that influence chain orientation: gly, pro; and
(8) aromatic; trp, tyr, phe.

The invention also envisions a peptide, polypeptide or fusion polypeptide with non-conservative substitutions.

Non-conservative substitutions entail exchanging a member of one of the classes described above for another.

Acid addition salts of the peptide, polypeptide or fusion polypeptide or of amino residues of the peptide, polypeptide or fusion polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

Formulations and Dosages

The polypeptides or fusions thereof, or nucleic acid encoding the polypeptide or fusion of the invention, can be formulated as pharmaceutical compositions and administered to a mammalian host, such as a human patient in a variety of forms adapted to the chosen route of administration, e.g., orally or parenterally, by intravenous, intramuscular, topical or subcutaneous routes. In one embodiment, the polypeptide or nucleic acid encoding the polypeptide is administered to a site of cartilage damage or suspected cartilage damage, or is administered prophylactically.

In one embodiment, the JP2 polypeptides or fusions thereof, or nucleic acid encoding the polypeptide or fusion, may be administered by infusion or injection. Solutions of the polypeptides or fusions thereof, or nucleic acid encoding the polypeptide or fusion or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion may include sterile aqueous solutions or dispersions or sterile powders comprising the active ingredient which are adapted for the extemporaneous preparation of sterile injectable or infusible solutions or dispersions, optionally encapsulated in liposomes. In al cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the methods of preparation include vacuum drying and the freeze drying techniques, which yield a powder of the active ingredient plus any additional desired ingredient present in the previously sterile-filtered solutions.

Useful solid carriers may include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as antimicrobial agents can be added to optimize the properties for a given use. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the polypeptides or fusions thereof, or nucleic acid encoding the polypeptide or fusion, can be determined by comparing their in vitro activity and in vivo activity in animal models thereof. Methods for the extrapolation of effective dosages in mice, and other animals, to humans are known to the art; for example, see U.S. Pat. No. 4,938,949.

Generally, the concentration of the polypeptides or fusions thereof, or nucleic acid encoding the polypeptide or fusion, in a liquid composition, may be from about 0.1-25 wt-%, e.g., from about 0.5-10 wt-%. The concentration in a semi-solid or solid composition such as a gel or a powder may be about 0.1-5 wt-%. e.g., about 0.5-2.5 wt-%.

The amount of the polypeptides or fusions thereof, or nucleic acid encoding the polypeptide or fusion required for use alone or with other agents will vary with the route of administration, the nature of the condition being treated and the age and condition of the patient and will be ultimately at the discretion of the attendant physician or clinician.

The polypeptides or fusions thereof, or nucleic acid encoding the polypeptide or fusion, may be conveniently administered in unit dosage form; for example, containing 5 to 1000 mg, conveniently 10 to 750 mg, or conveniently 50 to 500 mg of active ingredient per unit dosage form.

In general, however, a suitable dose may be in the range of from about 0.5 to about 100 mg/kg, e.g., from about 10 to about 75 mg/kg of body weight per day, such as 3 to about 50 mg per kilogram body weight of the recipient per day, for example in the range of 6 to 90 mg/kg/day, e.g., in the range of 15 to 60 mg/kg/day.

The invention will be described by the following non-limiting examples.

Example 1

Experimental Procedures

Human Heart Samples and Animal Studies

Samples from patients with ischemic heart disease were obtained from the University of Iowa Heart Failure Transplant Program. Rejected healthy donor hearts were obtained through the Donor Network. All human heart tissue samples were obtained under an organ research donation protocol that was approved by the institutional Review Board of the University of Iowa. Animal experiments were performed in accordance with the Guide for the Care and Use of Laboratory Animals (National Institutes of Health publication no. 85-23, revised 1996) and were approved by the Institutional Animal Care and Use Committee at the University of Iowa.

Cardiac-specific JP2 Knockdown (JP2-KD) was achieved with the use of transgenic mice conditionally expressing a JP2 shRNA (shJP2). Specifically, conditional shJP2 mice (provided by Dr. Wehrens) (van Oort et al., 2011) were crossed with mice carrying the cardiac-specific α-myosin heavy chain promoter upstream of Cre (% MHC-Cre, also FVB-Tg(Myh6-cre)2182Mds/J, The Jackson Laboratory). The shJP2 mice were maintained on a C57BL/6 background for more than 10 generations. The αMHC-Cre mice were maintained on an FVB background. PCR was used to genotype the offspring. The near complete depletion of JP2 protein in JP2-KD (αMHC-Cre X shJP2) hearts has been reported recently (Chen et al., 2013). JP2-KD mice were sacrificed at 2 months of age for isolation and culture of ventricular cardiomyocytes as described below.

In Vito and In Vivo I/R Protocols in Mouse Hearts

For in vitro I/R injury, hearts were excised rapidly from anesthetized mice and perfused with Krebs-Henseleit solution at 37° C. using a Langendorff apparatus at a constant pressure of 80 mm Hg with 95% $O_2$. 5% $CO_2$. After 20 minutes of equilibration, hearts were subjected to 35 minutes of global no-flow ischemia followed by 50 minutes of reperfusion. Some hearts were treated with MDL-28170 (10 μM) via perfusion 10 minutes before ischemia and after the onset of reperfusion. For in vivo I/R injury in mouse hearts, myocardial ischemia was produced by ligation of the left anterior descending coronary artery for 20 minutes, followed by reperfusion for 30 minutes (longer periods of ischemia/reperfusion lead to a high death rate under our conditions). Left ventricles were dissected for analysis by Western blotting.

Molecular Cloning, Mutagenesis, and Adenovirus Construction

Wild-type JP2 cDNA was provided by Dr. Takeshima (Takeshima et al., 2000). FLAG and HA epitope tags were added to 5' and 3' ends, respectively, in the same reading frame of the coding sequence of JP2 cDNA by PCR. The dual epitope-tagged cDNA was cloned into the pCMV-XL5 plasmid under the control of a CMV promoter. cDNAs of JP2 truncations were cloned using PCR. QuikChange II (Agilent) was used for site-directed mutagenesis. Adenoviruses containing full-length JP2 (Ad-JP2), truncated JP2(1-565) (Ad-JP2(1-565)), or JP2(566-end) (Ad-JP2(566-end)) or empty Ad5 virus (Ad-empty) were produced by the University of Iowa Gene Transfer Vector Core. In the adenovirus construct, the full-length JP2 and truncation JP2(1-565) were tagged with FLAG at the N terminus and HA at the C terminus. The truncation JP2(566-end) was tagged with HA at the C terminus.

Adult Cardiomyocyte Culture, Cell Transfection. and Adenovirus Infection

Genecarrier-1 (Epoch Lab) was used to transfect plasmids into HEK293T cells. Isolation and culture of cardiomyocytes were performed as described previously (Guo et al., 2012). Adenoviruses were applied at a multiplicity of infection of 100, which resulted in transfection of almost all cells, as confirmed by immunostaining of epitope tags. $Ca^{2+}$ Imaging experiments were performed 40 hours after adenoviral infection.

In Vitro Calpain-Mediated Proteolysis Reaction

Mouse and human heart tissues as well as HEK 293T cells (obtained from the ATCC and cultured according to the protocol of the manufacturer) overexpressing tagged JP2 were washed with PBS and homogenized in lysis buffer (20 mM Tris-HCl, 150 mM NaCl, 2 mM EDTA, and 1% Triton X-100), followed by sonication. Homogenates were centrifuged for 10 minutes at 14,000 rpm at 4° C. Protein content in the supernatant was determined using the BCA assay (Thermo Scientific). Cell extracts were diluted in ice-cold calpain reaction buffer (135 mM NaCl, 5 mM KCl, 1 mM $MgCl_2$, 10 mM glucose, 10 mM Hepes (pH 7.25), 2 mM lactacystin, and 10 mM 2-mercaptoethanol) to a concentration of 4 mg protein/ml. Just prior to starting the protease reaction, $CaCl_2$ was added to achieve a final concentration of 3 mM free $Ca^{2+}$ (in the presence of EDTA), as calculated by winmaxc32 (Stanford University). For some experiments, the free $Ca^{2+}$ concentration was adjusted to 500 μM, as calculated by winmaxc32. Purified human calpain I (Calbiochem) was added at a concentration of 1 mg of total protein/1 μg of calpain I. Reactions without $Ca^{2+}$ or without purified calpain I were used as controls. Reactions were incubated at 30° C. for the indicated time and stopped by adding EDTA to a final concentration of 10 mM and incubating for 5 minutes at 95° C. The reaction products were subjected to Western blotting.

Western Blot Analysis and Immunostaining

Western blotting and immunostaining of cardiomyocytes were performed as described previously (Guo et al., 2012) using antibodies to JP2 (catalog no. sc-51313, Santa Cruz Biotechnology) and epitope tags (anti-FLAG, catalog no. A00187, Genescript; anti-HA, catalog no. sc-805, Santa Cruz Biotechnology). Immunofluorescence was imaged by using a confocal microscope (Cari Zeiss MicroImaging Inc.).

Confocal $Ca^{2+}$ Imaging

Cells were loaded with Rhod-2AM at 37° C. for 20 minutes, followed by washing with Tyrode's solution at room temperature for 15 minutes before $Ca^{2+}$ imaging. Confocal images were acquired using a ×63, 1.3 numerical aperture oil immersion objective mounted on a Zeiss LSM 510 confocal microscope. Confocal line scanning was used to record $Ca^{2+}$ signals. Steady-state $Ca^{2+}$ transients were recorded in Tyrode's solution containing 1.8 mM $Ca^{2+}$ under field stimulation of 1 Hz. At least five steady-state transients for each cell were analyzed and averaged to represent $Ca^{2+}$ signals of the cell. $Ca^{2+}$ imaging data were analyzed by using a home-complied software, CaTeasy, which is coded in MATLAB 2013a (Mathworks). Briefly, the program normalizes $Ca^{2+}$ transient images on a column-by-column basis (512 columns/image). The characteristic parameters of normalized transients were detected automatically. The firing time of every scanning pixel was detected column by column on the basis of the maximum local variability of pixel intensity. The profile of the point-to-point firing time was indicated by a red line overlapping on the $Ca^{2+}$ image. Index of desynchronization, defined by the mean absolute deviation of firing time of each scanning pixel (with every 8 pixels binned), was used to evaluate the dyssynchrony of $Ca^{2+}$ transients. This automated software for calcium transient analysis is available upon request.

Statistics

Data are presented as mean±S.E. Analysis of variance and Student's t test were applied when appropriate. A p value of <0.05 was considered statistically significant.

Results

Figure 1B:
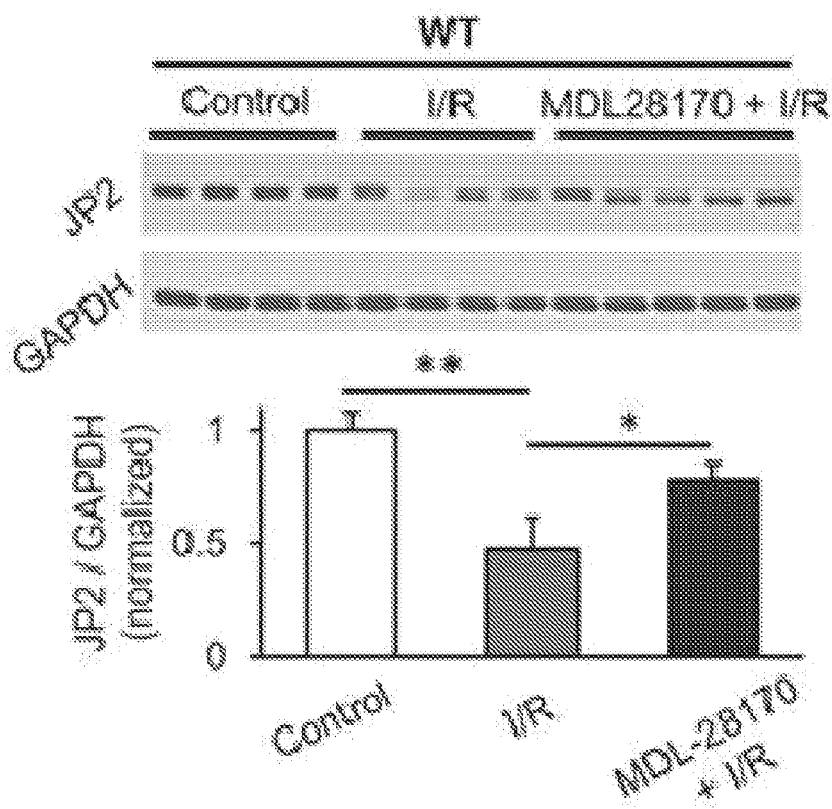
Figure 1C:
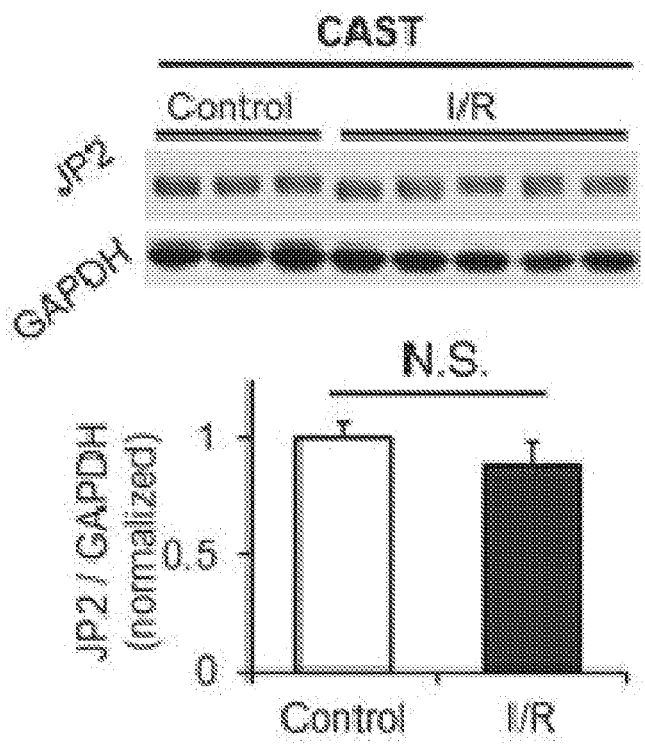
Figure 1D:
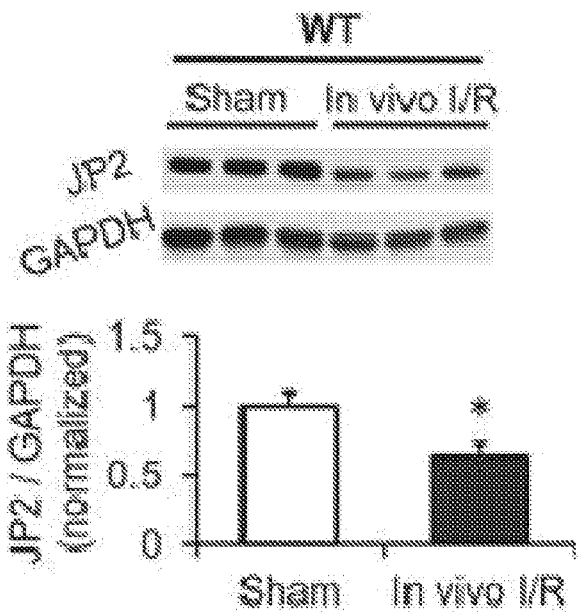
Figure 1E:
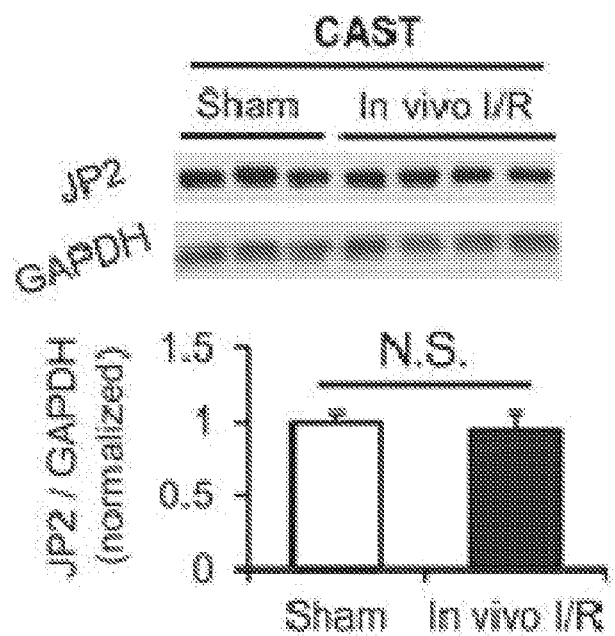

Calpain Mediates Down-Regulation of JP2 in Response to Cardiac Ischemia/Reperfusion Injury A Western blotting assay showed that JP2 protein was reduced by 60% in left ventricular lysates from end-stage heart failure patients with ischemic heart disease (FIG. 1A), similar to previous reports on human failing hearts of different etiologies, such as dilated and hypertrophied cardiomyopathies (Landstrom et al., 2011; Zhang et al., 2013). To dissect the molecular mechanisms responsible for JP2 down-regulation in disease, we used a murine model of acute cardiac stress. Following global cardiac I/R injury in Langendorff-perfused WT mouse hearts, we observed a significant down-regulation of JP2 protein in the left ventricle (FIG. 1B). JP2 down-regulation was also observed in an in vivo I/R model induced by in situ left anterior descending coronary artery ligation/reperfusion in mouse hearts (FIG. 1D). These data suggest that JP2 down-regulation is not solely accomplished by miRNA-mediated gene silencing (Xu et al., 2007), given that loss of JP2 expression was evident within the short time period of I/R injury in our study.

JP2 down-regulation was attenuated by perfusion with the calpain inhibitor MDL-28170 before and after ischemia (FIG. 1B). These data are in line with the observed increase in calpain activity under a variety of pathological conditions, such as pressure overload, myocardial infarction, I/R injury, and isoproterenol-induced cardiac disease (Chen et al., 2002; French et al., 2006; Inserte et al., 2012; Yoshida et al., 1995; Greyson et al., 2008; Hall et al., 2005; Li et al., 2011; Sandmann et al., 2001; Arthur and Belcastro; 1997; Patterson et al., 2011; Heidrich and Ehrlich, 2009; Letavernier et al., 2008). In the post-ischemic heart, calpain degrades a myriad of structural and myofilament proteins, resulting in cardiac dysfunction (Yoshida et al., 1995; Chen et al., 2001; Maekawa et al., 2003; Kashef et al., 2012). Next, studies were performed in transgenic mice overexpressing the endogenous calpain inhibitor protein calpastatin (CAST) (Li et al., 2009; Peltier et al., 2006). JP2 levels were statistically unchanged in hearts from CAST mice after both in vitro and in vivo I/R injury (FIGS. 1C and E), further suggesting that calpain contributes to the reduction in JP2 protein expression.

Figure 2A:
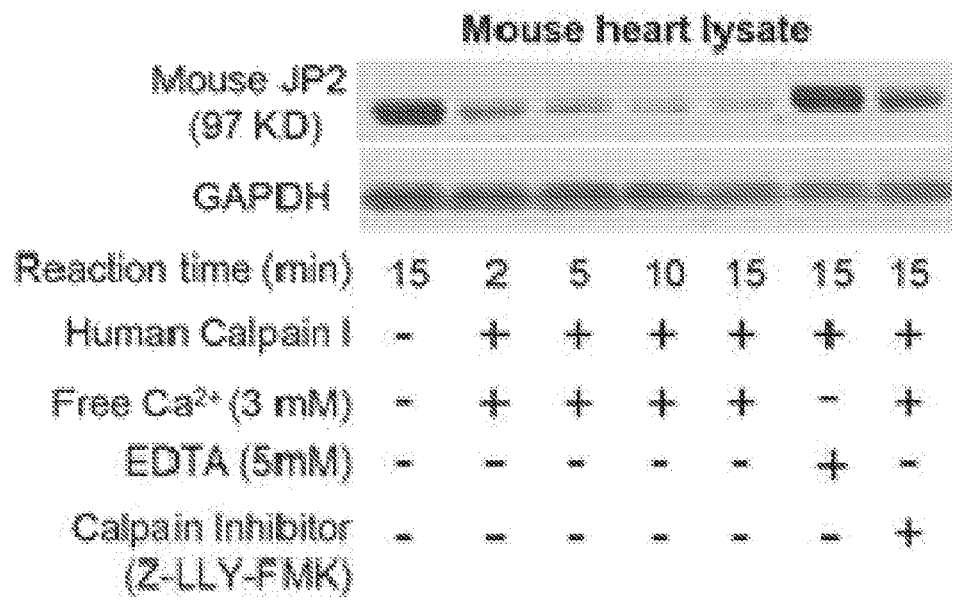
FIGS. 2A-C. In vitro calpain cleavage reactions identify calpain as the JP2 protease in mouse and human heart. A) and B) In vitro proteolysis of JP2 in mouse (A) and human (B) heart lysates (1 mg total protein) in the presence of human calpain I (1 µg of calpain I) and free $Ca^{2+}$ (3 mM) with or without EDTA (5 mM) or the calpain inhibitor Z-LLY-FMK (20 µM). C) Protein lysates from 293T cells overexpressing JP2 (untagged) were incubated with purified human calpain I in the presence or absence of $Ca^{2+}$ or calpain inhibitor. Data are representative of at least three independent experiments.
Figure 2B:
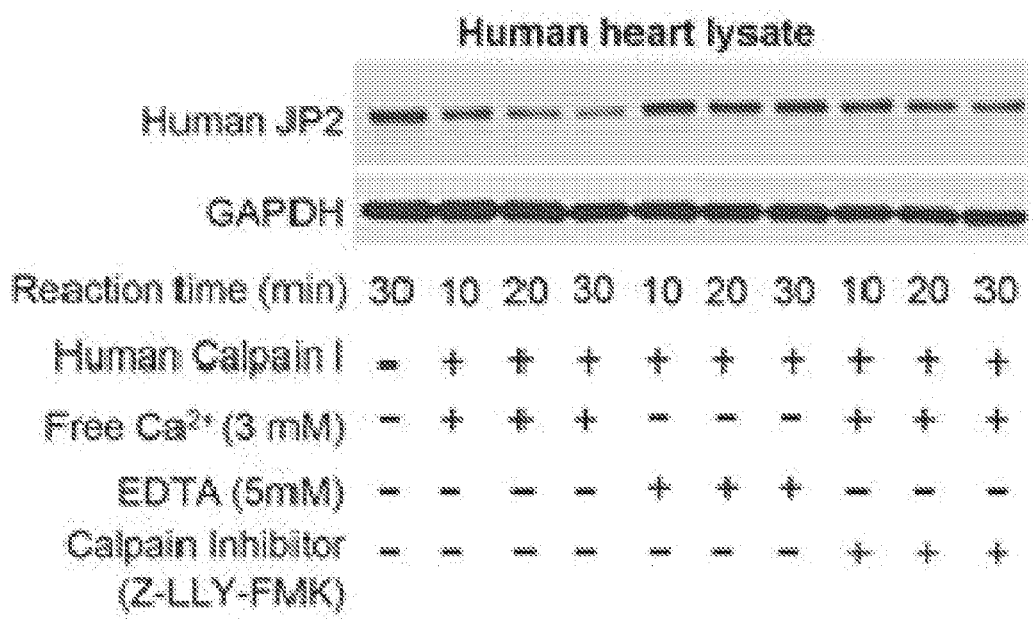

To determine whether calpain directly cleaves JP2, in vitro cleavage reactions were performed by incubating protein lysates from WT mouse hearts with purified human calpain 1. Blotting with a JP2 C-terminal antibody revealed a significant reduction in full-length JP2 upon addition of calpain I (FIG. 2A). The $Ca^{2+}$ chelator EDTA or the calpain inhibitor Z-LLY-FMK inhibited JP2 degradation. In vitro calpain cleavage assays using human heart lysates also showed a time-dependent and $Ca^{2+}$/calpain-dependent JP2 down-regulation, identifying JP2 as a direct substrate for calpain (FIG. 2B). These data provide direct evidence that, in cardiac tissue, JP2 is a substrate of the $Ca^{2+}$-dependent protease calpain.

Identification of Calpain Cleavage Sites on JP2

Figure 2C:
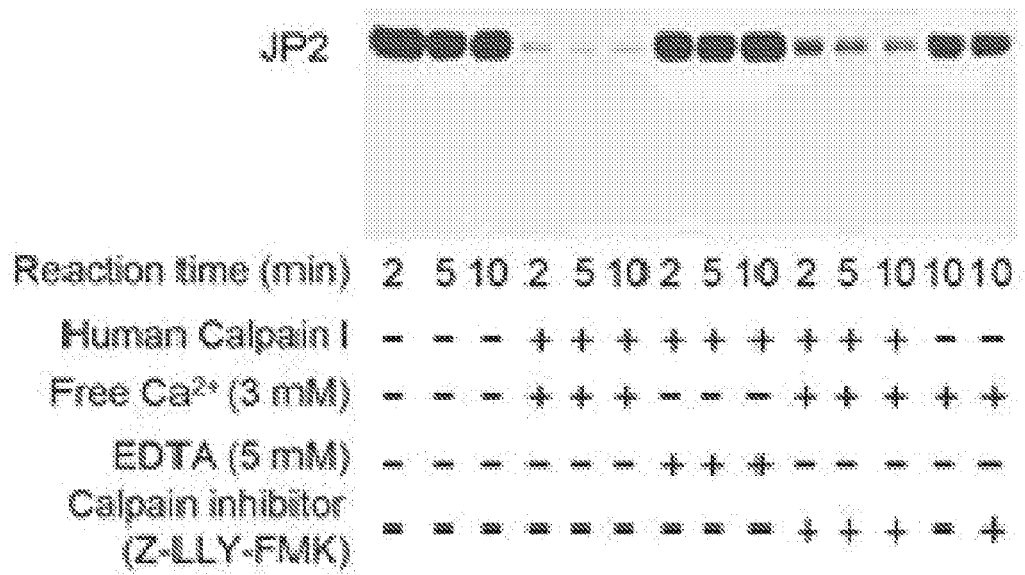

Murine JP2 was overexpressed in 293T cells and subjected lysates to a calpain proteolysis assay. Using an antibody against the JP2 C-terminal epitope, a dramatic decrease was detected in the amount of full-length JP2 but could not detect the faster-migrating species (FIG. 2C), indicating that calpain cleavage may have destroyed the antibody epitope.

Figure 3A:
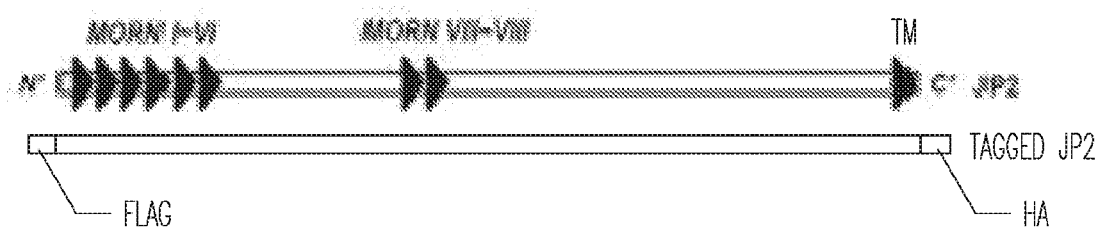
Figure 3D:
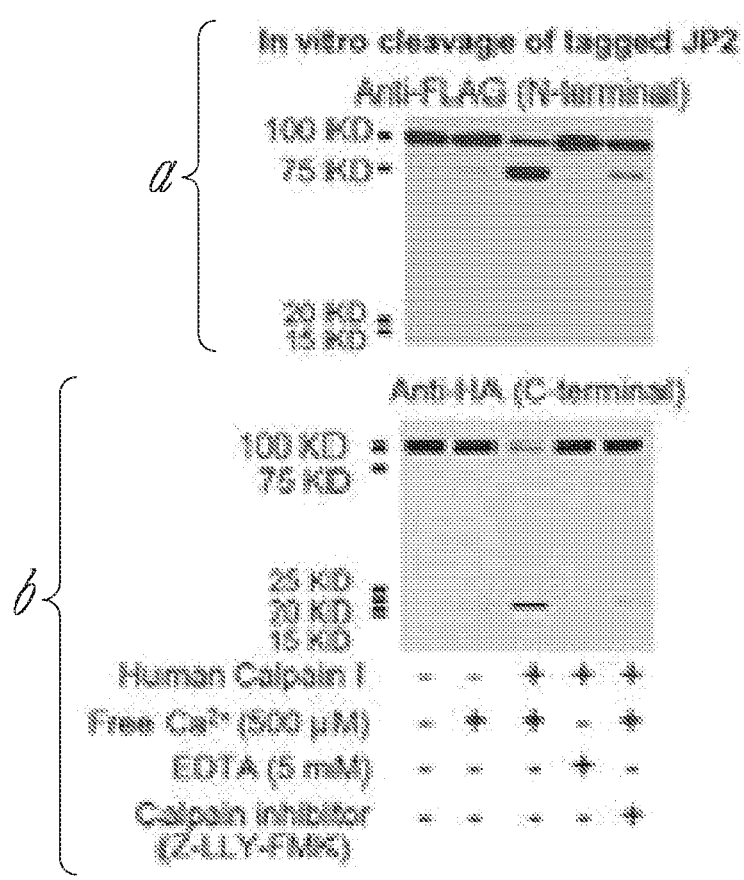

To determine the extent of JP2 proteolysis by calpain, a JP2 construct was generated with an N-terminal FLAG tag and a C-terminal HA tag (FIG. 3A). After cotransfection of the dually tagged JP2 and human calpain I into 293T cells, the $Ca^{2+}$ ionophore ionomycin was used to induce $Ca^{2+}$-dependent cleavage of JP2. Blotting with an antibody against the N-terminal FLAG tag demonstrated the calpain-dependent appearance of four N-terminal cleavage products, denoted N-I, II, III, and IV (FIG. 3B, a). The antibody against the HA tag detected one C-terminal cleavage product (denoted C-I, FIG. 3B, b). Treatment with the calpain inhibitor MDL-28170 resulted in a substantial reduction in the presence of both the N- and C-terminal leavage products and restored JP2 full-length levels to those observed in untreated cells (FIG. 3B, a and b). Cleavage products of a similar molecular weight were also observed in the in vitro calpain cleavage assays at 3 mM $Ca^{2+}$ (FIG. 3C) and 500 µM $Ca^{2+}$ (FIG. 3D). Removing $Ca^{2+}$ from the reaction or inhibition of calpain with Z-LLY-FMK resulted in a substantial reduction in cleavage products and preservation of full-length JP2 (FIGS. 3C and D). These data suggest that JP2 contains at least four calpain cleavage sites.

Figure 4A:
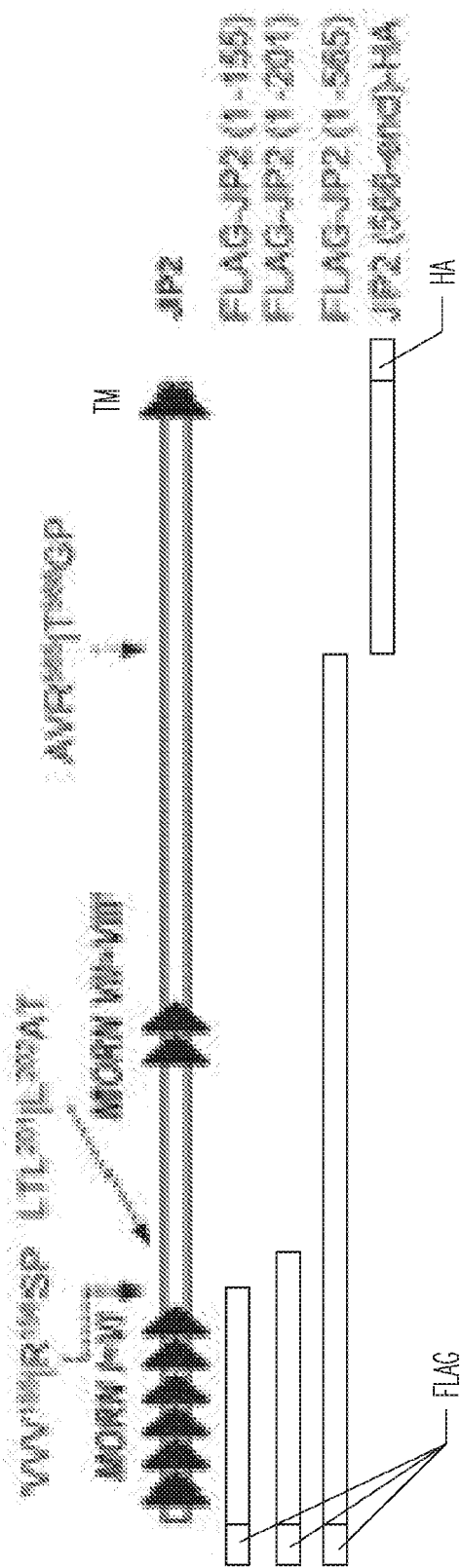
FIGS. 4A-D. C-terminal JP2 proteolysis at R565T is the primary site for calpain-mediated cleavage. A) Schematic of the N- or C-terminal epitope-tagged truncated JP2 constructs on the basis of putative calpain cleavage sites. These cleavage sites were predicted by using GPS-CCD 1.0 and CaMPDB. Arrows indicate these predicted cleavage sites relative to the MORN and TM domains. B) Expression of JP2 truncations in 293T cells. Where indicated, cells were pretreated with lactacystin (10 µM) after transfection. C) Western blot with anti-FLAG (N-terminal tag) following in vitro cleavage reaction with JP2(1-585) truncation. D) six to eight Amino acid deletions surrounding the predicted cleavage sites (V155R, Δ(153-158); L201L, Δ(198-205); R565T, Δ(563-568)) were introduced into the full-length JP2 construct with N-terminal FLAG and C-terminal HA epitope tags. Following expression of mutants in 293T cells, lysates were subjected to in vitro cleavage reactions. WT JP2 with tags was used as a control.
Figure 4B:
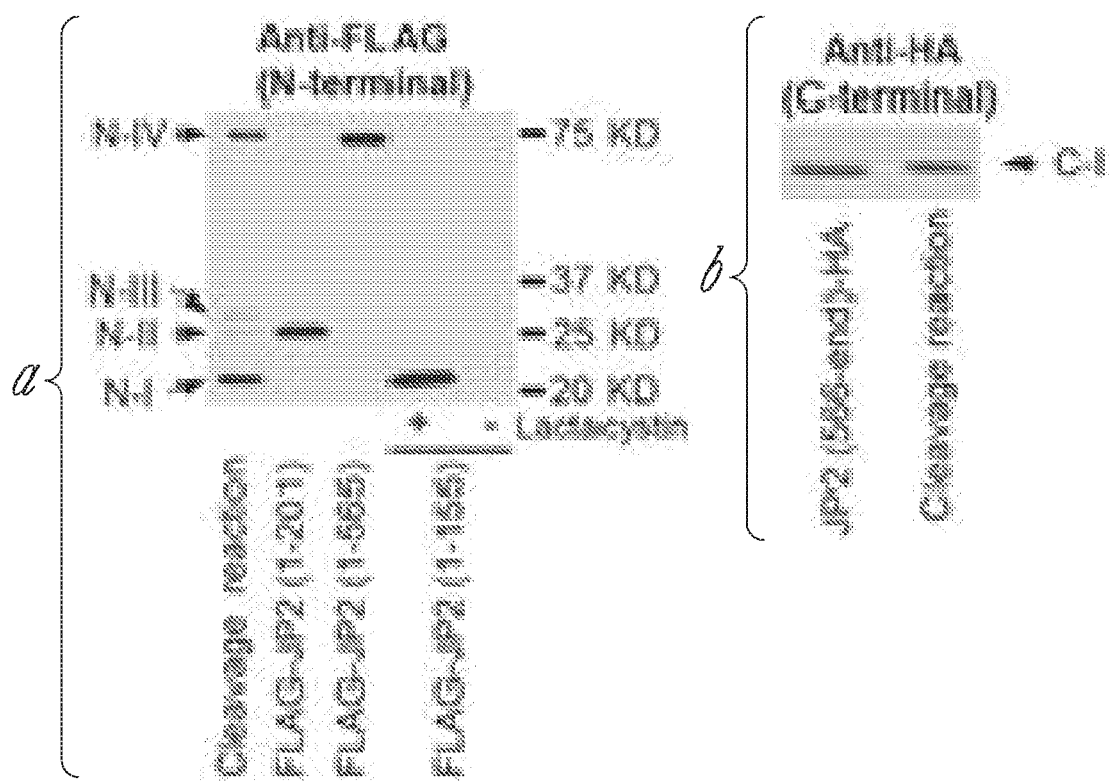
Figure 4C:
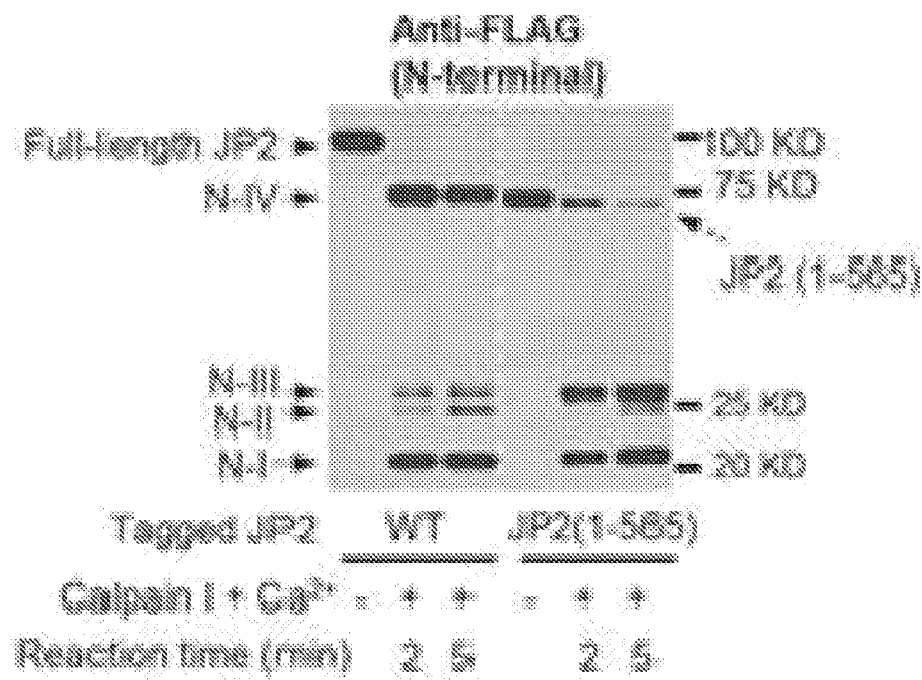

Using the computational tools CaMPDB (DuVerle et al., 2011) and GPS-CCD 1.0 (Liu et al., 2011), several putative calpain cleavage sites were identified in JP2. A panel of tagged JP2 truncations was generated on the basis of the predicted N- and C-terminal calpain cleavage sites (FIG. 4A). When expressed exogenously in 293T cells, JP2(1-155), JP2(1-201), and JP2(1-565) have a similar molecular weight as the cleavage products N-I, N-II, and N-IV, respectively (FIG. 4B, a). JP2(1-155), which corresponds to N-I, was only detectable in 293T cells treated with the proteasomal inhibitor lactacystin (FIG. 4B, a), suggesting that this cleavage product is not stable and undergoes further degradation by the proteasome (FIG. 4B, a). Note that JP2(566-end), which is the C-terminal counterpart of JP2(1-565), has a similar molecular weight as C-terminal cleavage product C-I (FIG. 4B, b), indicating N-IV and C-I may be generated by a single cleavage of JP2 at Arg-565/Thr-566. The susceptibility of JP2(1-565) to calpain-mediated proteolysis was examined and it was found that this fragment can be further processed by calpain to generate N-I, N-II, and N-III fragments (FIG. 4C). These data provide evidence that deletion of the extreme C-terminal tail of JP2 does not attenuate the calpain recognition of other cleavage sites.

Figure 4D:
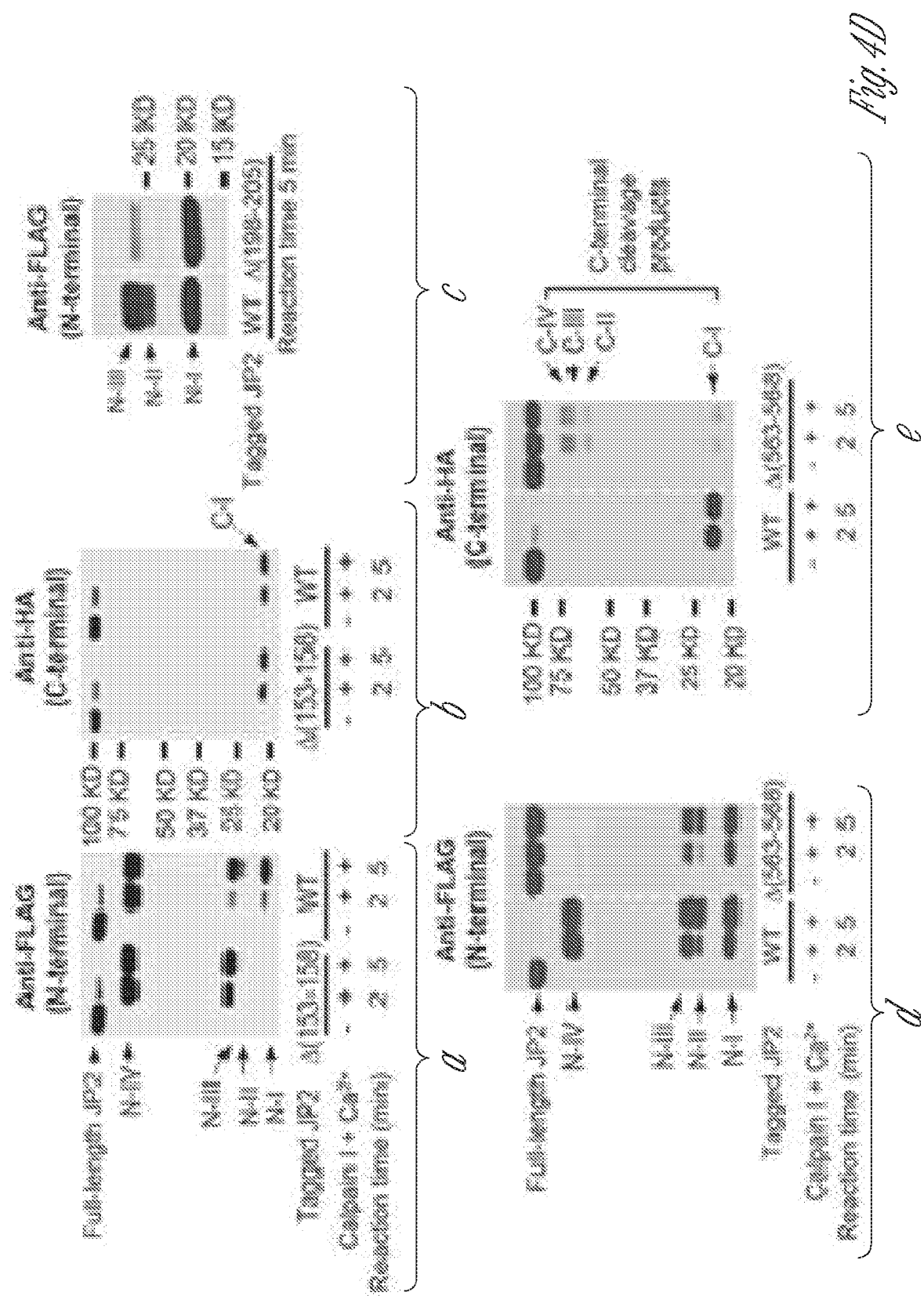

Next, the predicted calpain cleavage at Val-155/Arg-156, Leu-201/Leu-202, and Arg-565/Thr-566 was verified by creating site-directed deletions in the surrounding area. A six-residue deletion around the putative cleavage site Val-155/Arg-156 (Δ(153-158)) completely abolished the generation of N-I in the in vitro calpain cleavage assay (FIG. 4D, a), whereas cleavage at the extreme C terminus remained largely intact compared with WT JP2 (FIG. 4D, a and b). Next, an eight residue deletion around the putative cleavage site Leu-201/Leu-202 (Δ(198-205)) resulted in complete loss of the JP2 cleavage product N-II but had no effect on the generation of N-I (FIG. 4D, c), suggesting that cleavage at Val-155/Arg-156 is not dependent on prior cleavage at Leu-201/Leu-202. Finally, a six-amino acid deletion around the putative cleavage site Arg-565/Thr-566 (Δ(563-588)) led to complete loss of N-IV (FIG. 4D, d) and a severe reduction in C-I (FIG. 4D, e). Several C-terminal cleavage products (arrows. FIG. 4D, e), which may be counterparts of the cleavage products detected by anti-FLAG antibody, were detected by the anti-HA antibody in the in vitro calpain cleavage reaction of Δ(563-568) but not WT JP2 (FIG. 4D, e). Unlike loss of the N-terminal cleavage sites, loss of the C-terminal Arg-565/Thr-566 cleavage site preserved full-length JP2 (FIG. 4D, d and e), suggesting that the C-terminal Arg-565/Thr-566 cleavage site is more sensitive to calpain than the N-terminal cleavage sites. Taken together, these data identify Val-155/Arg-156, Leu-201/Leu-202, and Arg-565/Thr-566 as calpain cleavage sites that result in the generation of the cleavage products N-I, N-II and N-IV, and C-I, respectively.

Figure 5A:
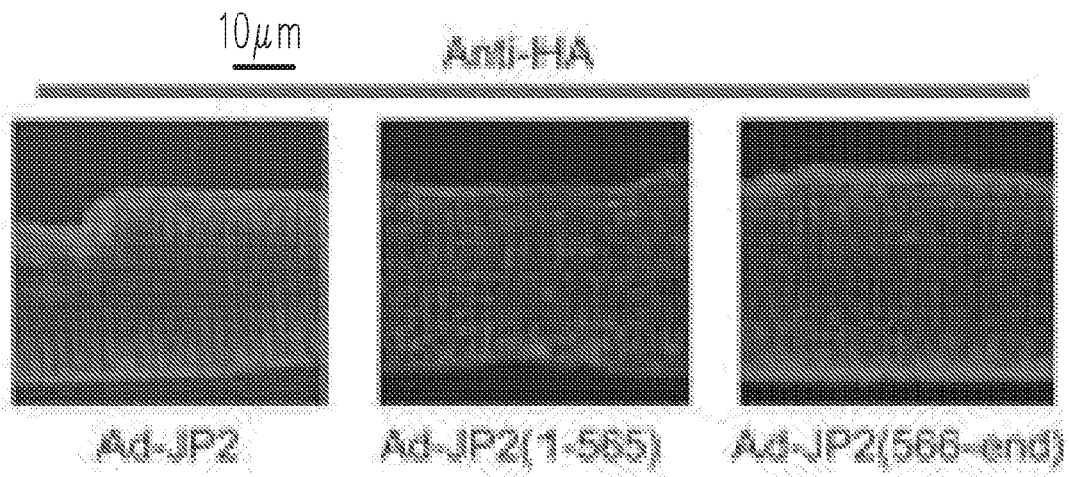
FIGS. 5A-H. JP2 truncations are nonfunctional in regulating $Ca^{2+}$ transients. A) An antibody against the HA tag was used to reveal the localization of adenoviral expression of tagged full-length JP2 and truncations, as indicated, in adult wild-type cardiomyocytes. All the three version of JP2 can be localized in the striated pattern. B) Full-length JP2 and JP2(1-565) forms complexes with RyR2 and Cav1.2 In vivo. An antibody against HA was used for immunoprecipitation (IF). The RyR2 and Cav1.2 that were pulled down were detected by Western blot analysis. Note that full-length JP2 and JP2(1-565) pulled down both RyR2 and Cav1.2, although JP(568-end) does not form complexes with RyR2 or Cav1.2. IB, immunoblot. C) Adenovirus-mediated expression of full-length JP2, FLAG-JP2(1-565)-HA, and JP2(566-end)-HA in JP2-KD) cardiomyocytes. D) Representative steady-state $Ca^{2+}$ transients under 1-Hz field stimulation. The fluorescence intensity (F) of $Ca^{2+}$ imaging was normalized to the baseline (FO). The red lines overlapping on $Ca^{2+}$ imaging show the profile of the moment of $Ca^{2+}$ transient firing on the scanning line in a point-by-point way. A straighter line means better synchronization of the $Ca^{2+}$ transients. Note that expression of full-length JP2, but not JP2 truncations, improves the amplitude and synchronization of $Ca^{2+}$ transients. E-G) Summary of $Ca^{2+}$ transient amplitude, index of desynchronization (mean absolute deviation of firing time), and duration of 50% decay ($T_5$) (n=68, 70, 70, and 52 for Ad-Empty, Ad-JP2, Ad-JP2(1-585), and Ad-JP2(566-end), respectively). Only full-length JP2 Improves the amplitude, synchronization, and decay of $Ca^{2+}$ transients. H) Summary of SR $Ca^{2+}$ content, which was assessed by caffeine-induced SR $Ca^{2+}$ release (n=17, 17, 17, and 12 for Ad-Empty, Ad-JP2, Ad-JP2(1-565), and Ad-JP2 (566-end), respectively). **, $p<0.01$ versus indicated groups; N.S., not significant.
Figure 5B:
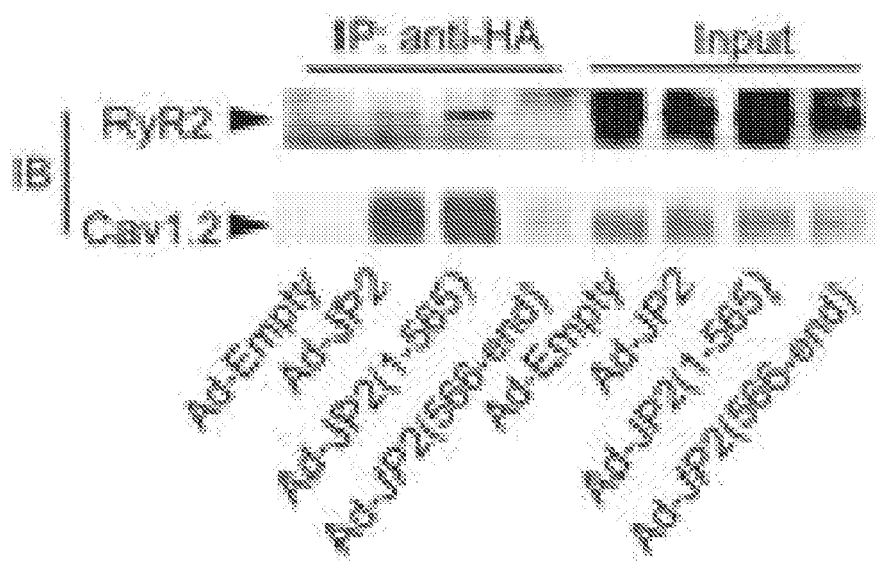

JP2 Fragments Corresponding to the Primary Cleavage Site (Arg-565/Thr-566) have No Effect on Cardiomyocyte $Ca^{2+}$ Handling Cleavage at the primary calpain proteolysis site (Arg-565/Thr-566) splits apart the C-terminal SR-binding TM domain and N-terminal plasma membrane-binding MORN domains of JP2. It is believed that intact JP2 is required for its normal function to tether the plasma membrane and SR together, but it is unknown whether truncated JP2 fragments exert any additional functions on myocyte $Ca^{2+}$ handling. To test this, epitope-tagged (see "Experimental Procedures") full-length JP2 and JP2 truncations corresponding to the primary calpain cleavage site were expressed in cardiomyocytes via adenoviruses. Immunostaining showed the striated pattern of these three versions of JP2 in infected mouse ventricular cardiomyocytes (FIG. 5A), indicating that the two truncations can still be localized to the T-tubule/SR junction via either MORN domains or TM domains, respectively. Coimmunoprecipitation showed that full-length JP2 and JP2(1-565), but not JP2(566-end), interact with RyR2 and Cav1.2 (FIG. 5B), demonstrating that JP2 Interacts with complexes of E-C coupling channels via its N terminus.

Figure 5C:
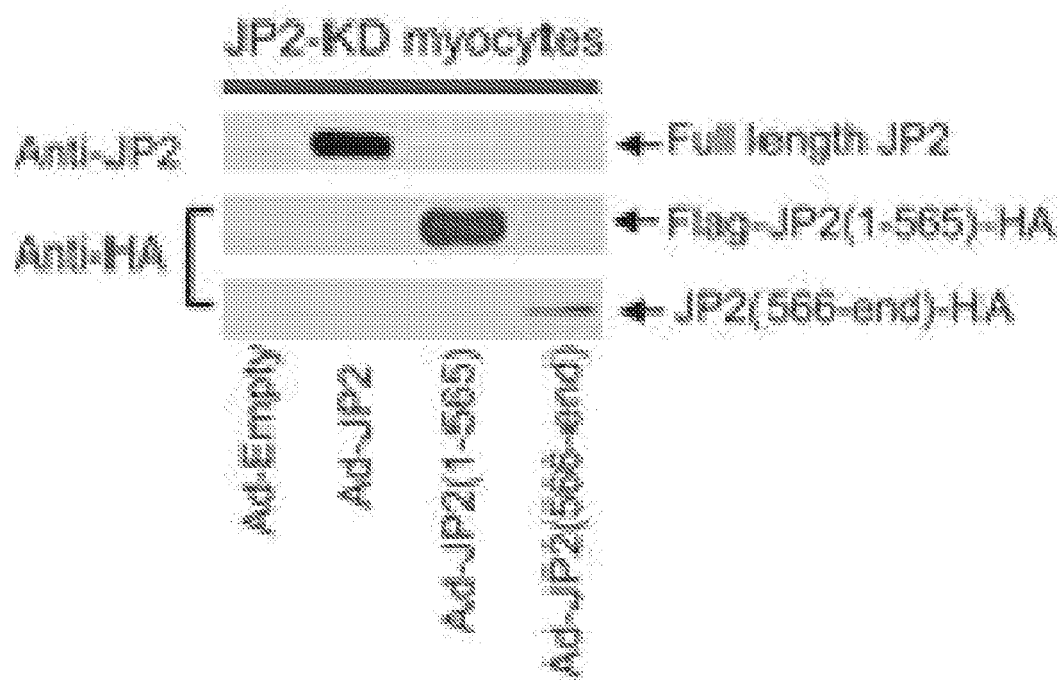
Figure 5D:
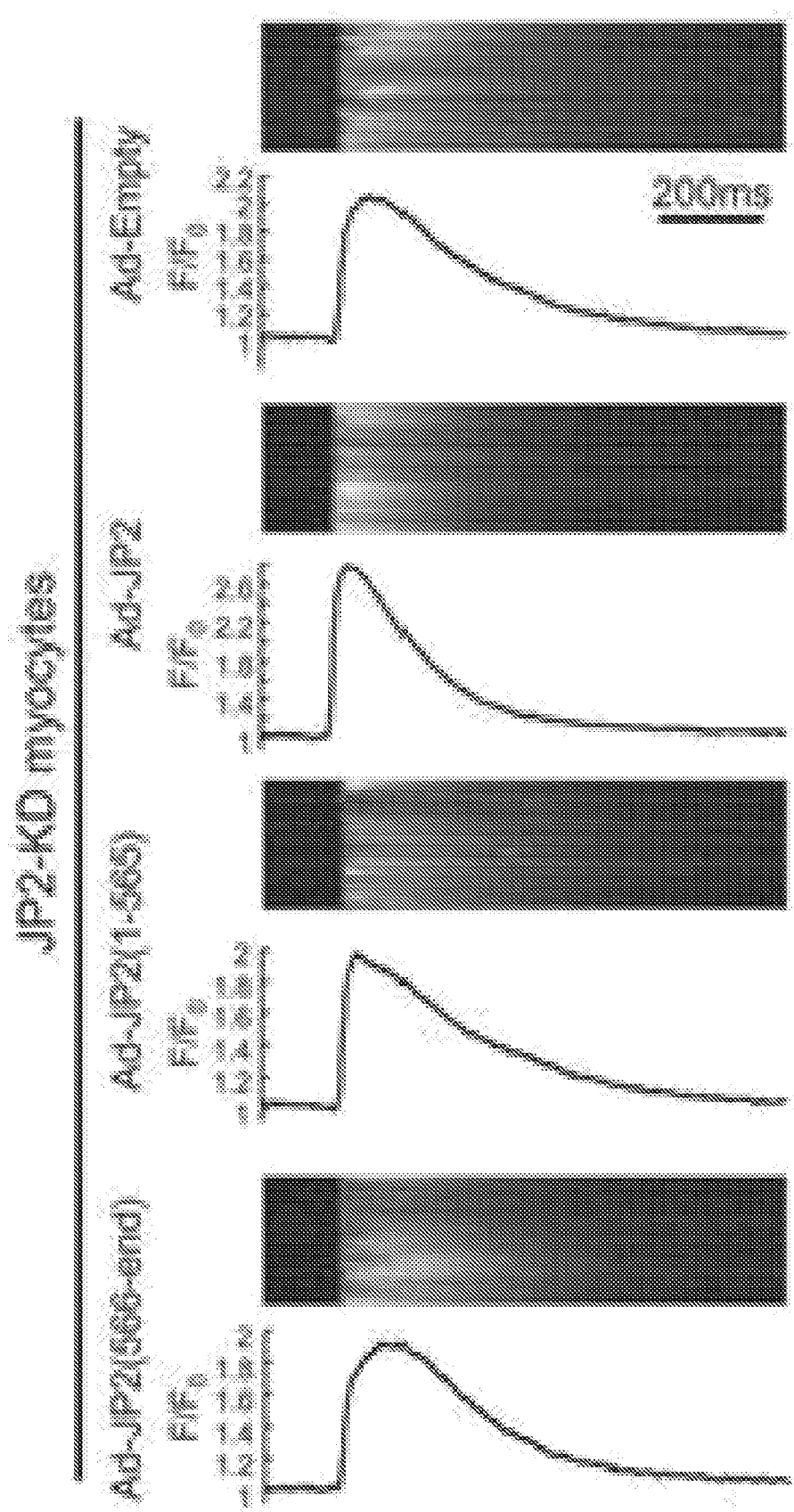
Figure 5E:
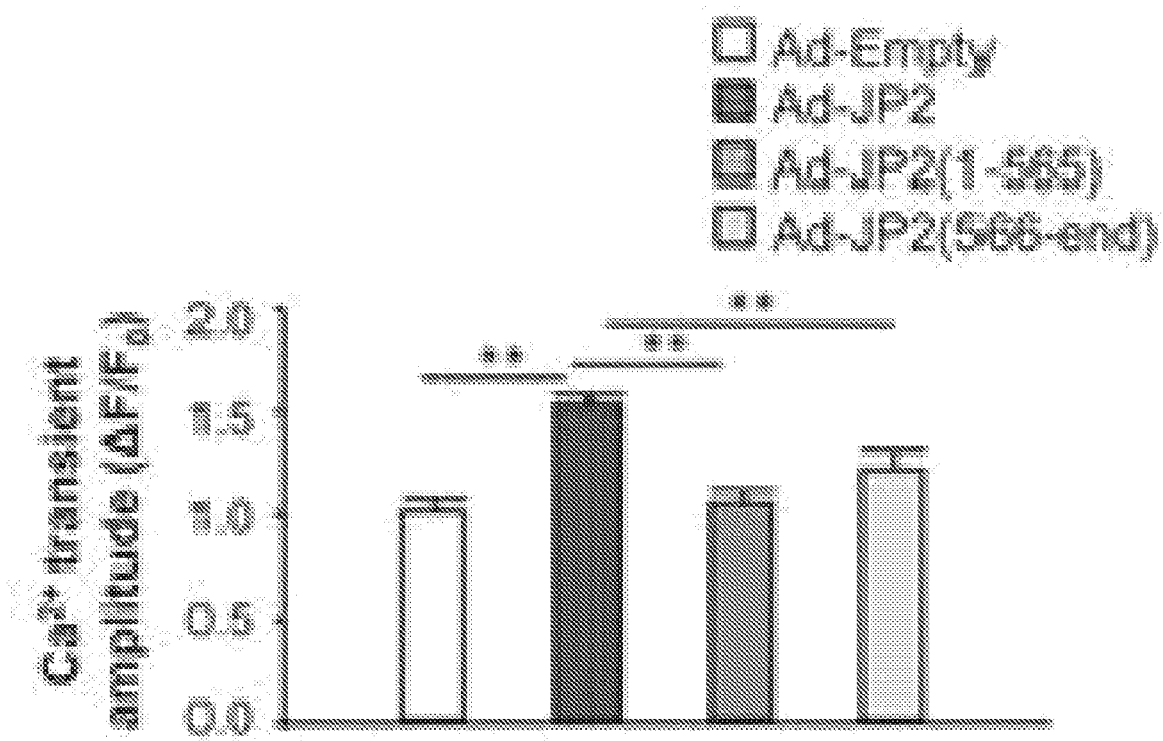
Figure 5F:
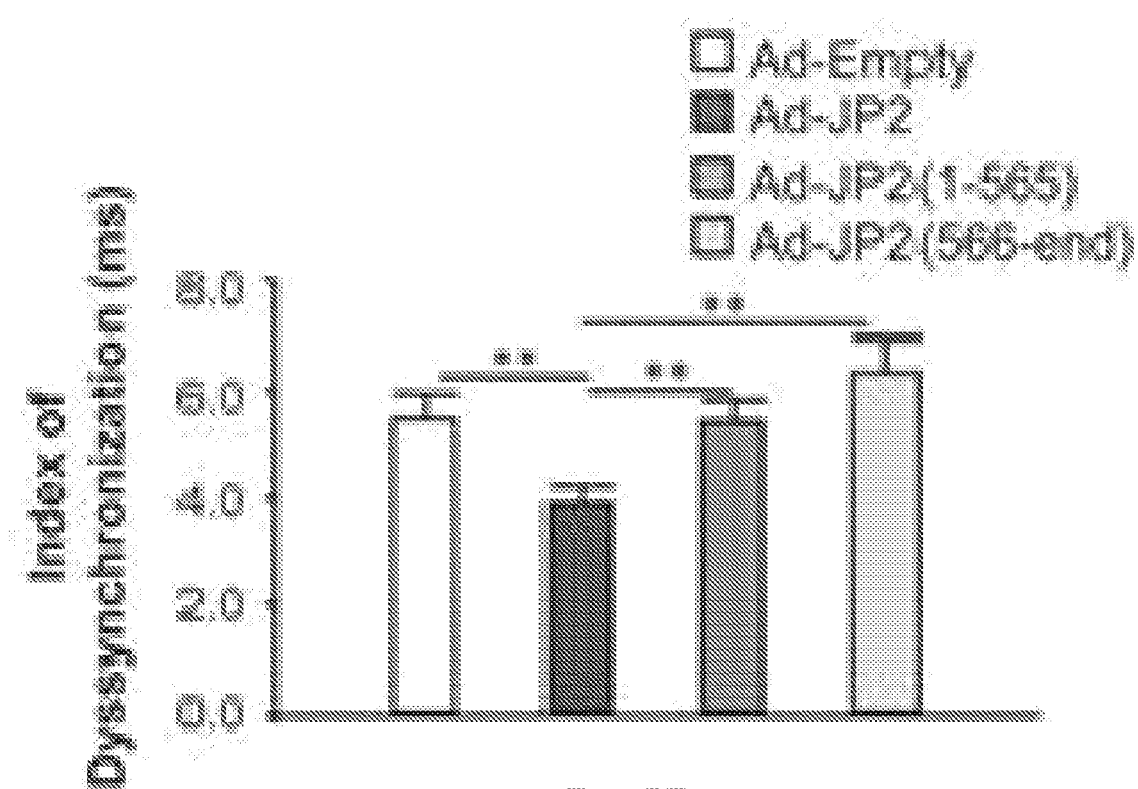
Figure 5G:
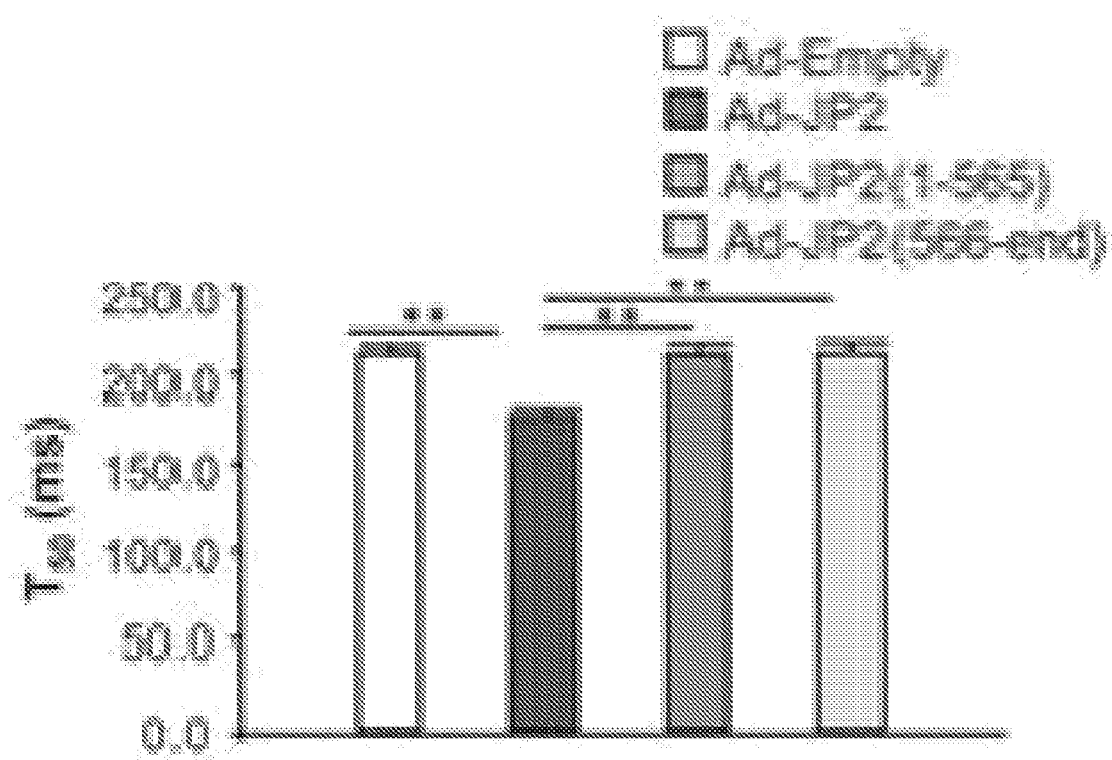
Figure 5H:
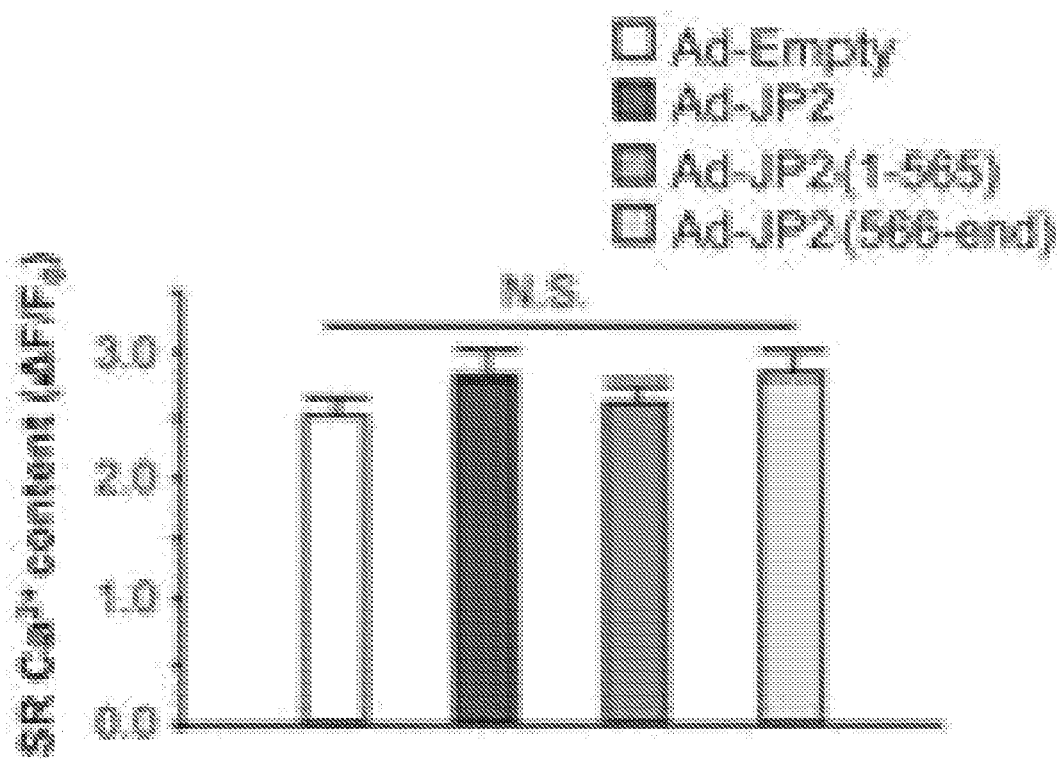
Figure 6A:
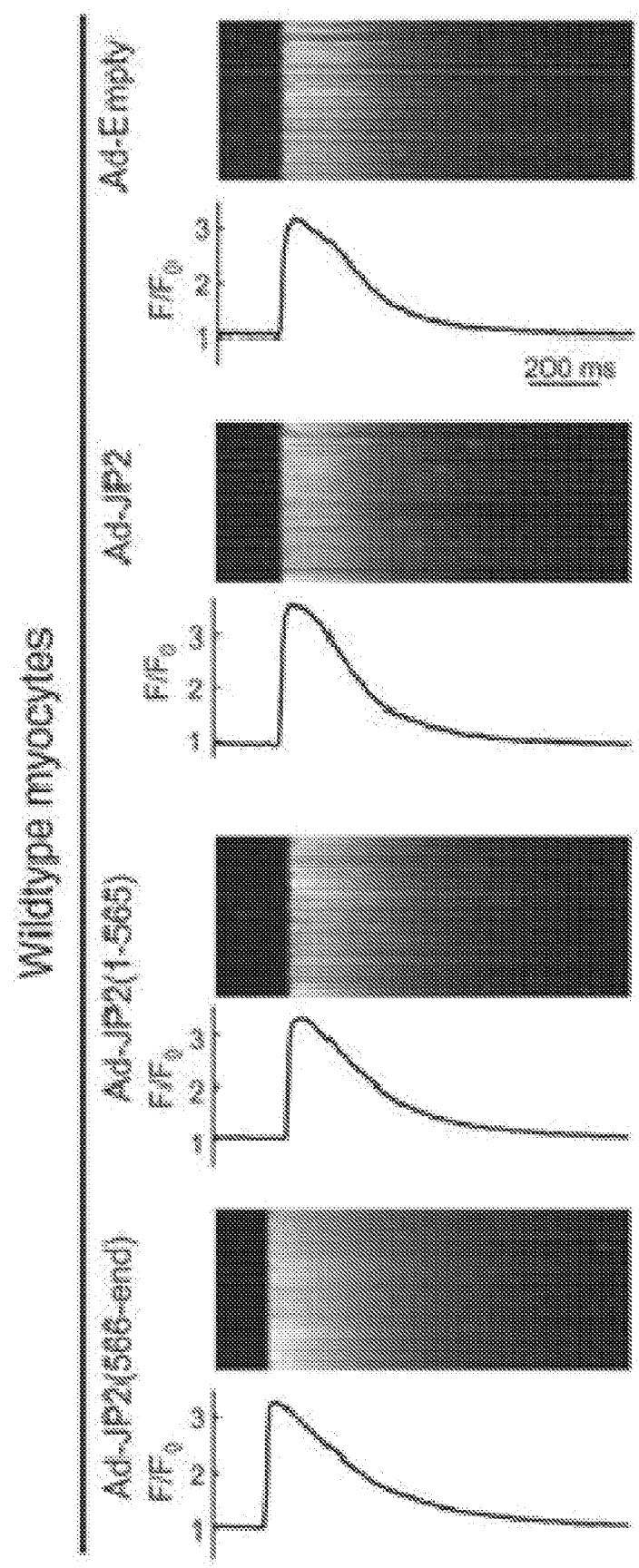
FIGS. 6A-E. JP2 truncations do not have a dominant negative effect on Ca-2 transients in wild-type cardiomyocytes. A) Representative steady-state $Ca^{2+}$ transients under 1-Hz field stimulation. See the legend of FIG. 5 for the definition of the red lines overlapping on $Ca^{2+}$ imaging. B-D) Summary of $Ca^{24}$ transient amplitude, index of desynchronization, and duration of 50% decay ($T_{50}$) (n=51, 52, 51, and 61 for Ad-Empty, Ad-JP2, Ad-JP2(1-565), and Ad-JP2(566-end), respectively). E) Summary of SR $Ca^{2+}$ content, which was assessed by caffeine-induced SR $Ca^{2+}$ release (n=24, 24, 29, and 33 for Ad-Empty, Ad-JP2, Ad-JP2 (1-565), and Ad-JP2(568-end), respectively).
Figure 6B:
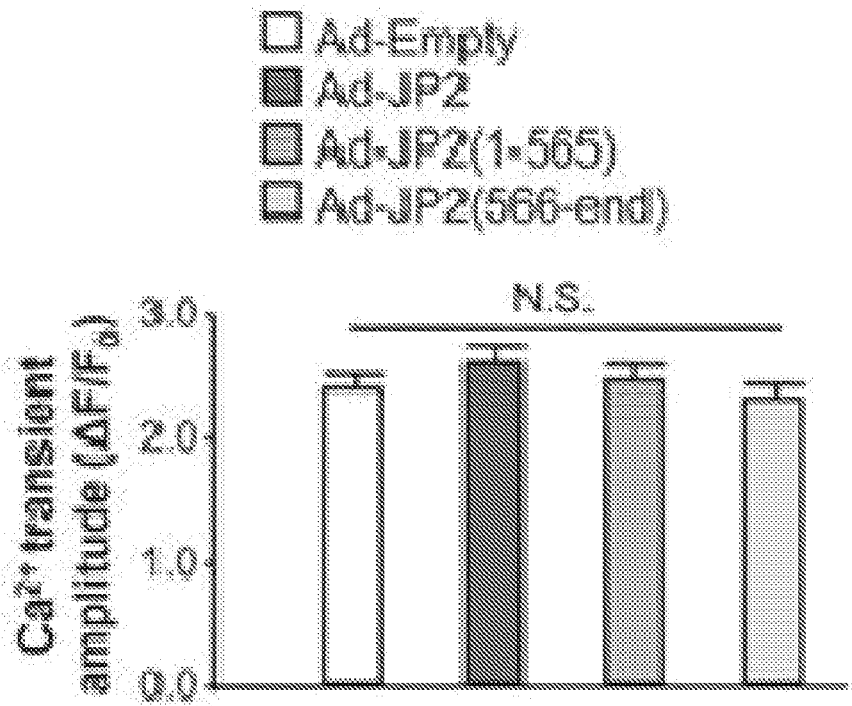
Figure 6C:
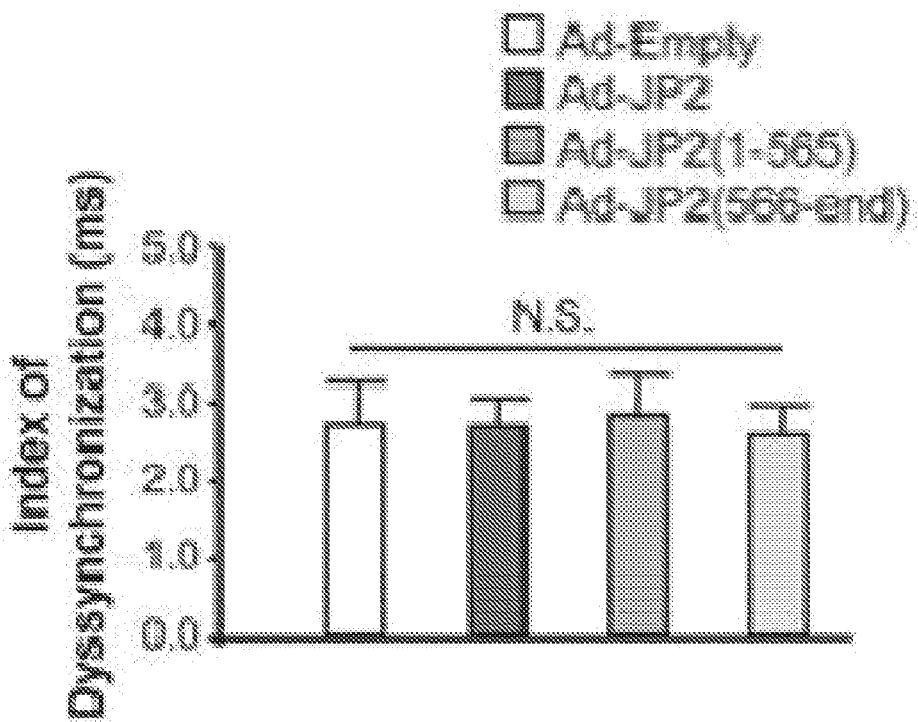
Figure 6D:
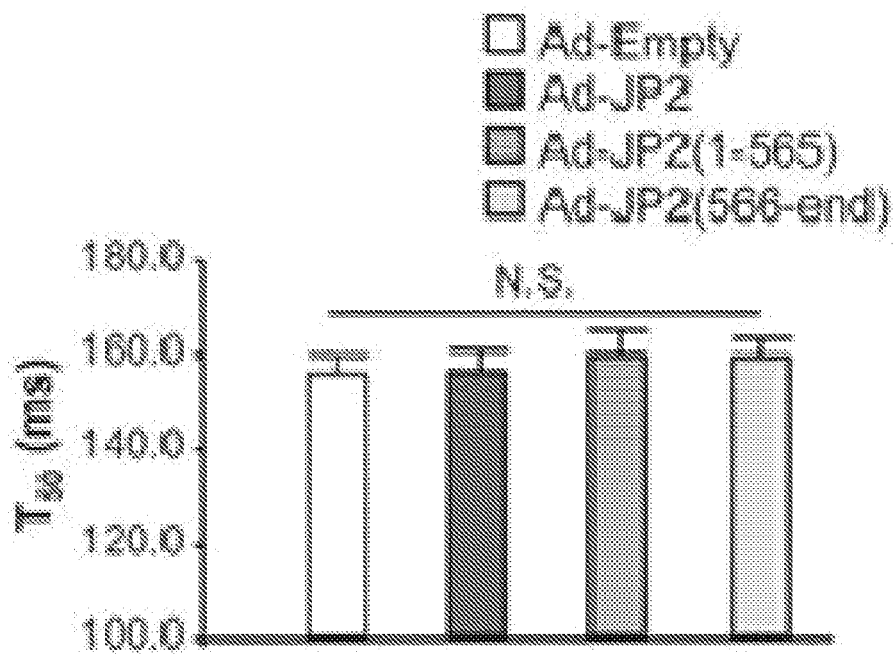
Figure 6E:
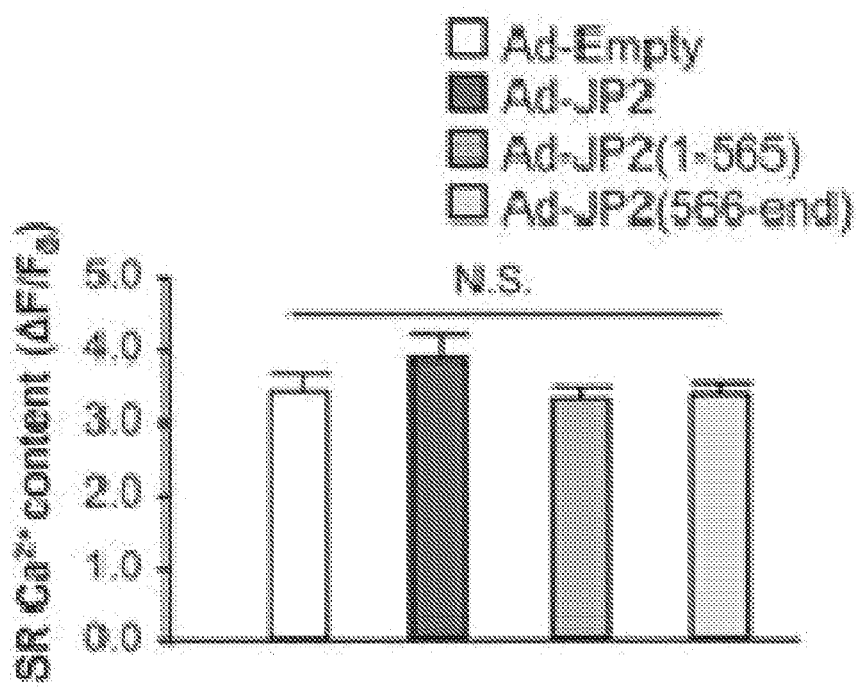

Next the potential role of JP2 truncates on $Ca^{2+}$ handling in cardiomyocytes was evaluated. Epitope-tagged full-length JP2, N-terminal truncation JP2(1-565) and C-terminal truncation JP2(568-end) expressed. In ventricular cardiomyocytes from mice with silenced endogenous JP2 (JP2-KD) (FIG. 5C). Expression of full-length JP2 in JP2-KD cardiomyocytes resulted in a significantly increased amplitude (by 50%) (FIGS. 5D and E), increased synchronization (quantified by the index of desynchronization, FIGS. 5D and F), as well as a shortened decay phase (T50) of $Ca^{2+}$ transients (FIG. 5G). In contrast, expression of JP2(1-565) or JP2(566-end) failed to restore $Ca^{2+}$ transients in JP2-KD cardiomyocytes (FIG. 5, E-G). SR $Ca^{2+}$ content of JP2-KD cardiomyocytes was not influenced by expression of full-length JP2 or JP2 truncations (FIG. 5H). Because JP2(1-585) and JP2(566-end) can still be localized to the striated T-tubule/SR junction, and because JP2(1-565) even interacts with RyR2 and Cav1.2, next it was tested whether these truncations have a dominant negative effect on $Ca^{2+}$ handling in WT cardiomyocytes. The data showed that overexpression of full-length JP2 or truncations from either terminus did not alter the kinetics of steady-state $Ca^{2+}$ transients under 1-Hz field stimulation and SR $Ca^{2+}$ loading in WT cardiomyocytes (FIG. 6). These data indicate that proteolysis of JP2 at the C terminus results in E-C coupling dysfunction.

Discussion

These data reveal, for the first time, the molecular determinants responsible for posttranslational calpain proteolysis of JP2, providing a molecular mechanism of JP2 down-regulation following cardiac injury. Sequence prediction of calpain cleavage sites identified several putative sites, three of which we confirmed by mutagenesis. The data suggest that C-terminal calpain cleavage of JP2 may be a prerequisite for proteolysis at N-terminal sites. It was found that neither N-terminal nor C-terminal truncations of JP2 are sufficient to restore $Ca^{2+}$ transients in cardiomyocytes in which endogenous JP2 has been knocked down. These data provide important insights into JP2 regulation in cardiomyocyte E-C coupling and may explain, in part, the significant cardiac phenotype associated with loss of JP2 in vivo and the protective effect of calpain inhibition (Li et al., 2011; Chen et al., 2001).

It has been reported that JP2 is required for maintaining T-tubule structural integrity in adult hearts (van Oort et al., 2011; Wei et al., 2010). More recently, JP2 was identified as an essential factor in T-tubule and E-C coupling maturation during development (Minamisawa et al., 2004). In another study, overexpression of JP2 was found to attenuate the transition from hypertrophy to heart failure, suggesting its significance as a potential therapeutic target (Guo et al., 2014). JP2 protein down-regulation has been observed in failing human hearts as well as multiple animal models of cardiac disease (Landstrom et al., 2011; Chen et al., 2012; Guo et al., 2013; Minamisawa et al., 2004; Wei et al., 2010; Xu et al., 2012; Xu et al., 2007; V W et al., 2014; Murphy et al., 2013; Zhang et al., 2013; Li et al., 2013). This loss of JP2 is associated with alterations in T-tubule ultrastructure and E-C coupling dysfunction, thereby contributing to the development of heart failure (van Oort et al., 2011; Chen et al., 2013; Landstrom et al., 2011; Xu et al., 2012). To date, miR-24-mediated translational repression and $Ca^{2+}$-dependent proteolysis have been implicated mechanistically in JP2 down-regulation (Xu at al., 2012; Song et al., 2012; Murphy et al., 2013; Li et al., 2013). The present data extend these latter findings by identifying calpain as the JP2 protease. Moreover, we define the molecular determinants of JP2 proteolysis and provide evidence for this mechanism in an animal model of cardiac stress.

Previous reports have suggested two mechanisms by which JP2 regulates E-C coupling. First, JP2 acts as a physical bridge between the T-tubule and SR membranes to maintain normal $Ca^{2+}$ handling in cardiomyocytes (van Oort et al., 2011; Chen et al., 2013). Second, JP2 has been shown to interact with RyR2 and Cav1.2 and regulate their gating function (van Oort et al., 2011; Golini et al., 2011). The data suggest that down-regulation of JP2 results in E-C coupling dysfunction primarily through disrupting the junctional complex. Specifically, it was found that the N-terminal truncation fragment of JP2 interacts with RyR2 and Cav1.2 but is not sufficient to restore $Ca^{2+}$ transients in JP2-KD cardiomyocytes. These data provide compelling evidence that full-length JP2 is required for normal E-C coupling function. Taken together, the study provides novel molecular insights into the structure and function of JP2 in cardiomyocytes.

Example 2

As described above, calpain protease primarily cleaves at the site Arg-565/Thr-566 of Junctophilin-2. This produces a shorter form of Junctophilin-2 including the first 565 amino acids of N-terminus of JP2 (noted as JP2(1-565) or JP2NT). A NLS was found in JP2 and JP2NT, e.g., KRPRP. A potential DNA binding domain was found in JP2 and JP2NT, e.g., KRRVLPLKSSKVRQKVEHGVEGAQRAAAIARQ-KAEIAASRTSHAKAKAEAAEQAALAA (SEQ ID NO:16, in human JP2, the correlate is KRRMLQLKSNKVRQKVEHSVEGAQRAAAIARQ-KAEIAASRTSHAKAKAEAAEQAALAA; SEQ ID NO:17) When the C-terminal transmembrane domain of JP2 was proteolytically removed, the NLS imported the C-terminal truncations of JP2 into the nucleus. Moreover, overexpression of JP2NT alters gene transcriptional profile in cardiomyocytes as revealed by microarray.

Figure 9A:
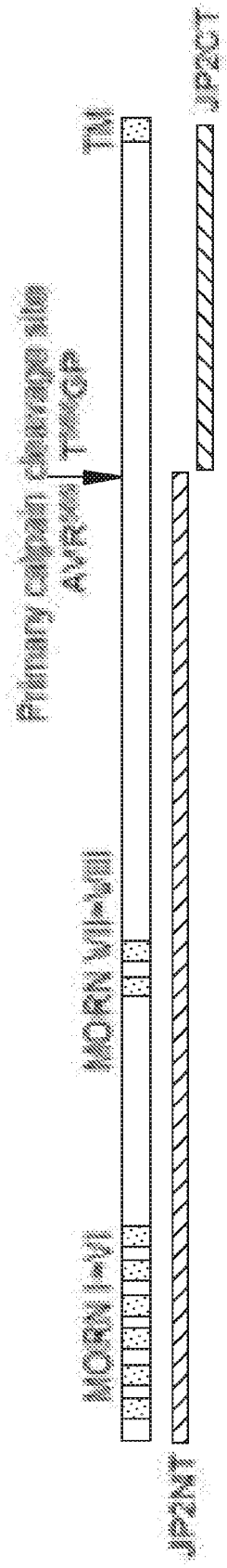
FIGS. 9A-J. JP2 N-terminal truncate (JP2NT) accumulates in the nucleus of stressed hearts. A) Schematic of JP2 and JP2 truncates. B) JP2NT is primarily present in nuclear fractions of murine heart lysates. H3; Histone H3. C) Increased endogenous JP2NT in soluble (Nu-S) and chromatin-containing (chromatin) nuclear fractions from calpain-overexpressing (OE) hearts. The Nu-S fraction was derived by treatment with micrococcal nuclease (MNASE), which cleaves DNA and releases chromatin-associated proteins. D) & E) Increased endogenous JP2NT levels in chronic cardiac stress models: D) isoproterenol (ISO, 1 week) minipump infusion; E) myocardial infarction (MI, 1 week). Calpain inhibitor MDL-28170 attenuated the elevation of nuclear JP2NT in both models. n≥3 for each group; *$p<0.05$; **$p<0.01$. F-J) Analysis of JP2NT nuclear localization using the rapamycin-inducible split tobacco etch virus protease (sTEVp) system. F) Schematic of the sTEVp system. The N- and C-terminal fragments of TEV protease were fused to FRB and FKBP12, respectively. Rapamycin induces reconstitution of TEV protease through the FKBP-rapamycin-FRB complex. A TEVp substrate recognition sequence (TRS) was inserted into the primary calpain cleavage site (Rm/Tw) of JP2 (eGFP-JP2TRS), allowing for inducible and site-specific rapid cleavage of substrates at the TRS. b-e, eGFP-JP2TRS was transfected into 293T cells alone (G, 1) or with sTEVp system (H, J), followed by treatment with DMSO control (G, H) or rapamycin (100 nM) for 1 hr (I, J).

A transgenic mouse line with cardiac specific overexpression of an exogenous protein sequence corresponding to JP2NT was prepared. JP2NT (JP2(1-565)) transgenic mice were generated based on a tet-off system. The Flag and HA tagged JP2NT cDNA was cloned downstream of tet-operated alpha-MHC promoter, enabling the cardiac specific and conditional expression of JP2NT (FIG. 9A). The plasmid (αMHC-JP2NT) was delivered by pronuclear injection into fertilized eggs to make transgenic founders. The transgenic mouse lines were backcrossed to C57 background for 9 generations. αMHC-JP2NT mice have been crossed with αMHC-tTA mice to generate double transgenic αMHC-tTA-JP2NT mice (noted as JP2NT OE mice). This allows for inducible and cardiac-specific expression of JP2NT, in which tTA binds to tet-operon and activates transcription of JP2NT. Thus, the expression and nuclear localization of JP2NT in transgenic mice have been confirmed. Moreover, these mice were found to be resistant to Angiotensin-li induced cardiac hypertrophy and pressure overload induced heart failure.

JP2NT binds to chromatin. In particular amino acids 330-400 (344-402 in SEQ ID NO:3 of murine JP2 (KRRVLPLKSSKVRQKVEHGVEGAQRAAAIARQ-KAEIAASRTSHAKAKAEAAEQAALAA; SEQ ID NO:16) represent a potential DNA binding domain. The data (see below) showed that this domain allows for chromatin or DNA binding of JP2NT. A series of JP2 truncations or mutants were transfected into 293 cells. The nuclei were isolated and the insoluble nuclear fraction, which represents chromatin, was extracted. Micrococcal DNASE (MNASE) was used to digest the DNA and solubilize the DNA/Chromatin binding proteins. Western blot showed that JP2NT is in the insoluble nuclear fraction and can be released into soluble fraction by MNASE treatment, indicating it is a chromatin associated protein. In addition, depletion of the DNA binding domain abolished the presence of JP2NT in the insoluble nuclear fraction, indicating this region is important for the DNA or chromatin binding of JP2NT. In vitro gel shift assay with purified JP2NT showed that JP2NT directly binds to DNA sequence of MEF2 binding site.

The DNA binding sites of JP2NT were also identified on a genome scale. Chromatin immunoprecipitation (CHIP) experiments were performed and the DNA fragments pulled down by JP2NT were sequenced. Genome wide DNA intervals were revealed by sequencing. These DNA intervals cover more than 10,000 genes. More importantly, most of these DNA sites are around transcription start sites of protein coding genes, providing a mechanism of transcription regulation by JP2NT Example 3

Methods
Animal Experiments

Animal experiments were performed in accordance with the Guide for the Care and Use of Laboratory Animals (National Institutes of Health publication 85-23, revised 1996) and were approved by the Institutional Animal Care and Use Committee at the University of Iowa. Cardiac specific JP2NT overexpression vector was constructed by subcloning mouse JP2NT cDNA (Guo et al., 2015) into a tet-operated αMHC transgenic vector, as described previously (Guo et al., 2014). The oocyte injection of transgenic vectors was carried out by University of Iowa transgenic core. The injected oocytes were transferred to pseudopregnant recipients. Transgenic offsprings were backcrossed with C57BL/6J mice for >9 generations to generate transgenic mice in a C57BL/6J background. These transgenic mice were crossed with αMHC-tTA (C57 background) (Guo et al., 2014) to generate double transgenic mice (JP2NT-OE) carrying both αMHC-JP2NT and αMHC-tTA. The non-overexpression single transgenic littermates were used as control. PCR was used to determine the genotype of transgenic mice. Nine to 10-wk-old male JP2NT-OE mice and their control littermates were subjected to pressure overload by transaortic banding (TAB) surgery, as described (Guo et al., 2014). Transthoracic echocardiograms were performed with conscious mice in the University of Iowa Cardiology Animal Phenotyping Core Laboratory, using a Vevo 2100 Imager (Visual Sonics), as described previously (Cheng et al., 1993).

Molecular Cloning, Mutagenesis, Adenovirus Construction

The strategy of molecular cloning and mutagenesis was the same as described in Guo et al. (2015). The sTEVp system were adopted from the work of Ikeda Lab (Williams et al., 2009). pBV-LUC vector was used to construct firefly reporters under the control of promoters specified in the paper. MRE-firefly reporter was described previously (Wysocka et al., 2001). SV40-reniulla reporter (pGL4.73) was from Promega. Adenoviruses carrying full-length JP2 (Ad-JP2). JP2NT (Ad-JP2NT). JP2NT$^{\Delta NLS}$, JP2NT$^{\Delta bNLS\Delta\Delta ARR}$ (JP2NTΔ(345-402)) or empty virus were produced by University of Iowa Gene Transfer Vector Core.

Protein Fractionation and Western Blotting

Ultracentrifuge based protein fractionation was performed following the protocol described previously (van Berlo et al., 2013). For some experiments, the soluble nuclear fraction (Nu-S) was separately extracted using nuclear extraction buffer (NEB) from the Tissue subcellular fractionation kit of Thermo Scientific, and the remaining insoluble fraction was subjected to MNASE digestion for chromatin fraction extraction. In some experiments, the whole nuclear fraction was harvested using RIPA and sonicated to include both soluble fraction and chromatin fraction in the same sample. The antibody used for detecting JP2NT was from Santa Cruz (H250, sc-134875). Antibodies against type 2 ryanodine receptors (Thermo Scientific), voltage-gated L-type Ca$^{24}$ channels (Alomone Labs), Pol II (Cell Signaling), TBP (Cell Signaling), MEF2C (Cell Signaling), Myc tag (DSHB Hybridoma Product 9E 10), HA tag (Santa Cruz) and GAPDH (Sigma-Aldrich) were used to specifically label the proteins of interest. HRP-linked anti-Mouse IgG (1:5,000), anti-Goat IgG (1:5,000), and anti-rabbit IgG (1:10,000) were used to visualize bound primary antibodies with the ECL substrate (GE).

Adult Cardiomyocyte Culture, Cell Transfection and Adenovirus Infection

Genecarrier-1 (Epoch Lab) was used to transfect plasmids into HEK293T cells. Isolation and culture of cardiomyocytes were performed as described previously (Guo et al., 2015). Adenoviruses were applied at a multiplicity of infection (MOI) of about 100, which results in transfection of almost all cells as confirmed by immunostaining of eptiope tags.

Luciferase Assay

Firefly and Renilla reporter plasmids and JP2NT variants were co-transfected into HEK293 cells. The protein of the cells was harvested 48 hours after transfection. Promega dual luciferase system was used to evaluate the luciferase activity.

Crosslinking Reversal Co-IP

Cells were first crosslinked by 1% formaldehyde for 10 minutes at RT before quenching by 0.75 M Tris. After washing with PBS, cells were lysized using RIPA buffer and sonication was applied to breakdown chromatin and shear DNA. Anti-HA resin (sigma) was used to pull down HA tagged protein complexes. The pulled-down protein complexes were boiled at 95° C. for 10 minutes to reverse the formaldehyde induced crosslinking between proteins. Western blot was used to assay the presence of bait and prey proteins.

RNA Extraction

RNA of cultured cardiomyocytes was extracted using RNAeasy (Qiagene). Myocardium RNA was extracted using Trizol. Total RNA was treated with DNASE-I to eliminate genomic DNA and then cleaned using RNA cleanup Kit (Qiagene).

RT-PCR

Superscript II were used for Reverse Transcription of mRNA. A QUANT STUDIO 3 real-time PCR machine was used to run qPCR. The primers used in RT-PCR were:

```
Gapdh
CATTTCCTGGTATGACAATGAATACG    (SEQ ID NO: 18)

TCCAGGGTTTCTTACTCCTTGGA       (SEQ ID NO: 19)

Myc
TGA AGG CTG GAT TTC CTT TG    (SEQ ID NO: 20)

TTC TCT TCC TCG TCG CAG AT    (SEQ ID NO: 21)

Ikbkg
AAG CAC CCC TGG AAG AAC C     (SEQ ID NO: 22)

CCT GCT CTG AAG GCA GAT GTA   (SEQ ID NO: 23)

Tgfbr1
TCTGCATTGCACTTATGCTGA         (SEQ ID NO: 24)

AAAGGGCGATCTAGTGATGGA         (SEQ ID NO: 25)

KLF4
ATCCTTTCCAACTCGCTAACCC        (SEQ ID NO: 26)

CGGATCGGATAGCTGAAGCTG         (SEQ ID NO: 27)

Myocardin
GATGGGCTCTCTCCAGATCAG         (SEQ ID NO: 28)

GGCTGCATCATTCTTGTCACTT        (SEQ ID NO: 29)

Nfkbia
TGAAGGACGAGGAGTACGAGC         (SEQ ID NO: 30)

TTCGTGGATGATTGCCAAGTG         (SEQ ID NO: 32)

Klf6
GTTTCTGCTCGGACTCCTGAT         (SEQ ID NO: 33)

TTCCTGGAAGATGCTACACATTG       (SEQ ID NO: 34)

IRS1
CGATGGCTTCTCAGACGTG           (SEQ ID NO: 35)

CAGCCCGCTTGTTGATGTTG          (SEQ ID NO: 36)

FOXO1
CCCAGGCCGGAGTTTAACC           (SEQ ID NO: 37)

GTTGCTCATAAAGTCGGTGCT         (SEQ ID NO: 38)

PIK3R1
ACACCACGGTTTGGACTATGG         (SEQ ID NO: 39)

GGCTACAGTAGTGGGCTTGG          (SEQ ID NO: 40)

FGFR1
TAATACCACCGACAAGGAAATGG       (SEQ ID NO: 41)

TGATGGGAGAGTCCGATAGAGT        (SEQ ID NO: 42)

CREBBP
GGCTTCTCCGCGAATGACAA          (SEQ ID NO: 43)

GTTTGGACGCAGCATCTGGA          (SEQ ID NO: 44)

RhoG
GCGCACCGTGAACCTAAAC           (SEQ ID NO: 45)

GTGGACTGGCAATGGAGAAAC         (SEQ ID NO: 46)

BNP
GTCTTGGCCTTTTGGCTTC           (SEQ ID NO: 47)

TTCCTCAGTCTGCTCACTC           (SEQ ID NO: 48)

ANP
AGGAGAAGATGCCGGTAGAAGA        (SEQ ID NO: 49)

GCTTCCTCAGTCTGCTCACTCA        (SEQ ID NO: 50)
```

Immunofluorescence and Confocal Imaging

Immunofluorescence was done as described previously (Guo et al., 2015). A Zeiss confocal microscope LSM510 was used for recording cell images.

Microarray

Microarray assay was performed by Affymetrix GeneChip® Mouse Genome 430 2.0 according to the standard procedure of cRNA preparation and Genechip hybridization. The R package limma (version 3.22.7) (Ritchie et al., 2015) was used for processing microarray data and identifying differentially expressed genes (the cutoff of significance was p value<0.01). David (Huang et al., 2009) was used for gene enrichment (GO) analysis. Ingenuity pathway analysis (IPA, Qiagen) was used for pathway analysis.

ChIP-Seq

ChIP-seq from transgenic myocardium was performed using the antibody against HA-tag, which pulls down the HA-tagged JP2NT. Sequencing libraries were prepared for the pulled-down DNA and input DNA (randomly fragmented genomic DNA), and then were subjected to Illumina sequencing (NextSeq 500 platform, 75 bp single end reads). The quality of sequencing reads was evaluated by FastQC (version 0.11.3) software (http://www.bioinformatics.babraham.ac.uk/projects/fastqc/) and the sequencing adaptor was trimmed by Cutadapt (version 1.8.1) software (Martin, 2011). Processed sequencing reads were aligned to mouse genome (mm10) by Bowtie 2 (version 2.2.5) software (Langmead et al., 2012) with the "-end-to-end" mode. MACS (version 1.4.2) software (Langmead et al., 2012) was used to call enriched peaks (the cutoff of significance was p value<1e-10). Homer (version 4.8.3) software (Heinz et al., 2010) was used to analyze the enriched genomic features of peaks, identify the target genes, and search the binding motifs.

RNA-Seq

Illumina TruSeq Stranded mRNA Library Prep Kit was used to prepare the sequencing library for myocardium samples. Sequencing was performed by Illumina HiSeq 2500 platform (2×125 bp paired-end). Kallisto (0.42.5) software (Bray et al., 2016) was used to quantify transcript abundance of mouse transcriptome (Grcm38). Sleuth (0.28.1) software (Pimentel et al., 2018) was used to investigate the differential expression of transcripts between groups (the cutoff of significance was p value<0.01).

Results

Nuclear Localization of JP2NT

Figure 9C:
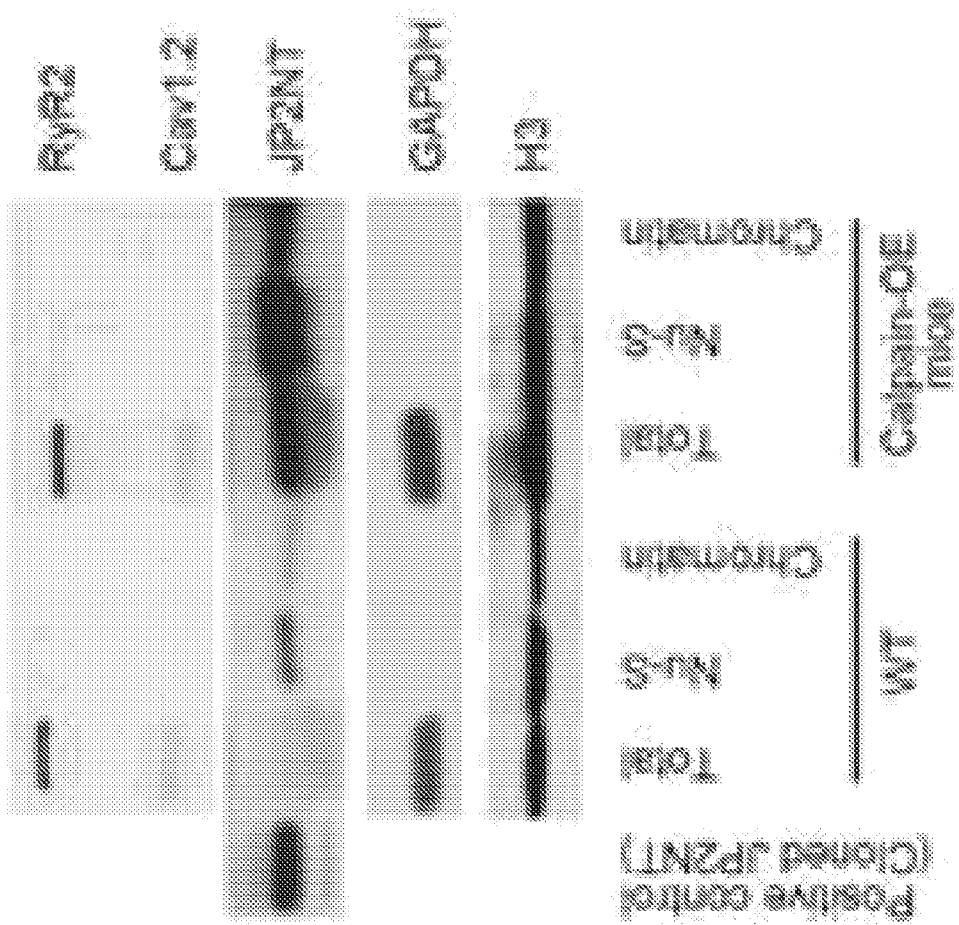
Figure 9B:
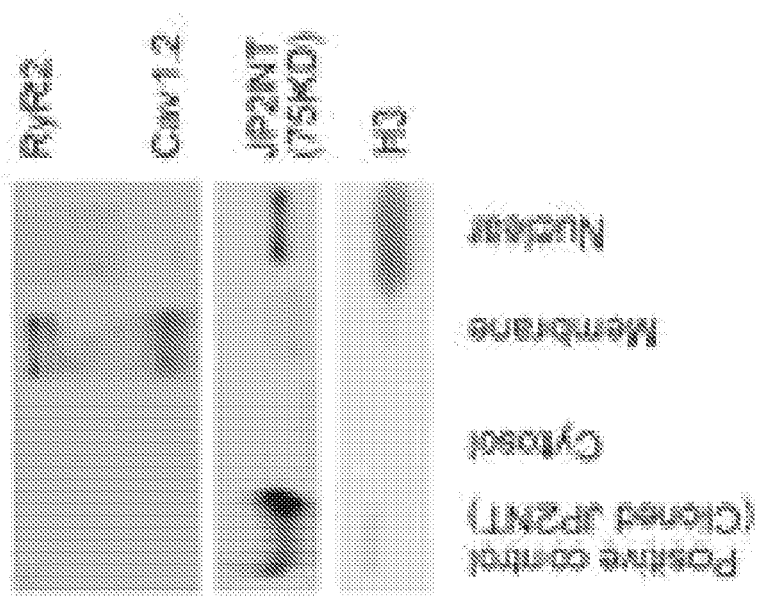
Figure 15A:
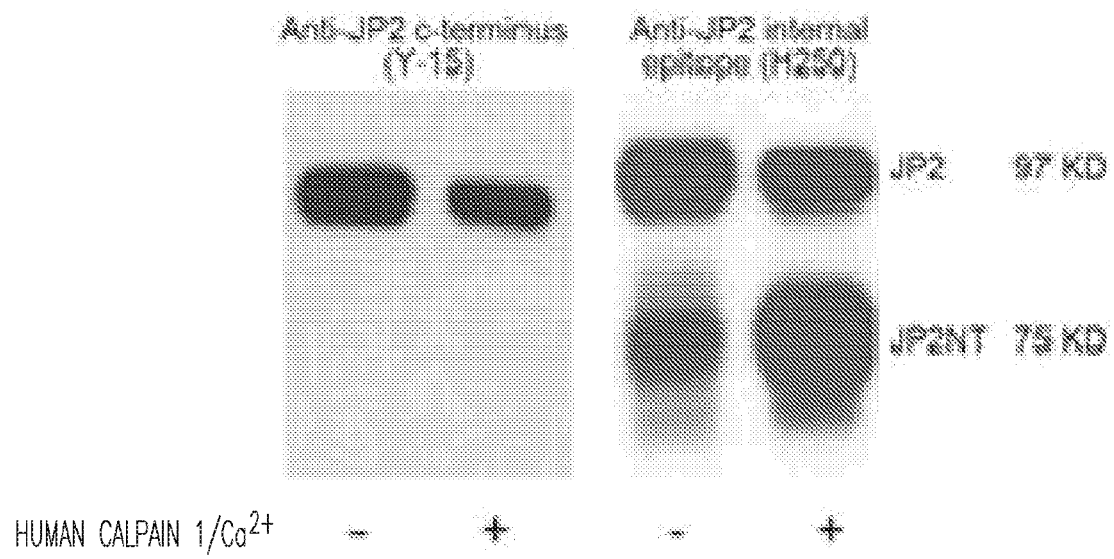
FIGS. 15A-D. A) An antibody against the internal epitope of JP2 (H250) detected both full-length JP2 and JP2NT induced by in vitro calpain cleavage. The same proteolysis reaction product was blotted by antibody again the C-terminus of JP2 (Y-15). This antibody did not detect cleaved product (JP2NT). B)-C), fractionation of myocardium of chronic cardiac stress models: B) isoproterenol (ISO, 1 week) minipump infusion; C) myocardial infarction (MI, 1 week). Note the increased endogenous JP2NT levels in nuclear fraction. D). Immunostaining of ventricular heart sections using the antibody against internal episode of JP2 (H250) detected a JP2 product in nuclei, which was observed more frequently under stressed conditions (a, ISO infusion in mice; b, MI in mice; c, human heart sections from healthy donors or patients with MI). Red arrows denote the presence of JP2(NT) in nuclei. N=3 hearts per group.
Figure 15B:
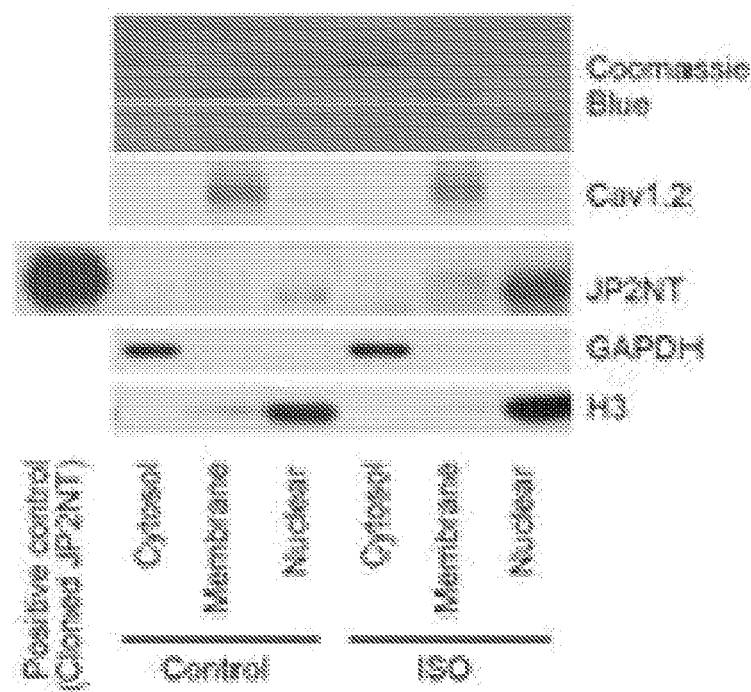
Figure 15C:
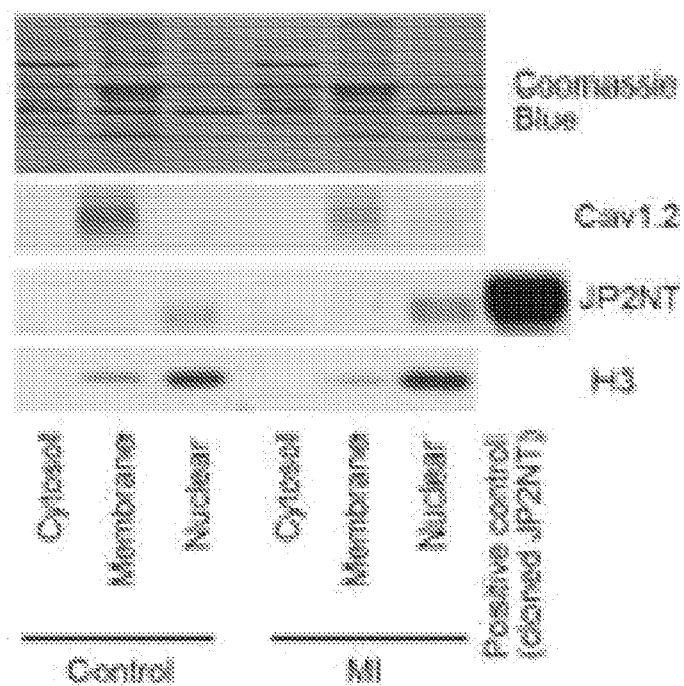
Figure 15D:
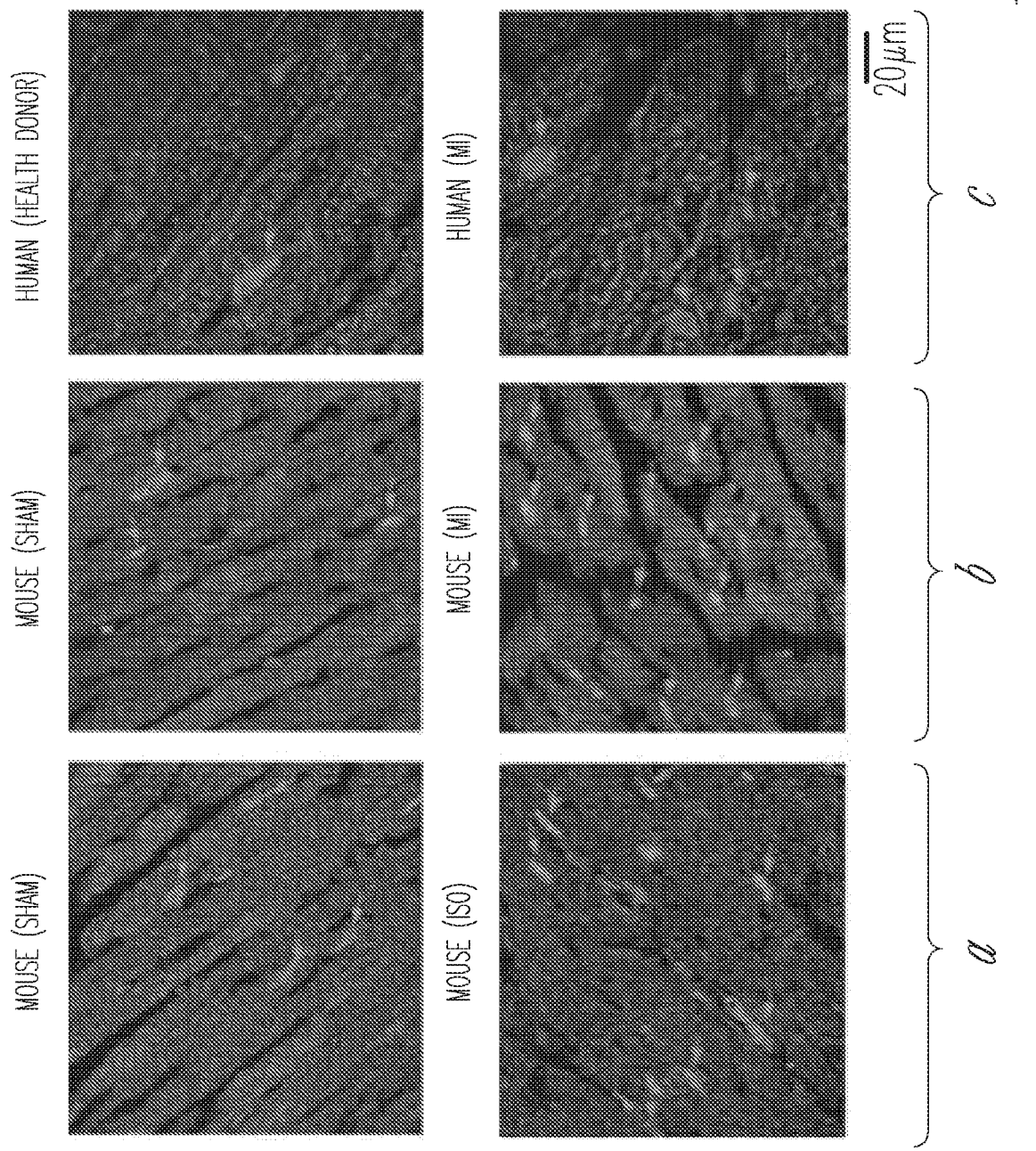

JP2 is a substrate of calpain, and the primary calpain proteolysis site in the C-terminal region of JP2 between residues R565/T568 (Example 1; Guo et al., 2015). Calpain cleavage creates an N-terminal truncate (residues 1-565, termed "JP2NT") that contains the plasma membrane-binding MORN motifs, and a C-terminal fragment containing the SR membrane anchoring TM domain (FIG. 9A). Western blotting was performed with an antibody against an internal epitope of JP2, which is not destroyed by calpain cleavage of JP2 (FIG. 15A). Analysis of subcellular fractions of mouse myocardium established that endogenous JP2NT (75 KD) is present and predominantly enriched in nuclear fractions (FIGS. 9B and 15B-C). Immunostainings of human and mouse myocardium sections using the same antibody also detected a JP2 product in nuclei (denoted by arrows in FIG. 15D). JP2NT was dramatically increased in myocardium from mice with cardiac-specific overexpression of calpain 1, and enriched in the nuclear fraction (FIG. 9C) (for calpain-OE mice, see Galvez et al. (2007)). In addition, treatment with micrococcal nuclease (MNASE), which cleaves DNA and releases chromatin-associated proteins, released JP2NT from the chromatin pellet into the soluble nuclear fraction (FIG. 9C), substantiating the nuclear localization of endogenous JP2NT in vivo and also suggesting that JP2NT is a chromatin-associated protein.

Figure 9D:
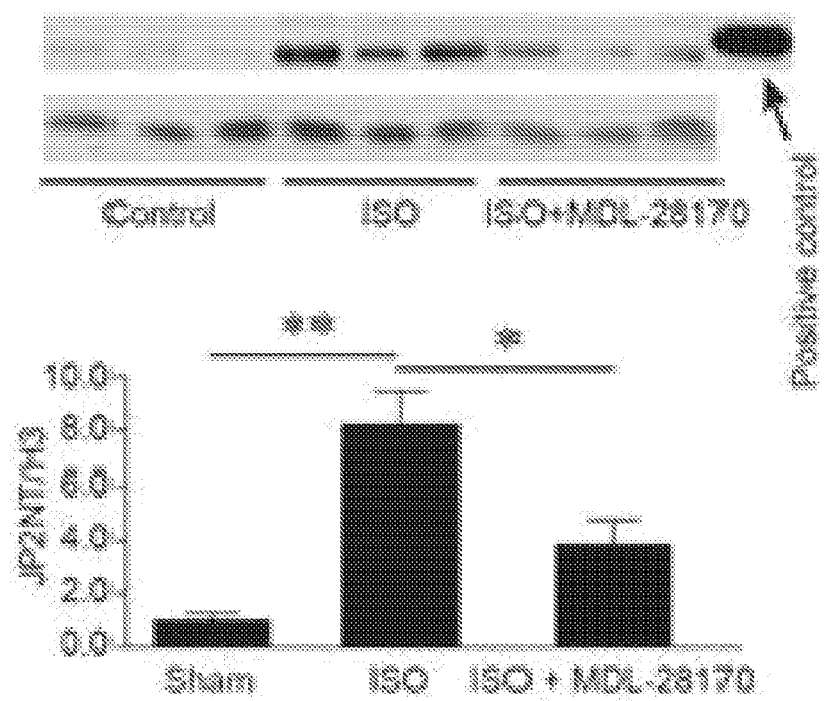
Figure 9E:
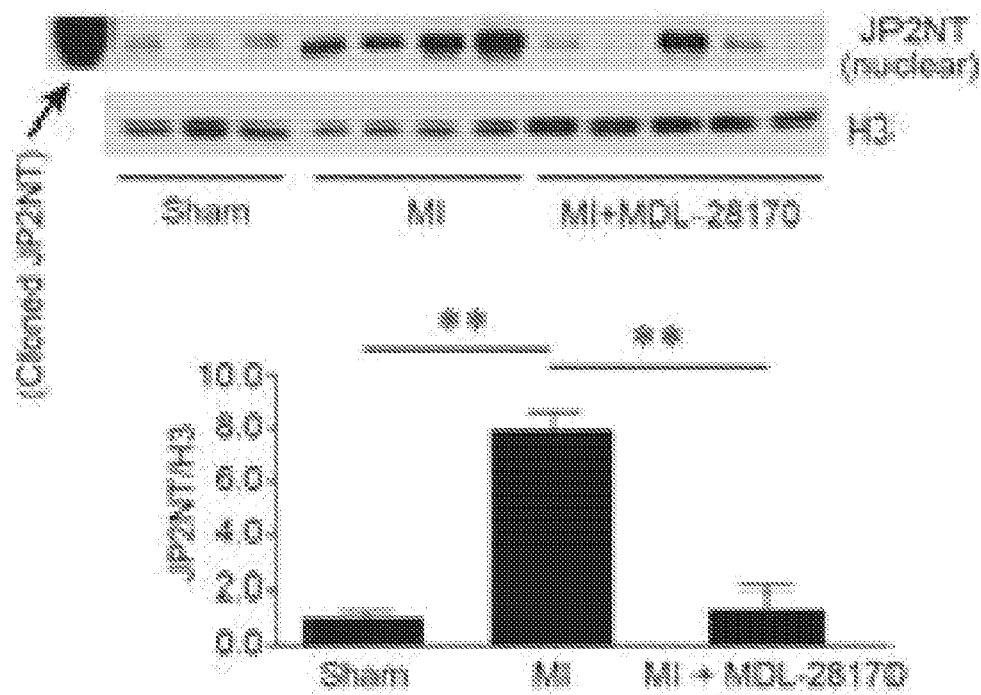

It was hypothesized that pathological stresses that activate calpain (Patterson et al., 2011) promote generation and nuclear accumulation of JP2NT. Consistent with this notion, both isoproterenol infusion (FIGS. 9D and 15B-Da) and myocardial infarction (FIGS. 9E, 15C and 15Db&c) increased the amount of JP2NT in nuclei of stressed hearts compared with (sham) controls. Conversely, administration of the calpain inhibitor MDL-28170 significantly attenuated stress-induced elevation in nuclear JP2NT (FIGS. 9D-E and 15B-C), further supporting that calpain-mediated proteolysis of full-length JP2 under cardiac stress results in accumulation of nuclear JP2NT.

Figure 9F:
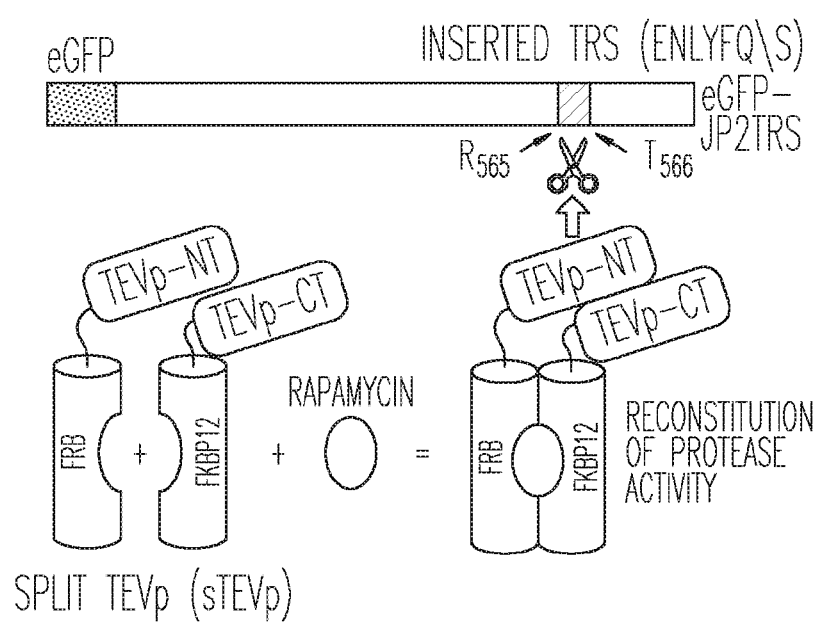
Figure 9G:
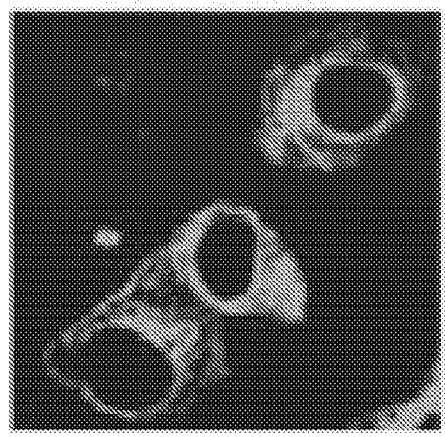
Figure 9H:
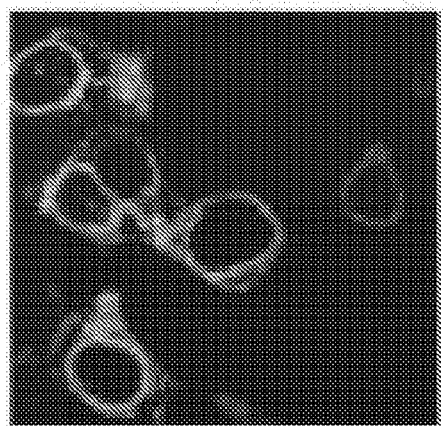
Figure 9I:
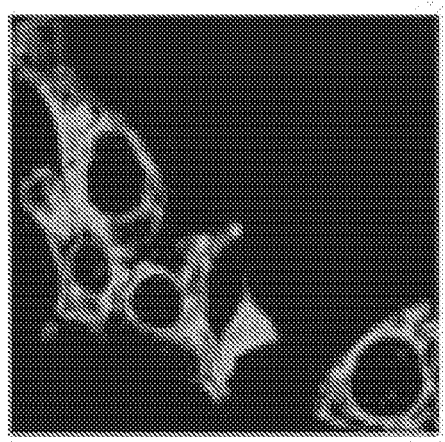
Figure 9J:
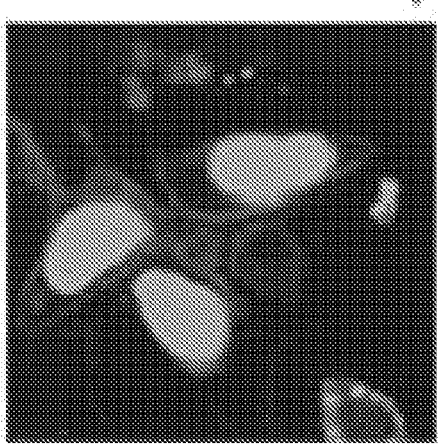

These data led to the postulate that the posttranslational removal of the C-terminus of JP2 is sufficient to promote JP2NT translocation into the nucleus. To recapitulate the process by which calpain-mediated proteolysis is associated with JP2NT translocation, an inducible tobacco etch virus protease (TEVp) system was employed (FIG. 9F) (Williams et al., 2009). A TEVp substrate recognition sequence was inserted into eGFP-JP2 in the primary calpain cleavage site (R565/T566) (eGFPJP2TRS, FIG. 9F). At baseline in HEK293T cells, eGFP-JP2TRS was localized at the cell membrane and an intracellular network-like structure that is likely the endoplasmic reticulum (FIG. 9G). In the absence of rapamycin, co-transfection of sTEVp did not affect the localization of eGFP-JP2TRS (FIG. 9H). In cells expressing sTEVp, rapamycin treatment rapidly and dramatically induced nuclear importation of the N-terminus of eGFP-JP2TRS (FIG. 9J). These data show that JP2 c-terminus functions to anchor the intact JP2 protein at the dyad, and removal of JP2 C-terminus is sufficient to traffic the N-terminal fragment into nuclei.

JP2NT has a NLS and a Chromatin/DNA Binding Region

Figure 10A:
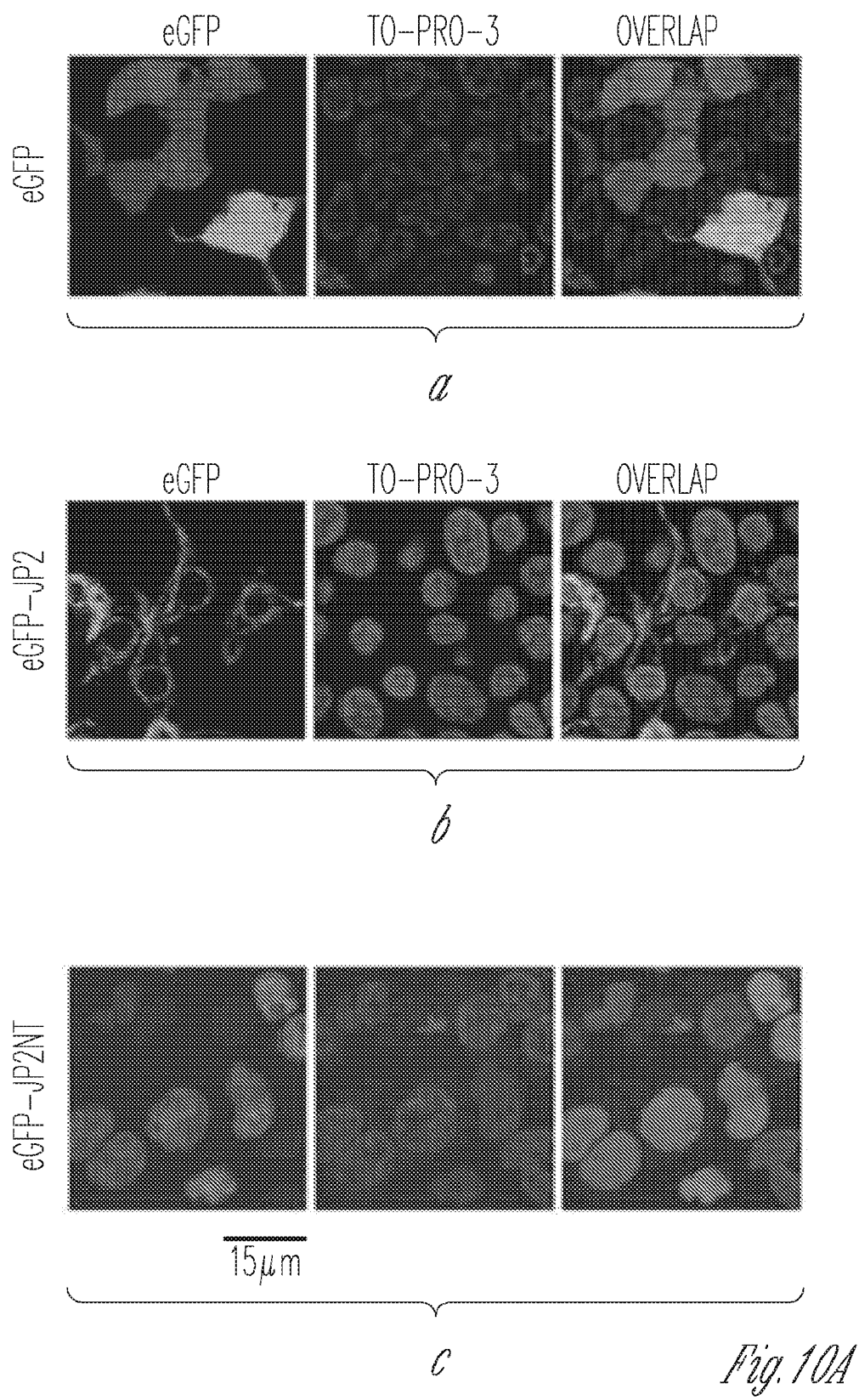
Figure 16A:
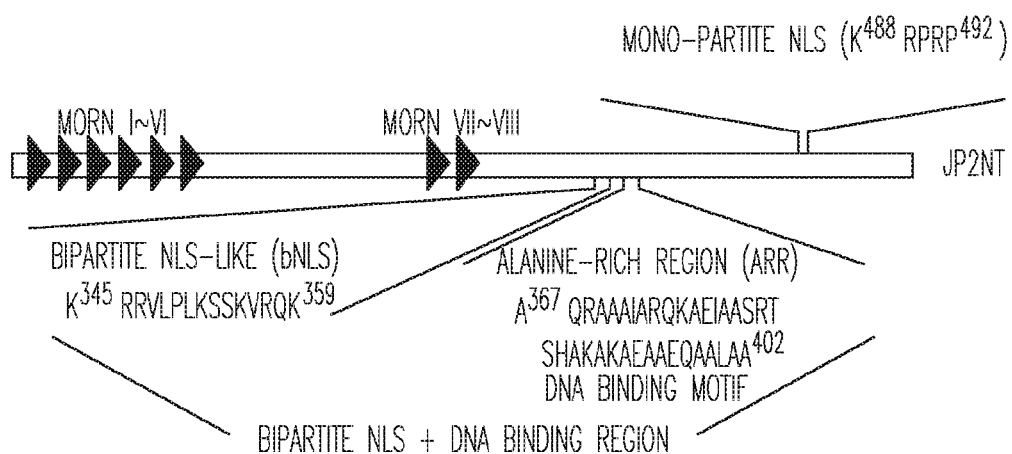
FIGS. 16A-E. Both the bi-partite NLS and the mono-partite NLS are sufficient to localize mCherry into nucleus. A) Schematic presentation of the bi-partite NLS (bNLS) like region and the mono-partite NLS on JP2NT. B) Conservation of the mono-partite NLS in several mammalian species (SEQ ID Nos. 75-80). C) Evolutionary conservation of the bNLS and ARR from JP2 of different species (SEQ ID Nos. 66-74). D) Effects of different fragments of JP2 on mCherry subcellular distribution in HEK293 cells. EGFP-JP2NT is used to indicate the nuclei. mCherry alone distributed all over the cells. Fusing the region including the monopartite-NLS to mCherry (JP2(478-502)-mCherry) brought mCherry Into nucleus. Fusing the region including the bipartite-NLS and ARR to mCherry (JP2(331-405)-mCherry) also brought mCherry into nuclei. E) Adenoviral transfection of JP2NT vs. JP2NTΔNLS and JP2NT$^{ΔnNLS/ΔARR}$ (all HA-tagged) in adult cardiomyocytes. JP2NT was concentrated in nuclei (stained with To-Pro-3), while JP2NT$^{ΔNLS}$ was completely absent in the nuclei. Deletion of bNLS and ARR did not prevent the nuclear importation of JP2NT in cardiomyocytes.
Figure 16B:
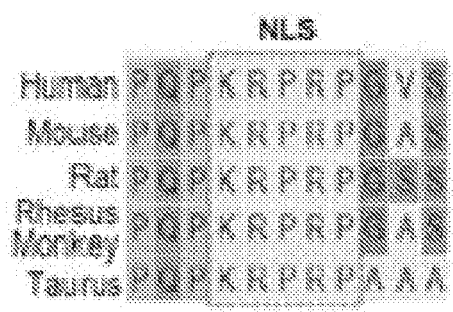
Figure 16C:
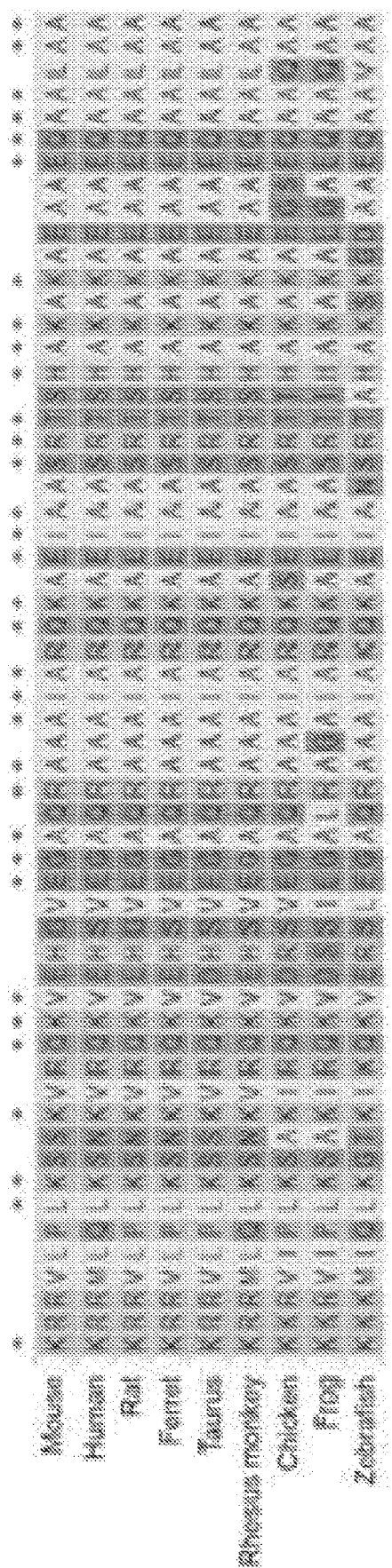
Figure 16D:
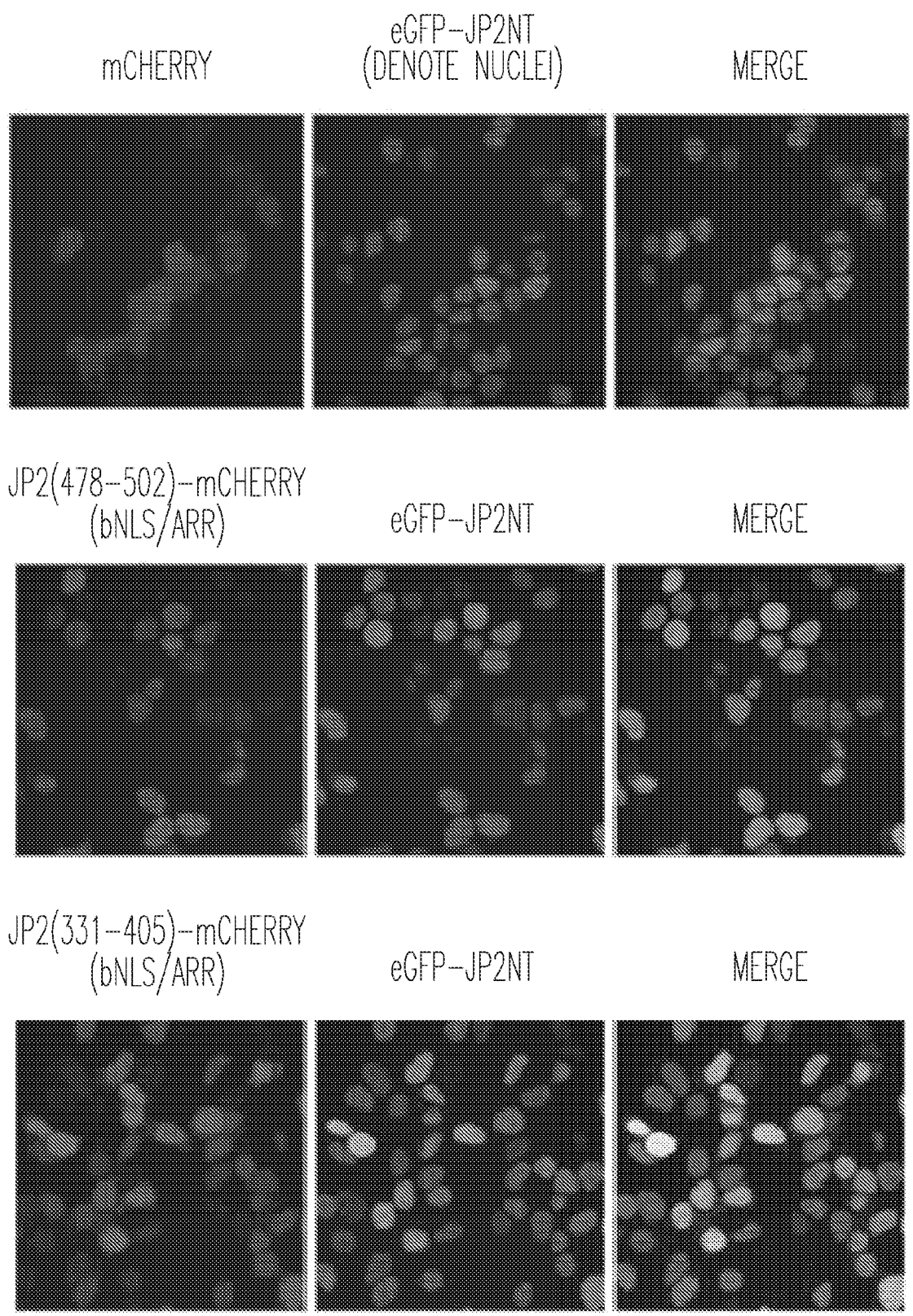
Figure 16E:
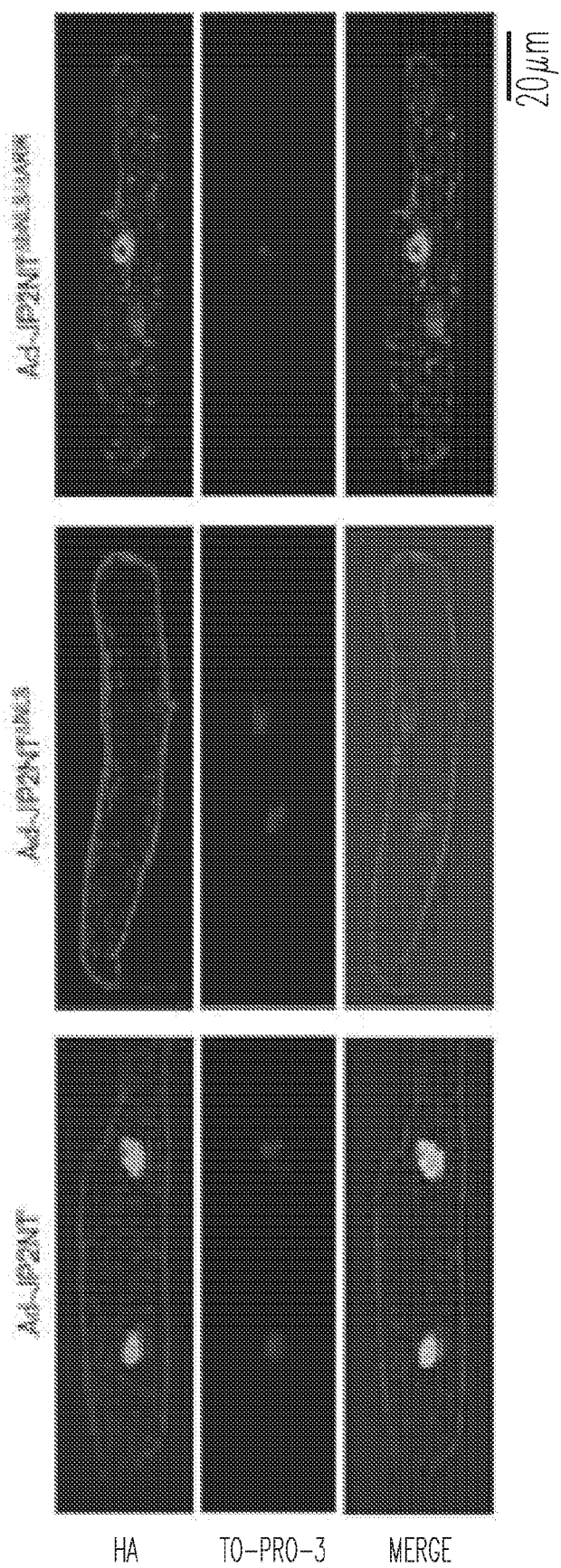

To Investigate the molecular mechanism of JP2NT nuclear importation, an in silico analysis (Sigrist et al., 2002) was performed. In JP2NT, a monopartite nuclear localization signal (NLS), K488RPRP492 and a bipartite NLS-like peptide (bNLS), K345RRVLPLKSSKVRQK359, adjacent to an alanine-rich region (ARR, A387-A402) (FIG. 18A) that shows characteristics of a helix-turn-helix structure (GYM 2.0 (Narasimhan et al., 2002)) were identified. These domains are evolutionarily conserved among species (FIGS. 18B-C). Fusion of a short peptide containing this monopartite NLS to mCherry resulted in nuclear enrichment of the fusion proteins (FIG. 16D). Deletion of this sequence (JP2NT$^{\Delta NLS}$) abolished nuclear localization of eGFP-JP2NT in HEK293T cells (FIG. 10Aa-c and Bd) and cardiomyocytes (FIG. 16E). Indicating this NLS is Indispensable for nuclear localization of JP2NT. A fusion protein containing mCherry and the bNLS peptide with the ARR was imported into nuclei (FIG. 16D). However, deletion of the bNLS sequence from JP2NT (eGFP-JP2NT$^{\Delta bNLS}$) did not prevent its nuclear importation in HEK293T cells (FIG. 10Ae) and cardiomyocytes (FIG. 16E), indicating that this region is not necessary for nuclear importation of JP2NT. Interestingly, the sub-nuclear localization of eGFP-JP2NT$^{\Delta bNLS}$ was mutually exclusive from To-Pro-3 staining, which labels genomic DNA (FIG. 10Be), suggesting physical dissociation of eGFP-JP2NT$^{\Delta bNLS}$ from genomic DNA. Deletion of the adjacent ARR from JP2NT (eGFP-JP2NT$^{\Delta ARR}$) induced greater separation of eGFP-JP2NT from DNA and was accompanied by accumulation of DNA at the nuclear periphery (FIG. 10Bf). These data indicate that bNLS and ARR are involved in DNA or chromatin binding.

Figure 10C:
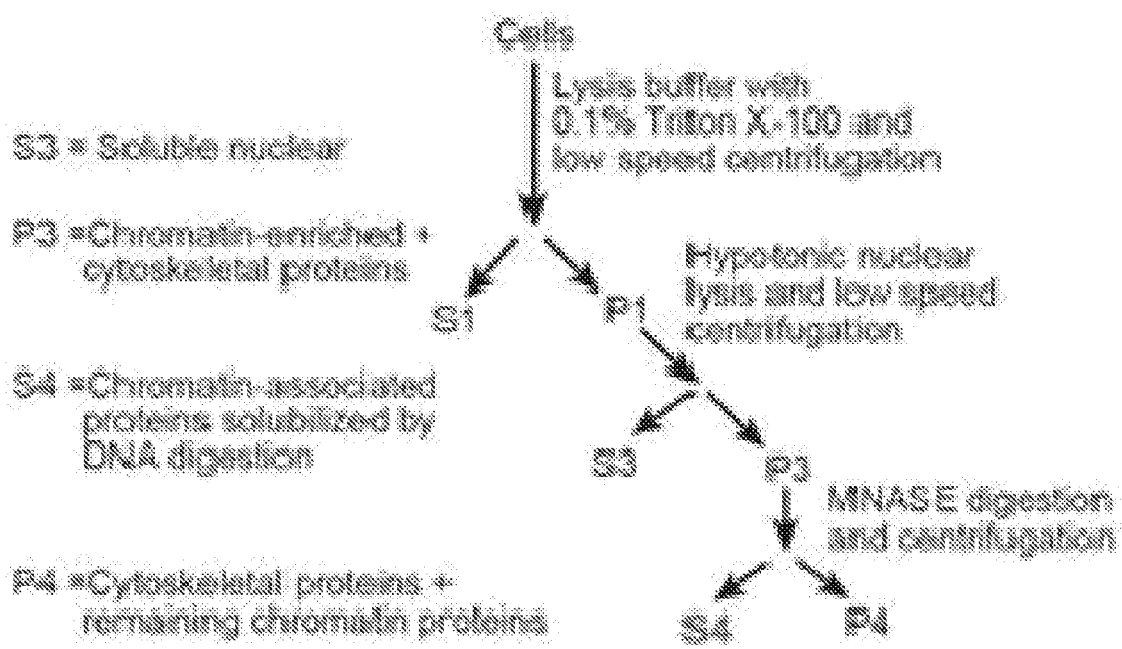
Figure 10D:
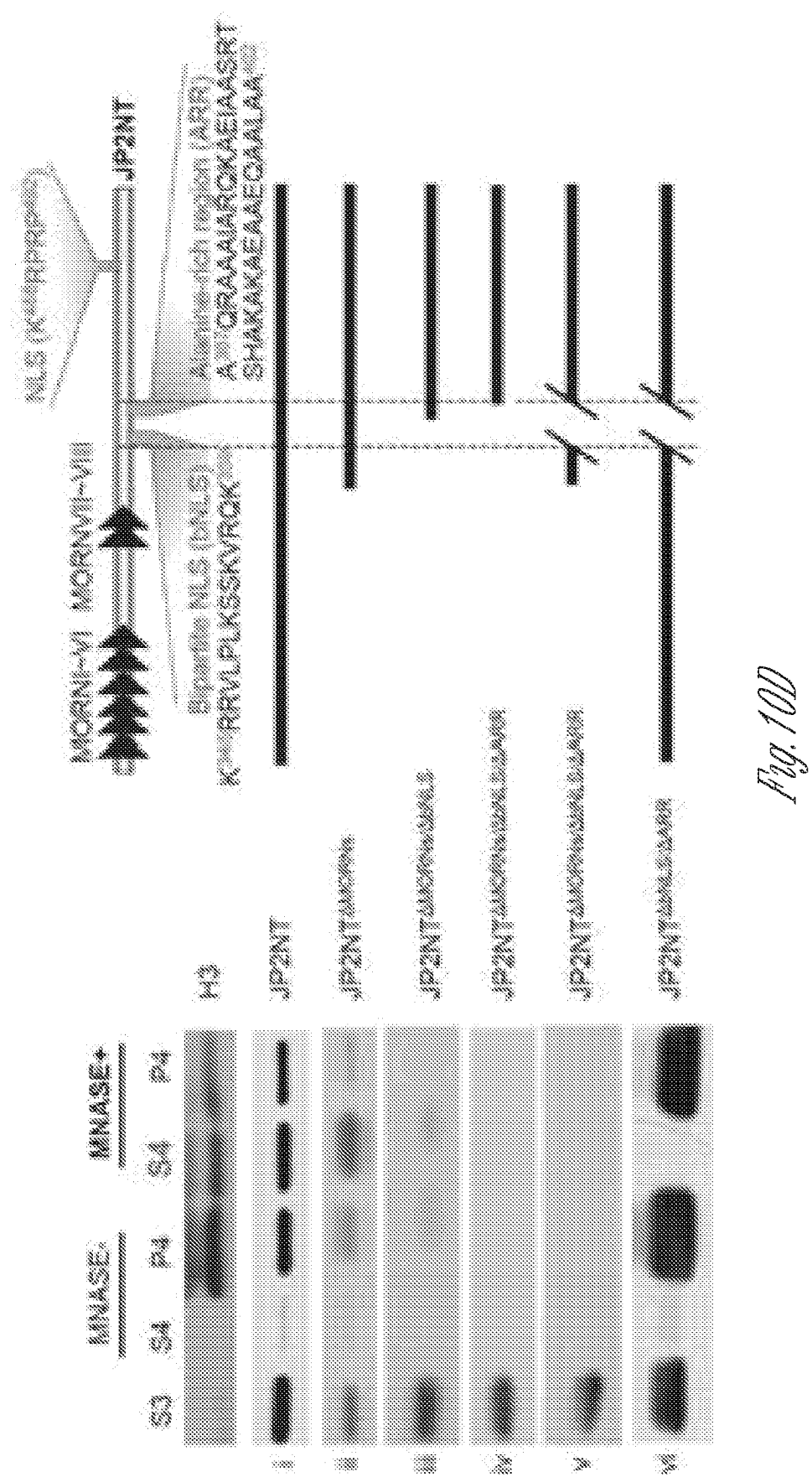
Figure 11A:
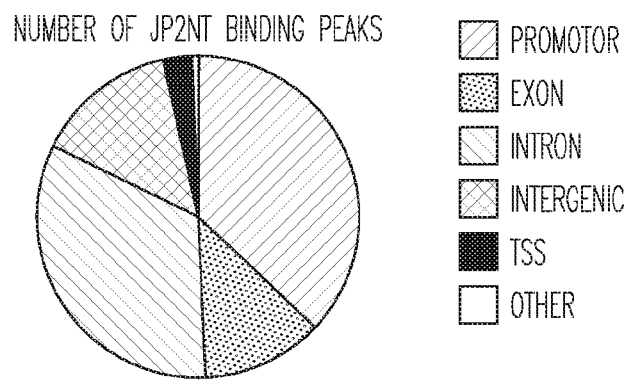
Figure 11B:
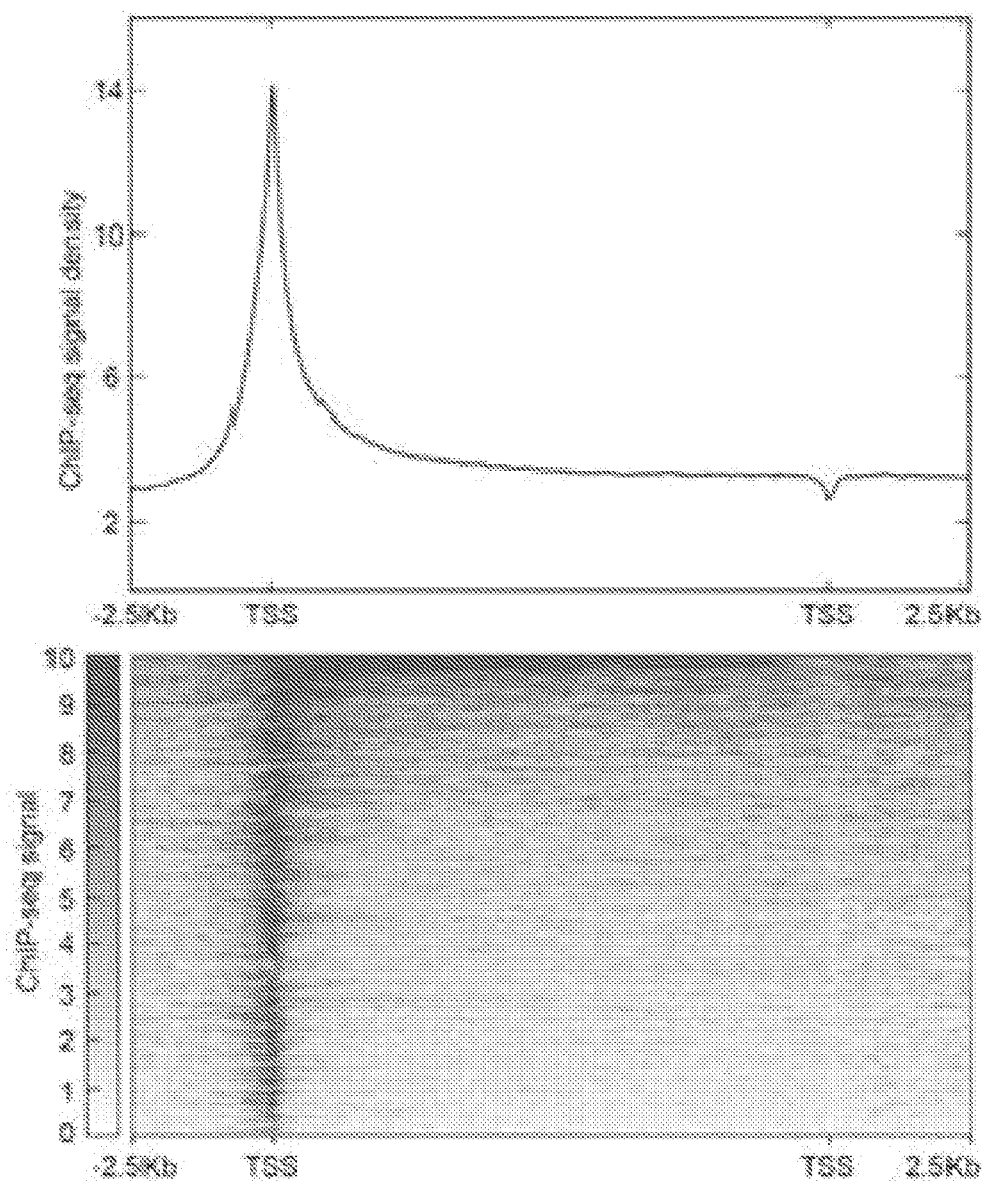
Figure 11C:
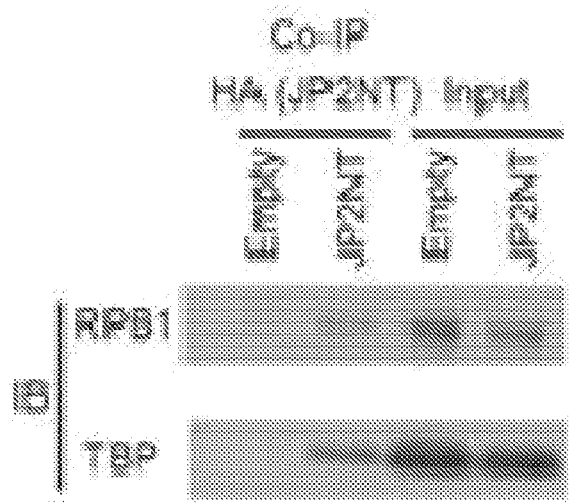

To further confirm the association of JP2NT with chromatin, a biochemical fractionation procedure (Wysocka et al., 2001) (FIG. 10C) was applied. JP2NT was detected in both soluble (S3) and chromatin containing insoluble (P4) nuclear fractions. MNASE-mediated DNA digestion released JP2NT from the insoluble chromatin fraction (MNASE+/S4) (FIGS. 10D-1). Deletion of the 8 MORN domains from JP2NT (JP2NT$^{\Delta MORNs}$) did not influence its distribution in the nucleus or its association with chromatin (FIGS. 10D-ii). In contrast, deletion of the bNLS-like signal from this construct (JP2NT$^{\Delta MORNs/\Delta bNLS}$) significantly reduced the association of JP2NT with chromatin (FIG. 10D-iii). Deletion of the alanine-rich domain in combination with the bNLS (JP2NT$^{\Delta MORNs/\Delta bNLS/\Delta ARR}$ or JP2NT$^{\Delta bNLS/\Delta ARR}$) completely prevented localization of JP2NT in the insoluble chromatin fraction (FIG. 10D-iv~vi). Based on these data, it was concluded that JP2NT associates with chromatin via a domain located at residues about 345-402, which is highly evolutionarily conserved in mammalian species as well as in vertebrate such as fish and birds (FIG. 11C).

JP2NT is Enriched at Transcription Start Sites

Figure 7:
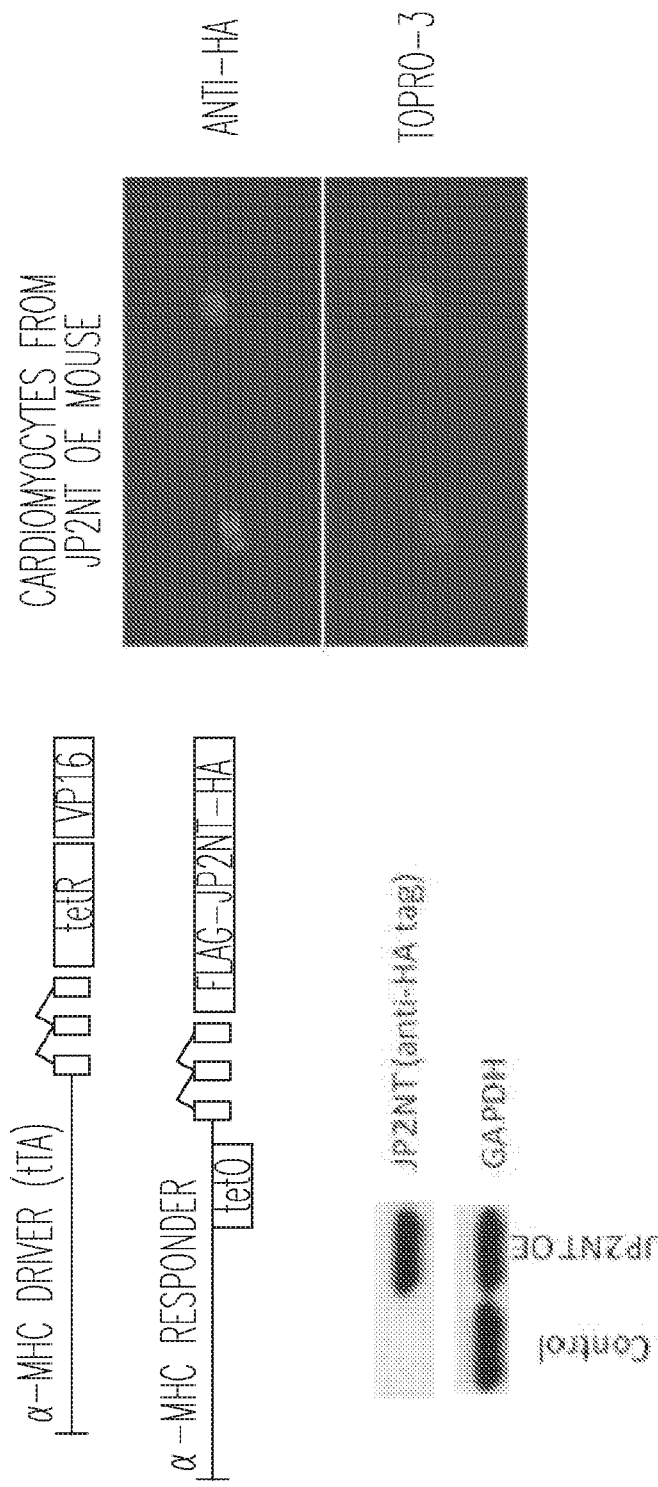
FIG. 7. Schematic of vectors used to express truncated JP2 in mice (upper left); expression analysis (upper right); and immunofluorescence of cells expressing the vectors that are stained with fluorophore labeled anti-HA or Topro3.

To systematically study the genomic targets of JP2NT, transgenic mice were generated with cardiac-specific overexpression of HA-tagged JP2NT. In these mice, JP2NT is predominantly localized in the nuclei of cardiomyocytes (FIG. 7). Hearts of the JP2NT overexpressing mice (JP2NT-OE) were subjected to ChIP-seq analysis using anti-HA antibody. 18,242 JP2NT-binding genomic DNA regions ($p<10^{-10}$) encompassing 10,587 genes were identified. The DNA binding profile revealed that JP2NT is concentrated in gene-enriched regions, especially the promoter and 5' UTR regions (FIG. 11A). Moreover, JP2NT is preferentially enriched at transcription start sites (TSS) (FIG. 11B), a characteristic of transcription regulators.

JP2NT is a TATA Box Binding Protein and Interacts with Transcription Machinery

Figure 11D:
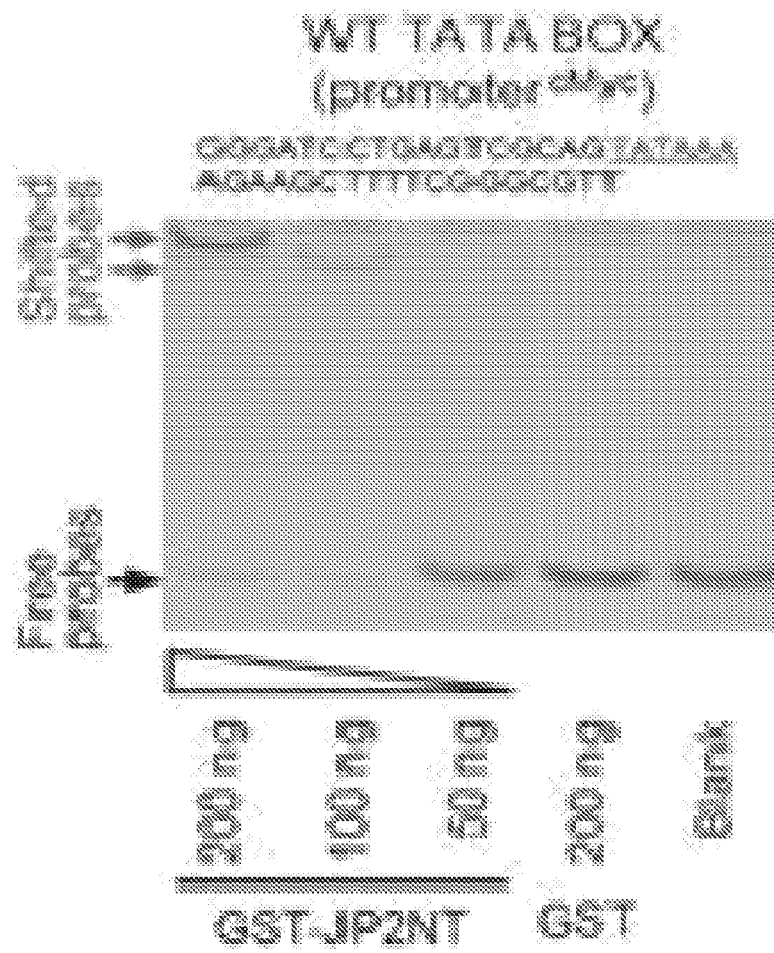
Figure 17A:
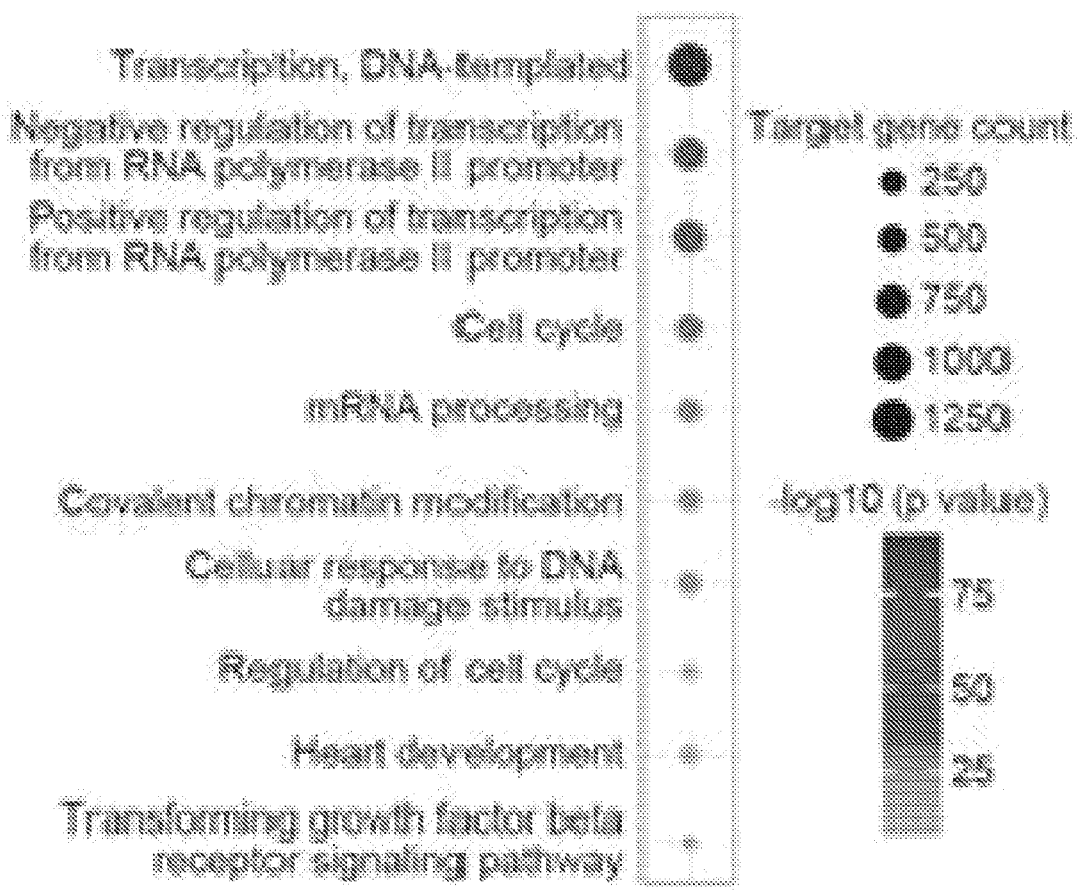
Figure 17B:
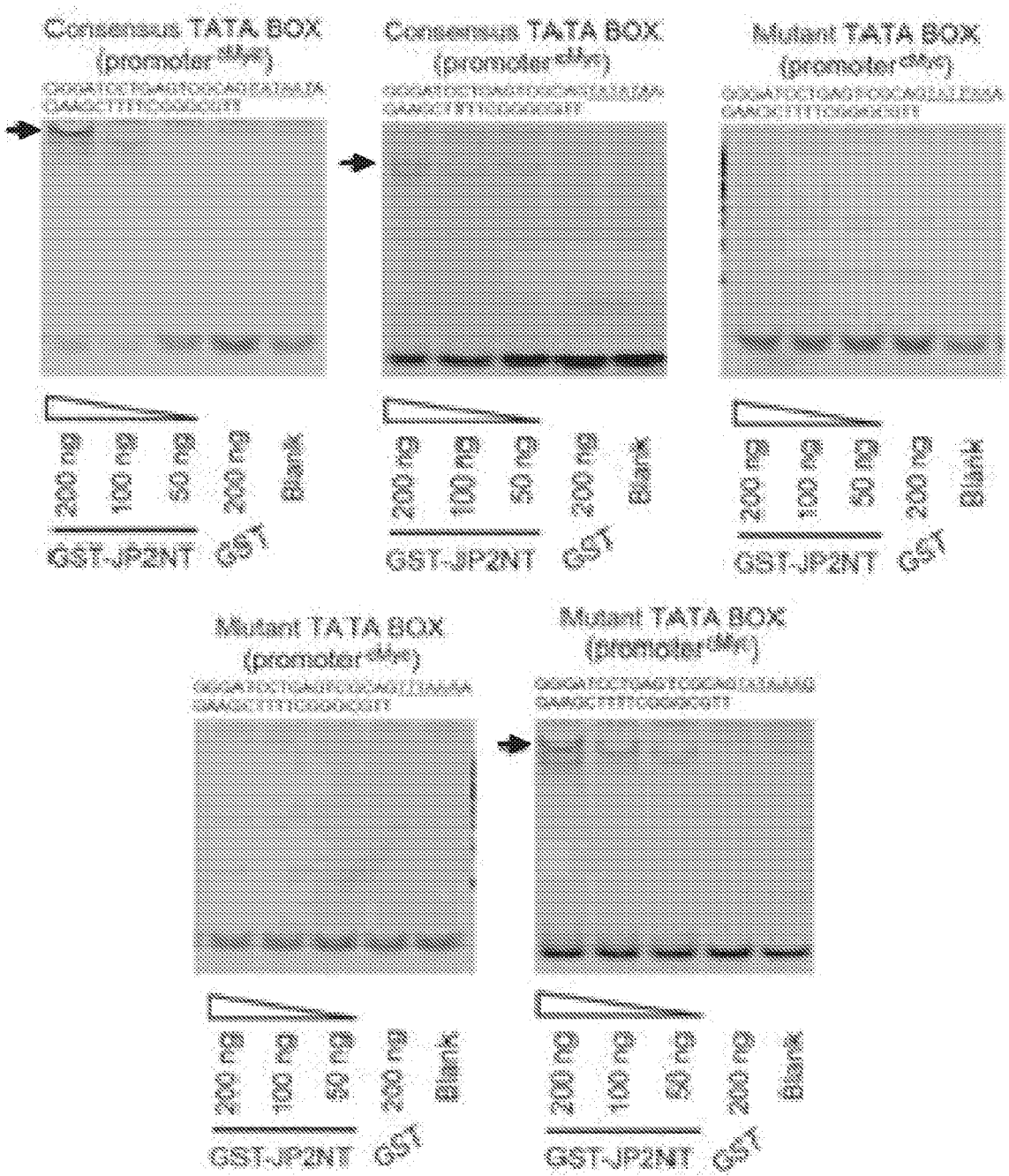

Based on these results, it was hypothesized that JP2NT may directly associate with core cis-regulatory elements that regulate transcription initiation. Crosslinking-reversal co-IP experiments in JP2NT-transfected 293T cells demonstrated that JP2NT associates with RNA polymerase II (RPB1) and TATA-box binding protein (TBP), both of which are components of the basic transcriptional machinery (FIG. 11C). TBP specifically binds to TATA boxes, eukaryotic core cis-regulatory elements localized at transcription start site. Subsequent in vitro analysis with purified recombinant GST-JP2NT revealed that JP2NT directly binds to the TATA box or variants (TATAAA, TATAAT and TATATA) from cMyc (FIGS. 11D and 17B) or the CMV promoter (FIG. 17C). This interaction was abrogated by mutation of the TATA box elements (FIGS. 11E&G and 17B). It was concluded that JP2NT is a DNA binding protein, binding to consensus TATA box represented as TATAA(A/T) or TATATA (FIG. 11F).

Figure 11H:
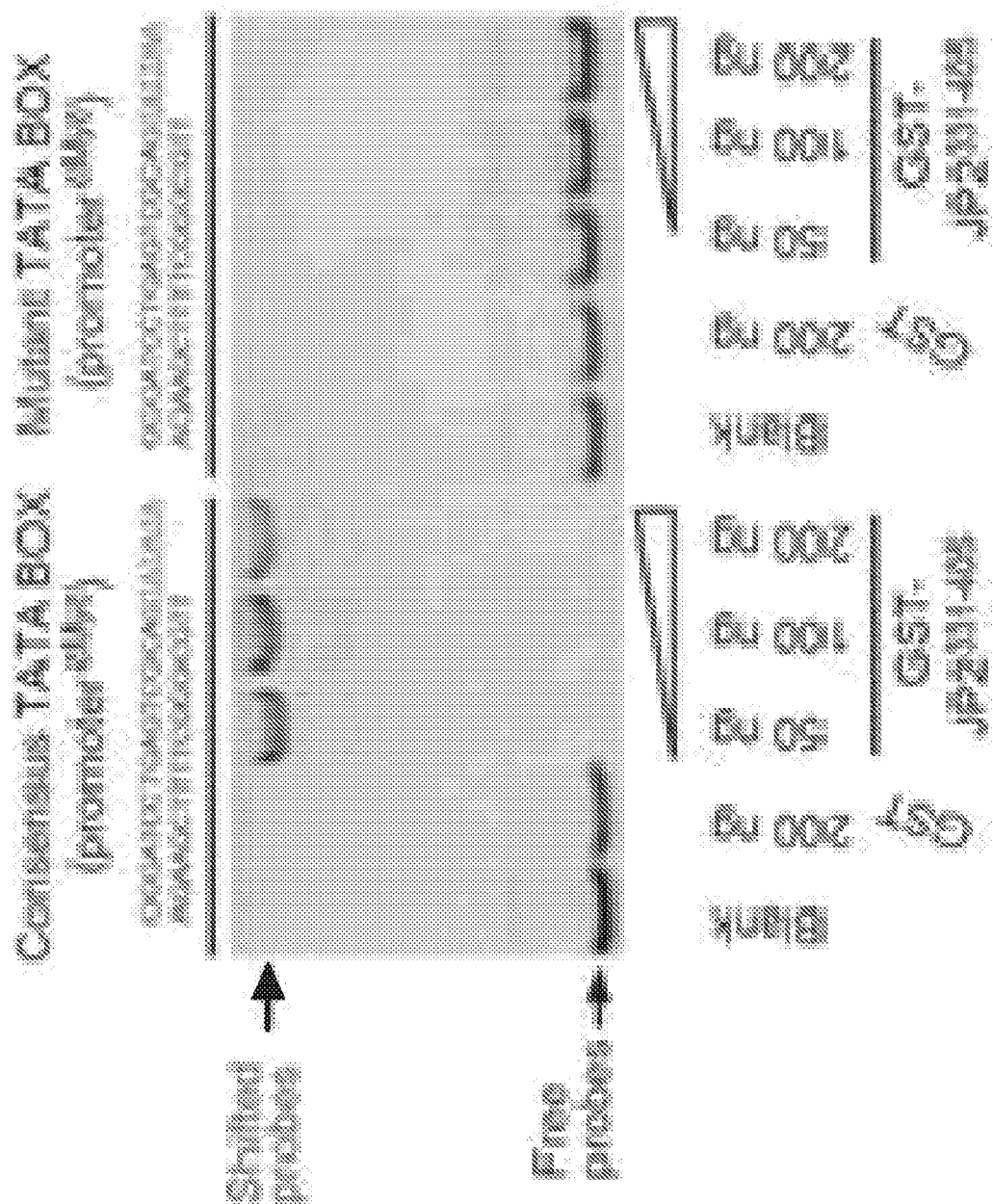

Deletion of N-terminal MORN domains alone from JP2NT (GST-JP2NT$^{\Delta MORNs}$) did not alter the interaction of JP2NT with the TATA box oligonucleotide (FIGS. 11G and 17C). However, deletion of the ARR from this construct (GST-JP2NT$^{\Delta MORNs/\Delta ARR}$) completely abrogated the association of JP2NT with TATA box elements (FIGS. 11G and 17C). Conversely, a purified peptide containing the ARR (GST-JP2$^{331-405}$) specifically bound to the consensus but not mutant TATA box (FIGS. 11H and 17D). Together, these data indicate that the ARR is responsible for TATA box binding.

Figure 12C:
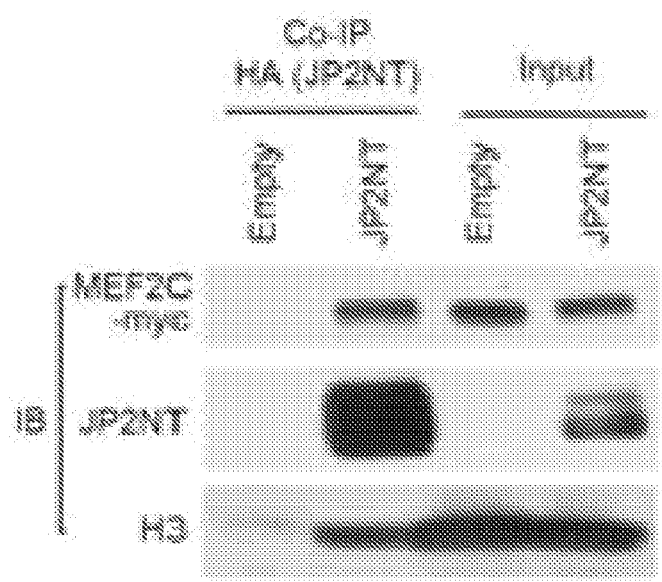
Figure 18:
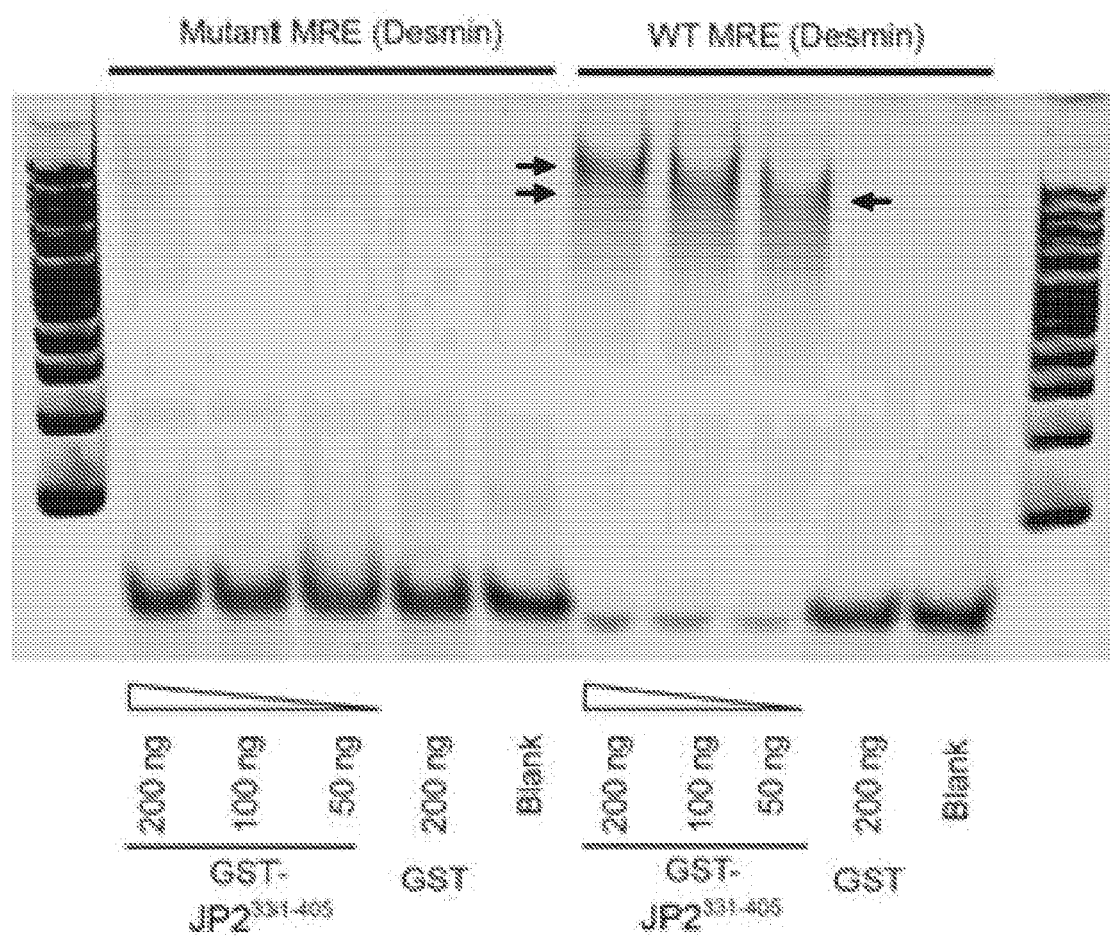
FIG. 18. Gel shift assay of a peptide containing the DNA binding domain of JP2NT binding to MEF2 response element (MRE).

JP2NT Represses MEF2C-Mediated Transcription Via Competing for MEF2 Binding Sites The MEF2 family, master regulators of hypertrophic genes in cardiomyocytes, binds to the A/T enriched consensus sequence (C/TTA(A/T)4TA G/A), which shares the same core sequence with TATA box. Thus, it was hypothesized that JP2NT directly interacts with MEF2 binding sites. Consistent with this hypothesis, MEF2 binding motifs were significantly enriched in the ChIP-seq dataset (FIG. 12A). Gel shift assay demonstrated that purified JP2NT or purified DNA binding domain of JP2NT (GST-JP2$^{331-405}$) interacts with a MEF2C Response Element (MRE) from the desmin enhancer (FIGS. 12B and 18). Co-IP of 293 cells transfected with Myc-tagged MEF2C and HA-tagged JP2NT demonstrated an interaction of the two proteins (FIG. 12C).

Figure 12D:
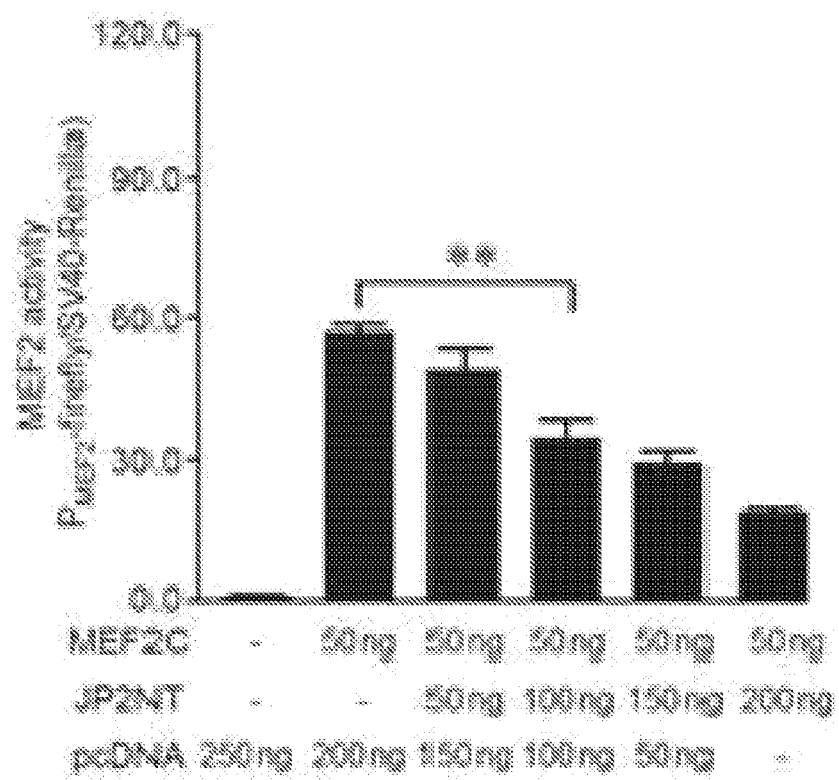
Figure 12E:
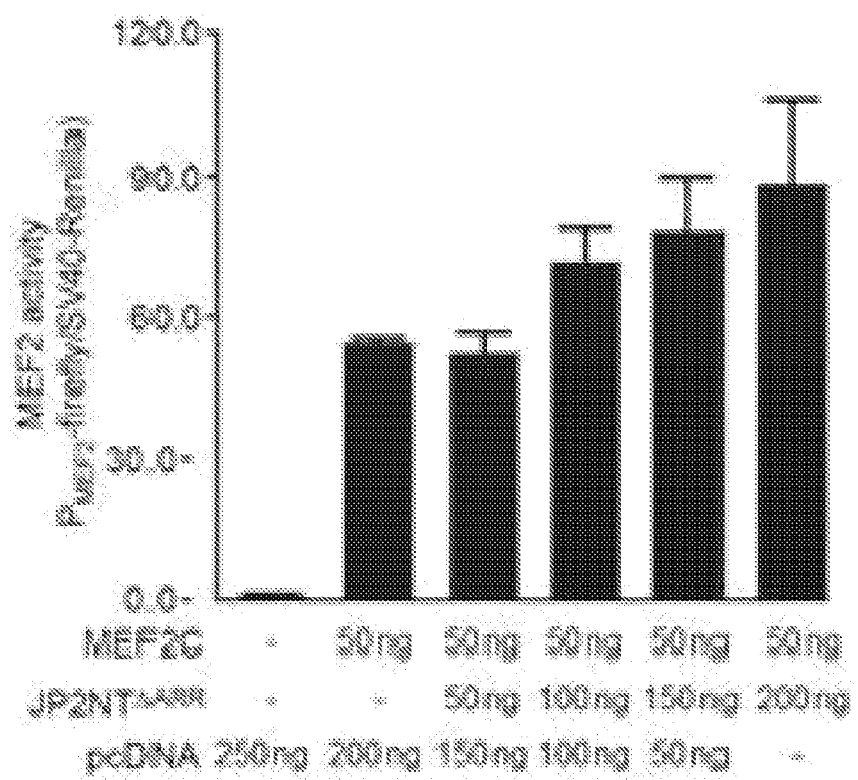

To examine whether JP2NT regulates MEF2-mediated transcription, a luciferase reporter system with firefly cDNA driven by the desmin enhancer-derived MEF2 binding site ($P_{MEF2}$-firefly) (Naya et al., 1999) was used. Co-transfection of plasmid expressing MEF2C and $P_{MEF2}$-firefly in 293 cells significantly increased the firefly luciferase signal relative to constitutive $P_{SV40}$-Renilla (FIGS. 12D-E). Co-transfection of JP2NT attenuated the MEF2-responsive signal in a dose-dependent manner (FIG. 12D). By contrast, MEF2C-mediated transcriptional activity was not altered in cells expressing a JP2NT construct lacking the ARR (JP2NT$^{\Delta ARR}$, FIG. 12E), which was found to be required for its association with chromatin and TATA box sequences. These data suggest that JP2NT competes with MEF2 for direct interaction with its consensus sequence at promoters to block MEF2-mediated transcription.

Figures 13A, 13B:
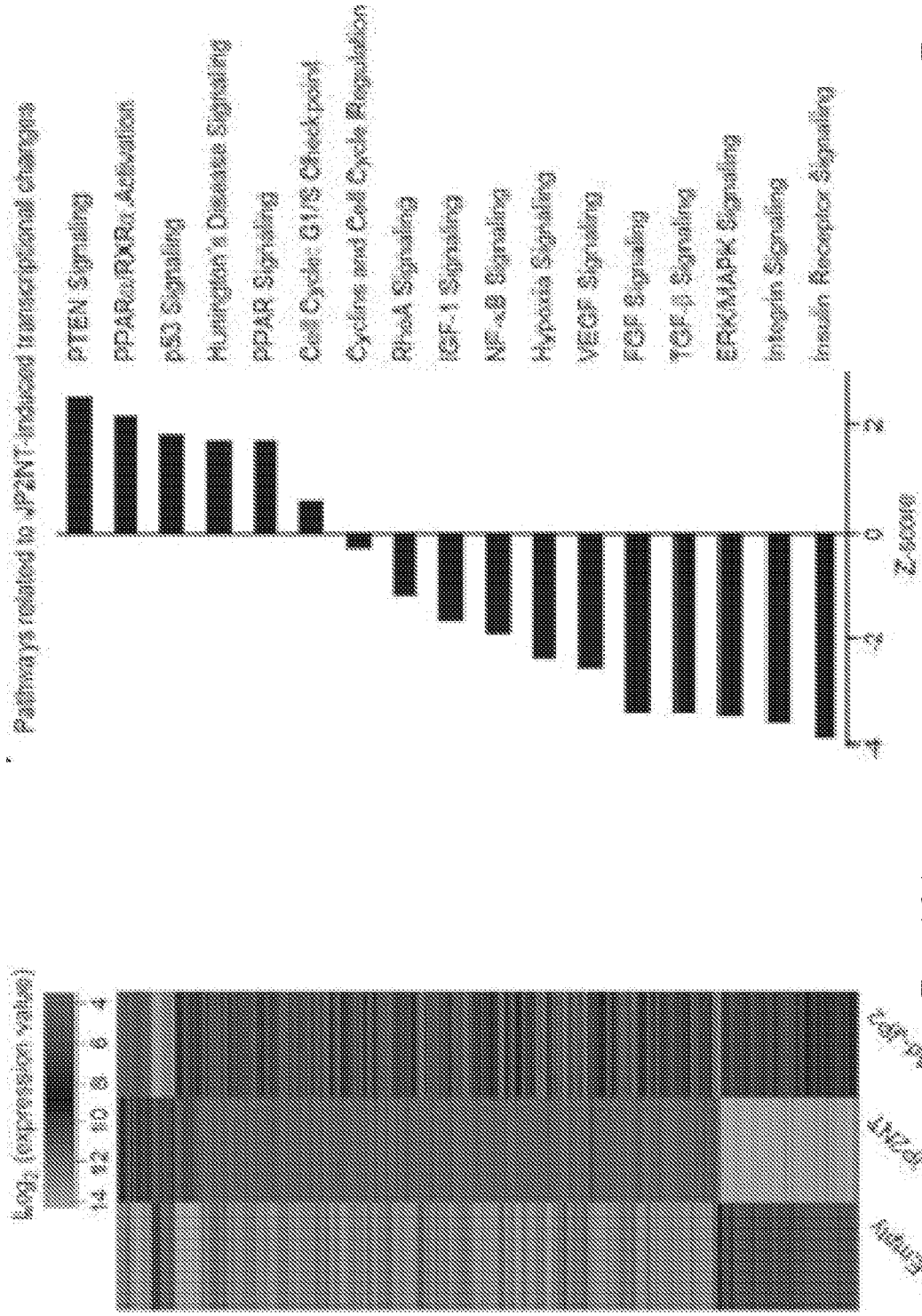
FIGS. 13A-D. JP2NT drives broad-spectrum transcriptional reprogramming in cultured cardiomyocytes. A) Heatmap of significantly altered genes in cultured adult murine cardiomyocytes expressing JP2 or JP2NT by adenovirus (Ad). B) IPA pathway enrichment analysis of significantly altered transcripts induced by JP2NT. C) RT-qPCR validation of genes that were significantly down-regulated by JP2NT as compared to Ad-Empty control. Note that deletion of the ARR (JP2NT$^{\Delta ARR}$) prevented JP2NT-mediated transcriptional repression. Data were calculated as the Log 2 fold change relative to cells transfected with Ad-Empty. Each transcript was assayed in n≥4 batches of independent cells. D) Transcriptional activity assays in which luciferase is under the control of the indicated promoters. n≥3 independent batches of cells, 3 transfection replications included in each batch; *, p<0.05, **p<0.01 vs. Ad-Empty.
Figure 19B:
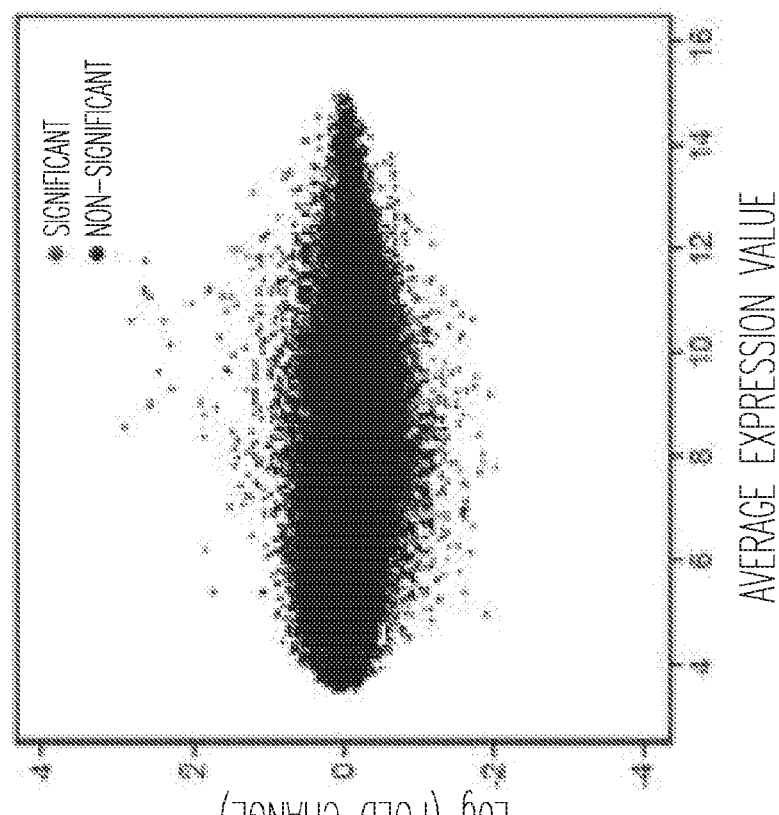
FIGS. 19A-D. A)-B) MA plots of genechip data. Notice that JP2NT overexpression (JP2NT-OE) Induced more significantly changed transcripts than JP2-OE. C)-D), GO enrichment of JP2NT-OE vs. JP2-OE induced differentially expressed genes.
Figure 19A:
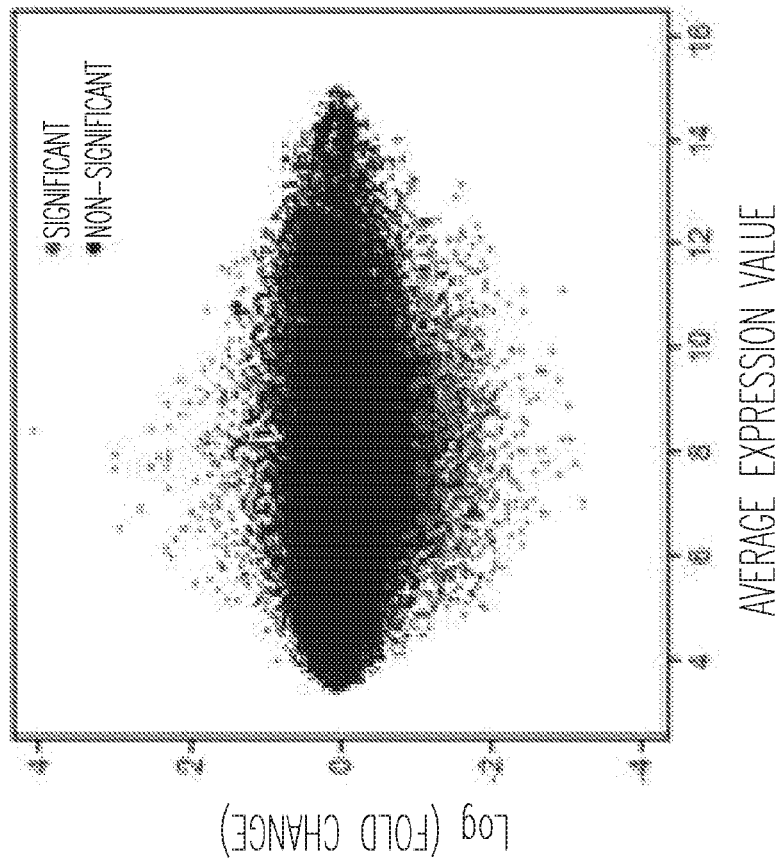

Overexpression of JP2NT in Cultured Cardiomyocytes Induces Profound Changes in Transcriptional Profile The association of JP2NT with DNA and transcription machinery led us to investigate whether JP2NT directly modulates the transcriptional profile in cardiomyocytes. Compared with cardiomyocytes expressing empty virus (Ad-Empty control), Affymetrix Genechip analysis revealed that the expression of 574 and 1996 known genes were significantly induced or repressed (p<0.01), respectively, in JP2NT-expressing cardiomyocytes (FIGS. 13A and 19A). Conversely, only 96 significantly induced and 264 significantly repressed genes were detected in cardiomyocytes with overexpression of full length JP2 (FIGS. 13A and 19B). Importantly, about 74% of the differentially expressed genes induced by JP2NT mapped to genomic loci where JP2NT was found to bind by ChIP-seq. These findings indicate that JP2NT represses transcription by binding to genomic regions, either directly through binding to TATA box elements or through interactions with transcription factors such as MEF2.

Figure 19C:
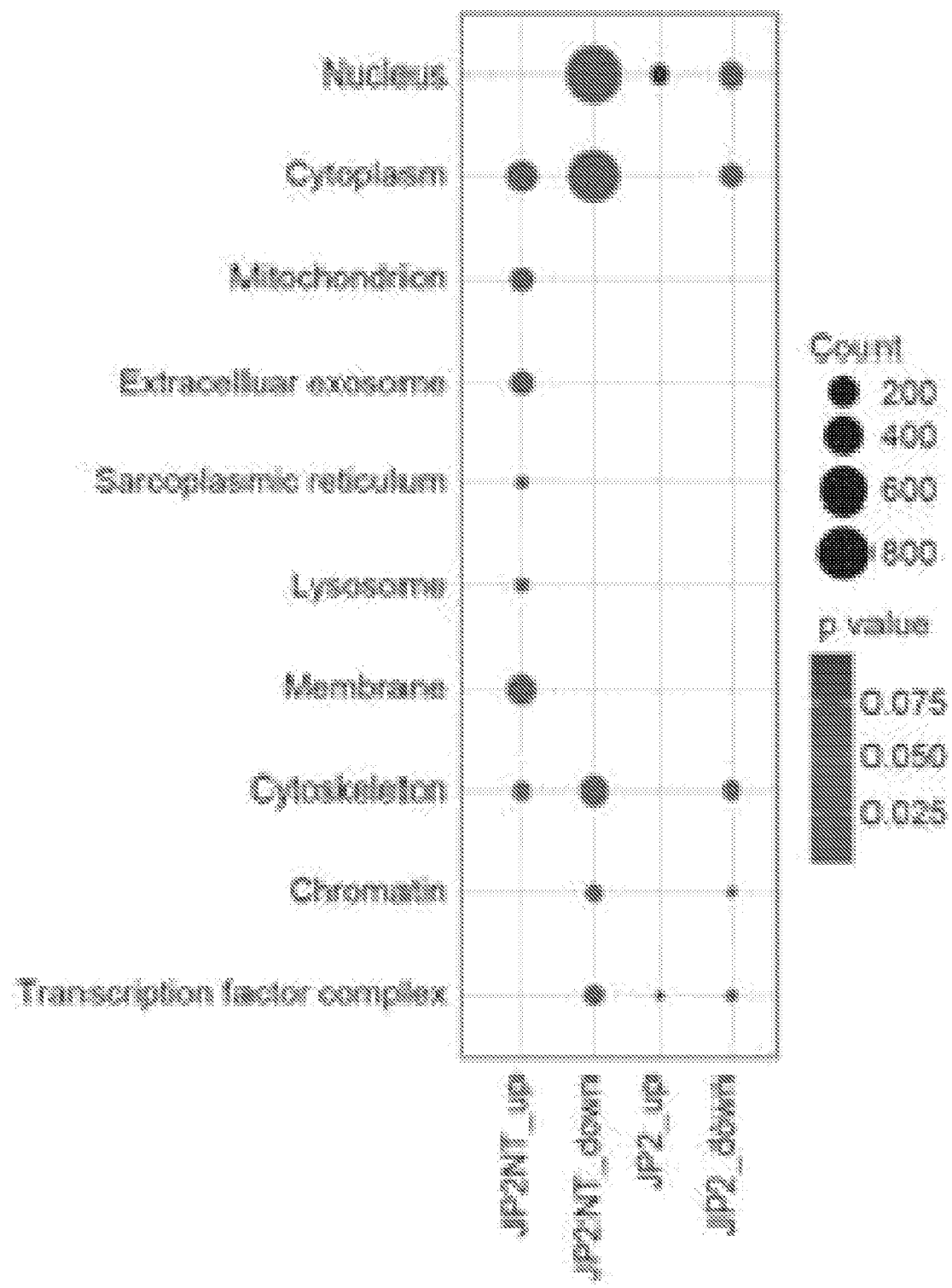
Figure 19D:
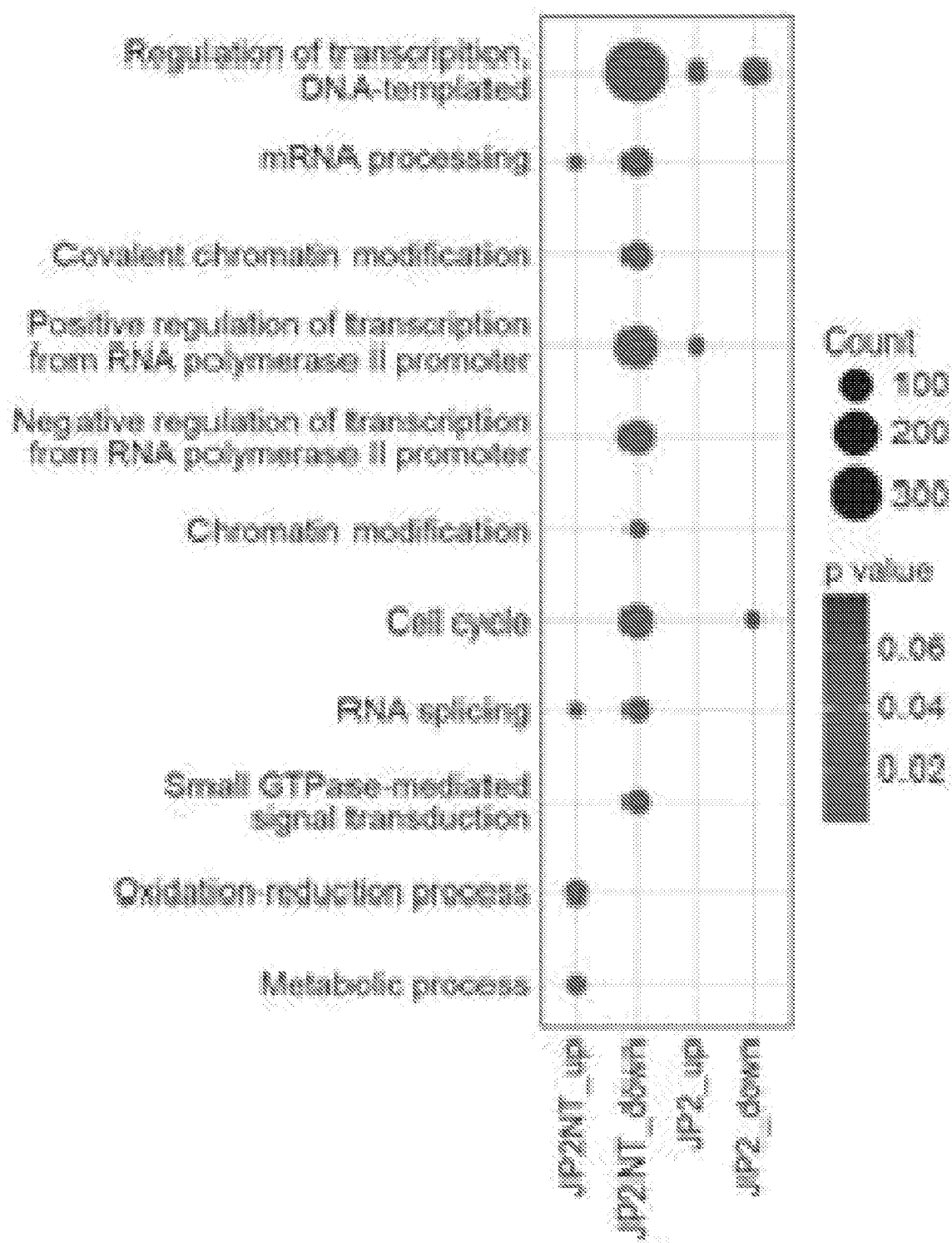

Many of the JP2NT-downregulated genes encode nuclear proteins (FIG. 19C) and proteins that are functionally enriched in nuclear events such as transcriptional regulation and chromatin modification (FIG. 19D). Ingenuity Pathway Analysis (IPA) of the differentially expressed genes induced by JP2NT identified pathways and regulators implicated in cardiac hypertrophy, fibrosis, cell growth and differentiation as well as inflammation. Specifically, ERK/MAPK, NF-κB, TGF-β and integrin signaling pathways were predicted to be inhibited in response to JP2NT overexpression (FIG. 13B).

Figure 13C:
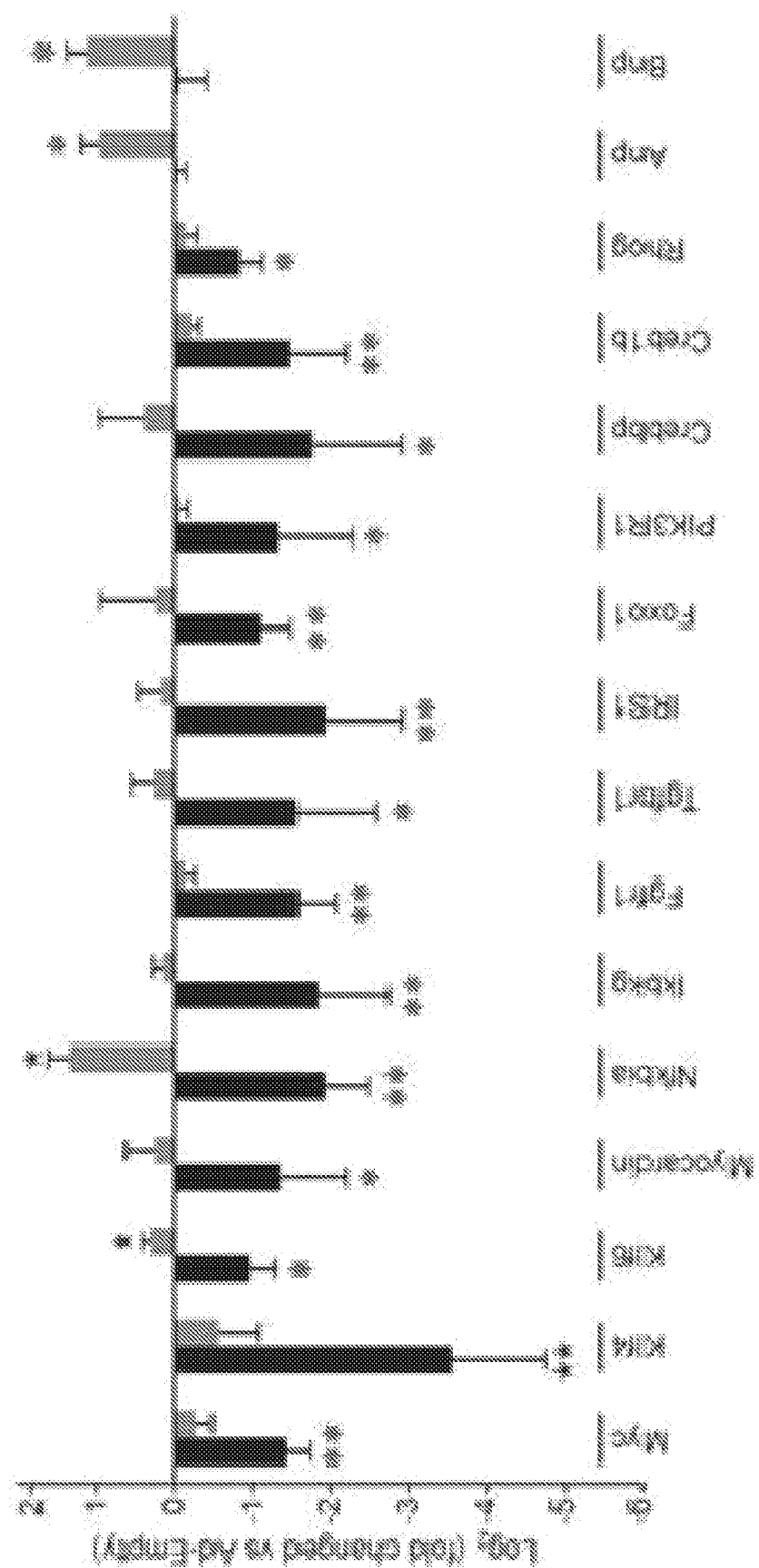

Confirming these GeneChip findings, mRNA levels of genes including KLF4, KLF6, Myc, TGFβR1, NFKBIA, FOXO1, PI3KR1 et al, were significantly decreased in cardiomyocytes expressing JP2NT compared with Ad-Empty infected cells (FIG. 13C). Deletion of the DNA binding region from JP2NT (JP2NT$^{\Delta bNLS/\Delta ARR}$) largely prevented the repressive effect of JP2NT (FIG. 13C). Interestingly, the cardiac hypertrophy markers ANP and BNP were not altered by JP2NT expression but were significantly increased by JP2NT$^{\Delta bNLS/\Delta ARR}$ (FIG. 13C).

Figure 13D:
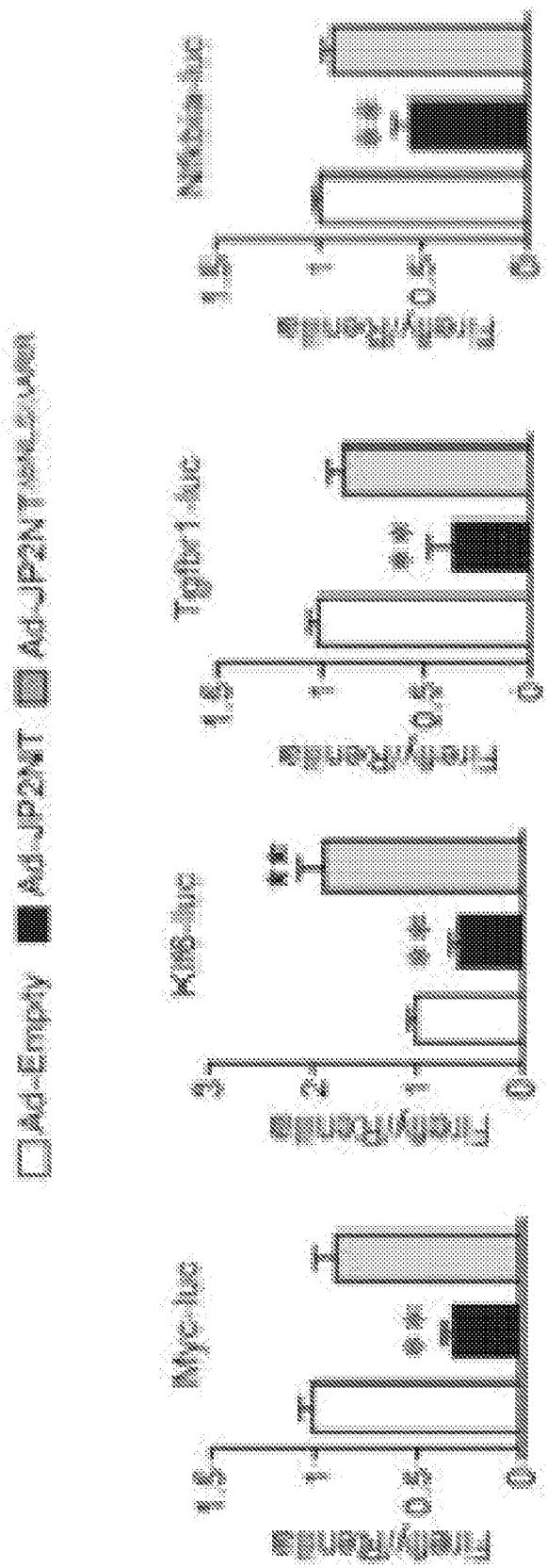

To further test whether JP2NT regulates transcription of these genes, luciferase reporters controlled by promoters of Myc, KLF6, TGFβR1 and NFKBIA were constructed. For all genes, promoter activity was significantly attenuated by co-expression of JP2NT (FIG. 13D). Consistent with the changes in mRNA levels, expression of JP2NT$^{\Delta bNLS/\Delta ARR}$ either had no effect on baseline firefly luciferase signal or increased promoter activity as compared to empty vector control (FIG. 13D), supporting that the DNA binding domain of JP2NT is important for its function as a transcriptional repressor.

JP2NT Attenuates Heart Failure in Mice

Figure 14A:
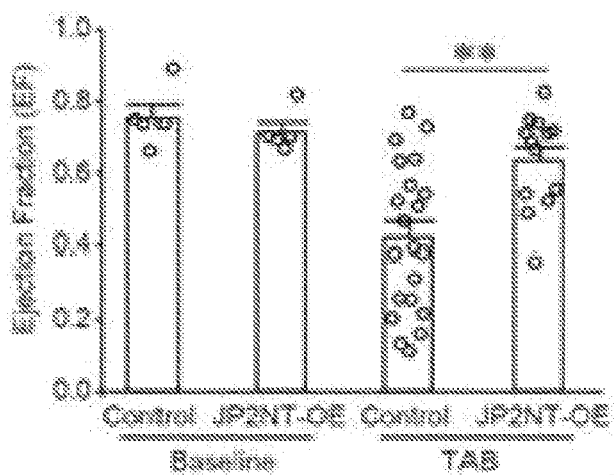
FIGS. 14A-F. JP2NT overexpression protects against pressure overload-induced heart failure. A) Cardiac specific overexpression of JP2NT (JP2NT-OE) preserved cardiac ejection fraction (EF) in mice 3 weeks after transverse aortic banding (TAB). B) JP2NT overexpression attenuated TAB-induced cardiac hypertrophy as evidenced by a decreased heart weight/body weight (HW/BW) ratio. C) Lung weight/body weight (LW/BW) ratio is significantly reduced in JP2NT-OE mice following TAB. n=5, 5, 22, 13 for each group respectively. D) Volcano plot of the effect of JP2NT overexpression on TAB-induced transcriptional remodeling. E) IPA pathway enrichment analysis of significantly altered transcripts in JP2NT-OE mice following TAB as compared to littermate controls. F) Schematic of the mechanism by which JP2NT converts stress signals to transcriptional reprogramming in stressed hearts. Left, E-C coupling under normal condition. Right, Under stress conditions, cardiac stress results in Ca$^{2+}$ overload (1), promoting calpain activation (2). Calpain cleavage of JP2 liberates JP2NT from the SR membrane (3). JP2NT translocates to the nucleus via a conserved NLS (4). JP2NT binds to TATA box elements via the ARR and associates with MEF2 to repress transcription of genes that control deleterious cardiac remodeling (5).
Figure 14B:
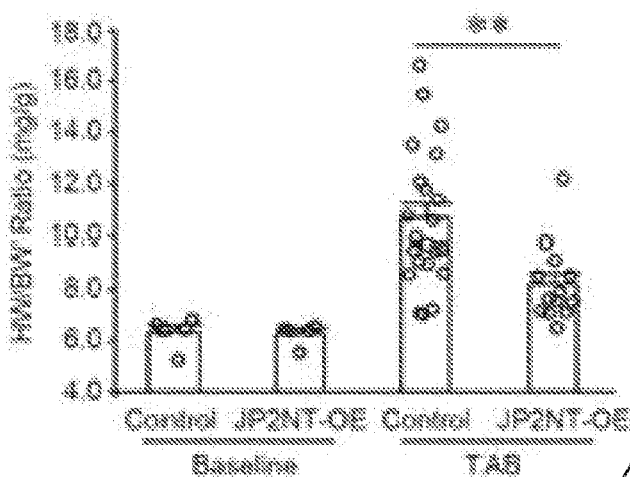
Figure 14C:
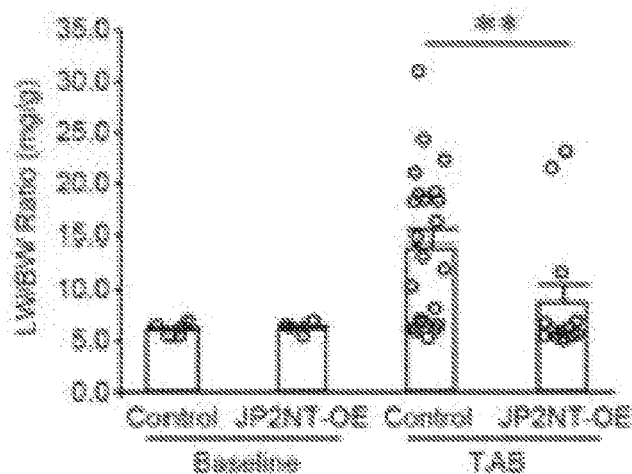

Since JP2NT represses transcription of key regulators of hypertrophy, fibrosis and inflammation, it was predicted JP2NT would exert a protective effect on stress-induced pathological cardiac remodeling. At baseline, JP2NT overexpression had no effect on cardiac morphology or function (FIGS. 14A-C). Surprisingly, under stress conditions induced by transaortic banding (TAB) surgery to induce pressure overload hypertrophy and heart failure, JP2NT-OE mice had improved cardiac function (FIG. 14A), lower heart weight/body weight ratio (FIG. 14B) and reduced lung edema indicated by the lung weight/body weight ratio (FIG. 14C) relative to wild-type controls.

Figure 14D:
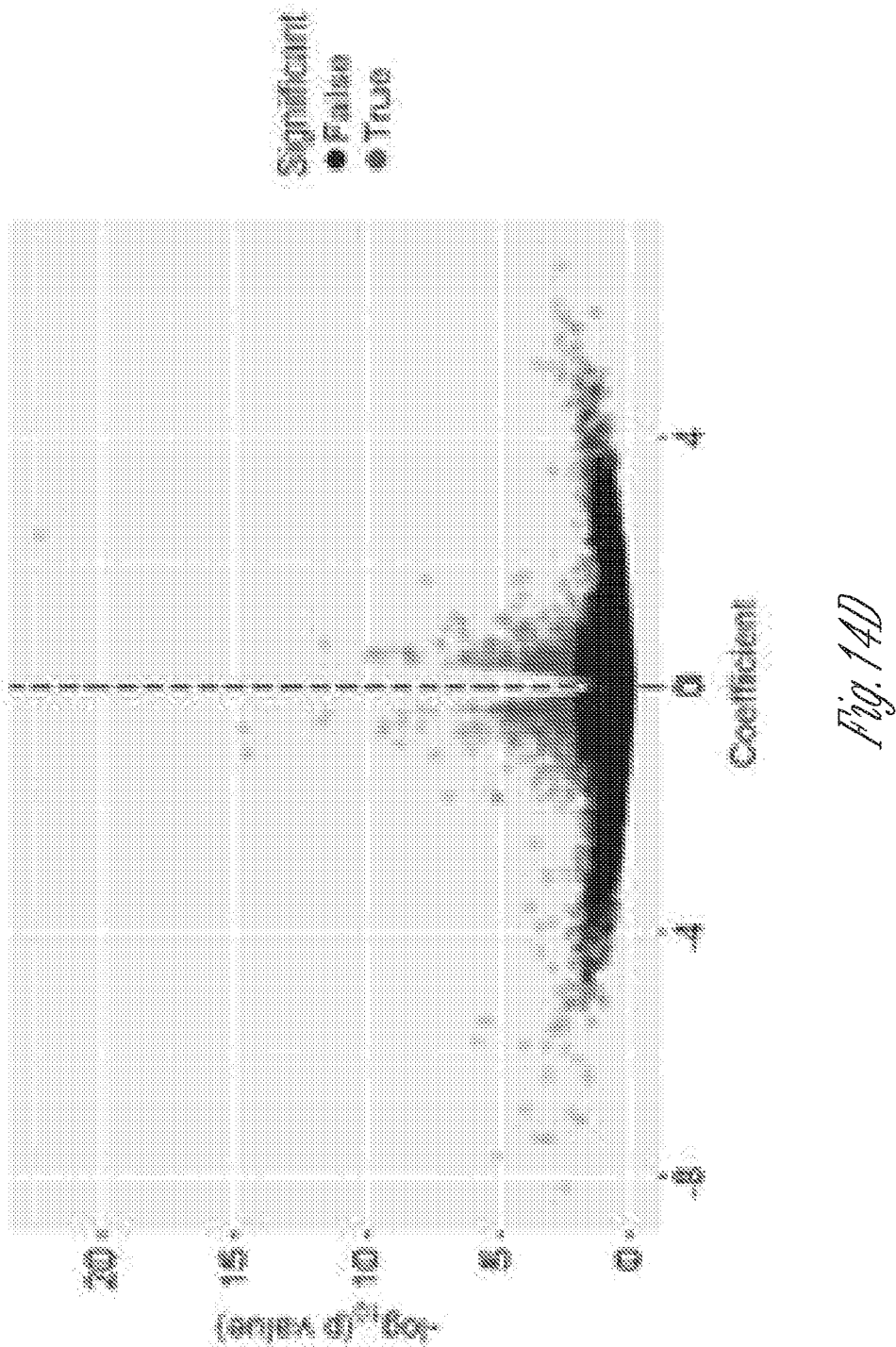
Figure 14E:
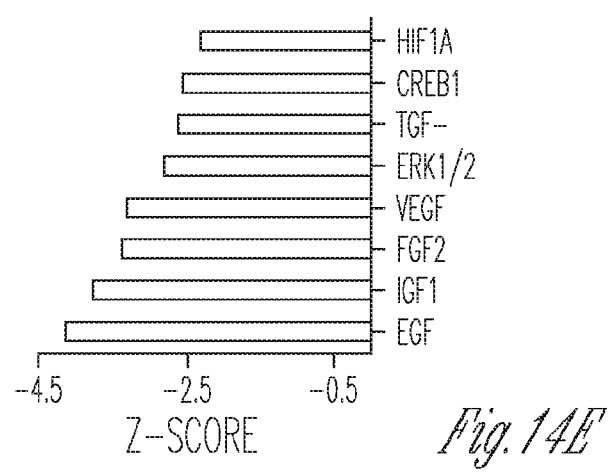
Figure 14H:
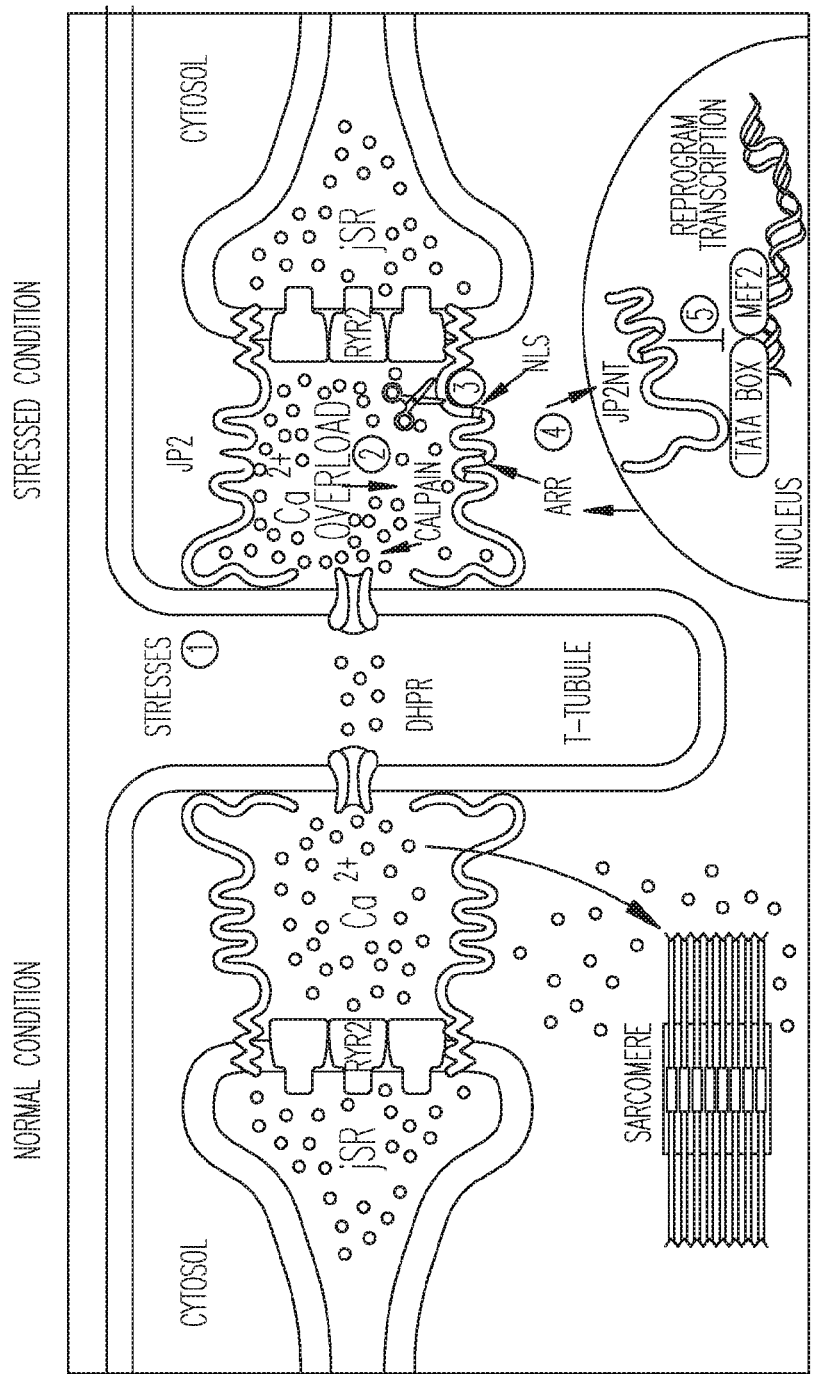
Figure 20A:
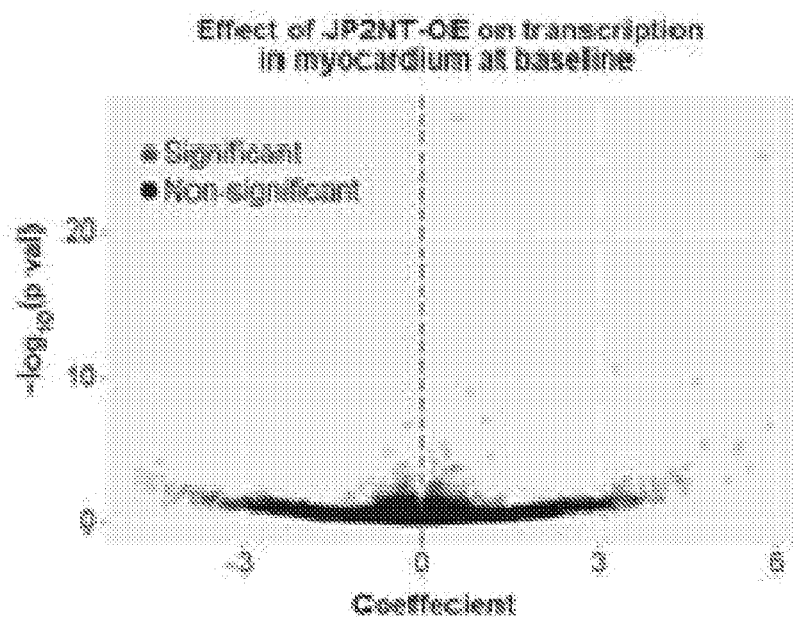
FIGS. 20A-C. A) Volcano plot of differentially expressed transcripts in JP2NT-OE mice compared with control mice under baseline condition. B) Volcano plot of differentially expressed transcripts in control mice under TAB and baseline condition. C) Volcano plot of differentially expressed transcripts in JP2NT-OE mice under TAB and baseline condition.
Figure 20B:
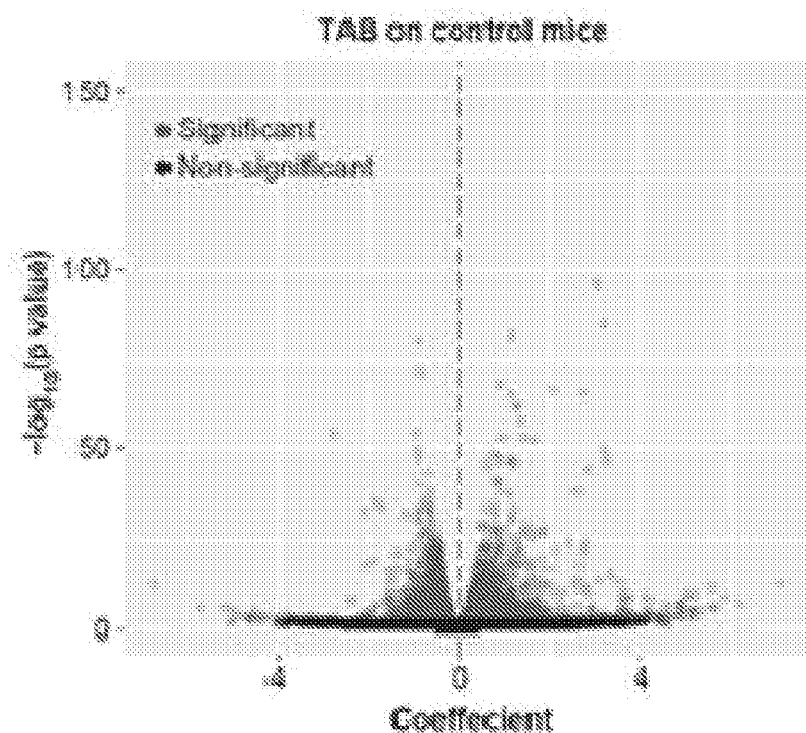
Figure 20C:
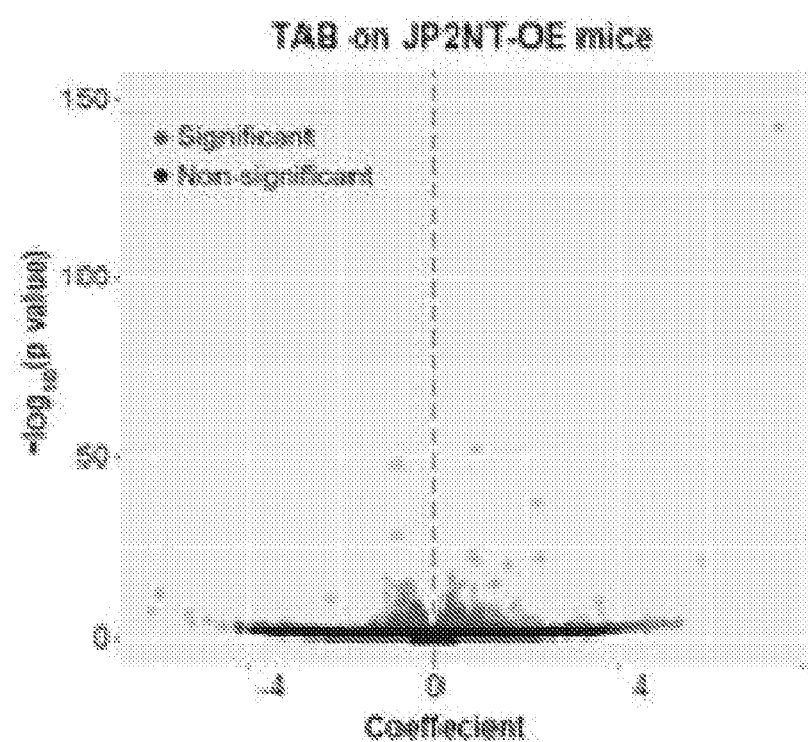

RNA-Seq demonstrated minor differences in the cardiac transcription profile of JP2NT-OE mice at baseline relative to control littermates (FIG. 20A), with only 49 significantly altered genes (p<0.01). TAB promoted a marked change in the transcriptome of control hearts as compared to sham surgery, with 4636 significantly altered transcripts derived from 3580 genes (FIG. 20B). Overexpression of JP2NT significantly modified the transcriptional profile in response to cardiac stress: a significant difference in 1082 transcripts derived from 954 known genes was detected based on a linear regression model (p<0.01, FIG. 14D). Among these, 540 transcripts (mapped to 481 known genes) were negatively influenced and 542 transcripts (mapped to 476 known genes) positively influenced by JP2NT overexpression, with a predicted inhibition of ERK, TGF-β, CREB and NFκ-B signaling pathways (FIGS. 14E and 21). These findings are in line with observations in cultured cardiomyocytes (FIG. 13) and substantiate a pivotal role for JP2NT in the cardiac response to stress by inhibiting transcriptional reprogramming.

Discussion

The data are likely the first evidence suggesting that an E-C coupling structural protein can also act as a transcriptional regulator. Herein it was demonstrated that regulated cleavage of JP2 converts it from a structural protein to a nuclear transcriptional regulator via an NLS and an ARR contained within JP2NT (FIG. 14F). JP2NT is enriched in the promoter region of genes in cardiomyocytes and primarily acts as a transcriptional repressor of genes implicated in cell growth and differentiation, hypertrophy, inflammation and fibrosis, with evidence for a specific interaction with the transcription factor MEF2. Cardiac-specific transgenic overexpression of JP2NT attenuates pressure overload induced development of heart failure, identifying JP2NT generation as a self-protective homeostatic mechanism that safeguards against the deleterious effects of cardiac stress. These discoveries reveal a signaling pathway that transduces membrane stresses into transcriptome changes in the setting of E-C uncoupling following cardiac stress.

JP2 was initially discovered as a structural protein with dual membrane anchoring domains that connect T-tubules and the SR membrane (Takeshima et al., 2000). Here it is disclosed that JP2 contains additional regulatory domains that extend beyond its role as a structural protein. An NLS in the N-terminal region of JP2 Is necessary for nuclear import of the calpain-generated JP2NT truncate. Thus, under stress conditions, calpain-mediated cleavage of JP2 serves two purposes: 1) impairs the bridging of T-tubules with the SR membrane (contributing to cardiomyocyte ultrastructural remodeling and E-C uncoupling (Wu et al., 2014)); and 2) liberates JP2NT, allowing JP2NT to translocate to the nucleus and mediate transcriptional reprogramming. In addition, the α-helix region of JP2 contains a DNA binding domain that mediates selective binding to canonical TATA box motifs. Interestingly, this DNA binding domain is evolutionarily conserved, suggestive of a dual function for JP2 as a structural protein and transcriptional regulator in other species.

The development and progression of heart failure involves diverse cellular and molecular mechanisms (Mudd et al., 2008; van Berto et al., 2013). The ChIP-seq and transcriptomic profiling data suggest that JP2NT suppresses gene transcription by targeting multiple signaling pathways such as inflammatory responses, fibrosis, myocyte hypotrophy, cell death, etc. Taken with the protective effect of JP2NT overexpression in the setting of cardiac stress, this study indicates that JP2NT is an endogenous self-protective stress transducer which conveys the E-C uncoupling signal to the nucleus, regulates transcriptional reprogramming and ultimately attenuates the progression of heart failure. As JP2 is abundant in all muscle cells (cardiac, skeletal and smooth muscle), JP2NT may serve as a general protective mechanism antagonizing stress-induced pathological remodeling related to many diseases.

REFERENCES

Arthur and Belcastro, Mol. Cell Biochem., 176:241 (1997).
Backs et al., J. Clin. Invest., 116:1853 (2006).
Bers, Nature, 415:198 (2002).
Bray et al., Nat. Biotechnol., 34:525 (2016).
Cannell et al., Science, 268:1045 (1995).
Chen et al., Cardiovasc. Res., 10:54 (2013).
Chen et al., FASEB J., 26:2531 (2012).
Chen et al., J. Biol. Chem., 276:30724 (2001).
Chen et al., J. Blol. Chem., 277:29181 (2002).
Cheng et al., Science, 262:740 (1993).
Clapham, Cell, 131:1047 (2007).
Colella et al., Proc. Natl. Acad. Sci. USA, 105:2859 (2008).
Cox et al., Nat. Protoc., 1:1872 (2006).
DuVerle et al., PLoS ONE, 6:e19035 (2011).
Franzini-Armstrong et al., Biophys. J., 77:1528 (1999).
French et al., Am. J. Physiol. Heart Circ. Physiol., 290:H128 (2006).
Frey et al. Nat. Med., 6:1221 (2000).
Galvez et al., Circ. Res., 100:1071 (2007).
Golini et al., J. Biol. Chem., 286:43717 (2011).
Gómez et al., Circulation, 104:688 (2001).
Gomez et al., Science, 276:800 (1997).
Greyson et al., J. Mol. Cell Cardiol., 44:59 (2008).
Guo et al., Cardiovasc. Res., 0.98:204 (2013).
Guo et al., J. Biol. Chem., 2K:16670 (2012).
Guo et al., J. Biol. Chem., 290:17946 (2015).
Guo et al., Proc. Natl. Acad. Sci. USA, 111:12240 (2014).
Hall et al., J. Heart Luna Transplant., 24:1639 (2005).
Heidrich and Ehrlich, Circ. Res., 104:19 (2009).
Heinz et al., Mol. Cell, 38:576 (2010).
Houser et al., Sci. Signal, 1:pe31 (2008).
Huang et al., Nat Protoc., 4:44 (2009).
Inserte et al., Cardiovasc. Res., 0.6:23 (2012).
Jayasinghe et al., Biophys. J., 102:L19 (2012).
Jiang et al., Heart Rhythm, 13:743 (2016).
Kashef et al., J. Biol. Chem., 287:30268 (2012).
Landstrom et al., Circ. Heart Fail., 4:214 (2011).
Landstrom et al., J. Mol. Cell Cardiol., 42:1026 (2007).
Langmead et al., Nat. Methods, 9:357 (2012).
Letavemier et al., Circ. Res., 102:720 (2008).
Li et al., Cardiovasc. Res., 83:72 (2009).
Li et al., Circ. Res., 2:601 (2013).
U et al., Diabetes, 60:2985 (2011).
Litwin et al., Circ. Res., 87:1040 (2000).
Liu et al., PLoS ONE. 6:e19001 (2011).
Lopez-Lopez et al., Science, 268:1042 (1995).
Maekawa et al., J. Mol. Cell Cardiol., 35:1277 (2003).
Martin, EMBnet.journal 17:3 (2011).
Minamisawa et al., Biochem. Biophys. Res. Commun., 2:852 (2004).
Molkentin et al., Cell, 93:215 (1998).
Mudd et al., Nature, 451:919 (2008).
Murphy et al., J. Physiol., 51:719 (2013).
Narasimhan et al., J. Comput. Blol., 9:707 (2002).
Naya at al., Development, 126:2045 (1999).
Nishi et al., Biochem. Biophys. Res. Commun., 273:920-927 (2000).
Page et al., Circ. Res., 45:260 (1979).
Passier et al., J. Clin, Invest., 105:1395 (2000).
Patterson et al., Circ. Res., 109:453 (2011).
Peltier et al., J. Am. Soc. Nephrol., 17:3415 (2006).
Pimentel ET AL., BioRxiv. http://dx.doi.org/10.1101/058164 (2016).
Ritchie et al., Nucleic Acids Res., 43:e47 (2015).
Sandmann et al., Br. J. Pharmacol., 132:767 (2001).
Sigrist et al., Brief Bioinform., 3:265 (2002).
Singh et al., J. Mol. Cell Cardiol., 37:101 (2004).
Song at al., Circ. Res., 111:816 (2012).
Song et al., Proc. Natl. Acad. Sci. USA, 103:4305 (2006).
Takeshima et al., Cell Calcium. 10.1016/j.ceca.2015.01.007 (2015).
Takeshima et al., Mol. Cell, 6:11 (2000).
van Berto et al., J. Clin. Invest., 123:37 (2013).
van Oort et al., Circulation, 123:979 (2011).
Wang et al., Nature, 410:592 (2001).
Wei et al., Circ. Res., 107:520 (2010).
Williams et al., PloS one, 4:e7474 (2009).
Wu et al., Cardiovasc. Res., 2:430 (2012).
Wu et al., J. Am. Heart Assoc., 3:e000527 (2014).
Wu et al., J. Clin. Invest., 116:675 (2006).
Wysocka et al., Mol. Cell. Biol., 21:3820 (2001).
Xu et al., Circ. Res., 111:837 (2012).
Xu et al., PLoS Biol., 5:e21 (2007).
Yoshida et al., Circ. Res., 77:603 (1995).
Zhang et al., Cardiovasc. Res., 98:269 (2013).

All publications, patents and patent applications are incorporated herein by reference. While in the foregoing specification, this invention has been described in relation to certain preferred embodiments thereof, and many details have been set forth for purposes of illustration, it win be apparent to those skilled in the art that the invention is susceptible to additional embodiments and that certain of the details herein may be varied considerably without departing from the basic principles of the invention.

What is claimed is:

1. A vector comprising a promoter operably linked to an open reading frame encoding an isolated soluble truncated junctophilin-2 (JP-2) protein having a DNA binding domain and a nuclear localization signal (NLS), which protein has at least 90% amino acid identity to SEQ ID NO:1, SEQ ID NO:2 or SEQ ID NO:3, or comprising an isolated transcriptional repressor DNA binding domain which has at least 90% amino acid identity to SEQ ID NO:16 or SEQ ID NO:17, wherein the soluble truncated JP-2 lacks a JP-2 membrane anchor domain.

2. The vector of claim 1, which is a viral vector.

3. The vector of claim 1 wherein the promoter is a tissue-specific promoter.

4. The vector of claim 1 further comprising an enhancer.

5. The vector of claim 4 wherein the enhancer is a tissue-specific enhancer.

6. The vector of claim 1 which is integrated into the genome of a non-human mammal.

7. The vector of claim 6 wherein the open reading frame is operably linked to a tissue-specific promoter or enhancer.

8. The vector of claim 6 wherein expression of the protein in the mammal is inducible.

* * * * *

```
                            SEQUENCE LISTING

<160> NUMBER OF SEQ ID NOS: 80

<210> SEQ ID NO 1
<211> LENGTH: 696
<212> TYPE: PRT
<213> ORGANISM: Homo sapiens

<400> SEQUENCE: 1

Met Ser Gly Gly Arg Phe Asp Phe Asp Asp Gly Gly Ala Tyr Cys Gly
1               5                   10                  15

Gly Trp Glu Gly Gly Lys Ala His Gly His Gly Leu Cys Thr Gly Pro
            20                  25                  30

Lys Gly Gln Gly Glu Tyr Ser Gly Ser Trp Asn Phe Gly Phe Glu Val
        35                  40                  45

Ala Gly Val Tyr Thr Trp Pro Ser Gly Asn Thr Phe Glu Gly Tyr Trp
    50                  55                  60

Ser Gln Gly Lys Arg His Gly Leu Gly Ile Glu Thr Lys Gly Arg Trp
65                  70                  75                  80

Leu Tyr Lys Gly Glu Trp Thr His Gly Phe Lys Gly Arg Tyr Gly Ile
                85                  90                  95

Arg Gln Ser Ser Ser Gly Ala Lys Tyr Glu Gly Thr Trp Asn Asn
            100                 105                 110

Gly Leu Gln Asp Gly Tyr Gly Thr Glu Thr Tyr Ala Asp Gly Gly Thr
        115                 120                 125

Tyr Gln Gly Gln Phe Thr Asn Gly Met Arg His Gly Tyr Gly Val Arg
    130                 135                 140

Gln Ser Val Pro Tyr Gly Met Ala Val Val Arg Ser Pro Leu Arg
145                 150                 155                 160

Thr Ser Leu Ser Ser Leu Arg Ser Glu His Ser Asn Gly Thr Val Ala
                165                 170                 175

Pro Asp Ser Pro Ala Ser Pro Ala Ser Asp Gly Pro Ala Leu Pro Ser
            180                 185                 190

Pro Ala Ile Pro Arg Gly Gly Phe Ala Leu Ser Leu Leu Ala Asn Ala
        195                 200                 205

Glu Ala Ala Arg Ala Pro Lys Gly Gly Leu Phe Gln Arg Gly
    210                 215                 220

Ala Leu Leu Gly Lys Leu Arg Arg Ala Glu Ser Arg Thr Ser Val Gly
225                 230                 235                 240

Ser Gln Arg Ser Arg Val Ser Phe Leu Lys Ser Asp Leu Ser Ser Gly
                245                 250                 255

Ala Ser Asp Ala Ala Ser Thr Ala Ser Leu Gly Glu Ala Ala Glu Gly
            260                 265                 270

Ala Asp Glu Ala Ala Pro Phe Glu Ala Asp Ile Asp Ala Thr Thr Thr
        275                 280                 285

Glu Thr Tyr Met Gly Glu Trp Lys Asn Asp Lys Arg Ser Gly Phe Gly
    290                 295                 300

Val Ser Glu Arg Ser Ser Gly Leu Arg Tyr Glu Gly Glu Trp Leu Asp
305                 310                 315                 320

Asn Leu Arg His Gly Tyr Gly Cys Thr Thr Leu Pro Asp Gly His Arg
                325                 330                 335

Glu Glu Gly Lys Tyr Arg His Asn Val Leu Val Lys Asp Thr Lys Arg
```

```
                340                 345                 350
Arg Met Leu Gln Leu Lys Ser Asn Lys Val Arg Gln Lys Val Glu His
            355                 360                 365
Ser Val Glu Gly Ala Gln Arg Ala Ala Ile Ala Arg Gln Lys Ala
        370                 375                 380
Glu Ile Ala Ala Ser Arg Thr Ser His Ala Lys Ala Lys Ala Glu Ala
385                 390                 395                 400
Ala Glu Gln Ala Ala Leu Ala Ala Asn Gln Glu Ser Asn Ile Ala Arg
                405                 410                 415
Thr Leu Ala Arg Glu Leu Ala Pro Asp Phe Tyr Gln Pro Gly Pro Glu
            420                 425                 430
Tyr Gln Lys Arg Arg Leu Leu Gln Glu Ile Leu Glu Asn Ser Glu Ser
        435                 440                 445
Leu Leu Glu Pro Pro Asp Arg Gly Ala Gly Ala Ala Gly Leu Pro Gln
    450                 455                 460
Pro Pro Arg Glu Ser Pro Gln Leu His Glu Arg Glu Thr Pro Arg Pro
465                 470                 475                 480
Glu Gly Gly Ser Pro Ser Pro Ala Gly Thr Pro Gln Pro Lys Arg
                485                 490                 495
Pro Arg Pro Gly Val Ser Lys Asp Gly Leu Leu Ser Pro Gly Ala Trp
            500                 505                 510
Asn Gly Glu Pro Ser Gly Glu Gly Ser Arg Ser Val Thr Pro Ser Glu
        515                 520                 525
Gly Ala Gly Arg Arg Ser Pro Ala Arg Pro Ala Thr Glu Arg Met Ala
    530                 535                 540
Ile Glu Ala Leu Gln Ala Pro Pro Ala Pro Ser Arg Glu Pro Glu Val
545                 550                 555                 560
Ala Leu Tyr Gln Gly Tyr His Ser Tyr Ala Val Arg Thr Thr Pro Pro
                565                 570                 575
Glu Pro Pro Pro Phe Glu Asp Gln Pro Glu Pro Glu Val Ser Gly Ser
            580                 585                 590
Glu Ser Ala Pro Ser Ser Pro Ala Thr Ala Pro Leu Gln Ala Pro Thr
        595                 600                 605
Leu Arg Gly Pro Glu Pro Ala Arg Glu Thr Pro Ala Lys Leu Glu Pro
    610                 615                 620
Lys Pro Ile Ile Pro Lys Ala Glu Pro Arg Ala Lys Ala Arg Lys Thr
625                 630                 635                 640
Glu Ala Arg Gly Leu Thr Lys Ala Gly Ala Lys Lys Ala Arg Lys
                645                 650                 655
Glu Ala Ala Leu Ala Ala Glu Ala Glu Val Glu Val Glu Glu Val Pro
            660                 665                 670
Asn Thr Ile Leu Ile Cys Met Val Ile Leu Leu Asn Ile Gly Leu Ala
        675                 680                 685
Ile Leu Phe Val His Leu Leu Thr
    690                 695

<210> SEQ ID NO 2
<211> LENGTH: 696
<212> TYPE: PRT
<213> ORGANISM: Homo sapiens

<400> SEQUENCE: 2

Met Ser Gly Gly Arg Phe Asp Phe Asp Asp Gly Gly Ala Tyr Cys Gly
1               5                   10                  15
```

-continued

```
Gly Trp Glu Gly Gly Lys Ala His Gly His Gly Leu Cys Thr Gly Pro
            20                  25                  30
Lys Gly Gln Gly Glu Tyr Ser Gly Ser Trp Asn Phe Gly Phe Glu Val
        35                  40                  45
Ala Gly Val Tyr Thr Trp Pro Ser Gly Asn Thr Phe Glu Gly Tyr Trp
    50                  55                  60
Ser Gln Gly Lys Arg His Gly Leu Gly Ile Glu Thr Lys Gly Arg Trp
65                  70                  75                  80
Leu Tyr Lys Gly Glu Trp Thr His Gly Phe Lys Gly Arg Tyr Gly Ile
                85                  90                  95
Arg Gln Ser Ser Ser Ser Gly Ala Lys Tyr Glu Gly Thr Trp Asn Asn
            100                 105                 110
Gly Leu Gln Asp Gly Tyr Gly Thr Glu Thr Tyr Ala Asp Gly Gly Thr
        115                 120                 125
Tyr Gln Gly Gln Phe Thr Asn Gly Met Arg His Gly Tyr Gly Val Arg
    130                 135                 140
Gln Ser Val Pro Tyr Gly Met Ala Val Val Arg Ser Pro Leu Arg
145                 150                 155                 160
Thr Ser Leu Ser Ser Leu Arg Ser Glu His Ser Asn Gly Thr Val Ala
                165                 170                 175
Pro Asp Ser Pro Ala Ser Pro Ala Ser Asp Gly Pro Ala Leu Pro Ser
            180                 185                 190
Pro Ala Ile Pro Arg Gly Gly Phe Ala Leu Ser Leu Leu Ala Asn Ala
        195                 200                 205
Glu Ala Ala Arg Ala Pro Lys Gly Gly Leu Phe Gln Arg Gly
    210                 215                 220
Ala Leu Leu Gly Lys Leu Arg Arg Ala Glu Ser Arg Thr Ser Val Gly
225                 230                 235                 240
Ser Gln Arg Ser Arg Val Ser Phe Leu Lys Ser Asp Leu Ser Ser Gly
                245                 250                 255
Ala Ser Asp Ala Ala Ser Thr Ala Ser Leu Gly Glu Ala Ala Glu Gly
            260                 265                 270
Ala Asp Glu Ala Ala Pro Phe Glu Ala Asp Ile Asp Ala Thr Thr Thr
        275                 280                 285
Glu Thr Tyr Met Gly Glu Trp Lys Asn Asp Lys Arg Ser Gly Phe Gly
    290                 295                 300
Val Ser Glu Arg Ser Ser Gly Leu Arg Tyr Glu Gly Glu Trp Leu Asp
305                 310                 315                 320
Asn Leu Arg His Gly Tyr Gly Cys Thr Thr Leu Pro Asp Gly His Arg
                325                 330                 335
Glu Glu Gly Lys Tyr Arg His Asn Val Leu Val Lys Asp Thr Lys Arg
            340                 345                 350
Arg Met Leu Gln Leu Lys Ser Asn Lys Val Arg Gln Lys Val Glu His
        355                 360                 365
Ser Val Glu Gly Ala Gln Arg Ala Ala Ile Ala Arg Gln Lys Ala
    370                 375                 380
Glu Ile Ala Ala Ser Arg Thr Ser His Ala Lys Ala Lys Ala Glu Ala
385                 390                 395                 400
Ala Glu Gln Ala Ala Leu Ala Ala Asn Gln Glu Ser Asn Ile Ala Arg
                405                 410                 415
Thr Leu Ala Arg Glu Leu Ala Pro Asp Phe Tyr Gln Pro Gly Pro Glu
            420                 425                 430
Tyr Gln Lys Arg Arg Leu Leu Gln Glu Ile Leu Glu Asn Ser Glu Ser
```

```
                    435                 440                 445
Leu Leu Glu Pro Pro Asp Arg Gly Ala Gly Ala Ala Gly Leu Pro Gln
    450                 455                 460

Pro Pro Arg Glu Ser Pro Gln Leu His Glu Arg Glu Thr Pro Arg Pro
465                 470                 475                 480

Glu Gly Gly Ser Pro Ser Pro Ala Gly Thr Pro Pro Gln Pro Lys Arg
                    485                 490                 495

Pro Arg Pro Gly Val Ser Lys Asp Gly Leu Leu Ser Pro Gly Ala Trp
                500                 505                 510

Asn Gly Glu Pro Ser Gly Glu Gly Ser Arg Ser Val Thr Pro Ser Glu
                515                 520                 525

Gly Ala Gly Arg Arg Ser Pro Ala Arg Pro Ala Thr Glu Arg Met Ala
            530                 535                 540

Ile Glu Ala Leu Gln Ala Pro Pro Ala Pro Ser Arg Glu Pro Glu Val
545                 550                 555                 560

Ala Leu Tyr Gln Gly Tyr His Ser Tyr Ala Val Arg Thr Thr Pro Pro
                    565                 570                 575

Glu Pro Pro Pro Phe Glu Asp Gln Pro Glu Pro Glu Val Ser Gly Ser
                580                 585                 590

Glu Ser Ala Pro Ser Ser Pro Ala Thr Ala Pro Leu Gln Ala Pro Thr
            595                 600                 605

Leu Arg Gly Pro Glu Pro Ala Arg Glu Thr Pro Ala Lys Leu Glu Pro
610                 615                 620

Lys Pro Ile Ile Pro Lys Ala Glu Pro Arg Ala Lys Ala Arg Lys Thr
625                 630                 635                 640

Glu Ala Arg Gly Leu Thr Lys Ala Gly Ala Lys Lys Ala Arg Lys
                    645                 650                 655

Glu Ala Ala Leu Ala Ala Glu Ala Glu Val Glu Val Glu Val Pro
                    660                 665                 670

Asn Thr Ile Leu Ile Cys Met Val Ile Leu Leu Asn Ile Gly Leu Ala
                675                 680                 685

Ile Leu Phe Val His Leu Leu Thr
    690                 695

<210> SEQ ID NO 3
<211> LENGTH: 696
<212> TYPE: PRT
<213> ORGANISM: Mus musculus

<400> SEQUENCE: 3

Met Ser Gly Gly Arg Phe Asp Phe Asp Asp Gly Gly Ala Tyr Cys Gly
1               5                   10                  15

Gly Trp Glu Gly Gly Lys Ala His Gly His Gly Leu Cys Thr Gly Pro
                20                  25                  30

Lys Gly Gln Gly Glu Tyr Ser Gly Ser Trp Asn Phe Gly Phe Glu Val
            35                  40                  45

Ala Gly Val Tyr Thr Trp Pro Ser Gly Asn Thr Phe Glu Gly Tyr Trp
        50                  55                  60

Ser Gln Gly Lys Arg His Gly Leu Gly Ile Glu Thr Lys Gly Arg Trp
65              70                  75                  80

Leu Tyr Lys Gly Glu Trp Thr His Gly Phe Lys Gly Arg Tyr Gly Ile
                85                  90                  95

Arg Gln Ser Thr Asn Ser Gly Ala Lys Tyr Glu Gly Thr Trp Asn Asn
            100                 105                 110
```

-continued

Gly Leu Gln Asp Gly Tyr Gly Thr Glu Thr Tyr Ala Asp Gly Gly Thr
            115                 120                 125

Tyr Gln Gly Gln Phe Thr Asn Gly Met Arg His Gly Tyr Gly Val Arg
        130                 135                 140

Gln Ser Val Pro Tyr Gly Met Ala Val Val Arg Ser Pro Leu Arg
145                 150                 155                 160

Thr Ser Leu Ser Ser Leu Arg Ser Glu His Ser Asn Gly Thr Val Ala
                165                 170                 175

Pro Asp Ser Pro Ala Ala Asp Gly Pro Met Leu Pro Ser Pro Pro Val
            180                 185                 190

Pro Arg Gly Gly Phe Ala Leu Thr Leu Leu Ala Thr Ala Glu Ala Ala
        195                 200                 205

Arg Pro Gln Gly Leu Phe Thr Arg Gly Thr Leu Leu Gly Arg Leu Arg
    210                 215                 220

Arg Ser Glu Ser Arg Thr Ser Leu Gly Ser Gln Arg Ser Arg Leu Ser
225                 230                 235                 240

Phe Leu Lys Ser Glu Leu Ser Ser Gly Ala Ser Asp Ala Ala Ser Thr
                245                 250                 255

Gly Ser Leu Ala Glu Gly Ala Glu Gly Pro Asp Ala Ala Ala Pro
            260                 265                 270

Phe Asp Ala Asp Ile Asp Ala Thr Thr Thr Glu Thr Tyr Met Gly Glu
        275                 280                 285

Trp Lys Asn Asp Lys Arg Ser Gly Phe Gly Val Ser Glu Arg Ser Ser
    290                 295                 300

Gly Leu Arg Tyr Glu Gly Glu Trp Leu Asp Asn Leu Arg His Gly Tyr
305                 310                 315                 320

Gly Arg Thr Thr Leu Pro Asp Gly His Arg Glu Gly Lys Tyr Arg
                325                 330                 335

His Asn Val Leu Val Lys Gly Thr Lys Arg Arg Val Leu Pro Leu Lys
            340                 345                 350

Ser Ser Lys Val Arg Gln Lys Val Glu His Gly Val Glu Gly Ala Gln
        355                 360                 365

Arg Ala Ala Ala Ile Ala Arg Gln Lys Ala Glu Ile Ala Ala Ser Arg
    370                 375                 380

Thr Ser His Ala Lys Ala Lys Ala Glu Ala Ala Glu Gln Ala Ala Leu
385                 390                 395                 400

Ala Ala Asn Gln Glu Ser Asn Ile Ala Arg Thr Leu Ala Lys Glu Leu
                405                 410                 415

Ala Pro Asp Phe Tyr Gln Pro Gly Pro Glu Tyr Gln Lys Arg Arg Leu
            420                 425                 430

Leu Gln Glu Ile Leu Glu Asn Ser Glu Ser Leu Leu Glu Pro Pro Glu
        435                 440                 445

Arg Gly Leu Gly Thr Gly Leu Pro Glu Arg Pro Arg Glu Ser Pro Gln
    450                 455                 460

Leu His Glu Arg Glu Thr Pro Gln Pro Glu Gly Gly Pro Pro Ser Pro
465                 470                 475                 480

Ala Gly Thr Pro Pro Gln Pro Lys Arg Pro Arg Pro Gly Ala Ser Lys
                485                 490                 495

Asp Gly Leu Leu Ser Pro Gly Ser Trp Asn Gly Glu Pro Gly Gly Glu
            500                 505                 510

Gly Ser Arg Pro Ala Thr Pro Ser Asp Gly Ala Gly Arg Arg Ser Pro
        515                 520                 525

Ala Arg Pro Ala Ser Glu His Met Ala Ile Glu Ala Leu Gln Pro Pro

```
            530                 535                 540
Pro Ala Pro Ser Gln Glu Pro Glu Val Ala Met Tyr Arg Gly Tyr His
545                 550                 555                 560

Ser Tyr Ala Val Arg Thr Gly Pro Pro Glu Pro Pro Leu Glu Asp
                565                 570                 575

Glu Gln Glu Pro Glu Pro Pro Glu Pro Val Arg Arg Ser Asp
            580                 585                 590

Ser Ala Pro Pro Ser Pro Val Ser Ala Thr Val Pro Glu Glu Glu Pro
                595                 600                 605

Pro Ala Pro Arg Ser Pro Val Pro Ala Lys Gln Ala Thr Leu Glu Pro
            610                 615                 620

Lys Pro Ile Val Pro Lys Ala Glu Pro Lys Ala Lys Ala Arg Lys Thr
625                 630                 635                 640

Glu Ala Arg Gly Leu Ser Lys Ala Gly Ala Lys Lys Lys Gly Arg Lys
                645                 650                 655

Glu Val Ala Gln Ala Lys Glu Ala Glu Val Glu Val Glu Val Pro
            660                 665                 670

Asn Thr Val Leu Ile Cys Met Val Ile Leu Leu Asn Ile Gly Leu Ala
                675                 680                 685

Ile Leu Phe Val His Leu Leu Thr
            690                 695

<210> SEQ ID NO 4
<211> LENGTH: 694
<212> TYPE: PRT
<213> ORGANISM: Oryctolagus cuniculus

<400> SEQUENCE: 4

Met Ser Gly Gly Arg Phe Asp Phe Asp Asp Gly Gly Ala Tyr Cys Gly
1               5                   10                  15

Gly Trp Glu Gly Gly Lys Ala His Gly His Gly Leu Cys Thr Gly Pro
                20                  25                  30

Lys Gly Gln Gly Glu Tyr Ser Gly Ser Trp Asn Phe Gly Phe Glu Val
            35                  40                  45

Ala Gly Val Tyr Thr Trp Pro Ser Gly Asn Thr Phe Glu Gly Tyr Trp
        50                  55                  60

Ser Gln Gly Lys Arg His Gly Leu Gly Ile Glu Thr Lys Gly Arg Trp
65                  70                  75                  80

Leu Tyr Lys Gly Glu Trp Thr His Gly Phe Lys Gly Arg Tyr Gly Thr
                85                  90                  95

Arg Gln Ser Thr Ser Ser Gly Ala Lys Tyr Glu Gly Thr Trp Asn Asn
            100                 105                 110

Gly Leu Gln Asp Gly Tyr Gly Thr Glu Thr Tyr Ala Asp Gly Gly Thr
        115                 120                 125

Tyr Gln Gly Gln Phe Thr Asn Gly Met Arg His Gly Tyr Gly Val Arg
130                 135                 140

Gln Ser Val Pro Tyr Gly Met Ala Val Val Val Arg Ser Pro Leu Arg
145                 150                 155                 160

Thr Ser Leu Ser Ser Leu Arg Ser Glu His Ser Asn Gly Thr Val Ala
                165                 170                 175

Pro Asp Ser Pro Ala Ser Pro Ala Ala Asp Gly Pro Ala Leu Pro Ser
            180                 185                 190

Pro Ala Ile Pro Arg Gly Gly Phe Ala Leu Ser Leu Leu Ala Asn Ala
        195                 200                 205
```

```
Glu Ala Ala Arg Ala Pro Lys Gly Gly Gly Leu Phe Pro Arg Gly Ala
            210                 215                 220

Leu Leu Gly Lys Leu Arg Arg Ala Glu Ser Arg Thr Ser Val Gly Ser
225                 230                 235                 240

Gln Arg Ser Arg Val Ser Phe Leu Lys Ser Asp Leu Ser Ser Gly Ala
                245                 250                 255

Ser Asp Ala Ala Ser Thr Ala Ser Leu Gly Glu Gly Ala Glu Gly Ala
            260                 265                 270

Asp Ala Ala Pro Phe Glu Ala Asp Ile Asp Ala Thr Thr Thr Glu
            275                 280                 285

Thr Tyr Met Gly Glu Trp Lys Asn Asp Lys Arg Ser Gly Phe Gly Val
290                 295                 300

Ser Glu Arg Ser Ser Gly Leu Arg Tyr Glu Gly Glu Trp Leu Asp Asn
305                 310                 315                 320

Leu Arg His Gly Tyr Gly Cys Thr Thr Leu Pro Asp Gly His Arg Glu
                325                 330                 335

Glu Gly Lys Tyr Arg His Asn Val Leu Val Lys Gly Thr Lys Arg Arg
            340                 345                 350

Val Leu Pro Leu Lys Ser Asn Lys Val Arg Gln Lys Val Glu His Ser
            355                 360                 365

Val Glu Gly Ala Gln Arg Ala Ala Ile Ala Arg Gln Lys Ala Glu
370                 375                 380

Ile Ala Val Ser Arg Thr Ser His Ala Arg Ala Lys Ala Glu Ala Ala
385                 390                 395                 400

Glu Gln Ala Ala Leu Ala Ala Asn Gln Glu Ser Asn Ile Ala Arg Ser
                405                 410                 415

Leu Ala Arg Glu Leu Ala Pro Asp Phe Tyr Gln Pro Gly Pro Glu Tyr
            420                 425                 430

Gln Lys Arg Arg Leu Leu Gln Glu Ile Leu Glu His Ser Glu Ser Leu
            435                 440                 445

Leu Glu Pro Pro Asp Arg Gly Ala Ala Gly Leu Pro Gln Pro Pro Arg
450                 455                 460

Glu Ser Pro Gln Leu His Glu Arg Glu Thr Pro Arg Pro Glu Gly Gly
465                 470                 475                 480

Pro Pro Ser Pro Ala Gly Thr Pro Pro Gln Pro Lys Arg Pro Arg Pro
                485                 490                 495

Gly Ala Ser Lys Asp Gly Leu Leu Gly Pro Gly Ala Trp Asn Gly Glu
            500                 505                 510

Pro Ser Gly Gly Ser Gly Gly Glu Gly Ser Arg Pro Ala Thr Pro Ala
            515                 520                 525

Ala Ala Gly Ala Gly Arg Arg Ser Pro Ala Arg Pro Ala Ser Glu His
530                 535                 540

Met Ala Ile Glu Ala Leu Gln Ala Pro Pro Ala Pro Ser Arg Glu Pro
545                 550                 555                 560

Glu Val Ala Leu Tyr Arg Gly Tyr His Ser Tyr Ala Val Arg Thr Ala
                565                 570                 575

Pro Pro Ala Pro Pro Phe Glu Asp Asp Pro Gln Pro Glu Ala Ala
            580                 585                 590

Asp Pro Asp Ser Ala Pro Ala Ser Pro Ala Thr Ala Pro Gly Gln Ala
            595                 600                 605

Pro Ala Leu Gly Asn Pro Glu Pro Ala Pro Glu Ser Pro Ala Lys Leu
610                 615                 620

Glu Pro Lys Pro Ile Val Pro Lys Ala Lys Ala Arg Lys Thr Glu Ala
```

```
            625                 630                 635                 640
Arg Gly Leu Ser Lys Thr Gly Ala Lys Lys Pro Arg Lys Glu Ala
                    645                 650                 655

Ala Gln Ala Ala Glu Ala Glu Val Glu Val Glu Val Pro Asn Thr
            660                 665                 670

Val Leu Ile Cys Met Val Ile Leu Leu Asn Ile Gly Leu Ala Ile Leu
            675                 680                 685

Phe Val His Leu Leu Thr
            690

<210> SEQ ID NO 5
<211> LENGTH: 5
<212> TYPE: PRT
<213> ORGANISM: Artificial Sequence
<220> FEATURE:
<223> OTHER INFORMATION: A synthetic peptide

<400> SEQUENCE: 5

His His His His His
1               5

<210> SEQ ID NO 6
<211> LENGTH: 6
<212> TYPE: PRT
<213> ORGANISM: Artificial Sequence
<220> FEATURE:
<223> OTHER INFORMATION: A synthetic peptide

<400> SEQUENCE: 6

His His His His His His
1               5

<210> SEQ ID NO 7
<211> LENGTH: 10
<212> TYPE: PRT
<213> ORGANISM: Artificial Sequence
<220> FEATURE:
<223> OTHER INFORMATION: A synthetic peptide

<400> SEQUENCE: 7

Glu Gln Lys Leu Ile Ser Glu Glu Asp Leu
1               5                   10

<210> SEQ ID NO 8
<211> LENGTH: 8
<212> TYPE: PRT
<213> ORGANISM: Artificial Sequence
<220> FEATURE:
<223> OTHER INFORMATION: A synthetic peptide

<400> SEQUENCE: 8

Asp Tyr Lys Asp Asp Asp Asp Lys
1               5

<210> SEQ ID NO 9
<211> LENGTH: 8
<212> TYPE: PRT
<213> ORGANISM: Artificial Sequence
<220> FEATURE:
<223> OTHER INFORMATION: A synthetic peptide

<400> SEQUENCE: 9

Trp Ser His Pro Gln Phe Glu Lys
1               5
```

<210> SEQ ID NO 10
<211> LENGTH: 9
<212> TYPE: PRT
<213> ORGANISM: Artificial Sequence
<220> FEATURE:
<223> OTHER INFORMATION: A synthetic peptide

<400> SEQUENCE: 10

Tyr Pro Tyr Asp Val Pro Asp Tyr Ala
1               5

<210> SEQ ID NO 11
<211> LENGTH: 5
<212> TYPE: PRT
<213> ORGANISM: Artificial Sequence
<220> FEATURE:
<223> OTHER INFORMATION: A synthetic peptide

<400> SEQUENCE: 11

Arg Tyr Ile Arg Ser
1               5

<210> SEQ ID NO 12
<211> LENGTH: 4
<212> TYPE: PRT
<213> ORGANISM: Artificial Sequence
<220> FEATURE:
<223> OTHER INFORMATION: A synthetic peptide

<400> SEQUENCE: 12

Phe His His Thr
1

<210> SEQ ID NO 13
<211> LENGTH: 17
<212> TYPE: PRT
<213> ORGANISM: Artificial Sequence
<220> FEATURE:
<223> OTHER INFORMATION: A synthetic peptide

<400> SEQUENCE: 13

Trp Glu Ala Ala Ala Arg Glu Ala Cys Cys Arg Glu Cys Cys Ala Arg
1               5                   10                  15

Ala

<210> SEQ ID NO 14
<211> LENGTH: 5
<212> TYPE: PRT
<213> ORGANISM: Artificial Sequence
<220> FEATURE:
<223> OTHER INFORMATION: A synthetic peptide

<400> SEQUENCE: 14

Lys Arg Pro Arg Pro
1               5

<210> SEQ ID NO 15
<211> LENGTH: 14
<212> TYPE: PRT
<213> ORGANISM: Artificial Sequence
<220> FEATURE:
<223> OTHER INFORMATION: A synthetic peptide

<400> SEQUENCE: 15

Arg Arg Val Leu Pro Leu Lys Ser Ser Lys Val Arg Gln Lys
1               5                   10

```
<210> SEQ ID NO 16
<211> LENGTH: 58
<212> TYPE: PRT
<213> ORGANISM: Artificial Sequence
<220> FEATURE:
<223> OTHER INFORMATION: A synthetic peptide

<400> SEQUENCE: 16

Lys Arg Arg Val Leu Pro Leu Lys Ser Ser Lys Val Arg Gln Lys Val
1               5                   10                  15

Glu His Gly Val Glu Gly Ala Gln Arg Ala Ala Ala Ile Ala Arg Gln
                20                  25                  30

Lys Ala Glu Ile Ala Ala Ser Arg Thr Ser His Ala Lys Ala Lys Ala
        35                  40                  45

Glu Ala Ala Glu Gln Ala Ala Leu Ala Ala
    50                  55

<210> SEQ ID NO 17
<211> LENGTH: 58
<212> TYPE: PRT
<213> ORGANISM: Artificial Sequence
<220> FEATURE:
<223> OTHER INFORMATION: A synthetic peptide

<400> SEQUENCE: 17

Lys Arg Arg Met Leu Gln Leu Lys Ser Asn Lys Val Arg Gln Lys Val
1               5                   10                  15

Glu His Ser Val Glu Gly Ala Gln Arg Ala Ala Ala Ile Ala Arg Gln
                20                  25                  30

Lys Ala Glu Ile Ala Ala Ser Arg Thr Ser His Ala Lys Ala Lys Ala
        35                  40                  45

Glu Ala Ala Glu Gln Ala Ala Leu Ala Ala
    50                  55

<210> SEQ ID NO 18
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 18
catttcctgg tatgacaatg aatacg                                      26

<210> SEQ ID NO 19
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 19
tccagggttt cttactcctt gga                                         23

<210> SEQ ID NO 20
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 20
```

```
tgaaggctgg atttcctttg                                          20

<210> SEQ ID NO 21
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 21
ttctcttcct cgtcgcagat                                          20

<210> SEQ ID NO 22
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 22
aagcacccct ggaagaacc                                           19

<210> SEQ ID NO 23
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 23
cctgctctga aggcagatgt a                                        21

<210> SEQ ID NO 24
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 24
tctgcattgc acttatgctg a                                        21

<210> SEQ ID NO 25
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 25
aaagggcgat ctagtgatgg a                                        21

<210> SEQ ID NO 26
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 26
atcctttcca actcgctaac cc                                       22

<210> SEQ ID NO 27
<211> LENGTH: 21
<212> TYPE: DNA
<213> ORGANISM: Artificial Sequence
```

```
<220> FEATURE:
<223> OTHER INFORMATION: A synthetic oligonucleotide

<400> SEQUENCE: 27
cggatcggat agctgaagct g                                              21

<210> SEQ ID NO 28
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 28
gatgggctct ctccagatca g                                              21

<210> SEQ ID NO 29
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 29
ggctgcatca ttcttgtcac tt                                             22

<210> SEQ ID NO 30
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 30
tgaaggacga ggagtacgag c                                              21

<210> SEQ ID NO 31

<400> SEQUENCE: 31

000

<210> SEQ ID NO 32
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 32
ttcgtggatg attgccaagt g                                              21

<210> SEQ ID NO 33
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 33
gtttctgctc ggactcctga t                                              21

<210> SEQ ID NO 34
<211> LENGTH: 23
<212> TYPE: DNA
<213> ORGANISM: Artificial Sequence
```

```
<220> FEATURE:
<223> OTHER INFORMATION: A synthetic oligonucleotide

<400> SEQUENCE: 34
ttcctggaag atgctacaca ttg                                              23

<210> SEQ ID NO 35
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 35
cgatggcttc tcagacgtg                                                   19

<210> SEQ ID NO 36
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 36
cagcccgctt gttgatgttg                                                  20

<210> SEQ ID NO 37
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 37
cccaggccgg agtttaacc                                                   19

<210> SEQ ID NO 38
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 38
gttgctcata aagtcggtgc t                                                21

<210> SEQ ID NO 39
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 39
acaccacggt ttggactatg g                                                21

<210> SEQ ID NO 40
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 40
ggctacagta gtgggcttgg                                                  20
```

<210> SEQ ID NO 41
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 41
taataccacc gacaaggaaa tgg                                          23

<210> SEQ ID NO 42
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 42
tgatgggaga gtccgataga gt                                           22

<210> SEQ ID NO 43
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 43
ggcttctccg cgaatgacaa                                              20

<210> SEQ ID NO 44
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 44
gtttggacgc agcatctgga                                              20

<210> SEQ ID NO 45
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 45
gcgcaccgtg aacctaaac                                               19

<210> SEQ ID NO 46
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 46
gtggactggc aatggagaaa c                                            21

<210> SEQ ID NO 47
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 47
gtcttggcct tttggcttc                                                                                 19

<210> SEQ ID NO 48
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 48
ttcctcagtc tgctcactc                                                                                 19

<210> SEQ ID NO 49
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 49
aggagaagat gccggtagaa ga                                                                             22

<210> SEQ ID NO 50
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 50
gcttcctcag tctgctcact ca                                                                             22

<210> SEQ ID NO 51
<211> LENGTH: 12
<212> TYPE: PRT
<213> ORGANISM: Artificial Sequence
<220> FEATURE:
<223> OTHER INFORMATION: A synthetic peptide

<400> SEQUENCE: 51

Met Val Ile Leu Leu Asn Ile Gly Leu Ala Ile Leu
1               5                   10

<210> SEQ ID NO 52
<211> LENGTH: 35
<212> TYPE: PRT
<213> ORGANISM: Artificial Sequence
<220> FEATURE:
<223> OTHER INFORMATION: A synthetic peptide

<400> SEQUENCE: 52

Leu Thr Pro Glu Gln Val Val Ala Ile Ala Ser Asn Ile Gly Gly Lys
1               5                   10                  15

Gln Ala Leu Glu Val Thr Val Gln Arg Leu Leu Pro Val Leu Leu Gln
            20                  25                  30

Ala His Gly
        35

<210> SEQ ID NO 53
<211> LENGTH: 14
<212> TYPE: PRT
<213> ORGANISM: Artificial Sequence
<220> FEATURE:

<223> OTHER INFORMATION: A synthetic peptide

<400> SEQUENCE: 53

Arg Arg Val Leu Pro Leu Lys Ser Ser Lys Val Arg Gln Lys
1               5                   10

<210> SEQ ID NO 54
<211> LENGTH: 35
<212> TYPE: PRT
<213> ORGANISM: Artificial Sequence
<220> FEATURE:
<223> OTHER INFORMATION: A synthetic peptide

<400> SEQUENCE: 54

Gln Arg Ala Ala Ala Ile Ala Arg Gln Lys Ala Glu Ile Ala Ala Ser
1               5                   10                  15

Arg Thr Ser His Ala Lys Ala Lys Ala Glu Ala Ala Glu Gln Ala Ala
            20                  25                  30

Lys Ala Ala
        35

<210> SEQ ID NO 55
<211> LENGTH: 4
<212> TYPE: PRT
<213> ORGANISM: Artificial Sequence
<220> FEATURE:
<223> OTHER INFORMATION: A synthetic peptide

<400> SEQUENCE: 55

Arg Pro Arg Pro
1

<210> SEQ ID NO 56
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 56
gggatctgag tcgcagtata aaagaagctt ttcgggcgtt                    40

<210> SEQ ID NO 57
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 57
ggggatcgtg agtcgcagta tattagaagc ttttcgggcg tt                 42

<210> SEQ ID NO 58
<211> LENGTH: 41
<212> TYPE: DNA
<213> ORGANISM: Artificial Sequence
<220> FEATURE:
<223> OTHER INFORMATION: A synthetic oligonucleotide

<400> SEQUENCE: 58
gggatcctga gtcgcagtat taaagaagct tttcgggcgt t                  41

<210> SEQ ID NO 59
<211> LENGTH: 42
<212> TYPE: DNA

```
<213> ORGANISM: Artificial Sequence
<220> FEATURE:
<223> OTHER INFORMATION: A synthetic oligonucleotide

<400> SEQUENCE: 59
ggcctttcct tctcctctat aaataccagc tctggtattt ca          42

<210> SEQ ID NO 60
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 60
ggcctttcct tctcctctat agcgaccagc tctggtattt ca          42

<210> SEQ ID NO 61
<211> LENGTH: 11
<212> TYPE: PRT
<213> ORGANISM: Homo sapiens

<400> SEQUENCE: 61

Pro Gln Pro Lys Arg Pro Arg Pro Gly Val Ser
1               5                   10

<210> SEQ ID NO 62
<211> LENGTH: 11
<212> TYPE: PRT
<213> ORGANISM: Mus musculus

<400> SEQUENCE: 62

Pro Gln Pro Lys Arg Pro Arg Pro Cys Ala Ser
1               5                   10

<210> SEQ ID NO 63
<211> LENGTH: 11
<212> TYPE: PRT
<213> ORGANISM: Rattus norvegicus

<400> SEQUENCE: 63

Pro Gln Pro Lys Arg Pro Arg Pro Gly Ser Ser
1               5                   10

<210> SEQ ID NO 64
<211> LENGTH: 11
<212> TYPE: PRT
<213> ORGANISM: Macaca mulatta

<400> SEQUENCE: 64

Pro Gln Pro Lys Arg Pro Arg Pro Gly Ala Ser
1               5                   10

<210> SEQ ID NO 65
<211> LENGTH: 11
<212> TYPE: PRT
<213> ORGANISM: Bos taurus

<400> SEQUENCE: 65

Pro Gln Pro Lys Arg Pro Arg Pro Ala Ala Ala
1               5                   10

<210> SEQ ID NO 66
<211> LENGTH: 58
<212> TYPE: PRT
```

<213> ORGANISM: Mus musculus

<400> SEQUENCE: 66

Lys Arg Arg Val Leu Pro Leu Lys Ser Ser Lys Val Arg Gln Lys Val
1               5                   10                  15

Glu His Gly Val Glu Gly Ala Gln Arg Ala Ala Ile Ala Arg Gln
            20                  25                  30

Lys Ala Glu Ile Ala Ala Ser Arg Thr Ser His Ala Lys Ala Lys Ala
        35                  40                  45

Glu Ala Ala Glu Gln Ala Ala Leu Ala Ala
        50                  55

<210> SEQ ID NO 67
<211> LENGTH: 58
<212> TYPE: PRT
<213> ORGANISM: Homo sapiens

<400> SEQUENCE: 67

Lys Arg Arg Met Leu Gln Leu Lys Ser Asn Lys Val Arg Gln Lys Val
1               5                   10                  15

Glu His Ser Val Glu Gly Ala Gln Arg Ala Ala Ile Ala Arg Gln
            20                  25                  30

Lys Ala Glu Ile Ala Ala Ser Arg Thr Ser His Ala Lys Ala Lys Ala
        35                  40                  45

Glu Ala Ala Glu Gln Ala Ala Leu Ala Ala
        50                  55

<210> SEQ ID NO 68
<211> LENGTH: 58
<212> TYPE: PRT
<213> ORGANISM: Rattus norvegicus

<400> SEQUENCE: 68

Lys Arg Arg Val Leu Pro Leu Lys Ser Asn Lys Val Arg Gln Lys Val
1               5                   10                  15

Glu His Gly Val Glu Gly Ala Gln Arg Ala Ala Ile Ala Arg Gln
            20                  25                  30

Lys Ala Glu Ile Ala Ala Ser Arg Thr Ser His Ala Lys Ala Lys Ala
        35                  40                  45

Glu Ala Ala Glu Gln Ala Ala Leu Ala Ala
        50                  55

<210> SEQ ID NO 69
<211> LENGTH: 58
<212> TYPE: PRT
<213> ORGANISM: Mustela putorius furo

<400> SEQUENCE: 69

Lys Arg Arg Val Leu Pro Leu Lys Ser Asn Lys Val Arg Gln Lys Val
1               5                   10                  15

Glu His Ser Val Glu Gly Ala Gln Arg Ala Ala Ile Ala Arg Gln
            20                  25                  30

Lys Ala Glu Ile Ala Ala Ser Arg Thr Ser His Ala Lys Ala Lys Ala
        35                  40                  45

Glu Ala Ala Glu Gln Ala Ala Leu Ala Ala
        50                  55

<210> SEQ ID NO 70
<211> LENGTH: 58

```
<212> TYPE: PRT
<213> ORGANISM: Bos taurus

<400> SEQUENCE: 70

Lys Arg Arg Val Leu Pro Leu Lys Ser Ser Lys Val Arg Gln Lys Val
1               5                   10                  15

Asp His Ser Val Glu Gly Ala Gln Arg Ala Ala Ala Ile Ala Arg Gln
            20                  25                  30

Lys Ala Glu Ile Ala Ala Ser Arg Thr Ser His Ala Lys Ala Lys Ala
        35                  40                  45

Glu Ala Ala Glu Gln Ala Ala Leu Ala Ala
    50                  55

<210> SEQ ID NO 71
<211> LENGTH: 58
<212> TYPE: PRT
<213> ORGANISM: Macaca mulatta

<400> SEQUENCE: 71

Lys Arg Arg Met Leu Gln Leu Lys Ser Asn Lys Val Arg Gln Lys Val
1               5                   10                  15

Glu His Ser Val Glu Gly Ala Gln Arg Ala Ala Ala Ile Ala Arg Gln
            20                  25                  30

Lys Ala Glu Ile Ala Ala Ser Arg Thr Ser His Ala Lys Ala Lys Ala
        35                  40                  45

Glu Ala Ala Glu Gln Ala Ala Leu Ala Ala
    50                  55

<210> SEQ ID NO 72
<211> LENGTH: 58
<212> TYPE: PRT
<213> ORGANISM: Gallus gallus domesticus

<400> SEQUENCE: 72

Lys Lys Arg Val Ile Pro Leu Lys Ser Ala Lys Ile Arg Gln Lys Val
1               5                   10                  15

Asp Arg Ser Val Glu Gly Ala Gln Arg Ala Ala Ala Ile Ala Arg Gln
            20                  25                  30

Lys Ser Glu Ile Ala Ala Ser Arg Thr Thr His Ala Lys Ala Lys Ala
        35                  40                  45

Glu Gly Ser Glu Gln Ala Ala Gln Ala Ala
    50                  55

<210> SEQ ID NO 73
<211> LENGTH: 58
<212> TYPE: PRT
<213> ORGANISM: Rana Temporaria

<400> SEQUENCE: 73

Lys Lys Arg Val Ile Pro Leu Lys Ser Ala Lys Ile Arg Gln Lys Val
1               5                   10                  15

Asp Ser Ser Ile Glu Gly Ala Leu Arg Ala Gly Ala Ile Ala Arg Gln
            20                  25                  30

Lys Ala Glu Ile Ala Ala Ser Arg Thr Thr His Ala Lys Ala Lys Ala
        35                  40                  45

Glu Gly Ala Glu Gln Ala Ala Gln Ala Ala
    50                  55

<210> SEQ ID NO 74
```

```
<211> LENGTH: 58
<212> TYPE: PRT
<213> ORGANISM: Danio rerio

<400> SEQUENCE: 74

Lys Lys Lys Met Ile Gln Leu Lys Gly Thr Lys Ile Lys Gln Lys Val
1               5                   10                  15

Glu Arg Ser Leu Glu Gly Ala Gln Arg Ala Ala Ile Ala Lys Gln
            20                  25                  30

Lys Ala Glu Ile Ala Asn Ser Arg Thr Ala His Ala Lys Ser Lys Gly
        35                  40                  45

Asp Ala Ala Glu Gln Ala Ala Val Ala Ala
    50                  55

<210> SEQ ID NO 75
<211> LENGTH: 11
<212> TYPE: PRT
<213> ORGANISM: Homo sapiens

<400> SEQUENCE: 75

Pro Gln Pro Lys Arg Pro Arg Pro Gly Val Ser
1               5                   10

<210> SEQ ID NO 76
<211> LENGTH: 11
<212> TYPE: PRT
<213> ORGANISM: Mus musculus

<400> SEQUENCE: 76

Pro Gln Pro Lys Arg Pro Arg Pro Gly Ala Ser
1               5                   10

<210> SEQ ID NO 77
<211> LENGTH: 11
<212> TYPE: PRT
<213> ORGANISM: Rattus norvegicus

<400> SEQUENCE: 77

Pro Gln Pro Lys Arg Pro Arg Pro Gly Ser Ser
1               5                   10

<210> SEQ ID NO 78
<211> LENGTH: 11
<212> TYPE: PRT
<213> ORGANISM: Macaca mulatta

<400> SEQUENCE: 78

Pro Gln Pro Lys Arg Pro Arg Pro Gly Ala Ser
1               5                   10

<210> SEQ ID NO 79
<211> LENGTH: 11
<212> TYPE: PRT
<213> ORGANISM: Chlorocebus aethiops

<400> SEQUENCE: 79

Pro Gln Pro Lys Arg Pro Arg Pro Gly Ala Ser
1               5                   10

<210> SEQ ID NO 80
<211> LENGTH: 11
<212> TYPE: PRT
<213> ORGANISM: Bos taurus
```

```
<400> SEQUENCE: 80

Pro Gln Pro Lys Arg Pro Arg Pro Ala Ala Ala
1               5                   10
```